(12) United States Patent
Bagal et al.

(10) Patent No.: US 8,134,007 B2
(45) Date of Patent: Mar. 13, 2012

(54) PYRIDINE DERIVATIVES

(75) Inventors: Sharanjeet Kaur Bagal, Sandwich (GB); Karl Richard Gibson, Sandwich (GB); Mark Ian Kemp, Sandwich (GB); Cedric Poinsard, Sandwich (GB); Blanda Luzia Stammen, Sandwich (GB); Stephen Martin Denton, Sandwich (GB); Melanie Susanne Glossop, Sandwich (GB)

(73) Assignee: Pfizer Inc., New York, NY (US)

( * ) Notice: Subject to any disclaimer, the term of this patent is extended or adjusted under 35 U.S.C. 154(b) by 954 days.

(21) Appl. No.: 12/114,258

(22) Filed: May 2, 2008

(65) Prior Publication Data

US 2009/0048306 A1  Feb. 19, 2009

Related U.S. Application Data

(60) Provisional application No. 60/915,745, filed on May 3, 2007, provisional application No. 60/957,536, filed on Aug. 23, 2007.

(51) Int. Cl.
- *C07D 413/12* (2006.01)
- *C07D 413/14* (2006.01)
- *C07D 401/12* (2006.01)
- *C07D 401/14* (2006.01)
- *A61K 31/4418* (2006.01)
- *A61K 31/4427* (2006.01)
- *A61K 31/443* (2006.01)
- *A61K 31/4439* (2006.01)

(52) U.S. Cl. ............... 546/269.1; 546/272.1; 546/272.4; 514/340; 514/341; 514/342

(58) Field of Classification Search .................. None
See application file for complete search history.

(56) References Cited

U.S. PATENT DOCUMENTS

| | | | |
|---|---|---|---|
| 5,494,911 A | 2/1996 | Bartlett et al. | |
| 6,011,051 A | 1/2000 | Müllner et al. | 514/378 |
| 6,020,357 A | 2/2000 | Pinto et al. | 514/406 |
| 6,060,491 A | 5/2000 | Pruitt et al. | 514/355 |
| 6,689,779 B2 | 2/2004 | Lee et al. | 514/235.8 |
| 2003/0017166 A1 | 1/2003 | Lindner | 424/184.1 |
| 2006/0106011 A1 | 5/2006 | Bock et al. | 514/227.5 |
| 2007/0105904 A1 | 5/2007 | Tanaka et al. | 514/332 |

FOREIGN PATENT DOCUMENTS

| | | |
|---|---|---|
| CA | 2354266 | 6/2000 |
| CA | 2629964 | 6/2007 |
| EP | 1137438 | 6/2002 |
| EP | 0821952 | 3/2004 |
| EP | 1275638 | 6/2006 |
| EP | 1764093 | 3/2007 |
| EP | 1764095 | 3/2007 |
| WO | WO 9414780 | 7/1994 |
| WO | WO 9618616 | 6/1996 |
| WO | WO 9618617 | 6/1996 |
| WO | WO 0123887 | 4/2001 |
| WO | WO 0157024 | 8/2001 |
| WO | WO 0168612 | 9/2001 |
| WO | WO 0209648 | 2/2002 |
| WO | WO 03022276 | 3/2003 |
| WO | WO 03022285 | 3/2003 |
| WO | WO 03051366 | 6/2003 |
| WO | WO 03037274 | 8/2003 |
| WO | WO 03068747 | 8/2003 |
| WO | 2004080999 | 9/2004 |
| WO | WO 2004099148 | 11/2004 |
| WO | 2005004866 | 1/2005 |
| WO | WO 2005030753 | 4/2005 |
| WO | WO 2005084368 | 9/2005 |
| WO | WO 2006011050 | 2/2006 |
| WO | WO 2006051311 | 5/2006 |
| WO | WO 2007026920 | 3/2007 |
| WO | WO 2007039297 | 4/2007 |
| WO | WO 2007028654 | 5/2007 |
| WO | WO 2007051981 | 5/2007 |
| WO | WO 2007051982 | 5/2007 |
| WO | WO 2007052123 | 5/2007 |
| WO | WO 2007056341 | 5/2007 |
| WO | WO 2007058990 | 5/2007 |
| WO | WO 2007063925 | 6/2007 |
| WO | WO 2007083239 | 7/2007 |
| WO | WO 2007087442 | 8/2007 |
| WO | WO 2007089904 | 8/2007 |
| WO | WO 2007093901 | 8/2007 |
| WO | WO 2007126957 | 11/2007 |
| WO | WO 2008021388 | 2/2008 |
| WO | WO 2008079277 | 7/2008 |
| WO | WO 2008086014 | 7/2008 |
| WO | WO 2008106692 | 9/2008 |
| WO | WO 2008135830 | 11/2008 |

OTHER PUBLICATIONS

Pillie, et al., J. Org. Chem., vol. 48(7); pp. 1084-1091 (1983).

*Primary Examiner* — Kamal Saeed
*Assistant Examiner* — Nyeemah A Grazier
(74) *Attorney, Agent, or Firm* — J. Michael Dixon; Gregg C. Benson

(57) ABSTRACT

The present invention relates to compounds of the formula (I):

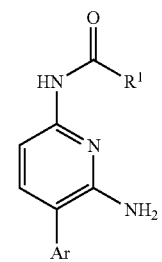

and pharmaceutically acceptable salts thereof, to processes for the preparation of, intermediates used in the preparation of, and compositions containing such compounds and the uses of such compounds for the treatment of pain.

23 Claims, 3 Drawing Sheets

PYRIDINE DERIVATIVES

CROSS-REFERENCE TO RELATED APPLICATION

This application claims the benefit of U.S. Provisional Application No. 60/915,745 filed May 3, 2007, and U.S. Provisional Application No. 60/957,536 filed Aug. 23, 2007, both of which applications are incorporated by reference herein in their entirety.

This invention relates to pyridine derivatives. More particularly, this invention relates to heteroaryl substituted N-[6-amino-5-aryl-pyridin-2-yl]-carboxamide derivatives and to processes for the preparation of, intermediates used in the preparation of, compositions containing and the uses of, such derivatives.

The pyridine derivatives of the present invention are sodium channel modulators and have a number of therapeutic applications, particularly in the treatment of pain. More particularly, the pyridine derivatives of the invention are $Na_{v1.8}$ modulators. Preferred pyridine derivatives of the invention show an affinity for the $Na_{v1.8}$ channel which is greater than their affinity for the $Na_{v1.5}$ channel and the tetrodotoxin-sensitive sodium channels (TTX-S).

The $Na_{v1.8}$ channel is a voltage-gated sodium channel which is expressed in nociceptors, the sensory neurones responsible for transducing painful stimuli. The rat channel and the human channel have been cloned in 1996 and 1998 respectively (*Nature* 1996; 379: 257-262; *Pain* 1998 (November); 78(2):107-114). The $Na_{v1.8}$ channel was previously known as SNS (sensory neurone specific) and PN3 (peripheral nerve type 3). The $Na_{v1.8}$ channel is atypical in that it shows resistance to the blocking effects of the puffer fish toxin tetrodotoxin and it is believed to underlie the slow-voltage-gated and tetrodotoxin-resistant (TTX-R) sodium currents recorded from dorsal root ganglion neurones. The closest molecular relative to the $Na_{v1.8}$ channel is the $Na_{v1.5}$ channel, which is the cardiac sodium channel, with which it shares approximately 60% homology. The $Na_{v1.8}$ channel is expressed most highly in the 'small cells' of the dorsal root ganglia (DRG). These are thought to be the C- and A-delta cells which are the putative polymodal nociceptors, or pain sensors. Under normal conditions, the $Na_{v1.8}$ channel is not expressed anywhere other than subpopulations of DRG neurones. The $Na_{v1.8}$ channels are thought to contribute to the process of DRG sensitisation and also to hyperexcitability due to nerve injury. Inhibitory modulation of the $Na_{v1.8}$ channels is aimed at reducing the excitability of nociceptors, by preventing them from contributing to the excitatory process.

Studies have shown that $Na_{v1.8}$ knock-out leads to a blunted pain phenotype, mostly to inflammatory challenges (A. N. Akopian et al., *Nat. Neurosci.* 1999; 2; 541-548) and that $Na_{v1.8}$ knockdown reduces pain behaviours, in this case neuropathic pain (J. Lai et al., *Pain,* 2002 (January); 95(1-2): 143-152). Coward et al. and Yiangou et al., have shown that $Na_{v1.8}$ appears to be expressed in pain conditions (*Pain.* 2000 (March); 85(1-2): 41-50 and FEBS Lett. 2000 (Feb. 11); 467(2-3): 249-252).

The $Na_{v1.8}$ channel has also been shown to be expressed in structures relating to the back and tooth pulp and there is evidence for a role in causalgia, inflammatory bowel conditions and multiple sclerosis (Bucknill et al., *Spine.* 2002 (Jan. 15); 27(2):135-140: Shembalker et al., *Eur J Pain.* 2001; 5(3): 319-323: Laird et al., *J Neurosci.* 2002 (Oct. 1); 22(19): 8352-8356: Black et al., *Neuroreport.* 1999 (Apr. 6); 10(5): 913-918 and *Proc. Natl. Acad. Sci. USA* 2000: 97: 11598-11602).

Several sodium channel modulators are known for use as anticonvulsants or antidepressants, such as carbamazepine, amitriptyline, lamotrigine and riluzole, all of which target brain tetradotoxin-sensitive (TTX-S) sodium channels. Such TTX-S agents suffer from dose-limiting side effects, including dizziness, ataxia and somnolence, primarily due to action at TTX-S channels in the brain.

WO-A-2006/011050 discusses 6-amino-2-aminocarbonyl-5-phenyl-pyridine derivatives.

Figure 1:
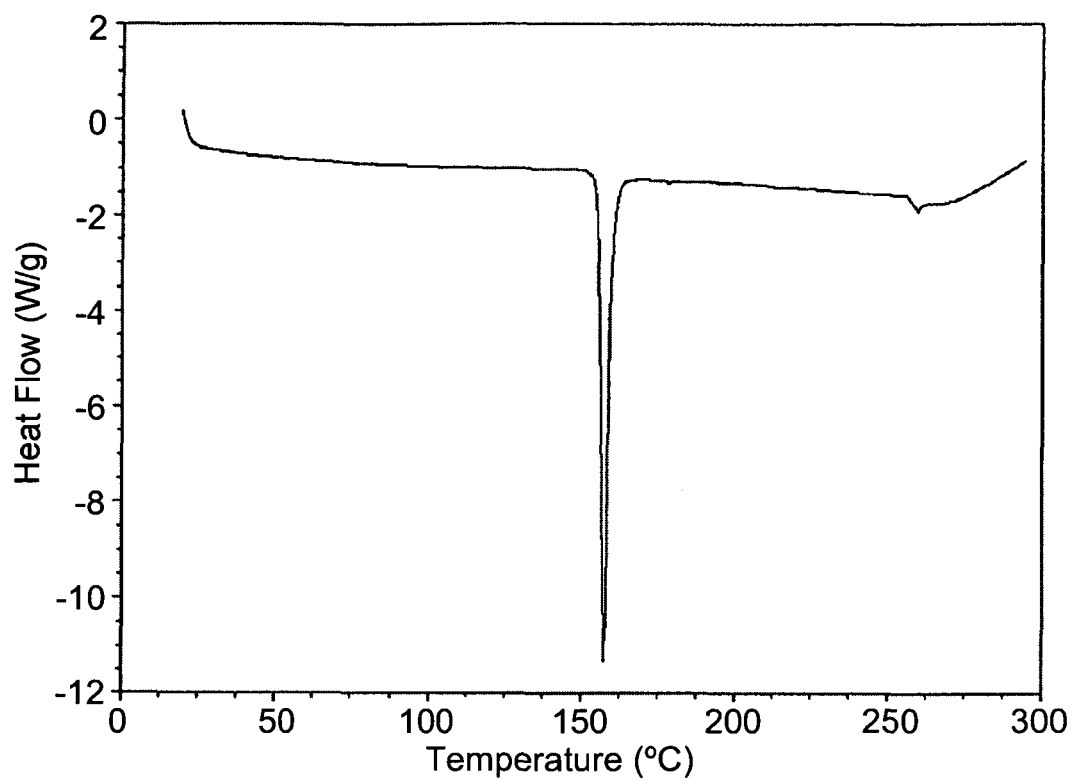
FIG. 1 shows a DSC thermogram for a crystalline form of N-{6-amino-5-[2-(trifluoromethoxy)phenyl]pyridin-2-yl}-3-methylisoxazole-4-carboxamide.

It is an objective of the invention to provide new $Na_{v1.8}$ channel modulators that are good drug candidates. Preferred compounds should bind potently to the $Na_{v1.8}$ channel whilst showing little affinity for other sodium channels, particularly $Na_{v1.5}$ and the TTX-S channels, and show functional activity as $Na_{v1.8}$ channel modulators. They should be well absorbed from the gastrointestinal tract, be metabolically stable and possess favourable pharmacokinetic properties. They should be non-toxic and demonstrate few side-effects. Furthermore, the ideal drug candidate will exist in a physical form that is stable, non-hygroscopic and easily formulated. Preferred pyridine derivatives of the present invention are selective for the $Na_{v1.8}$ channel over $Na_{v1.5}$ and the tetradotoxin-sensitive (TTX-S) sodium channels, leading to improvements in the side-effect profile.

The pyridine derivatives of the present invention are therefore potentially useful in the treatment of a wide range of disorders, particularly pain, acute pain, chronic pain, neuropathic pain, inflammatory pain, visceral pain, nociceptive pain including post-surgical pain, and mixed pain types involving the viscera, gastrointestinal tract, cranial structures, musculoskeletal system, spine, urogenital system, cardiovascular system and CNS, including cancer pain, back and orofacial pain.

Other conditions that may be treated with the pyridine derivatives of the present invention include multiple sclerosis, neurodegenerative disorders, irritable bowel syndrome, osteoarthritis, rheumatoid arthritis, neuropathological disorders, functional bowel disorders, inflammatory bowel diseases, pain associated with dysmenorrhea, pelvic pain, cystitis, pancreatitis, migraine, cluster and tension headaches, diabetic neuropathy, peripheral neuropathic pain, sciatica, fibromyalgia, causalgia, and conditions of lower urinary tract dysfunction.

The invention provides a pyridine derivative of the formula (I):

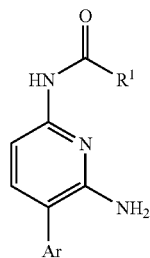

or a pharmaceutically acceptable salt or solvate thereof, wherein:
$R^1$ is selected from:
(i) phenyl, optionally substituted by one or more substituents each independently selected from halo, cyano, $(C_1-C_4)$ alkyl, $(C_1-C_4)$alkoxy, halo$(C_1-C_4)$alkyl, halo$(C_1-C_4)$ alkoxy, $(C_1-C_4)$alkoxy$(C_1-C_4)$alkyl, $(C_1-C_4)$alkylamino and di-$((C_1-C_4)$alkyl)amino; and
(ii) a 5-membered heteroaryl group comprising either (a) from 1 to 4 nitrogen atoms or (b) one oxygen or one sulphur atom and 1 or 2 nitrogen atoms, and wherein the heteroaryl group is optionally substituted by one substituent selected from $(C_1-C_4)$alkyl, $(C_1-C_4)$alkoxy, halo$(C_1-C_4)$alkyl, halo $(C_1-C_4)$alkoxy, $(C_1-C_4)$alkoxy$(C_1-C_4)$alkyl, $(C_1-C_4)$alkylamino and di-$((C_1-C_4)$alkyl)amino; with the proviso that $R^1$ is not imidazolyl, oxazolyl or 1,2,4-triazolyl;
Ar is

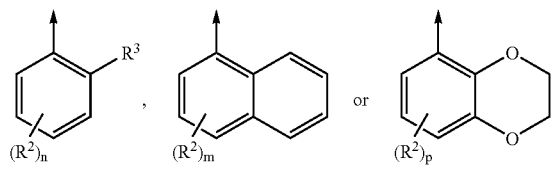

wherein →indicates the point of attachment to the pyridine ring;
each $R^2$ is independently $(C_1-C_4)$alkyl, $OR^4$, $(C_1-C_4)$alkoxy $(C_1-C_4)$alkyl, halo$(C_1-C_4)$alkyl, cyano or halo;
n is 0 to 4;
m is 0 to 7;
p is 0 to 3;
$R^3$ is hydrogen, $(C_1-C_4)$alkyl, $OR^4$, $(C_1-C_4)$alkoxy$(C_1-C_4)$ alkyl, halo$(C_1-C_4)$alkyl, cyano or halo;
$R^4$ is hydrogen, $(C_1-C_4)$alkyl, halo$(C_1-C_4)$alkyl, $(C_1-C_4)$ alkoxy$(C_1-C_4)$alkyl, $(C_3-C_6)$cycloalkyl, $(C_3-C_6)$cycloalkyl$(C_1-C_4)$alkyl, $Het^1$-, or $Het^1(C_1-C_4)$alkyl-; and
$Het^1$ is a saturated 5- or 6-membered heterocyclic ring comprising one oxygen atom.

In the above definitions, halo means fluoro, chloro, bromo or iodo. Alkyl, and alkoxy groups, containing the requisite number of carbon atoms, can be unbranched or branched. Examples of alkyl include methyl, ethyl, propyl (n-propyl and i-propyl) and butyl (n-butyl, i-butyl, sec-butyl and t-butyl). Examples of alkoxy include methoxy, ethoxy, propoxy (n-propoxy and i-propoxy) and butoxy (n-butoxy, i-butoxy, sec-butoxy and t-butoxy). Haloalkyl and haloalkoxy refers to an alkyl or alkoxy group, containing the requisite number of carbon atoms, which is substituted with one or more halogen atoms. Examples of haloalkyl include trifluoromethyl and 2,2,2-trifluoroethyl. Examples of haloalkoxy include trifluoromethoxy and 2,2,2-trifluoroethoxy.

In a preferred aspect (A), the invention provides a pyridine derivative of the formula (I), or a pharmaceutically acceptable salt or solvate thereof, wherein Ar is

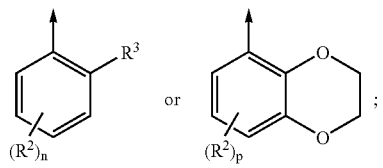

and n, $R^1$, $R^2$ and $R^3$ are as defined above. Preferably, n is 0, 1 or 2 and p is 0, 1 or 2.

In a preferred aspect (B), the invention provides a pyridine derivative of the formula (I), or a pharmaceutically acceptable salt or solvate thereof, wherein Ar, n, m, p, $R^1$ and $R^3$ are as defined above, either in the broadest aspect or in preferred aspects under (A); and each $R^2$ is independently $(C_1-C_4)$ alkyl, $OR^4$, $(C_1-C_4)$alkoxy$(C_1-C_4)$alkyl, halo$(C_1-C_4)$alkyl, and halo; and wherein $R^4$ is hydrogen, $(C_1-C_4)$alkyl, halo$(C_1-C_4)$alkyl, $(C_1-C_4)$alkoxy$(C_1-C_4)$alkyl, $(C_3-C_6)$cycloalkyl, or $(C_3-C_6)$cycloalkyl$(C_1-C_4)$alkyl; more preferably, each $R^2$ is independently methyl, ethyl, propyl, hydroxy, methoxy, ethoxy, propoxy, butoxy, cyclopropyloxy, methoxymethyl, methoxyethoxy, methoxypropoxy, cyclopropylmethoxy, difluoromethyl, trifluoromethyl, 2,2,2-trifluoroethyl, difluoromethoxy, trifluoromethoxy, 2,2,2-trifluoroethoxy, chloro or fluoro; most preferably each $R^2$ is independently hydroxy, methoxy, ethoxy, propoxy, cyclopropyloxy, methoxymethyl, methoxyethoxy, methoxypropoxy, cyclopropylmethoxy, difluoromethyl, trifluoromethyl, 2,2,2-trifluoroethyl, difluoromethoxy, trifluoromethoxy, 2,2,2-trifluoroethoxy, chloro or fluoro.

In an alternative preferred aspect (B1), the invention provides a pyridine derivative of the formula (I), or a pharmaceutically acceptable salt or solvate thereof, wherein Ar, n, m, p, $R^1$ and $R^3$ are as defined above, either in the broadest aspect or in preferred aspects under (A); and each $R^2$ is independently $(C_1-C_4)$alkyl, $(C_1-C_4)$alkoxy, halo$(C_1-C_4)$alkyl, halo $(C_1-C_4)$alkoxy, cyano or halo; more preferably, each $R^2$ is independently $(C_1-C_4)$alkyl, $(C_1-C_4)$alkoxy, halo$(C_1-C_4)$ alkyl, halo$(C_1-C_4)$alkoxy, or halo; more preferably, each $R^2$ is independently methyl, ethyl, propyl, methoxy, ethoxy, propoxy, difluoromethyl, trifluoromethyl, 2,2,2-trifluoroethyl, difluoromethoxy, trifluoromethoxy, 2,2,2-trifluoroethoxy, chloro or fluoro.

In preferred aspect (C), the invention provides a pyridine derivative of the formula (I), or a pharmaceutically acceptable salt or solvate thereof, wherein when Ar is

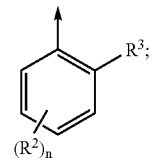

n, $R^1$ and $R^2$ are as defined above, either in the broadest aspect or in preferred aspects under (A), (B) or (B1), and $R^3$ is not hydrogen; more preferably, $R^3$ is halo, halo$(C_1-C_4)$alkyl, halo $(C_1-C_4)$alkoxy, $(C_1-C_4)$alkoxy, $(C_1-C_4)$alkyl, hydroxy, $(C_1-C_4)$alkoxy$(C_1-C_4)$alkyl, $(C_3-C_6)$cycloalkyl$(C_1-C_4)$alkoxy, $(C_3-C_6)$cycloalkyloxy or $(C_1-C_4)$alkoxy$(C_1-C_4)$alkoxy; more preferably, $R^3$ is methyl, ethyl, propyl, hydroxy, methoxy, ethoxy, propoxy, butoxy, cyclopropyloxy, methoxymethyl, methoxyethyl, methoxypropoxy, cyclopropylmethoxy, difluoromethyl, trifluoromethyl, 2,2,2-trifluoroethyl, difluoromethoxy, trifluoromethoxy, 2,2,2-trifluoroethoxy, chloro or fluoro; most preferably, R³ is ethoxy, propoxy, cyclopropyloxy, methoxyethyl, cyclopropylmethoxy, difluoromethyl, trifluoromethyl, 2,2,2-trifluoroethyl, difluoromethoxy, trifluoromethoxy, 2,2,2-trifluoroethoxy, chloro or fluoro.

In an alternative preferred aspect (C1), the invention provides a pyridine derivative of the formula (I), or a pharmaceutically acceptable salt or solvate thereof, wherein when Ar is

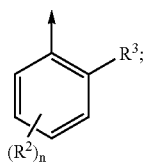

n, R¹ and R² are as defined above, either in the broadest aspect or in preferred aspects under (A), (B) or (B1), and R³ is halo, halo(C₁-C₄)alkyl, halo(C₁-C₄)alkoxy, (C₁-C₄)alkoxy or (C₁-C₄)alkyl; more preferably chloro, fluoro, methyl, ethyl, propyl, methoxy, ethoxy, propoxy, butoxy, difluoromethyl, trifluoromethyl, 2,2,2-trifluoroethyl, difluoromethoxy, trifluoromethoxy or 2,2,2-trifluoroethoxy; more preferably chloro, fluoro, difluoromethyl, trifluoromethyl, 2,2,2-trifluoroethyl, difluoromethoxy, trifluoromethoxy or 2,2,2-trifluoroethoxy; most preferably chloro, trifluoromethyl, or trifluoromethoxy.

In an alternative preferred aspect (C2), the invention provides a pyridine derivative of the formula (I), or a pharmaceutically acceptable salt or solvate thereof, wherein Ar is

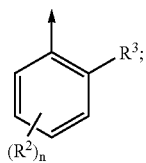

n, R¹ and R² are as defined above, either in the broadest aspect or in preferred aspects under (A), (B) or (B1), and R³ is OR⁴ or (C₁-C₄)alkoxy(C₁-C₄)alkyl, wherein R⁴ is hydrogen, (C₁-C₄)alkoxy(C₁-C₄)alkyl, (C₃-C₆)cycloalkyl, (C₃-C₆)cycloalkyl(C₁-C₄)alkyl, Het¹-, or Het¹(C₁-C₄)alkyl-; more preferably R³ is hydroxy, (C₁-C₄)alkoxy(C₁-C₄)alkyl, (C₃-C₆)cycloalkyl(C₁-C₄)alkoxy, (C₃-C₆)cycloalkyloxy or (C₁-C₄)alkoxy(C₁-C₄)alkoxy; more preferably R³ is (C₃-C₆)cycloalkyl(C₁-C₄)alkoxy or (C₃-C₆)cycloalkyloxy [for example cyclopropyloxy, or cyclopropylmethoxy]; more preferably R³ is (C₃-C₆)cycloalkyloxy; even more preferably R³ is cyclopropyloxy.

In an alternative preferred aspect (C3), the invention provides a pyridine derivative of the formula (I), or a pharmaceutically acceptable salt or solvate thereof, wherein Ar is

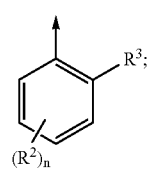

n, R¹ and R² are as defined above, either in the broadest aspect or in preferred aspects under (A), (B) or (B1), and R³ is halo, more preferably chloro.

In a preferred aspect (D), the invention provides a pyridine derivative of the formula (I), or a pharmaceutically acceptable salt or solvate thereof, wherein Ar, n, m, p, R¹, R² and R³ are as defined above, either in the broadest aspect or in a preferred aspect under (A), (B), (B1), (C), (C1), (C2) or (C3); and specific examples of R¹ include phenyl, pyrrolyl, pyrazolyl, isoxazolyl, thiazolyl, isothiazolyl, 1,2,3-triazolyl, oxadiazolyl, thiadiazolyl and tetrazolyl (each optionally substituted as specified above):

preferably R¹ is selected from:
(i) phenyl, optionally substituted by one or more substituents each independently selected from halo, cyano, (C₁-C₄)alkyl, (C₁-C₄)alkoxy, halo(C₁-C₄)alkyl, or (C₁-C₄)alkoxy(C₁-C₄)alkyl; and
(ii) a 5-membered heteroaryl group selected from pyrazolyl, isoxazolyl, oxadiazolyl, and 1,2,3-triazolyl, each being optionally substituted with (C₁-C₄)alkyl, halo(C₁-C₄)alkyl, or (C₁-C₄)alkoxy(C₁-C₄)alkyl:

more preferably, R¹ is a 5-membered heteroaryl group selected from

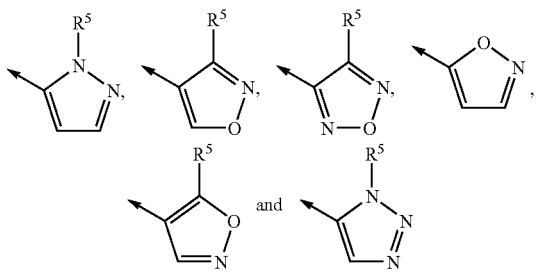

wherein→indicates the point of attachment to the carbonyl moiety and wherein each R⁵ is independently (C₁-C₄)alkyl, halo(C₁-C₄)alkyl, or (C₁-C₄)alkoxy(C₁-C₄)alkyl; more R⁵ is preferably methyl, ethyl, propyl, trifluoromethyl or methoxymethyl; most preferably R⁵ is methyl or ethyl.

Specific preferred pyridine derivatives according to the invention are those listed in the Examples section below, and the pharmaceutically acceptable salts and solvates thereof.

The compounds of formula (I), being $Na_{V1.8}$ channel modulators, are potentially useful in the treatment of a range of disorders. The treatment of pain, particularly chronic, inflammatory, neuropathic, nociceptive and visceral pain, is a preferred use.

Physiological pain is an important protective mechanism designed to warn of danger from potentially injurious stimuli from the external environment. The system operates through a specific set of primary sensory neurones and is activated by noxious stimuli via peripheral transducing mechanisms (see Millan, 1999, Prog. Neurobiol., 57, 1-164 for a review). These sensory fibres are known as nociceptors and are characteristically small diameter axons with slow conduction velocities. Nociceptors encode the intensity, duration and quality of noxious stimulus and by virtue of their topographically organised projection to the spinal cord, the location of the stimulus. The nociceptors are found on nociceptive nerve fibres of which there are two main types, A-delta fibres (myelinated) and C fibres (non-myelinated). The activity generated by nociceptor input is transferred, after complex processing in the dorsal horn, either directly, or via brain stem relay nuclei, to the ventrobasal thalamus and then on to the cortex, where the sensation of pain is generated.

Pain may generally be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain are neuropathic pain (e.g. painful diabetic neuropathy, postherpetic neuralgia), carpal tunnel syndrome, back pain, headache, cancer pain, arthritic pain and chronic post-surgical pain.

When a substantial injury occurs to body tissue, via disease or trauma, the characteristics of nociceptor activation are altered and there is sensitisation in the periphery, locally around the injury and centrally where the nociceptors terminate. These effects lead to a heightened sensation of pain. In acute pain these mechanisms can be useful, in promoting protective behaviours which may better enable repair processes to take place. The normal expectation would be that sensitivity returns to normal once the injury has healed. However, in many chronic pain states, the hypersensitivity far outlasts the healing process and is often due to nervous system injury. This injury often leads to abnormalities in sensory nerve fibres associated with maladaptation and aberrant activity (Woolf & Salter, 2000, Science, 288, 1765-1768).

Clinical pain is present when discomfort and abnormal sensitivity feature among the patient's symptoms. Patients tend to be quite heterogeneous and may present with various pain symptoms. Such symptoms include: 1) spontaneous pain which may be dull, burning, or stabbing; 2) exaggerated pain responses to noxious stimuli (hyperalgesia); and 3) pain produced by normally innocuous stimuli (allodynia—Meyer et al., 1994, Textbook of Pain, 13-44). Although patients suffering from various forms of acute and chronic pain may have similar symptoms, the underlying mechanisms may be different and may, therefore, require different treatment strategies. Pain can also therefore be divided into a number of different subtypes according to differing pathophysiology, including nociceptive, inflammatory and neuropathic pain.

Nociceptive pain is induced by tissue injury or by intense stimuli with the potential to cause injury. Pain afferents are activated by transduction of stimuli by nociceptors at the site of injury and activate neurons in the spinal cord at the level of their termination. This is then relayed up the spinal tracts to the brain where pain is perceived (Meyer et al., 1994, Textbook of Pain, 13-44). The activation of nociceptors activates two types of afferent nerve fibres. Myelinated A-delta fibres transmit rapidly and are responsible for sharp and stabbing pain sensations, whilst unmyelinated C fibres transmit at a slower rate and convey a dull or aching pain. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain may be chronic pain such as tumour related pain (e.g. bone pain, headache, facial pain or visceral pain) or pain associated with cancer therapy (e.g. postchemotherapy syndrome, chronic postsurgical pain syndrome or post radiation syndrome). Cancer pain may also occur in response to chemotherapy, immunotherapy, hormonal therapy or radiotherapy. Back pain may be due to herniated or ruptured intervertebral discs or abnormalities of the lumber facet joints, sacroiliac joints, paraspinal muscles or the posterior longitudinal ligament. Back pain may resolve naturally but in some patients, where it lasts over 12 weeks, it becomes a chronic condition which can be particularly debilitating.

Neuropathic pain is currently defined as pain initiated or caused by a primary lesion or dysfunction in the nervous system. Nerve damage can be caused by trauma and disease and thus the term 'neuropathic pain' encompasses many disorders with diverse aetiologies. These include, but are not limited to, peripheral neuropathy, diabetic neuropathy, post herpetic neuralgia, trigeminal neuralgia, back pain, cancer neuropathy, HIV neuropathy, phantom limb pain, carpal tunnel syndrome, central post-stroke pain and pain associated with chronic alcoholism, hypothyroidism, uremia, multiple sclerosis, spinal cord injury, Parkinson's disease, epilepsy and vitamin deficiency. Neuropathic pain is pathological as it has no protective role. It is often present well after the original cause has dissipated, commonly lasting for years, significantly decreasing a patient's quality of life (Woolf and Mannion, 1999, Lancet, 353, 1959-1964). The symptoms of neuropathic pain are difficult to treat, as they are often heterogeneous even between patients with the same disease (Woolf & Decosterd, 1999, Pain Supp., 6, S141-S147; Woolf and Mannion, 1999, Lancet, 353, 1959-1964). They include spontaneous pain, which can be continuous, and paroxysmal or abnormal evoked pain, such as hyperalgesia (increased sensitivity to a noxious stimulus) and allodynia (sensitivity to a normally innocuous stimulus).

The inflammatory process is a complex series of biochemical and cellular events, activated in response to tissue injury or the presence of foreign substances, which results in swelling and pain (Levine and Taiwo, 1994, Textbook of Pain, 45-56). Arthritic pain is the most common inflammatory pain. Rheumatoid disease is one of the commonest chronic inflammatory conditions in developed countries and rheumatoid arthritis is a common cause of disability. The exact aetiology of rheumatoid arthritis is unknown, but current hypotheses suggest that both genetic and microbiological factors may be important (Grennan & Jayson, 1994, Textbook of Pain, 397-407). It has been estimated that almost 16 million Americans have symptomatic osteoarthritis (OA) or degenerative joint disease, most of whom are over 60 years of age, and this is expected to increase to 40 million as the age of the population increases, making this a public health problem of enormous magnitude (Houge & Mersfelder, 2002, Ann Pharmacother., 36, 679-686; McCarthy et al., 1994, Textbook of Pain, 387-395). Most patients with osteoarthritis seek medical attention because of the associated pain. Arthritis has a significant impact on psychosocial and physical function and is known to be the leading cause of disability in later life. Ankylosing spondylitis is also a rheumatic disease that causes arthritis of the spine and sacroiliac joints. It varies from intermittent episodes of back pain that occur throughout life to a severe chronic disease that attacks the spine, peripheral joints and other body organs.

Another type of inflammatory pain is visceral pain which includes pain associated with inflammatory bowel disease (IBD). Visceral pain is pain associated with the viscera, which encompass the organs of the abdominal cavity. These organs include the sex organs, spleen and part of the digestive system. Pain associated with the viscera can be divided into digestive visceral pain and non-digestive visceral pain. Commonly encountered gastrointestinal (GI) disorders that cause pain include functional bowel disorder (FBD) and inflammatory bowel disease (IBD). These GI disorders include a wide range of disease states that are currently only moderately controlled, including, in respect of FBD, gastro-esophageal reflux, dyspepsia, irritable bowel syndrome (IBS) and functional abdominal pain syndrome (FAPS), and, in respect of IBD, Crohn's disease, ileitis and ulcerative colitis, all of which regularly produce visceral pain. Other types of visceral pain include the pain associated with dysmenorrhea, cystitis and pancreatitis and pelvic pain.

It should be noted that some types of pain have multiple aetiologies and thus can be classified in more than one area, e.g. back pain and cancer pain have both nociceptive and neuropathic components.

Other types of pain include:
pain resulting from musculo-skeletal disorders, including myalgia, fibromyalgia, spondylitis, sero-negative (non-rheumatoid) arthropathies, non-articular rheumatism, dystrophinopathy, glycogenolysis, polymyositis and pyomyositis;
heart and vascular pain, including pain caused by angina, myocardical infarction, mitral stenosis, pericarditis, Raynaud's phenomenon, scleredoma and skeletal muscle ischemia;
head pain, such as migraine (including migraine with aura and migraine without aura), cluster headache, tension-type headache mixed headache and headache associated with vascular disorders; and
orofacial pain, including dental pain, otic pain, burning mouth syndrome and temporomandibular myofascial pain.

The pyridine derivatives of formula (I) are also expected to be useful in the treatment of multiple sclerosis.

The invention also relates to therapeutic use of the pyridine derivatives of formula (I) as agents for treating or relieving the symptoms of neurodegenerative disorders. Such neurodegenerative disorders include, for example, Alzheimer's disease, Huntington's disease, Parkinson's disease, and Amyotrophic Lateral Sclerosis. The present invention also covers treating neurodegenerative disorders termed acute brain injury. These include but are not limited to: stroke, head trauma, and asphyxia. Stroke refers to a cerebral vascular disease and may also be referred to as a cerebral vascular accident (CVA) and includes acute thromboembolic stroke. Stroke includes both focal and global ischemia. Also, included are transient cerebral ischemic attacks and other cerebral vascular problems accompanied by cerebral ischemia. These vascular disorders may occur in a patient undergoing carotid endarterectomy specifically or other cerebrovascular or vascular surgical procedures in general, or diagnostic vascular procedures including cerebral angiography and the like. Other incidents are head trauma, spinal cord trauma, or injury from general anoxia, hypoxia, hypoglycemia, hypotension as well as similar injuries seen during procedures from embole, hyperfusion, and hypoxia. The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

The compounds of the present invention are useful in the treatment of conditions of lower urinary tract dysfunction including but not exclusively restricted to overactive bladder, increased daytime frequency, nocturia, urgency, urinary incontinence (any condition in which there is an involuntary leakage of urine), including stress urinary incontinence, urge urinary incontinence and mixed urinary incontinence, overactive bladder with associated urinary incontinence, enuresis, nocturnal enuresis, continuous urinary incontinence, and situational urinary incontinence such as incontinence during sexual intercourse. Activity of such compounds on lower urinary tract function, and thus their potential usefulness in treating conditions involving lower urinary tract dysfunction, can be investigated and assessed utilising a number of standard in vivo models known to those skilled in the art and frequently described in the literature (Morrison, J., et al., Neurophysiology and Neuropharmacology. In: Incontinence, Ed. Abrams, P., Cardozo, C., Khoury, S, and Wein, A. Report of the World Health Organisation Consensus Conference. Paris, France: Health Publications Ltd., 2002: 83-163; Brune M E et al. Comparison of alpha 1-adrenoceptor agonists in canine urethral pressure profilometry and abdominal leak point pressure models. J Urol. 2001, 166:1555-9).

The invention also relates to therapeutic use of the pyridine derivatives of formula (I) as agents for treating rheumatoid arthritis. Rheumatoid arthritis (RA) is considered a chronic autoimmune and inflammatory disease producing inflamed joints, which eventually swell, become painful, and experience degradation of cartilage, bone, and ligaments of the joint. A result of RA is deformity, instability, and stiffness of the joint and scarring within the joint. The joints deteriorate at a highly variable rate. Many factors, including genetic predisposition, may influence the pattern of the disease. People with rheumatoid arthritis may have a mild course, occasional flare-ups with long periods of remission without disease, or a steadily progressive disease, which may be slow or rapid. Rheumatoid arthritis may start suddenly, with many joints becoming inflamed at the same time. More often, it starts subtly, gradually affecting different joints. Usually, the inflammation is symmetric, with joints on both sides of the body affected. Typically, the small joints in the fingers, toes, hands, feet, wrists, elbows, and ankles become inflamed first, followed by the knees and hips.

Compounds of the present invention would be useful in treating arthritis, including rheumatoid arthritis, osteoarthritis, reactive arthritis (Reiter's Syndrome), infectious arthritis, psoriatic arthritis, polyarthritis, juvenile arthritis, juvenile rheumatoid arthritis, juvenile reactive arthritis and juvenile psoriatic arthritis Joint pain, also called arthralgia, can affect one or more joints. Joint pain can be caused by many types of injuries or conditions, including rheumatoid arthritis, osteoarthritis, and bursitis (i.e., inflammation of the bursae).

Other conditions that could be treated with the pyridine derivatives of the present invention include ankylosing spondylitis; rheumatism; gonococcal arthritis; sickle cell disease; joint infection; Lyme disease; psoriasis; polymyalgia rheumatica; hemophilia; cancer; hormonal disorder; nervous system disorder; syphilis; undifferentiated spondyloarthropathy (USpA); gout; Crohn's disease; multiple sclerosis; neurodegenerative disorders; irritable bowel syndrome; neuropathalogical disorders; functional bowel disorders; inflammatory bowel disease; pain associated with dysmenorrheal; pelvic pain; cystitis; pancreatitis; migraine; cluster and tension headaches; diabetic neuropathy; peripheral neuropathic pain; sciatica; fibromyalgia; causalgia; conditions of lower urinary tract dysfunction; myasthenia gravis; Guillain-Barre; autoimmune uveitis; autoimmune hemolytic anemia; pernicious anemia; autoimmune thrombocytopenia; temporal arteritis; anti-phospholipid syndrome; vasculitides such as Wegener's granulomatosis; Behcet's disease; psoriasis; dermatitis herpetiformis; pemphigus vulgaris; vitiligo; primary biliary cirrhosis; autoimmune hepatitis; Type 1 or immune-mediated diabetes mellitus; allergic rhinitis; sinusitis; rhinosinusitis; chronic otitis media; recurrent otitis media; allergic drug reactions; allergic insect sting reactions; allergic latex reactions; conjunctivitis; urticaria; anaphylaxis reactions; anaphylactoid reactions; atopic dermatitis; asthma; food allergies; Grave's disease; Hashimoto's thyroiditis; autoimmune oophoritis and orchitis; autoimmune disorder of the adrenal gland; systemic lupus erythematosus; scleroderma; polymyositis; dermatomyositis; ankylosing spondylitis; Sjogren's syndrome and ulcerative colitis.

The pyridine derivatives of formula (I) are also useful in the treatment of:

asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolitis; and obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension.

Pharmaceutically acceptable salts of the compounds of formula (I) include the acid addition and base salts thereof.

Suitable acid addition salts are formed from acids which form non-toxic salts. Examples include the acetate, adipate, aspartate, benzoate, besylate, bicarbonate/carbonate, bisulphate/sulphate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I); or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in a continuum of solid states ranging from fully amorphous to fully crystalline. The term 'amorphous' refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterised by a change of state, typically second order ('glass transition'). The term 'crystalline' refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterised by a phase change, typically first order ('melting point').

The compounds of the invention may also exist in unsolvated and solvated forms. The term 'solvate' is used herein to describe a molecular complex comprising the compound of the invention and one or more pharmaceutically acceptable solvent molecules, for example, ethanol. The term 'hydrate' is employed when said solvent is water.

A currently accepted classification system for organic hydrates is one that defines isolated site, channel, or metal-ion coordinated hydrates—see *Polymorphism in Pharmaceutical Solids* by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Also included within the scope of the invention are multi-component complexes (other than salts and solvates) wherein the drug and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallisation, by recrystallisation from solvents, or by physically grinding the components together—see Chem Commun, 17, 1889-1896, by O. Almarsson and M. J. Zaworotko (2004). For a general review of multi-component complexes, see J Pharm Sci, 64 (8), 1269-1288, by Haleblian (August 1975).

The compounds of the invention may also exist in a mesomorphic state (mesophase or liquid crystal) when subjected to suitable conditions. The mesomorphic state is intermediate between the true crystalline state and the true liquid state (either melt or solution). Mesomorphism arising as the result of a change in temperature is described as 'thermotropic' and that resulting from the addition of a second component, such as water or another solvent, is described as 'lyotropic'. Compounds that have the potential to form lyotropic mesophases are described as 'amphiphilic' and consist of molecules which possess an ionic (such as —COO$^-$Na$^+$, —COO$^-$K$^+$, or —SO$_3^-$Na$^+$) or non-ionic (such as —N$^-$N$^+$(CH$_3$)$_3$) polar head group. For more information, see *Crystals and the Polarizing Microscope* by N. H. Hartshorne and A. Stuart, 4$^{th}$ Edition (Edward Arnold, 1970).

Hereinafter all references to compounds of formula (I) include references to salts, solvates, multi-component complexes and liquid crystals thereof and to solvates, multi-component complexes and liquid crystals of salts thereof.

The compounds of the invention include compounds of formula (I) as hereinbefore defined, including all polymorphs and crystal habits thereof, prodrugs and isomers thereof (including optical, geometric and tautomeric isomers) as hereinafter defined and isotopically-labeled compounds of formula (I).

As one aspect, the present invention provides a compound of formula (I) which is an essentially pure, crystalline form of N-{6-amino-5-[2-(trifluoromethoxy)phenyl]pyridin-2-yl}-3-methylisoxazole-4-carboxamide.

As a further aspect, the present invention provides a compound of formula (I) which is an essentially pure, crystalline form of N-{6-amino-5-[2-(trifluoromethoxy)phenyl]pyridin-2-yl}-3-methylisoxazole-4-carboxamide which is characterised by a powder X-ray diffraction pattern (PXRD) obtained by irradiation with Cu Kα radiation (wavelength 1.5418 Ångstroms) which includes main peaks at 2-Theta° 16.6, 16.8, 23.1, 24.1 and 27.0+/−0.1.

The crystalline form of N-{6-amino-5-[2-(trifluoromethoxy)phenyl]pyridin-2-yl}-3-methylisoxazole-4-carboxamide is further characterised by differential scanning calorimetry (DSC) in which it exhibits a sharp endothermic peak at 158° C.±2° C.

The crystalline form of N-{6-amino-5-[2-(trifluoromethoxy)phenyl]pyridin-2-yl}-3-methylisoxazole-4-carboxamide is further characterised by a Fourier transform infrared (FT-IR) spectrum which includes absorption bands at 1453, 1167, 998 and 760 (+/−2) cm$^{-1}$.

The crystalline form of N-{6-amino-5-[2-(trifluoromethoxy)phenyl]pyridin-2-yl}-3-methylisoxazole-4-carboxamide is further characterised by a Fourier transform (FT) Raman spectrum which includes absorption bands at 1612, 1328, 749 and 686 (+/−2) cm$^{-1}$.

The expression 'essentially pure' when used herein means at least 95% by weight purity. More preferably, 'essentially pure' means at least 98% by weight purity, and most preferably at least 99% by weight purity.

As indicated, so-called 'prodrugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (Ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985).

Some examples of prodrugs in accordance with the invention include where the compound of formula (I) contains a primary or secondary amino functionality (—NH$_2$ or —NHR where R≠H), an amide thereof, for example, a compound wherein, as the case may be, one or both hydrogens of the amino functionality of the compound of formula (I) is/are replaced by (C$_1$-C$_{10}$)alkanoyl.

Further examples of replacement groups in accordance with the foregoing examples and examples of other prodrug types may be found in the aforementioned references.

Moreover, certain compounds of formula (I) may themselves act as prodrugs of other compounds of formula (I).

Also included within the scope of the invention are metabolites of compounds of formula (I), that is, compounds formed in vivo upon administration of the drug. Some examples of metabolites in accordance with the invention include (i) where the compound of formula (I) contains a methyl group, an hydroxymethyl derivative thereof (—CH$_3$->—CH$_2$OH):
(ii) where the compound of formula (I) contains an alkoxy group, an hydroxy derivative thereof (—OR->—OH);
(iii) where the compound of formula (I) contains a phenyl moiety, a phenol derivative thereof (-Ph->-PhOH); and Compounds of formula (I) containing one or more asymmetric carbon atoms can exist as two or more stereoisomers. Where structural isomers are interconvertible via a low energy barrier, tautomeric isomerism ('tautomerism') can occur. This can take the form of so-called valence tautomerism in compounds which contain an aromatic moiety. It follows that a single compound may exhibit more than one type of isomerism. Included within the scope of the present invention are all stereoisomers and tautomeric forms of the compounds of formula (I), including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, *Stereochemistry of Organic Compounds* by E. L. Eliel and S. H. Wilen (Wiley, 1994).

The present invention includes all pharmaceutically acceptable isotopically-labelled compounds of formula I wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and 14C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. 14C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (I) can generally be prepared by conventional techniques known to those skilled in the art or by processes analogous to those described in the accompanying Examples and Preparations using an appropriate isotopically-labeled reagent in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

The compounds of formula (I) should be assessed for their biopharmaceutical properties, such as solubility and solution stability (across pH), permeability, etc., in order to select the most appropriate dosage form and route of administration for treatment of the proposed indication.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences*, 19th Edition (Mack Publishing Company, 1995).

The compounds of the invention may be administered orally. Oral administration may involve swallowing, so that the compound enters the gastrointestinal tract, and/or buccal, lingual, or sublingual administration by which the compound enters the blood stream directly from the mouth.

Formulations suitable for oral administration include solid, semi-solid and liquid systems such as tablets; soft or hard capsules containing multi- or nano-particulates, liquids, or powders; lozenges (including liquid-filled); chews; gels; fast dispersing dosage forms; films; ovules; sprays; and buccal/mucoadhesive patches.

Liquid formulations include suspensions, solutions, syrups and elixirs. Such formulations may be employed as fillers in soft or hard capsules (made, for example, from gelatin or hydroxypropylmethylcellulose) and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in *Pharmaceutical Dosage Forms: Tablets*, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (I), a film-forming polymer, a binder, a solvent, a humectant, a plasticiser, a stabiliser or emulsifier, a viscosity-modifying agent and a solvent. Some components of the formulation may perform more than one function.

The compound of formula (I) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (I) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in *Pharmaceutical Technology On-line*, 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular, intrasynovial and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (I) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a suspension or as a solid, semi-solid, or thixotropic liquid for administration as an implanted depot providing modified release of the active compound. Examples of such formulations include drug-coated stents and semi-solids and suspensions comprising drug-loaded poly(dl-lactic-coglycolic)acid (PGLA) microspheres.

The compounds of the invention may also be administered topically, (intra)dermally, or transdermally to the skin or mucosa. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958, by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler, as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane, or as nasal drops. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (I), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff". The overall daily dose may be administered in a single dose or, more usually, as divided doses throughout the day.

The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, gels, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

For administration to human patients, the total daily dose of the compounds of the invention is typically in the range 0.1 mg to 1000 mg depending, of course, on the mode of administration. The total daily dose may be administered in single or divided doses and may, at the physician's discretion, fall outside of the typical range given herein.

These dosages are based on an average human subject having a weight of about 60 kg to 70 kg. The physician will readily be able to determine doses for subjects whose weight falls outside this range, such as infants and the elderly.

For the avoidance of doubt, references herein to "treatment" include references to curative, palliative and prophylactic treatment.

A $Na_{V1.8}$ channel modulator may be usefully combined with another pharmacologically active compound, or with two or more other pharmacologically active compounds, particularly in the treatment of pain. For example, a $Na_{V1.8}$ channel modulator, particularly a compound of formula (I), or a pharmaceutically acceptable salt or solvate thereof, as defined above, may be administered simultaneously, sequentially or separately in combination with one or more agents selected from:

an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

a barbiturate sedative, e.g. amobarbital, aprobarbital, butabarbital, butabital, mephobarbital, metharbital, methohexital, pentobarbital, phenobartital, secobarbital, talbutal, theamylal or thiopental;

a benzodiazepine having a sedative action, e.g. chlordiazepoxide, clorazepate, diazepam, flurazepam, lorazepam, oxazepam, temazepam or triazolam;

an $H_1$ antagonist having a sedative action, e.g. diphenhydramine, pyrilamine, promethazine, chlorpheniramine or chlorcyclizine;

a sedative such as glutethimide, meprobamate, methaqualone or dichloralphenazone;

a skeletal muscle relaxant, e.g. baclofen, carisoprodol, chlorzoxazone, cyclobenzaprine, methocarbamol or orphrenadine;

an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®, a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl)quinazoline;

a tricyclic antidepressant, e.g. desipramine, imipramine, amitriptyline or nortriptyline;

an anticonvulsant, e.g. carbamazepine, lamotrigine, topiratmate or valproate;

a tachykinin (NK) antagonist, particularly an NK-3, NK-2 or NK-1 antagonist, e.g. (αR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)$_2$-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

a muscarinic antagonist, e.g. oxybutynin, tolterodine, propiverine, tropsium chloride, darifenacin, solifenacin, temiverine and ipratropium;

a COX-2 selective inhibitor, e.g. celecoxib, rofecoxib, parecoxib, valdecoxib, deracoxib, etoricoxib, or lumiracoxib;

a coal-tar analgesic, in particular paracetamol;

a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

a vanilloid receptor agonist (e.g. resinferatoxin) or antagonist (e.g. capsazepine);

a beta-adrenergic such as propranolol;

a local anaesthetic such as mexiletine;

a corticosteroid such as dexamethasone;

a 5-HT receptor agonist or antagonist, particularly a 5-HT$_{1B/1D}$ agonist such as eletriptan, sumatriptan, naratriptan, zolmitriptan or rizatriptan;

a 5-HT$_{2A}$ receptor antagonist such as R(+)-alpha-(2,3-dimethoxy-phenyl)-1-[2-(4-fluorophenylethyl)]-4-piperidinemethanol (MDL-100907);

a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

Tramadol®;

a PDEV inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

an alpha-2-delta ligand such as gabapentin, pregabalin, 3-methylgabapentin, (1α,3α,5α)(3-amino-methyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

a cannabinoid;

metabotropic glutamate subtype 1 receptor (mGluR1) antagonist;

a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuprorion, nomifensine and viloxazine (Vivalan®), especially a selective noradrenaline reuptake inhibitor such as reboxetine, in particular (S,S)-reboxetine;

a dual serotonin-noradrenaline reuptake inhibitor, such as venlafaxine, venlafaxine metabolite O-desmethylvenlafaxine, clomipramine, clomipramine metabolite desmethylclomipramine, duloxetine, milnacipran and imipramine;

an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-5-chloro-3-pyridinecarbonitrile; 2-[[(1R,3S)-3-amino-4-hydroxy-1-(5-thiazolyl)butyl]thio]-4-chlorobenzonitrile, (2S, 4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3 pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, or guanidinoethyldisulfide;

an acetylcholinesterase inhibitor such as donepezil;

a prostaglandin E₂ subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(1S)-1-({[5-chloro-2-(3-fluorophenoxy)pyridin-3-yl]carbonyl}amino)ethyl] benzoic acid;

a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870, a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3, 5-trimethyl-6-(3-pyridylmethyl), 1,4-benzoquinone (CV-6504);

a sodium channel blocker, such as lidocaine;

a 5-HT3 antagonist, such as ondansetron;

and the pharmaceutically acceptable salts and solvates thereof.

Such combinations offer significant advantages, including synergistic activity, in therapy.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (I) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example, oral and parenteral, for administering the separate compositions at different dosage intervals, or for titrating the separate compositions against one another. To assist compliance, the kit typically comprises directions for administration and may be provided with a so-called memory aid.

All of the pyridine derivatives of the formula (I) can be prepared by the procedures described in the general methods presented below or by routine modifications thereof. The present invention also encompasses any one or more of these processes for preparing the pyridine derivatives of formula (I), in addition to any novel intermediates used therein.

In the following general methods, Ar and R¹ are as previously defined for a pyridine derivative of the formula (I) unless otherwise stated. Where ratios of solvents are given, the ratios are by volume.

According to a first process, compounds of formula (I) may be prepared from compounds of formula (IV), as illustrated by Scheme 1.

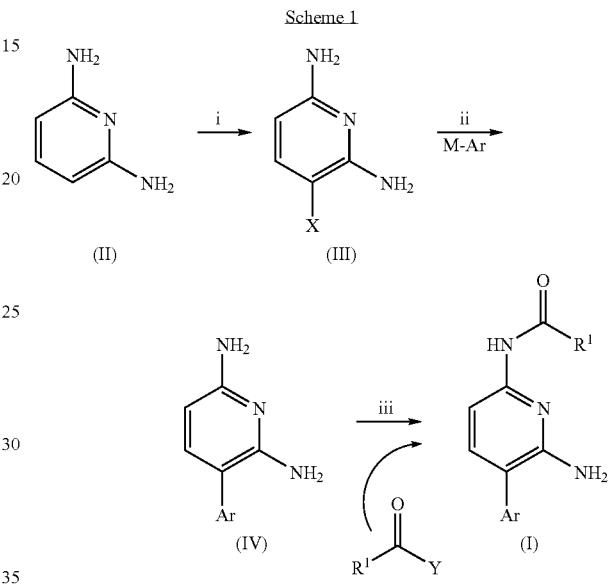

M is an optionally substituted/ligated metal or boron group suitable for cross-coupling reactions such as a trialkylstannane, dihydroxyborane, dialkoxyborane or halozinc.

X is a suitable group for cross-coupling reactions, typically Br or I

Y is a suitable leaving group, typically Cl

Compound (II) is commercially available.

Compounds of formula (III) may be prepared by an electrophilic halogenation reaction according to reaction step (i). Typical conditions comprise reaction of 2,6-diaminopyridine with a halogen, optionally in the presence of an organic or inorganic base, or according to the literature *J. Org, Chem.* 2006, 71, 2922-2925 and *J. C. S. Chem. Comm* 1980, 1139-1140. Preferred conditions comprise iodine and potassium carbonate in 2-methyl-tetrahydrofuran or iodine and triethylamine in ethanol/industrial methylated spirit (3-5% methanol in ethanol).

Compounds of formula (IV) can be prepared from compounds of formula (III) by process step (ii), a cross-coupling reaction, with ArM, in the presence of a suitable catalyst system, (e.g. palladium or nickel), and base. Typically 'Suzuki' conditions are used, comprising 1.2-3 equivalents of boronic acid, base and 0.01-0.25 equivalents of a palladium catalyst with phosphine based ligands in an organic solvent at a temperature of from 50° C. to 100° C. Preferred conditions comprise 2 equivalents of boronic acid, 1 equivalent of Cs₂CO₃ and 0.1 equivalents Pd(PPh₃)₄ in 2:1 1,4-dioxane/water at 80° C. or 1.1 equivalents of boronic acid, 1 equivalent of sodium or potassium carbonate, 0.015 equivalents tris(dibenzylideneacetone)dipalladium (0), and 0.045 equivalents tri-tertbutylphosphine in ethanol/water at 80° C.

Compounds of formula (I) can be prepared from compounds of formula (IV) according to process step (iii), an amide coupling using an acid chloride or a carboxylic acid activated by a suitable agent, optionally in the presence of a catalyst, in a suitable solvent. Typical conditions comprise acid chloride and an amine of formula (IV), with an excess of a suitable organic base, such as triethylamine, 2,6-lutidine or pyridine, in a suitable solvent, at a temperature of from room temperature to 80° C. Preferred conditions comprise 1.5 equivalents acid chloride in pyridine at 60° C., or 1.1 equivalents acid chloride and 1.3 eq 2,6-lutidine in acetonitrile at room temperature.

According to a second process, compounds of formula (I) may be prepared from compounds of formula (V), as illustrated by Scheme 2.

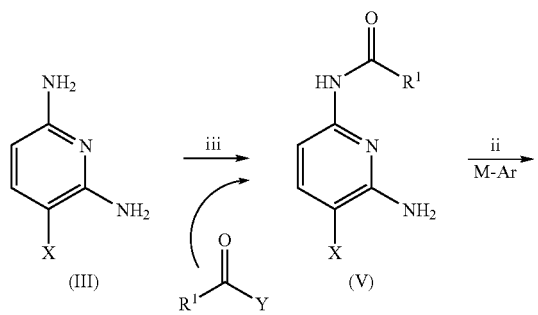

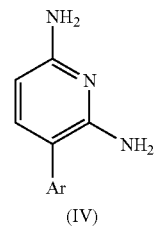

wherein M and X are as defined for Scheme 1.

Compounds of formula (VI) can be prepared from compounds of formula (III) by process step (iv), a metallation or boronation reaction optionally in the presence of a catalyst in a suitable solvent. Typical conditions comprise bis(pinacolato)diboron in the presence of potassium acetate and Pd(dppf)Cl$_2$ in dimethylformamide at 80° C.

Compounds of formula (IV) can be prepared from compounds of formula (VI) by a cross-coupling reaction according to process step (ii) as described above for Scheme 1.

According to a fourth process, compounds of formula (I) may be prepared from compounds of formula (VII), as illustrated by Scheme 4.

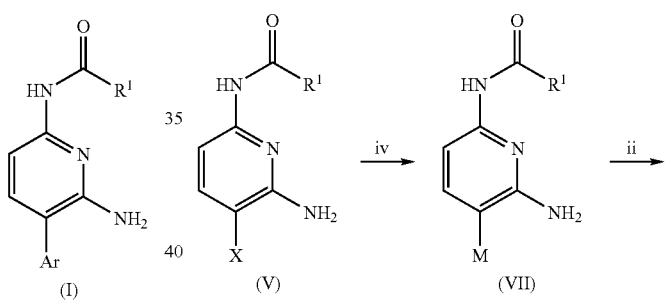

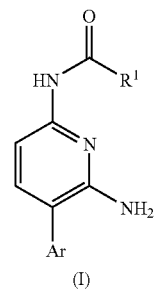

wherein M and X are as defined for Scheme 1.

Compounds of formula (VII) can be prepared from compounds of formula (V) by a metallation or boronation reaction according to process step (iv) as described above for Scheme 3.

Compounds of formula (I) can be prepared from compounds of formula (VII) by a cross-coupling reaction according to process step (ii) as described above for Scheme 1.

wherein M, X and Y are as defined for Scheme 1.

Compounds of formula (V) can be prepared from compounds of formula (III) by an amide coupling reaction according to process step (iii) as described above for Scheme 1.

Compounds of formula (I) can be prepared from compounds of formula (V) by a cross-coupling reaction according to process step (ii) as described above for Scheme 1.

According to a third process, compounds of formula (IV) may be prepared from compounds of formula (VI), as illustrated by Scheme 3.

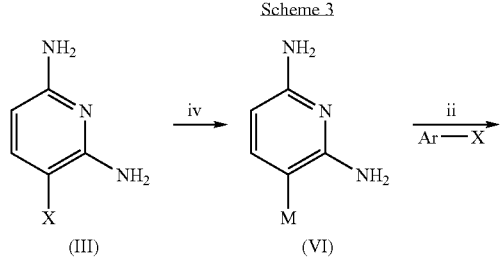

According to a fifth process, compounds of formula (III) may be prepared from compounds of formula (X), as illustrated by Scheme 5.

Scheme 5

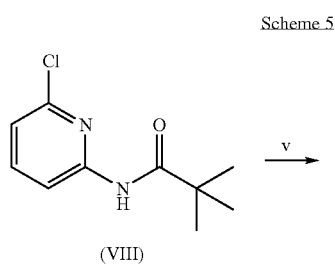

(VIII)

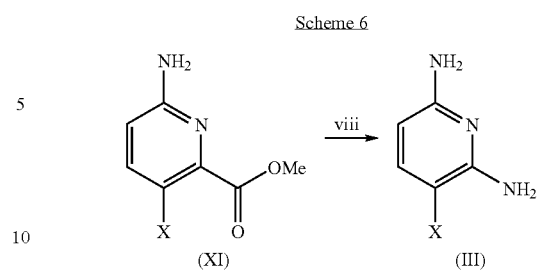

Scheme 6

(XI) → (III)

wherein X is as defined for Scheme 1.

Compounds of formula (XI) are known in the literature (*J. Org. Chem.* 1996, 61, 4623-4633).

Compounds of formula (III) can be prepared from compounds of formula (XI) according to process step (viii), by a hydrolysis reaction under basic or acidic conditions followed by a Curtius rearrangement or by displacement of the methyl ester with ammonia followed by a Hoffman rearrangement. Typical conditions comprise LiOH.H$_2$O in methanol/water at 75° C. followed by generation of an acyl azide using diphenylphosphoryl azide. Preferred conditions comprise 1.1 equivalents of diphenylphosphoryl azide, 1.1 equivalents triethylamine with 1.1 equivalents tert-butanol in toluene at 90° C., followed by deprotection under acidic conditions using HCl in 1,4-dioxane.

Referring to the general methods above, it will be readily understood to the skilled person that where protecting groups are present, these will be generally interchangeable with other protecting groups of a similar nature, e.g. where an amine is described as being protected with a tert-butoxycarbonyl group, this may be readily interchanged with any suitable amine protecting group. Suitable protecting groups are described in 'Protective Groups in Organic Synthesis' by T. Greene and P. Wuts (3$^{rd}$ edition, 1999, John Wiley and Sons).

The present invention also relates to novel intermediate compounds as defined above, all salts, solvates and complexes thereof and all solvates and complexes of salts thereof as defined hereinbefore for pyridine derivatives of formula (I). The invention includes all polymorphs of the aforementioned species and crystal habits thereof.

When preparing pyridine derivatives of formula (I) in accordance with the invention, it is open to a person skilled in the art to routinely select the best order of steps with which to synthesise the intermediates, and to choose the form of the intermediate compounds which provides the best combination of features for this purpose. Such features include the melting point, solubility, processability and yield of the intermediate form and the resulting ease with which the product may be purified on isolation. The skilled person may undertake the synthetic steps described above in any suitable order in order to arrive at the compounds of formula (I).

The invention is illustrated by the following representative Examples.

$^1$H Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad. The mass spectra (MS) were recorded using either electrospray ionisation (ESI) or atmospheric pressure chemical ionisation (APCI). The following abbreviations and chemical formulae have been used for common solvents: CDCl$_3$, deuterochloroform; D$_6$-DMSO, deuterodimethylsulphoxide; CD$_3$OD, deuterwherein X is as defined for Scheme 1.

Compounds of formula (VIII) are either commercially available, or known in the literature (*J. Org. Chem.* 2005, 70, 1711-1779).

Compounds of formula (IX) can be prepared from compounds of formula (VIII) by directed ortho-metallation followed by electrophilic halogenation according to process step (v). Typical conditions comprise an excess of tert-BuLi in THF at –78 C followed by the addition of dibromoethane, with warming to room temperature.

Compounds of formula (X) can be prepared from compounds of formula (IX) by displacement of the halogen by ammonia or a suitably protected form of ammonia according to process step (vi). Typical conditions comprise 4 equivalents RNH$_2$ (R=a suitable protecting group), 2 equivalents diisopropylethylamine in iso-propanol, heated at 160° C. for 4 hours. Where a protected form of ammonia is used, suitable deprotection would be required.

Compound of formula (III) can be prepared from compounds of formula (X) according to process step (vii), a deprotection reaction under basic or acidic conditions. Typical conditions are base mediated, using an alkali metal base such as KOH in 1,4-dioxane at 100° C.

According to a sixth process, compounds of formula (III) may be prepared from compounds of formula (XI), as illustrated by Scheme 6.

omethanol; THF, tetrahydrofuran. LCMS indicates liquid chromatography mass spectrometry ($R_t$=retention time). Where ratios of solvents are given, the ratios are by volume.

Certain compounds of the Examples and Preparations were purified using Automated Preparative High Performance Liquid Chromatography (HPLC). Reversed-phase HPLC conditions were on FractionLynx systems. Samples were submitted dissolved in 1 mL of DMSO. Depending on the nature of the compounds and the results of a pre-analysis, the purification was performed under either acidic conditions or basic conditions at ambient temperature. Acidic runs were carried out on a Sunfire Prep C18 OBD column (19×50 mm, 5 μm), basic runs were carried out on a Xterra Prep MS C18 (19×50 mm, 5 μm), both from Waters. A flow rate of 18 mL/min was used with mobile phase A: water+0.1% modifier (v/v) and B: acetonitrile+0.1% modifier (v/v). For acidic runs the modifier was formic acid, for basic run the modifier was diethylamine. A Waters 2525 binary LC pump supplied a mobile phase with a composition of 5% B for 1 min then ran from 5% to 98% B over 6 min followed by a 2 min hold at 98% B.

Detection was achieved using a Waters 2487 dual wavelength absorbance detector set at 225 nm followed in series by a Polymer Labs PL-ELS 2100 detector and a Waters ZQ 2000 4 way MUX mass spectrometer in parallel. The PL 2100 ELSD was set at 30° C. with 1.6/min supply of Nitrogen. The Waters ZQ MS was tuned with the following parameters:
ES+Cone voltage: 30 v Capillary: 3.20 kv
ES−Cone voltage: −30 v Capillary: −3.00 kv
Desolvation gas: 600 L/hr
Source Temp: 120° C.
Scan range 150-900 Da The fraction collection was triggered by both MS and ELSD.

Quality control analysis was performed using a LCMS method orthogonal to the preparative method. Acidic runs were carried out on a Sunfire C18 (4.6×50 mm, 5 μm), basic runs were carried out on a Xterra C18 (4.6×50 mm, 5 μm), both from Waters. A flow rate of 1.5 mL/min was used with mobile phase A: water+0.1% modifier (v/v) and B: acetonitrile+0.1% modifier (v/v). For acidic runs the modifier was formic acid, for basic run the modifier was diethylamine. A Waters 1525 binary LC pump ran a gradient elution from 5% to 95% B over 3 min followed by a 1 min hold at 95% B. Detection was achieved using a Waters MUX UV 2488 detector set at 225 nm followed in series by a Polymer Labs PL-ELS 2100 detector and a Waters ZQ 2000 4 way MUX mass spectrometer in parallel. The PL 2100 ELSD was set at 30° C. with 1.6/min supply of Nitrogen. The Waters ZQ MS was tuned with the following parameters:
ES+Cone voltage: 25 v Capillary: 3.30 kv
ES−Cone voltage: −30 v Capillary: −2.50 kv
Desolvation gas: 800 L/hr
Source Temp: 150° C.
Scan range 160-900 Da Unless otherwise noted, LCMS conditions were run according to the 6 minute LCMS gradient:
6 Minute LC-MS Gradient and Instrument Conditions
  Acid run:
A: 0.1% formic acid in water
B: 0.1% formic acid in acetonitrile
Column: C18 phase Phenomenex Gemini 50×4.6 mm with 5 micron particle size
Gradient: 95-5% A over 3 min, 1 min hold, 1 ml/min
UV: 210 nm-450 nm DAD
Temperature: 50 C
2 Minute LC-MS Gradient and Instrument Conditions
  Acid run:
A: 0.1% formic acid in water
B: 0.1% formic acid in acetonitrile
Column: C18 phase Fortis Pace 20×2.1 mm with 3 micron particle size
Gradient: 70-2% A over 1.8 min, 0.2 min hold, 1.8 ml/min
UV: 210 nm-450 nm DAD
Temperature: 75 C
C18 30 Minute Method LC-MS Gradient and Instrument Conditions
A: 0.1% formic acid in H2O
B: 0.1% formic acid in MeCN
Column: Phenomenex C18 phase Gemini 150×4.6 mm with 5 micron particle size
Gradient: 98-2% A over 18 min, 2 min hold, 1 ml/min
UV: 210 nm-450 nm DAD
Temperature: 50 C
Phenyl Hexyl 30 Minute Method LC-MS Gradient and Instrument Conditions
A: 10 mM ammonium acetate in H2O
B: 10 mM ammonium acetate in MeOH
Column: Phenomenex Phenyl Hexyl 150×4.6 mm with 5 micron particle size
Gradient: 98-2% A over 18 min, 2 min hold, 1 ml/min
UV: 210 nm-450 nm DAD
Temperature: 50 C

EXAMPLE 1

N-[6-Amino-5-(2-chlorophenyl)pyridin-2-yl]-1-methyl-1H-pyrazole-5-carboxamide

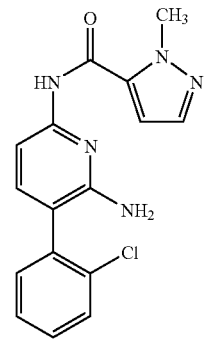

Method A

Oxalyl chloride (0.453 g, 3.57 mmol) was added to a slurry of 1-methyl-1H-pyrazole-5-carboxylic acid (0.150 g, 1.19 mmol) in dichloromethane (7 ml). One drop dimethylformamide was added and the reaction left to stir at room temperature for 2.5 hours. The reaction was concentrated in vacuo and azeotroped with dichloromethane. The residue was dissolved in $CH_3CN$ to make a 1M solution. 0.260 ml of the 1M solution of acid chloride (0.260 mmol) in $CH_3CN$ was added to a cooled solution of the 3-(2-chlorophenyl)-pyridine-2,6-diamine (Preparation 5, 0.055 g, 0.250 mmol) and lutidine (0.035 ml, 0.300 mmol) in $CH_3CN$ (2 ml). The reaction was warmed to room temperature and stirred for 18 hours. A further 0.130 ml of the acid chloride in $CH_3CN$ (0.130 mmol) and 0.017 ml lutidine (0.15 mmol) were added to the reaction, and stirred at room temperature for a further 18 hours before concentration in vacuo. The residue was taken up in 60 ml ethyl acetate and washed with 20 ml of a saturated aqueous solution of $NaHCO_3$ before drying over $Na_2SO_4$ and concentrating in vacuo to afford a golden oil. The residue was dissolved in 1 ml dimethylsulfoxide and purified using preparative HPLC.

LCMS Rt=3.03 min

MS m/z 328 [MH]+

$^1$HNMR (d$_6$-DMSO): 4.08 (s, 3H), 7.15 (s, 1H), 7.28 (d, 1H), 7.31-7.44 (m, 4H), 7.47 (s, 1H), 7.54 (m, 1H)

EXAMPLE 2

N-{6-Amino-5-[2-(trifluoromethyl)phenyl]pyridin-2-yl}-3-methylisoxazole-4-carboxamide

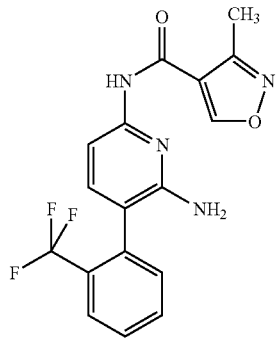

Method B

N-(6-Amino-5-iodopyridin-2-yl)-3-methylisoxazole-4-carboxamide (Preparation 15, 0.040 g, 0.12 mmol) was combined with 2-(trifluoromethyl)phenylboronic acid (0.044 g, 0.232 mmol) and cesium carbonate (0.038 g, 0.116 mmol) and suspended in a mixture of 1,4-dioxane (2 ml) and water (1 ml). The reaction was heated to 80° C. in a small, sealed, reaction vial (Reacti-vial™) then palladium tetrakis(triphenylphosphine) (0.010 g, 0.0087 mmol) added. The reaction was heated for 4 hours before cooling to room temperature and concentrating in vacuo. The residue was partitioned between dichloromethane and a saturated aqueous solution of Na$_2$CO$_3$ before filtering through a phase separation cartridge and concentrating in vacuo. The residue was purified by preparative HPLC to afford the title compound LCMS Rt=3.54 min MS m/z 363 [MH]+

EXAMPLE 3

N-[6-Amino-5-(2,5-dichlorophenyl)pyridin-2-yl]-1-methyl-1H-pyrazole-5-carboxamide

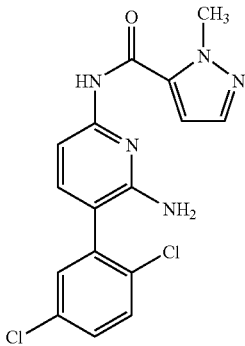

Method C

Oxalyl chloride (4.53 g, 35.7 mmol) was added to a slurry of 1-methyl-1H-pyrazole-5-carboxylic acid (3.00 g, 23.8 mmol) in dichloromethane (150 ml). Five drops dimethylformamide were added and the reaction left to stir at room temperature for 4 hours. The reaction was concentrated in vacuo to half the volume of dichloromethane. 0.825 ml of acid chloride solution in dichloromethane was added to a cooled solution of the 3-(2,5-dichloro)-pyridine-2,6-diamine (Preparation 7, 0.376 g, 1.485 mmol) in anhydrous pyridine (5 ml) and stirred at room temperature for 16 hours. The reaction was concentrated in vacuo, then partitioned between NaHCO$_3$ (20 ml) and dichloromethane (20 ml). The dichloromethane was washed with a saturated solution of brine (20 ml) before drying over Na$_2$SO$_4$ and concentrating in vacuo. The residue was purified by silica gel column chromatography eluting with 50:50 ethyl acetate:heptane to afford the title compound (0.146 g, 27% yield).

LCMS Rt=3.37 min

MS m/z 362 [MH]+

$^1$HNMR (CDCl$_3$): 4.26 (s, 3H), 4.32 (br s, 2H), 6.71 (s, 1H), 7.31-7.51 (m, 5H), 7.72 (d, 1H), 8.13 (br s, 1H)

EXAMPLE 4

N-[6-Amino-5-(2,3,5-trichlorophenyl)pyridin-2-yl]-1-methyl-1H-pyrazole-5-carboxamide

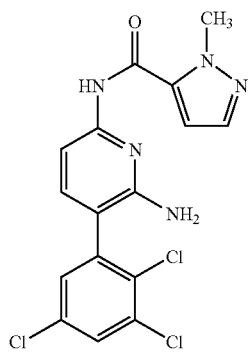

Method D

Oxalyl chloride (0.088 g, 0.693 mmol) was added to a slurry of 1-methyl-1H-pyrazole-5-carboxylic acid (0.066 g, 0.523 mmol) in dichloromethane (2 ml). One drop dimethylformamide was added and the reaction left to stir at room temperature for 2 hours. The reaction was concentrated in vacuo and azeotroped with dichloromethane. The residue was dissolved in THF (2 ml) and to this was added diisopropylethylamine (0.0956 g, 0.693 mmol) and 4-pyrrolidinopyridine (0.005 g, 0.035 mmol). The solution was cooled in an ice/acetone bath and 3-(2,3,5-trichlorophenyl)pyridine-2,6-diamine (Preparation 6, 0.100 g, 0.347 mmol) added portionwise over 1 minute. The reaction was warmed to room temperature and stirred for 18 hours. The reaction was diluted with dichloromethane and washed with a saturated aqueous solution of NH$_4$Cl (10 ml), followed by a saturated aqueous solution of NaHCO$_3$ (10 ml) and then water (10 ml) before drying over MgSO$_4$ and concentrating in vacuo to afford a brown gum. The residue was purified by trituration with pentane to afford the title compound as a yellow oil.

$^1$HNMR (d$_6$-DMSO): 4.09 (s, 3H), 5.60 (br s, 2H), 7.22 (d, 1H), 7.33 (d, 1H), 7.38 (d, 1H), 7.42 (d, 1H), 7.50 (d, 1H), 7.84 (d, 1H), 10.30 (br s, 1H)

EXAMPLE 5

N-[6-Amino-5-(2-chloro-5-methoxyphenyl)pyridin-2-yl]-1-methyl-1H-pyrazole-5-carboxamide

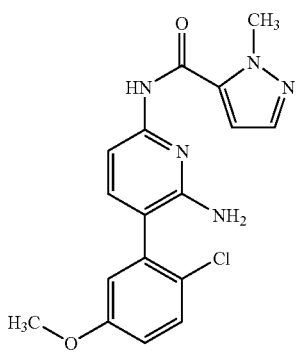

To a solution of 1-methyl-1H-pyrazole-5-carboxylic acid (5.28 g, 41.9 mmol) in dichloromethane (55 ml) was added oxalyl chloride (9.14 ml, 104.8 mmol) followed by 3 drops of dimethylformamide. The reaction was stirred at room temperature for 18 hours before concentration in vacuo. The residue was dissolved in acetonitrile (42 ml) and added dropwise to a cooled solution of 3-(2-chloro-5-methoxyphenyl)pyridine-2,6-diamine (preparation 1, 9.5 g, 38 mmol) and lutidine (6.6 ml, 57.1 mmol) in acetonitrile (650 ml). The reaction was allowed to warm to room temperature and stirred under nitrogen for 2 hours. The reaction was quenched by the addition of water (300 ml) and concentrated to low volume in vacuo. The aqueous residue was washed with dichloromethane (2×300 ml), dried (MgSO$_4$) and concentrated in vacuo. The residue was purified by silica gel column chromatography eluting with ethylacetate:heptane 1:4 to furnish a solid. This was recrystallised from toluene (100 ml) to afford 6.7 g of the title product.

LCMS Rt=1.88 min
MS m/z 358 [MH]+
$^1$HNMR (d-DMSO): 3.75 (s, 3H), 4.05 (s, 3H), 5.3 (br s, 2H), 6.9 (m, 1H), 6.95 (m, 1H), 7.2 (m, 1H), 7.3 (m, 1H), 7.35 (m, 1H), 7.45 (m, 1H), 7.5 (m, 1H), 10.3 (br s, 1H).

The following examples of the general formula:

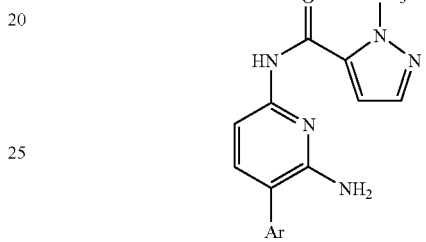

were prepared by methods analogous to Methods A, B and D, as described for Examples 1, 2 and 4 above. Unless otherwise noted, preparation details are as described for the method referred to.

| Example No. Name | Ar | Data | Preparation Information |
|---|---|---|---|
| 6 N-[6-Amino-5-(2-chloro-5-fluorophenyl)pyridin-2-yl]-1-methyl-1H-pyrazole-5-carboxamide | 2-chloro-5-fluorophenyl | LCMS Rt = 3.23 min MS m/z 346 [MH]+ | Method A, using 3-(2-chloro-5-fluorophenyl)pyridine-2,6-diamine (Preparation 3) and 1.1 equivalents acid chloride prepared from 1-methyl-1H-pyrazole-5-carboxylic acid. Stirred for 18 hours. Further 0.24 equivalents acid chloride added. Stirred for 4 hours. |
| 7 N-[6-Amino-5-(2,3-dichloro-5-methoxyphenyl)pyridin-2-yl]-1-methyl-1H-pyrazole-5-carboxamide | 2,3-dichloro-5-methoxyphenyl | LCMS Rt = 3.39 min MS m/z 391 [MH]+ $^1$HNMR (d$_6$-DMSO): 3.79 (s, 3H), 4.08 (s, 3H), 5.47 (br s, 2H), 6.89 (d, 1H), 7.20-7.31 (m, 3H), 7.38 (d, 1H), 7.49 (s, 1H), 10.32 (s, 1H) | Method A, using 3-(2,3-dichloro-5-methoxyphenyl)pyridine-2,6-diamine (Preparation 8), 1.6 equivalents lutidine and 1.3 equivalents acid chloride prepared from 1-methyl-1H-pyrazole-5-carboxylic acid. Purified by silica gel column chromatography, eluting with 75:25 ethyl acetate:heptane. Residue then further purified by preparative HPLC. |
| 8 N-[6-Amino-5-(2,5-dichloro-3-methoxyphenyl)pyridin- | 2,5-dichloro-3-methoxyphenyl | $^1$HNMR (d$_6$-DMSO): 3.91 (s, 3H), 4.08 (s, 3H), 5.43 (br s, | Method A, using 3-(2,5-dichloro-3-methoxyphenyl)pyridine-2,6-diamine (Preparation |

-continued

| Example No. Name | Ar | Data | Preparation Information |
|---|---|---|---|
| 2-yl]-1-methyl-1H-pyrazole-5-carboxamide | | 2H), 6.96 (s, 1H), 7.21 (s, 1H), 7.25 (s, 1H), 7.28 (d, 1H), 7.38 (d, 1H), 7.49 (s, 1H), 10.30 (s, 1H) | 4), 1.3 equivalents lutidine and 1.1 equivalents acid chloride prepared from 1-methyl-1H-pyrazole-5-carboxylic acid. Stirred for 72 hours. Purified by silica gel column chromatography, eluting with 15:85 to 50:50 ethyl acetate:heptane. |
| 9 N-[6-Amino-5-(2,3-dichlorophenyl)pyridin-2-yl]-1-methyl-1H-pyrazole-5-carboxamide | 2,3-dichlorophenyl | MS m/z 362 [MH]+ $^1$HNMR (d$_6$-DMSO): 4.1 (s, 3H), 5.4 (br s, 2H), 7.2 (d, 1H), 7.3 (m, 2H), 7.4 (m, 2H), 7.5 (d, 1H), 7.65 (d, d, 1H), 10.3 (br s, 1H) | Method D, using 3-(2,3-dichlorophenyl)pyridine-2,6-diamine (Preparation 14). Purified by silica gel column chromatography, eluting with 50:50 ethyl acetate:heptane. |
| 10 N-[6-Amino-5-(2-chloro-4-fluorophenyl)pyridin-2-yl]-1-methyl-1H-pyrazole-5-carboxamide | 2-chloro-4-fluorophenyl | LCMS Rt = 3.13 min MS m/z 346 [MH]+ | Method B, using N-(6-amino-5-iodopyridin-2-yl)-1-methyl-1H-pyrazole-5-carboxamide (Preparation 16), 2-chloro-4-fluorophenyl boronic acid and 0.074 equivalents palladium tetrakis(triphenylphosphine). Stirred for 5 hours. |
| 11 N-{6-Amino-5-[2-(trifluoromethoxy)pheny]-pyridin-2-yl}-1-methyl-1H-pyrazole-5-carboxamide | 2-(trifluoromethoxy)-phenyl | LCMS Rt = 3.59 min MS m/z 378 [MH]+ | Method B, using N-(6-amino-5-iodopyridin-2-yl)-1-methyl-1H-pyrazole-5-carboxamide (Preparation 16), 2-(trifluoromethoxy)phenyl boronic acid and 0.074 equivalents palladium tetrakis(triphenylphosphine). Stirred for 5 hours. |
| 12 N-{6-Amino-5-[5-fluoro-2-(trifluoromethyl)phenyl]-pyridin-2-yl}-1-methyl-1H-pyrazole-5-carboxamide | 5-fluoro-2-(trifluoromethyl)-phenyl | LCMS Rt = 3.36 min MS m/z 380 [MH]+ | Method B, using N-(6-amino-5-iodopyridin-2-yl)-1-methyl-1H-pyrazole-5-carboxamide (Preparation 16), 5-fluoro-2-(trifluoromethyl)phenyl boronic acid and 0.074 equivalents palladium tetrakis(triphenylphosphine). Stirred for 5 hours. |
| 13 N-[6-Amino-5-(2-chloro-3-fluorophenyl)pyridin-2-yl]-1-methyl-1H-pyrazole-5-carboxamide | 2-chloro-3-fluorophenyl | $^1$HNMR (d$_6$-DMSO): 4.06 (s, 3H), 5.46 (br s, 2H), 7.17-7.22 (m, 2H), 7.31 (d, 1H), 7.36-7.47 (m, 3H), 7.49 (d, 1H), 10.31 (br s, 1H) | Method B, using N-(6-amino-5-iodopyridin-2-yl)-1-methyl-1H-pyrazole-5-carboxamide (Preparation 16), 2-chloro-3-fluorophenyl boronic acid and 0.074 equivalents palladium tetrakis(triphenylphosphine). Stirred for 5 hours. Purified by trituration with dichloromethane. |
| 14 N-{6-Amino-5-[2-(trifluoromethyl)phenyl]-pyridin-2-yl}-1-methyl-1H-pyrazole-5-carboxamide | 2-(trifluoromethyl)-phenyl | LCMS Rt = 3.29 min MS m/z 362 [MH]+ | Method B, using N-(6-amino-5-iodopyridin-2-yl)-1-methyl-1H-pyrazole-5-carboxamide (Preparation 16), 2-(trifluoromethyl)phenylboronic acid and 0.074 equivalents palladium tetrakis(triphenylphosphine). Stirred for 5 hours. |
| 15 N-[6-Amino-5-(2,4- | 2,4-dichlorophenyl | $^1$HNMR (CDCl$_3$): 4.26 (s, 3H), | Method A, using 3-(2,4-dichlorophenyl)pyridine- |

-continued

| Example No. Name | Ar | Data | Preparation Information |
|---|---|---|---|
| dichlorophenyl)pyridin-2-yl]-1-methyl-1H-pyrazole-5-carboxamide | | 4.6 (br s, 2H), 6.7 (s, 1H), 7.3 (m, 1H), 7.4 (m, 2H), 7.55 (m, 2H), 7.7 (d, 1H), 8.1 (br s, 1H) LCMS Rt = 3.03 min MS m/z 362 [MH]+ | 2,6-diamine (Preparation 10), 1.5 equivalents lutidine and 1.3 equivalents acid chloride prepared from 1-methyl-1H-pyrazole-5-carboxylic acid. Purified by silica gel column chromatography, eluting with 95:5 dichloromethane:methanol Residue then further purified by preparative HPLC. |
| 16 N-{6-Amino-5-[5-chloro-2-(trifluoromethoxy)phenyl]-pyridin-2-yl}-1-methyl-1H-pyrazole-5-carboxamide | 5-chloro-2-(trifluoromethoxy)-phenyl | LCMS Rt = 3.60 min MS m/z 412 [MH]+ | Method A, using 3-[5-chloro-2-(trifluoromethoxy)phenyl]-pyridine-2,6-diamine (Preparation 12), 1.7 equivalents lutidine and 1.1 equivalents acid chloride prepared from 1-methyl-1H-pyrazole-5-carboxylic acid. |
| 17 N-{6-Amino-5-[2-fluoro-5-(trifluoromethoxy)phenyl]-pyridin-2-yl}-1-methyl-1H-pyrazole-5-carboxamide | 2-fluoro-5-(trifluoromethoxy)-phenyl | LCMS Rt = 3.45 min MS m/z 396 [MH]+ | Method A, using 3-[2-fluoro-5-(trifluoromethoxy)phenyl]-pyridine-2,6-diamine (Preparation 13), 1.8 equivalents lutidine and 1.4 equivalents acid chloride prepared from 1-methyl-1H-pyrazole-5-carboxylic acid. |
| 18 N-{6-Amino-5-[2-chloro-5-(trifluoromethoxy)phenyl]-pyridin-2-yl}-1-methyl-1H-pyrazole-5-carboxamide | 2-chloro-5-(trifluoromethoxy)-phenyl | LCMS Rt = 3.52 min MS m/z 412 [MH]+ | Method A, using 3-[2-chloro-5-(trifluoromethoxy)phenyl]-pyridine-2,6-diamine (Preparation 11), 3.0 equivalents lutidine and 1.1 equivalents acid chloride prepared from 1-methyl-1H-pyrazole-5-carboxylic acid. |

EXAMPLE 19

N-{6-Amino-5-[2-(difluoromethoxy)phenyl]pyridin-2-yl}-1-methyl-1H-pyrazole-5-carboxamide

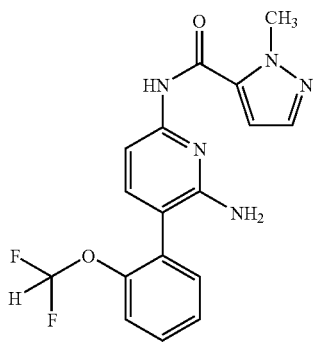

Method E

To a suspension of N-(6-amino-5-iodopyridin-2-yl)-1-methyl-1H-pyrazole-5-carboxamide (Preparation 16, 0.075 g, 0.22 mmol) in 1,4-dioxane (2 ml) and water (1 ml) was added cesium carbonate (0.071 g, 0.218 mmol), 2-[2-(difluoromethoxy)phenyl]-4,4,5,5-tetramethyl-1,3,2-dioxaborolane (Preparation 30, 0.117 g, 0.436 mmol) and palladium tetrakis(triphenylphosphine) (0.0252 g, 0.0218 mmol). The reaction vessel was purged with nitrogen, then sealed and heated in a Biotage microwave for 5 minutes at 120° C. The reaction was then diluted with ethyl acetate (50 ml) and washed with a dilute aqueous solution of NaHCO$_3$ before drying over Na$_2$SO$_4$ and concentrating in vacuo. The residue was purified by preparative HPLC to afford the title compound.

LCMS Rt=2.99 min
MS m/z 360 [MH]+

The following examples of the general formula:

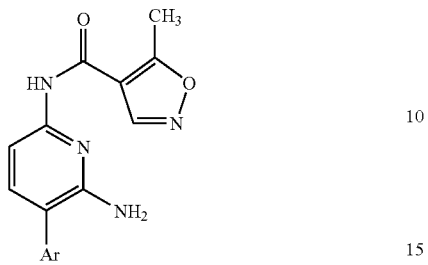

were prepared by methods analogous to Methods A, C and D, as described for Examples 1, 3 and 4 above. Unless otherwise noted, preparation details are as described for the method referred to.

| Example No. Name | Ar | Data | Preparation Information |
|---|---|---|---|
| 20 N-[6-Amino-5-(2-chlorophenyl)pyridin-2-yl]-5-methylisoxazole-4-carboxamide | 2-chlorophenyl | LCMS Rt = 3.26 min MS m/z 329 [MH]+ | Method A, using 3-(2-chlorophenyl)pyridine-2,6-diamine (Preparation 5) and acid chloride prepared from 5-methylisoxazole-4-carboxylic acid. |
| 21 N-[6-Amino-5-(2,5-dichlorophenyl)pyridin-2-yl]-5-methylisoxazole-4-carboxamide | 2,5-dichlorophenyl | LCMS Rt = 2.80 min MS m/z 363 [MH]+ | Method C, using 3-(2,5-dichlorophenyl)pyridine-2,6-diamine (Preparation 7) and 1.5 equivalents acid chloride prepared from 5-methylisoxazole-4-carboxylic acid. Reaction heated in a small, sealed reaction vial (Reacti-vial ™) at 60° C. Purified by preparative HPLC. |
| 22 N-[6-Amino-5-(2,3,5-trichlorophenyl)pyridin-2-yl]-5-methylisoxazole-4-carboxamide | 2,3,5-trichlorophenyl | $^1$HNMR ($d_6$-DMSO): 2.69 (s, 3H), 5.57 (br s, 2H), 7.31 (d, 1H), 7.42 (m, 2H), 7.85 (s, 1H), 9.19 (s, 1H), 10.31 (br s, 1H) | Method D, using acid chloride prepared from 5-methylisoxazole-4-carboxylic acid. Purified by recrystallisation from ethyl acetate. |
| 23 N-{6-Amino-5-[2-(trifluoromethoxy)phenyl]-pyridin-2-yl}-5-methylisoxazole-4-carboxamide | 2-(trifluoromethoxy)-phenyl | LCMS Rt = 3.28 min MS m/z 379 [MH]+ | Method A, using 3-[2-(trifluoromethoxy)phenyl]pyridine-2,6-diamine (Preparation 2), 1.32 equivalents lutidine and 1.10 equivalents acid chloride prepared from 5-methylisoxazole-4-carboxylic acid. |

EXAMPLE 24

N-[6-Amino-5-(2-chloro-5-methoxyphenyl)pyridin-2-yl]-3-methylisoxazole-4-carboxamide

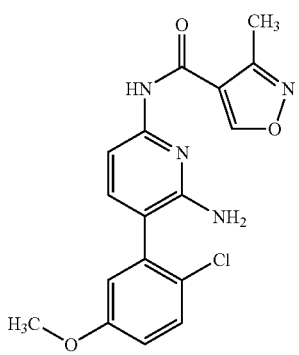

To a suspension of 3-methylisoxazole-4-carboxylic acid (2.73 g, 21.48 mmol) in dichloromethane (10 ml) was added oxalyl chloride (2.62 ml, 30.1 mmol) followed by 2 drops of dimethylformamide. The reaction was stirred at room temperature for 18 hours before concentration in vacuo. The residue was azeotroped with dichloromethane, dissolved in acetonitrile (15 ml) and added dropwise to a cooled solution of 3-(2-chloro-5-methoxyphenyl)pyridine-2,6-diamine (preparation 1, 5.2 g, 20.82 mmol) and lutidine (3.15 ml, 27.1 mmol) in acetonitrile (150 ml). The reaction was allowed to warm to room temperature and stirred under nitrogen for 30 minutes. The reaction was quenched by the addition of water (100 ml), extracted into ethyl acetate (200 ml), dried ($MgSO_4$) and concentrated in vacuo. The residue was purified by silica gel column chromatography eluting with ethylacetate:heptane 1:2 to furnish a pale yellow solid. This was triturated with t-butylmethylether, filtered, and recrystallised from ethyl acetate to furnish the title product as a white solid.

LCMS Rt=2.92 min

MS m/z 359 [MH]+

$^1$HNMR ($d_6$-DMSO): 2.4 (s, 3H), 3.95 (s, 3H), 5.3 (br s, 2H), 6.5 (m, 1H), 6.95 (m, 1H), 7.3 (m, 1H), 7.4-7.45 (m, 2H), 9.55 (s, 1H), 10.4 (br s, 1H).

The following examples of the general formula:

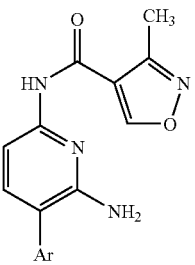

were prepared by methods analogous to Methods A, B and D as described for Examples 1, 2 and 4 above. Unless otherwise noted, preparation details are as described for the method referred to.

| Example No. Name | Ar | Data | Preparation Information |
|---|---|---|---|
| 25 N-[6-Amino-5-(2,5-dichlorophenyl)pyridin-2-yl]-3-methylisoxazole-4-carboxamide | 2,5-dichlorophenyl | LCMS Rt = 3.37 min MS m/z 363 [MH]+ | Method A, using 3-(2,5-dichlorophenyl)pyridine-2,6-diamine (Preparation 7), 2 equivalents lutidine and 1.5 equivalents acid chloride prepared from 3-methylisoxazole-4-carboxylic acid. |
| 26 N-[6-Amino-5-(2-chlorophenyl)pyridin-2-yl]-3-methylisoxazole-4-carboxamide | 2-chlorophenyl | LCMS Rt = 2.59 min MS m/z 329 [MH]+ $^1$HNMR ($CDCl_3$): 2.60 (s, 3H), 4.28 (br s, 2H), 7.32-7.43 (m, 4H), 7.51 (m, 1H), 7.67 (d, 1H), 7.84 (br s, 1H), 8.81 (s, 1H) | Method A, using 3-(2-chlorophenyl)pyridine-2,6-diamine (Preparation 5) and acid chloride prepared from 3-methylisoxazole-4-carboxylic acid. Stirred for 72 hours. Purified by silica gel column chromatography, eluting with 70:30 ethyl acetate:heptane. |
| 27 N-[6-Amino-5-(2,5-dichloro-3-methoxyphenyl)pyridin-2-yl]-3-methylisoxazole-4-carboxamide | 2,5-dichloro-3-methoxyphenyl | LCMS Rt = 2.91 min MS m/z 393 [MH]+ $^1$HNMR ($d_6$-DMSO): 2.47 (s, 3H), 3.91 (s, 3H), 5.41 (s, 2H), 6.96 (s, 1H), 7.26 (m, 2H), 7.37 (d, 1H), 9.54 (s, 1H) 10.40 (s, 1H) | Method A, using 3-(2,5-dichloro-3-methoxyphenyl)pyridine-2,6-diamine (Preparation 4), 1.3 equivalents lutidine and 1 equivalent acid chloride prepared from 3-methylisoxazole-4-carboxylic acid. Stirred for 72 hours. Residue purified by trituration with dichloromethane. |
| 28 N-[6-Amino-5-(2,3,5-trichlorophenyl)pyridin- | 2,3,5-trichlorophenyl | $^1$HNMR ($d_6$-DMSO): 2.42 (s, 3H), 5.55 (br s, 2H), 7.31 (d, | Method D, using acid chloride prepared from 3-methylisoxazole-4-carboxylic acid. Purified |

-continued

| Example No. Name | Ar | Data | Preparation Information |
|---|---|---|---|
| 2-yl]-3-methylisoxazole-4-carboxamide | | 1H), 7.39 (m, 2H), 7.83 (s, 1H), 9.54 (s, 1H), 10.38 (br s, 1H) | by preparative HPLC. |
| 29 N-[6-Amino-5-(2,3-dichloro-5-methoxyphenyl)pyridin-2-yl]-3-methylisoxazole-4-carboxamide | 2,3-dichloro-5-methoxyphenyl | LCMS Rt = 3.50 min M/S m/z 393 [MH]+ | Method A, using 3-(2,3-dichloro-5-methoxyphenyl)pyridine-2,6-diamine (Preparation 8), 1.6 equivalents lutidine and 1.5 equivalents acid chloride prepared from 3-methylisoxazole-4-carboxylic acid. |
| 30 N-[6-Amino-5-(7-chloro-2,3-dihydro-1,4-benzodioxin-5-yl)pyridin-2-yl]-3-methylisoxazole-4-carboxamide | 7-chloro-2,3-dihydro-1,4-benzodioxin-5-yl | LCMS Rt = 3.52 min MS m/z 387 [MH]+ | Method B, using N-(6-amino-5-iodopyridin-2-yl)-3-methylisoxazole-4-carboxamide (Preparation 15), (7-chloro-2,3-dihydro-1,4-benzodioxin-5-yl) boronic acid (Preparation 29) and 0.074 equivalents palladium tetrakis(triphenylphosphine). |
| 31 N-[6-Amino-5-(3,5-dichlorophenyl)pyridin-2-yl]-3-methylisoxazole-4-carboxamide | 3,5-dichlorophenyl | MS m/z 363 [MH]+ $^1$HNMR (d$_6$-DMSO): 2.4 (s, 3H), 5.6 (br s, 2H), 7.4 (m, 4H), 7.5 (m, 1H), 9.55 (s, 1H), 10.4 (s, 1H) | Method D, using 3-(3,5-dichlorophenyl)pyridine-2,6-diamine (Preparation 9) and 2 equivalents acid chloride prepared from 3-methylisoxazole-4-carboxylic acid. Purified by silica gel column chromatography, eluting with 50:50 ethyl acetate:heptane. |
| 32 N-{6-Amino-5-[5-chloro-2-(trifluoromethoxy)phenyl]-pyridin-2-yl}-3-methylisoxazole-4-carboxamide | 5-chloro-2-(trifluoromethoxy)phenyl | LCMS Rt = 3.70 min MS m/z 413 [MH]+ | Method A, using 3-[5-chloro-2-(trifluoromethoxy)phenyl]-pyridine-2,6-diamine (Preparation 12), 1.7 equivalents lutidine and acid chloride prepared from 3-methylisoxazole-4-carboxylic acid. |
| 33 N-[6-Amino-5-(2-fluorophenyl)pyridin-2-yl]-3-methylisoxazole-4-carboxamide | 2-fluorophenyl | LCMS Rt = 3.09 min MS m/z 313 [MH]+ | Method B, using N-(6-amino-5-iodopyridin-2-yl)-3-methylisoxazole-4-carboxamide (Preparation 15), 2-fluorophenyl boronic acid and 0.1 equivalents palladium tetrakis(triphenylphosphine). Stirred for 6 hours. Reaction performed in a round-bottom flask. |
| 34 N-[6-Amino-5-(2,5-difluorophenyl)pyridin-2-yl]-3-methylisoxazole-4-carboxamide | 2,5-difluorophenyl | LCMS Rt = 3.29 min MS m/z 331 [MH]+ | Method B, using N-(6-amino-5-iodopyridin-2-yl)-3-methylisoxazole-4-carboxamide (Preparation 15), 2,5-difluorophenyl boronic acid and 0.1 equivalents palladium tetrakis(triphenylphosphine). Stirred for 6 hours. Reaction performed in a round-bottom flask. |
| 35 N-[6-Amino-5-(2,3-dihydro-1,4-benzodioxin-5-yl)pyridin-2-yl]-3-methylisoxazole-4-carboxamide | 2,3-dihydro-1,4-benzodioxin-5-yl | LCMS Rt = 2.84 min MS m/z 353 [MH]+ | Method B, using N-(6-amino-5-iodopyridin-2-yl)-3-methylisoxazole-4-carboxamide (Preparation 15), 2,3-dihydro-1,4-benzodioxin-5-yl boronic acid and 0.1 |

-continued

| Example No. Name | Ar | Data | Preparation Information |
|---|---|---|---|
| | | | equivalents palladium tetrakis(triphenylphosphine). Stirred for 6 hours. Reaction performed in a round-bottom flask. |
| 36 N-{6-Amino-5-[2-fluoro-5-(trifluoromethoxy)phenyl]-pyridin-2-yl}-3-methylisoxazole-4-carboxamide | 2-fluoro-5-(trifluoromethoxy)phenyl | LCMS Rt = 3.61 min MS m/z 397 [MH]+ | Method A, using 3-[2-fluoro-5-(trifluoromethoxy)phenyl]-pyridine-2,6-diamine (Preparation 13), 1.8 equivalents lutidine and 1.4 equivalents acid chloride prepared from 3-methylisoxazole-4-carboxylic acid. |
| 37 N-{6-Amino-5-[2-chloro-5-(trifluoromethoxy)phenyl]-pyridin-2-yl}-3-methylisoxazole-4-carboxamide | 2-chloro-5-(trifluoromethoxy)phenyl | LCMS Rt = 3.70 min MS m/z 413 [MH]+ | Method A, using 3-[2-chloro-5-(trifluoromethoxy)phenyl]-pyridine-2,6-diamine (Preparation 11), 3.0 equivalents lutidine and 1.1 equivalents acid chloride prepared from 3-methylisoxazole-4-carboxylic acid. |
| 38 N-{6-Amino-5-[2-(difluoromethoxy)phenyl]-pyridin-2-yl}-3-methylisoxazole-4-carboxamide | 2-(difluoromethoxy)-phenyl | LCMS Rt = 3.11 min MS m/z 359 [M]− | Method B, using N-(6-amino-5-iodopyridin-2-yl)-3-methylisoxazole-4-carboxamide (Preparation 15), 2-[2-(difluoromethoxy)phenyl]-4,4,5,5-tetramethyl-1,3,2-dioxaborolane (Preparation 30) and 0.1 equivalents palladium tetrakis(triphenylphosphine). Stirred for 1 hour at 60° C. Reaction performed in a round-bottom flask. |
| 39 N-{6-Amino-5-[5-fluoro-2-(trifluoromethyl)phenyl]-pyridin-2-yl}-3-methylisoxazole-4-carboxamide | 5-fluoro-2-(trifluoromethyl)-phenyl | LCMS Rt = 3.54 min MS m/z 381 [MH]+ | Method B, using N-(6-amino-5-iodopyridin-2-yl)-3-methylisoxazole-4-carboxamide (Preparation 15), 5-fluoro-2-(trifluoromethyl)phenyl boronic acid and 0.1 equivalents palladium tetrakis(triphenylphosphine). Stirred for 3 hours. Reaction performed in a round-bottom flask. |
| 40 N-[6-Amino-5-(4-fluorophenyl)pyridin-2-yl]-3-methylisoxazole-4-carboxamide | 4-fluorophenyl | LCMS Rt = 2.88 min MS m/z 313 [MH]+ | Method B, using N-(6-amino-5-iodopyridin-2-yl)-3-methylisoxazole-4-carboxamide (Preparation 15), 4-fluorophenyl boronic acid and 0.1 equivalents palladium tetrakis(triphenylphosphine). Stirred at 60° C. for 2 hours. |
| 41 N-[6-Amino-5-(2-chloro-5-fluorophenyl)pyridin-2-yl]-3-methylisoxazole-4-carboxamide | 2-chloro-5-fluorophenyl | LCMS Rt = 3.30 min MS m/z 347 [MH]+ | Method B, using N-(6-amino-5-iodopyridin-2-yl)-3-methylisoxazole-4-carboxamide (Preparation 15), 2-chloro-5-fluorophenyl boronic acid and 0.1 equivalents palladium tetrakis(triphenylphosphine). Stirred at 60° C. for 2 hours. |

| Example No. Name | Ar | Data | Preparation Information |
|---|---|---|---|
| 42<br>N-[6-Amino-5-[2-(difluoromethyl)phenyl]-pyridin-2-yl]-3-methylisoxazole-4-carboxamide | 2-(difluoromethyl)-phenyl | LCMS Rt = 2.80 min<br>MS m/z<br>345 [MH]+<br>$^1$HNMR (CDCl$_3$):<br>2.61 (s, 3H),<br>4.25 (br s, 2H),<br>6.50 (br t, 1H),<br>7.34 (d, 1H),<br>7.40 (d, 1H),<br>7.56 (m, 2H),<br>7.69 (d, 1H),<br>7.80 (d, 1H),<br>7.86 (br s, 1H),<br>8.83 (s, 1H) | Method B, using N-(6-amino-5-iodopyridin-2-yl)-3-methylisoxazole-4-carboxamide (Preparation 15), 3-equivalents 2-[2-(difluoromethyl)phenyl]-4,4,5,5-tetramethyl-1,3,2-dioxaborolane (Preparation 31) and 0.08 equivalents palladium tetrakis(triphenylphosphine). Stirred at 80° C. for 3 hours. Purified by column chromatography, eluting with 70:30 ethyl acetate:heptane. |

EXAMPLE 43

N-{6-Amino-5-[2-(trifluoromethoxy)phenyl]pyridin-2-yl}-3-methylisoxazole-4-carboxamide

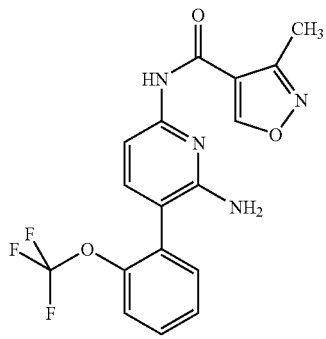

a) Oxalyl chloride (1.46 g, 11.5 mmol) was added to a slurry of 3-methylisoxazole-4-carboxylic acid (0.50 g, 3.93 mmol) in dichloromethane (30 ml). Two drops dimethylformamide were added and the reaction left to stir at room temperature for 18 hours. The reaction was concentrated in vacuo and azeotroped with dichloromethane. The residue was dissolved in CH$_3$CN to make a 1M solution. 2.5 ml of the 1M solution of acid chloride (2.50 mmol) in CH$_3$CN was added to a cooled solution of the 3-[2-(trifluoromethoxy)phenyl]pyridine-2,6-diamine (Preparation 2, 0.50 g, 1.86 mmol) and lutidine (0.33 ml, 2.97 mmol) in CH$_3$CN (30 ml). The reaction was warmed to room temperature and stirred for 19 hours before concentrating in vacuo. The residue was taken up in ethyl acetate and washed with a saturated aqueous solution of NaHCO$_3$ before concentrating in vacuo. The residue was purified by silica gel column chromatography eluting with 15:85 to 50:50 ethyl acetate:heptane to afford the title compound (0.565 g, 80% yield).

$^1$HNMR (d$_6$-DMSO): 2.42 (s, 3H), 5.34 (br s, 2H), 7.30 (d, 1H), 7.39-7.54 (m, 5H), 9.55 (s, 1H), 10.40 (br s, 1H)

LCMS Rt=3.10 min

MS m/z 379 [MH]+ b) N-{6-Amino-5-[2-(trifluoromethoxy)phenyl]pyridin-2-yl}-3-methylisoxazole-4-carboxamide can also be prepared according to the following method:

To a suspension of 3-methylisoxazole-4-carboxylic acid (2.58 g, 20 mmol) in isopropylacetate (26 ml) was added thionyl chloride (2.4 g, 1.47 ml, 20 mmol) and the reaction heated to 70° C. for 5 hours before cooling to room temperature. 11/12$^{ths}$ of this solution was added dropwise to a solution of 3-[2-(trifluoromethoxy)phenyl]pyridine-2,6-diamine (Preparation 2, 4.56 g, 16.9 mmol) and 2,6-lutidine (3.98 g, 4.3 ml, 37.2 mmol) in isopropylacetate (23 ml). The reaction was stirred at room temperature for 30 minutes during which a slurry was formed caused by crystallisation of lutidine hydrochloride. 20% w/w citric acid (46 ml) was added, the biphasic mixture stirred for 10 minutes before separation. The organic phase was washed with saturated sodium bicarbonate solution (46 ml), water (46 ml) and then reduced in volume to 16 ml. Toluene was then added (2×46 ml) and the volume reduced again to 20 ml. The resultant white solid was collected by filtration, washed with toluene (10 ml) and dried to afford the title compound in 46% yield. The white solid (2.1 g) was slurried in toluene (10 ml, 5 ml/g) and heated to reflux to form a solution. The resultant solution was cooled to 0° C. and granulated for 1 hour. The solid was collected by filtration, washed with toluene (6 ml, 3 ml/g) and dried overnight to yield 1.8 g of crystalline material.

The following examples of the general formula:

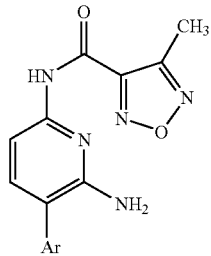

were prepared by methods analogous to Methods A or C, as described for Example 1 and 3 above. Unless otherwise noted, preparation details are as described for the method referred to.

| Example No. Name | Ar | Data | Preparation Information |
|---|---|---|---|
| 44 N-[6-Amino-5-(2,5-dichlorophenyl)pyridin-2-yl]-4-methyl-1,2,5-oxadiazole-3-carboxamide | 2,5-dichlorophenyl | LCMS Rt = 3.39 min MS m/z 364 [MH]+ $^1$HNMR (CDCl$_3$): 2.68 (s, 3H), 4.42 (br s, 2H), 7.27-7.46 (m, 4H), 7.68 (d, 1H), 8.96 (br s, 1H) | Method C, using 3-(2,5-dichlorophenyl)pyridine-2,6-diamine (Preparation 7), 1 equivalent acid chloride prepared from 4-methyl-1,2,5-oxadiazole-3-carboxylic acid. Acid chloride prepared using neat thionyl chloride at 50° C. for 16 hours. |
| 45 N-[6-Amino-5-(2-chloro-5-methoxyphenyl)pyridin-2-yl]-4-methyl-1,2,5-oxadiazole-3-carboxamide | 2-chloro-5-methoxyphenyl | LCMS Rt = 3.52 min MS m/z 360 [MH]+ | Method A, using 3-(2-chloro-5-methoxyphenyl)pyridine-2,6-diamine (Preparation 1), 2 equivalents lutidine and 1.5 equivalents acid chloride prepared from 4-methyl-1,2,5-oxadiazole-3-carboxylic acid. Acid chloride prepared using neat thionyl chloride at 50° C. for 16 hours. |
| 46 N-[6-Amino-5-(2-chlorophenyl)pyridin-2-yl]-4-methyl-1,2,5-oxadiazole-3-carboxamide | 2-chlorophenyl | LCMS Rt = 3.47 min MS m/z 330 [MH]+ | Method A, using 3-(2-chlorophenyl)pyridine-2,6-diamine (Preparation 5) and 1.1 equivalents acid chloride prepared from 4-methyl-1,2,5-oxadiazole-3-carboxylic acid. Stirred for 18 hours. Further 0.4 equivalents acid chloride and 0.5 equivalents lutidine added and stirred for 4 hours. Further 0.2 equivalents acid chloride and 0.3 equivalents lutidine added and stirred for 20 hours. |
| 47 N-[6-Amino-5-(2-chloro-5-fluorophenyl)pyridin-2-yl]-4-methyl-1,2,5-oxadiazole-3-carboxamide | 2-chloro-5-fluorophenyl | LCMS Rt = 3.61 min MS m/z 346 [M]− | Method A, using 3-(2-chloro-5-fluorophenyl)pyridine-2,6-diamine (Preparation 3) and 1.1 equivalents acid chloride prepared from 4-methyl-1,2,5-oxadiazole-3-carboxylic acid. Stirred for 18 hours. Further 0.7 equivalents acid chloride added and stirred for a further 4 hours. Further 0.6 equivalents of lutidine and 0.6 equivalents acid chloride added and stirred for 18 hours. |
| 48 N-[6-Amino-5-(2,3-dichloro-5-methoxyphenyl)pyridin-2-yl]-4-methyl-1,2,5-oxadiazole-3-carboxamide | 2,3-dichloro-5-methoxyphenyl | LCMS Rt = 3.23 min MS m/z 394 [MH]+ $^1$HNMR (d$_6$-DMSO): 2.51 (s, 3H), 3.79 (s, 3H), 6.90 (d, 1H), 7.30 (m, 2H), 7.39 (d, 1H), 10.83 (br s, 1H) | Method A, using 3-(2,3-dichloro-5-methoxyphenyl)pyridine-2,6-diamine (Preparation 8), 1.6 equivalents lutidine and 1 equivalent acid chloride prepared from 4-methyl-1,2,5-oxadiazole-3-carboxylic acid. Crystallized from dichloromethane. |
| 49 N-[6-Amino-5-(2,4-dichlorophenyl)pyridin-2-yl]-4-methyl-1,2,5-oxadiazole-3-carboxamide | 2,4-dichlorophenyl | LCMS Rt = 3.41 min MS m/z 364 [MH]+ $^1$HNMR (CDCl$_3$): 2.68 (s, 3H), 4.39 (br s, 2H), 7.26-7.54 (m, | Method C, using 3-(2,4-dichlorophenyl)pyridine-2,6-diamine (Preparation 10) and 1 equivalent acid chloride prepared from 4-methyl-1,2,5-oxadiazole-3-carboxylic acid. Stirred |

-continued

| Example No. Name | Ar | Data | Preparation Information |
|---|---|---|---|
| | | 3H), 7.54 (s, 1H), 7.67 (d, 1H), 8.95 (br s, 1H) | for 27 hours. Purified by preparative thin layer chromatography. |
| 50 N-{6-Amino-5-[2-(trifluoromethoxy)phenyl]-pyridin-2-yl}-4-methyl-1,2,5-oxadiazole-3-carboxamide | 2-(trifluoromethoxy)-phenyl | LCMS Rt = 3.62 min MS m/z 380 [MH]+ | Method A, using 3-[2-(trifluoromethoxy)phenyl]-pyridine-2,6-diamine (Preparation 2), 1.32 equivalents lutidine and 1.25 equivalents acid chloride prepared from 4-methyl-1,2,5-oxadiazole-3-carboxylic acid. |

EXAMPLE 51

N-[6-Amino-5-(2,5-dichloro-3-methoxyphenyl)pyridin-2-yl]-4-methyl-1,2,5-oxadiazole-3-carboxamide

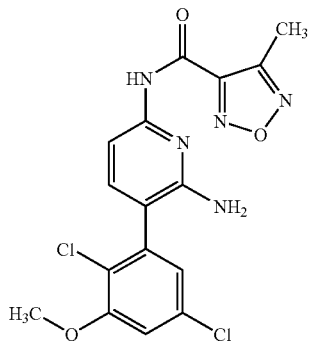

4-Methyl-1,2,5-oxadiazole-3-carboxylic acid (0.3 g, 2.34 mmol) was stirred in thionyl chloride (10 ml) at 50° C. for 18 hours. A further 3 ml oxalyl chloride and 2 drops of dimethylformamide were added and the reaction stirred for a further 1.5 hours at 50° C. The reaction was concentrated in vacuo and azeotroped with dichloromethane. The residue (0.134 g, 0.915 mmol) was dissolved in $CH_3CN$ (1.83 ml) and added to a solution of 3-(2,5-dichloro-3-methoxyphenyl)-pyridine-2,6-diamine (Preparation 4, 0.200 g, 0.704 mmol) in anhydrous pyridine (10 ml). The reaction was heated at 60° C. for 24 hours. A further 0.88 equivalents of the acid chloride in $CH_3CN$ (0.091 g, in 1.2 ml) was added and the reaction stirred for a further 24 hours at 60° C. The reaction was partitioned between dichloromethane and a saturated aqueous solution of $NaHCO_3$ before drying over $Na_2SO_4$ and concentrating in vacuo. The residue was purified by silica gel column chromatography eluting with 5:95 to 30:70 ethyl acetate:heptane to afford the title compound (0.050 g, 18% yield).

$^1$HNMR ($d_6$-DMSO): 2.51 (s, 3H), 3.90 (s, 3H), 5.62 (br s, 2H), 6.96 (d, 1H), 7.26 (d, 1H), 7.31 (s, 2H), 10.65 (br s, 1H)

LCMS Rt=3.51 min

MS m/z 394 [MH]+

EXAMPLE 52

N-[6-Amino-5-(2-chloro-5-methoxyphenyl)pyridin-2-yl]-1-ethyl-1H-pyrazole-5-carboxamide

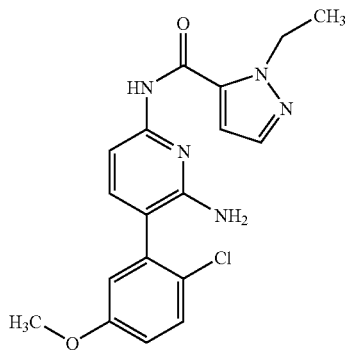

To an ice-cooled solution of 1-ethyl-1H-pyrazole-5-carboxylic acid (0.140 g, 1 mmol) in dichloromethane (2 ml) and tetrahydrofuran (2 ml) was added oxalyl chloride (0.262 ml, 3 mmol) followed by 1 drop of dimethylformamide. The reaction was stirred at room temperature for 1 hour before concentration in vacuo. The residue was azeotroped with dichloromethane, dissolved in acetonitrile (4 ml) and 2 ml was added dropwise to a cooled solution of 3-(2-chloro-5-methoxyphenyl)pyridine-2,6-diamine (preparation 1, 0.100 g, 0.4 mmol) and lutidine (0.070 ml, 0.6 mmol) in acetonitrile (4 ml). The reaction was allowed to warm to room temperature and stirred under nitrogen for 72 hours. The reaction was concentrated in vacuo and partitioned between dichloromethane (10 ml) and water (10 ml). The organic was dried ($MgSO_4$) and concentrated in vacuo. The residue was purified by silica gel column chromatography eluting with ethylacetate:heptane 1:3 to 3:1 to furnish 30 mg white solid as the desired compound.

MS m/z 372 [MH]+

$^1$HNMR ($CDCl_3$): 1.48 (t, 3H), 3.81 (s, 3H), 4.35 (br s, 2H), 4.65 (q, 2H), 6.68 (s, 1H), 6.88 (m, 2H), 7.41 (m, 2H), 7.52 (s, 1H), 7.70 (d, 1H), 8.14 (br s, 1H)

The following examples of the general formula:

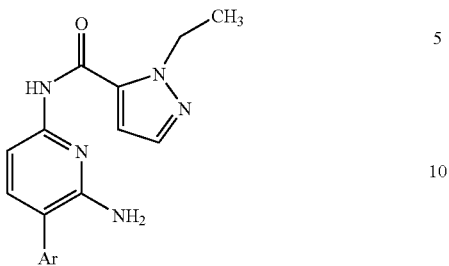

were prepared by methods analogous to Methods A and B, as described for Examples 1 and 2 above. Unless otherwise noted, preparation details are as described for the method referred to.

| Example No. Name | Ar | Data | Preparation Information |
|---|---|---|---|
| 53 N-[6-Amino-5-(2-chlorophenyl)pyridin-2-yl]-1-ethyl-1H-pyrazole-5-carboxamide | 2-chlorophenyl | LCMS Rt = 3.22 min MS m/z 340 [M]− | Method A, using 3-(2-chlorophenyl)pyridine-2,6-diamine (Preparation 5) and 1.05 equivalents acid chloride prepared from 1-ethyl-1H-pyrazole-5-carboxylic acid. |
| 54 N-[6-Amino-5-(2-chloro-5-fluorophenyl)pyridin-2-yl]-1-ethyl-1H-pyrazole-5-carboxamide | 2-chloro-5-fluorophenyl | LCMS Rt = 3.38 min MS m/z 360 [MH]+ | Method A, using 3-(2-chloro-5-fluorophenyl)pyridine-2,6-diamine (Preparation 3) and 1.1 equivalents acid chloride prepared from 1-ethyl-1H-pyrazole-5-carboxylic acid. |
| 55 N-[6-Amino-5-(2-chloro-4-fluorophenyl)pyridin-2-yl]-1-ethyl-1H-pyrazole-5-carboxamide | 2-chloro-4-fluorophenyl | LCMS Rt = 3.35 min MS m/z 360 [MH]+ | Method B, using N-(6-amino-5-iodopyridin-2-yl)-1-ethyl-1H-pyrazole-5-carboxamide (Preparation 17), 2-chloro-4-fluorophenyl boronic acid, 1.05 equivalents cesium carbonate and 0.077 equivalents palladium tetrakis(triphenylphosphine). Stirred for 5 hours. |
| 56 N-[6-Amino-5-(2,5-dichlorophenyl)pyridin-2-yl]-1-ethyl-1H-pyrazole-5-carboxamide | 2,5-dichlorophenyl | LCMS Rt = 3.58 min MS m/z 376 [MH]+ | Method B, using N-(6-amino-5-iodopyridin-2-yl)-1-ethyl-1H-pyrazole-5-carboxamide (Preparation 17), 2,5-dichlorophenyl boronic acid, 1.05 equivalents cesium carbonate and 0.077 equivalents palladium tetrakis(triphenylphosphine). Stirred for 5 hours. |
| 57 N-{6-Amino-5-[5-fluoro-2-(trifluoromethyl)phenyl]-pyridin-2-yl}-1-ethyl-1H-pyrazole-5-carboxamide | 5-fluoro-2-(trifluoromethyl)phenyl | LCMS Rt = 3.45 min MS m/z 394 [MH]+ | Method B, using N-(6-amino-5-iodopyridin-2-yl)-1-ethyl-1H-pyrazole-5-carboxamide (Preparation 17), 5-fluoro-2-(trifluoromethyl)phenyl boronic acid, 1.05 equivalents cesium |

-continued

| Example No. Name | Ar | Data | Preparation Information |
|---|---|---|---|
| | | | carbonate and 0.077 equivalents palladium tetrakis(triphenylphosphine). Stirred for 5 hours. |
| 58 N-[6-Amino-5-(2-chloro-3-fluorophenyl)pyridin-2-yl]-1-ethyl-1H-pyrazole-5-carboxamide | 2-chloro-3-fluorophenyl | LCMS Rt = 3.40 min MS m/z 360 [MH]+ | Method B, using N-(6-amino-5-iodopyridin-2-yl)-1-ethyl-1H-pyrazole-5-carboxamide (Preparation 17), 2-chloro-3-fluorophenyl boronic acid, 1.05 equivalents cesium carbonate and 0.077 equivalents palladium tetrakis(triphenylphosphine). Stirred for 5 hours. |
| 59 N-{6-Amino-5-[2-(trifluoromethoxy)phenyl]-pyridin-2-yl}-1-ethyl-1H-pyrazole-5-carboxamide | 2-(trifluoromethoxy)-phenyl | LCMS Rt = 3.44 min MS m/z 392 [MH]+ | Method B, using N-(6-amino-5-iodopyridin-2-yl)-1-ethyl-1H-pyrazole-5-carboxamide (Preparation 17), 2-(trifluoromethoxy)phenyl boronic acid, 1.05 equivalents cesium carbonate and 0.077 equivalents palladium tetrakis(triphenylphosphine). Stirred for 5 hours. |
| 60 N-{6-Amino-5-[2-(trifluoromethyl)phenyl]-pyridin-2-yl}-1-ethyl-1H-pyrazole-5-carboxamide | 2-(trifluoromethyl)-phenyl | LCMS Rt = 3.51 min MS m/z 376 [MH]+ | Method B, using N-(6-amino-5-iodopyridin-2-yl)-1-ethyl-1H-pyrazole-5-carboxamide (Preparation 17), 2-(trifluoromethyl)phenyl boronic acid and 0.077 equivalents palladium tetrakis(triphenylphosphine). Stirred for 5 hours. |
| 61 N-[6-Amino-5-(2,3-dichloro-5-methoxyphenyl)pyridin-2-yl]-1-ethyl-1H-pyrazole-5-carboxamide | 2,3-dichloro-5-methoxyphenyl | LCMS Rt = 3.58 min MS m/z 406 [MH]+ | Method A, using 3-(2,3-dichloro-5-methoxyphenyl)pyridine-2,6-diamine (Preparation 8), 1.6 equivalents lutidine and 1.5 equivalents acid chloride prepared from 1-ethyl-1H-pyrazole-5-carboxylic acid. Acid chloride prepared using neat thionyl chloride at 80° C. for 4 hours. |
| 62 N-[6-Amino-5-(2,5-dichloro-3-methoxyphenyl)pyridin-2-yl]-1-ethyl-1H-pyrazole-5-carboxamide | 2,5-dichloro-3-methoxyphenyl | LCMS Rt = 3.50 min MS m/z 406 [MH]+ | Method A, using 3-(2,5-dichloro-3-methoxyphenyl)pyridine-2,6-diamine (Preparation 4), 1.6 equivalents lutidine and 1.4 equivalents acid chloride prepared from 1-ethyl-1H-pyrazole-5-carboxylic acid. |
| 63 N-{6-Amino-5-[5-chloro-2-(trifluoromethoxy)phenyl]-pyridin-2-yl}-1-ethyl-1H-pyrazole-5-carboxamide | 5-chloro-2-(trifluoromethoxy)-phenyl | LCMS Rt = 3.83 min MS m/z 426 [MH]+ | Method A, using 3-[5-chloro-2-(trifluoromethoxy)phenyl]-pyridine-2,6-diamine (Preparation 12), 1.7 equivalents lutidine and 1.1 equivalents acid chloride prepared from 1-ethyl-1H-pyrazole-5-carboxylic acid. |
| 64 N-{6-Amino-5-[2-fluoro-5-(trifluoromethoxy)phenyl]-pyridin-2-yl}-1-ethyl-1H- | 2-fluoro-5-(trifluoromethoxy)-phenyl | LCMS Rt = 3.59 min MS m/z 410 [MH]+ | Method A, using 3-[2-fluoro-5-(trifluoromethoxy)phenyl]-pyridine-2,6-diamine (Preparation 13), 1.8 equivalents lutidine and |

| Example No. Name | Ar | Data | Preparation Information |
|---|---|---|---|
| pyrazole-5-carboxamide | | | 1.4 equivalents acid chloride prepared from 1-ethyl-1H-pyrazole-5-carboxylic acid. |
| 65 N-{6-Amino-5-[2-chloro-5-(trifluoromethoxy)phenyl]-pyridin-2-yl}-1-ethyl-1H-pyrazole-5-carboxamide | 2-chloro-5-(trifluoromethoxy)-phenyl | LCMS Rt = 3.74 min MS m/z 426 [MH]+ | Method A, using 3-[2-chloro-5-(trifluoromethoxy)phenyl]-pyridine-2,6-diamine (Preparation 11), 3.0 equivalents lutidine and 1.1 equivalents acid chloride prepared from 1-ethyl-1H-pyrazole-5-carboxylic acid. |

The following examples of the general formula:

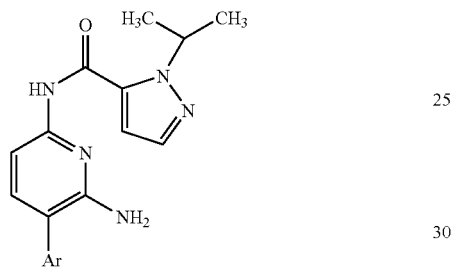

were prepared by methods analogous to Method A, as described for Example 1 above. Unless otherwise noted, preparation details are as described for the method referred to.

| Example No. Name | Ar | Data | Preparation Information |
|---|---|---|---|
| 66 N-[6-Amino-5-(2-chlorophenyl)pyridin-2-yl]-1-isopropyl-1H-pyrazole-5-carboxamide | 2-chlorophenyl | LCMS Rt = 3.62 min MS m/z 356 [MH]+ | Using 3-(2-chlorophenyl)pyridine-2,6-diamine (Preparation 5), 1 equivalent lutidine and 0.6 equivalents acid chloride prepared from 1-isopropyl-1H-pyrazole-5-carboxylic acid. Stirred for 18 hours. Further 0.4 equivalents acid chloride added. Stirred for 18 hours. |
| 67 N-[6-Amino-5-(2-chloro-5-fluorophenyl)pyridin-2-yl]-1-isopropyl-1H-pyrazole-5-carboxamide | 2-chloro-5-fluorophenyl | LCMS Rt = 3.58 min MS m/z 374 [MH]+ | Using 3-(2-chloro-5-fluorophenyl)pyridine-2,6-diamine (Preparation 3) and 1.07 equivalents acid chloride prepared from 1-isopropyl-1H-pyrazole-5-carboxylic acid. |
| 68 N-{6-Amino-5-[2-(trifluoromethoxy)-phenyl]pyridin-2-yl}-1-isopropyl-1H- | 2-(trifluoromethoxy)-phenyl | LCMS Rt = 3.59 min MS m/z 406 [MH]+ | Using 3-[2-(trifluoromethoxy)phenyl]-pyridine-2,6-diamine (Preparation 2), 1.32 equivalents lutidine and |

| Example No. Name | Ar | Data | Preparation Information |
|---|---|---|---|
| pyrazole-5-carboxamide | | | 1.10 equivalents acid chloride prepared from 1-isopropyl-1H-pyrazole-5-carboxylic acid. |
| 69 N-{6-Amino-5-[2-chloro-5-(trifluoromethoxy)-phenyl]pyridin-2-yl}-1-isopropyl-1H-pyrazole-5-carboxamide | 2-chloro-5-(trifluoromethoxy)-phenyl | LCMS Rt = 3.91 min MS m/z 440 [MH]+ | Using 3-[2-chloro-5-(trifluoromethoxy)phenyl]-pyridine-2,6-diamine (Preparation 11), 3.0 equivalents lutidine and 2.5 equivalents acid chloride prepared from 1-isopropyl-1H-pyrazole-5-carboxylic acid. Purified by silica gel column chromatography eluting with 40:60 ethyl acetate:heptane, followed by preparative HPLC. |

EXAMPLE 70

N-[6-Amino-5-(2,3,5-trichlorophenyl)pyridin-2-yl]-1-methyl-1H-pyrazole-3-carboxamide

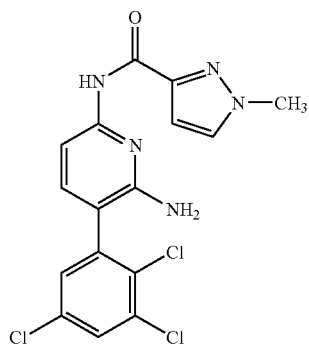

N-[6-Amino-5-(2,3,5-trichlorophenyl)pyridin-2-yl]-1-methyl-1H-pyrazole-3-carboxamide was prepared by a method analogous to Method D, as described for Example 4 above, using acid chloride prepared from 1-methyl-1H-pyrazole-3-carboxylic acid. The resulting product was purified by silica gel column chromatography, eluting with 60:40 ethyl acetate:cyclohexane.

$^1$HNMR (d$_6$-DMSO): 3.95 (s, 3H), 5.73 (s, 1H), 5.78 (br s, 2H), 6.79 (s, 1H), 7.32 (d, 1H), 7.39 (d, 1H), 7.81 (s, 1H), 7.86 (s, 1H), 9.02 (br s, 1H)

EXAMPLE 71

N-[6-Amino-5-(2,5-dichlorophenyl)pyridin-2-yl]-1,2,5-oxadiazole-3-carboxamide

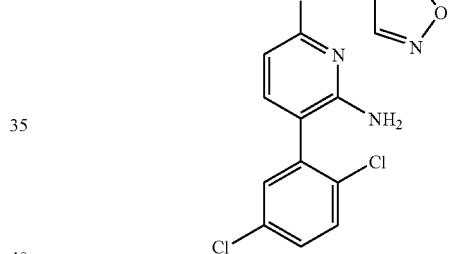

N-[6-Amino-5-(2,5-dichlorophenyl)pyridin-2-yl]-1,2,5-oxadiazole-3-carboxamide was prepared by a method analogous to Method A, as described for Example 1 above, using 3-(2,5-dichlorophenyl)pyridine-2,6-diamine (Preparation 7), 1 equivalent lutidine and 1 equivalent acid chloride prepared from 1,2,5-oxadiazole-3-carboxylic acid.

LCMS Rt=3.24 min

MS m/z 350 [MH]+

The following examples of the general formula:

were prepared by methods analogous to Method A, as described for Example 1 above. Unless otherwise noted, preparation details are as described for the method referred to.

| Example No. Name | Ar | Data | Preparation Information |
|---|---|---|---|
| 72 N-[6-Amino-5-(2,5-dichlorophenyl)pyridin-2-yl]isoxazole-3-carboxamide | 2,5-dichlorophenyl | LCMS Rt = 3.36 min MS m/z 349 [MH]+ | Using 3-(2,5-dichlorophenyl)pyridine-2,6-diamine (Preparation 7), 2 equivalents lutidine and 1.5 equivalents acid chloride prepared from isoxazole-3-carboxylic acid. |
| 73 N-[6-Amino-5-(2-chloro-5-methoxyphenyl)pyridin-2-yl]isoxazole-3-carboxamide | 2-chloro-5-methoxyphenyl | LCMS Rt = 2.69 min MS m/z 345 [MH]+ | Using 3-(2-chloro-5-methoxyphenyl)pyridine-2,6-diamine (Preparation 1), 2 equivalents lutidine and 1.5 equivalents acid chloride prepared from isoxazole-3-carboxylic acid. |
| 74 N-[6-Amino-5-(2-chlorophenyl)pyridin-2-yl]isoxazole-3-carboxamide | 2-chlorophenyl | LCMS Rt = 3.41 min MS m/z 315 [MH]+ | Using 3-(2-chlorophenyl)pyridine-2,6-diamine (Preparation 5) and 1 equivalent acid chloride prepared from isoxazole-3-carboxylic acid. Stirred for 18 hours. Further 0.5 equivalents lutidine and 0.4 equivalents acid chloride added and stirred for 4 hours. Further 0.34 equivalents lutidine and 0.19 equivalents acid chloride added and stirred for 20 hours. |

The following examples of the general formula:

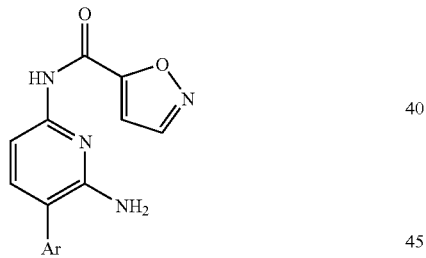

35

40

45 were prepared by methods analogous to Methods A and D, as described for Examples 1 and 4 above. Unless otherwise noted, preparation details are as described for the method referred to.

| Example No. Name | Ar | Data | Preparation Information |
|---|---|---|---|
| 75 N-[6-Amino-5-(2,5-dichlorophenyl)pyridin-2-yl]isoxazole-5-carboxamide | 2,5-dichlorophenyl | LCMS Rt = 3.24 min MS m/z 349 [MH]+ | Method A, using 3-(2,5-dichlorophenyl)pyridine-2,6-diamine (Preparation 7), 2 equivalents lutidine and 1.5 equivalents acid chloride prepared from isoxazole-5-carboxylic acid. |
| 76 N-[6-Amino-5-(2-chloro-5-methoxyphenyl)pyridin- | 2-chloro-5-methoxyphenyl | MS m/z 345 [MH]+ $^1$HNMR (CDCl$_3$): 3.74 (s, 3H), | Method A, using 3-(2-chloro-5-methoxyphenyl)pyridine-2,6-diamine (Preparation |

| Example No. Name | Ar | Data | Preparation Information |
|---|---|---|---|
| 2-yl]isoxazole-5-carboxamide | | 4.33 (br s, 2H), 6.78-6.84 (m, 2H), 6.98 (s, 1H), 7.32-7.34 (m, 2H), 7.63 (d, 1H), 8.32 (s, 1H), 8.60 (br s, 1H) | 1), 2 equivalents lutidine and 1.5 equivalents acid chloride prepared from isoxazole-3-carboxylic acid. Purified by silica gel column chromatography eluting with dichloromethane, followed by preparative HPLC. |
| 77 N-[6-Amino-5-(2-chlorophenyl)pyridin-2-yl]isoxazole-5-carboxamide | 2-chlorophenyl | LCMS Rt = 3.08 min MS m/z 315 [MH]+ | Method A, using 3-(2-chlorophenyl)pyridine-2,6-diamine (Preparation 5) and acid chloride prepared from isoxazole-3-carboxylic acid. Stirred for 18 hours. Further 0.4 equivalents lutidine and 0.37 equivalents acid chloride added and stirred for 18 hours. |
| 78 N-[6-Amino-5-(2,3,5-trichlorophenyl)pyridin-2-yl]isoxazole-5-carboxamide | 2,3,5-trichlorophenyl | MS m/z 383 [MH]+ $^1$HNMR (d$_6$-DMSO): 5.67 (br s, 2H), 7.35-7.43 (m, 4H), 7.83 (s, 1H), 8.77 (s, 1H), 10.66 (br s, 1H) | Method D, using acid chloride prepared from isoxazole-3-carboxylic acid. Purified by silica gel column chromatography, eluting with 20:80 to 60:40 ethyl acetate:cyclohexane. |

The following examples of the general formula:

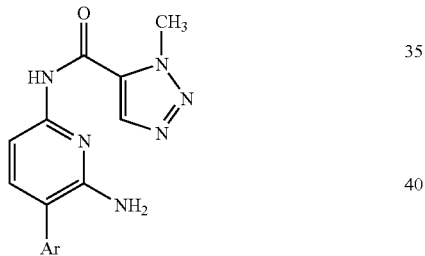

were prepared by methods analogous to Methods A and C, as described for Examples 1 and 3 above, using an acid chloride prepared from 1-methyl-1H-1,2,3-triazole-5-carboxylic acid (Preparation 34). Unless otherwise noted, preparation details are as described for the method referred to.

| Example No. Name | Ar | Data | Preparation Information |
|---|---|---|---|
| 79 N-[6-Amino-5-(2,4-dichlorophenyl)pyridin-2-yl]-1-methyl-1H-1,2,3-triazole-5-carboxamide | 2,4-dichlorophenyl | LCMS Rt = 3.46 min MS m/z 725 [M$_2$H]+ | Method A, using 3-(2,4-dichlorophenyl)pyridine-2,6-diamine (Preparation 10), 2 equivalents lutidine and 2 equivalents acid chloride. Stirred for 18 hours at 50° C., then refluxed for 2 hours. |
| 80 N-[6-Amino-5-(2,5-dichlorophenyl)pyridin-2-yl]-1-methyl-1H-1,2,3-triazole-5-carboxamide | 2,5-dichlorophenyl | LCMS Rt = 3.27 min MS m/z 363 [MH]+ | Method C, using 3-(2,5-dichlorophenyl)pyridine-2,6-diamine (Preparation 7) and 1 equivalent acid chloride. Stirred at 60° C. for 1 hour. Purified by preparative HPLC. |

-continued

| Example No. Name | Ar | Data | Preparation Information |
|---|---|---|---|
| 81 N-[6-Amino-5-(2,3-dichloro-5-methoxyphenyl)pyridin-2-yl]-1-methyl-1H-1,2,3-triazole-5-carboxamide | 2,3-dichloro-5-methoxyphenyl | LCMS Rt = 3.46 min MS m/z 785 [M$_2$H]+ | Method C, using 3-(2,3-dichloro-5-methoxyphenyl)pyridine-2,6-diamine (Preparation 8) and 2 equivalents acid chloride. Stirred at 60° C. for 1.5 hours. Purified by preparative HPLC. |
| 82 N-[6-Amino-5-(2-chlorophenyl)pyridin-2-yl]-1-methyl-1H-1,2,3-triazole-5-carboxamide | 2-chlorophenyl | LCMS Rt = 3.02 min MS m/z 329 [MH]+ | Method C, using 3-(2-chlorophenyl)pyridine-2,6-diamine (Preparation 5) and 1 equivalent acid chloride. Stirred at 60° C. for 1 hour. Purified by preparative HPLC. |
| 83 N-[6-Amino-5-(2-chloro-5-methoxyphenyl)pyridin-2-yl]-1-methyl-1H-1,2,3-triazole-5-carboxamide | 2-chloro-5-methoxyphenyl | LCMS Rt = 3.15 min MS m/z 359 [MH]+ | Method C, using 3-(2-chloro-5-methoxyphenyl)pyridine-2,6-diamine (Preparation 1) and 1 equivalent acid chloride. Stirred at 60° C. for 1 hour. Purified by preparative HPLC. |
| 84 N-[6-Amino-5-(2,3,5-trichlorophenyl)pyridin-2-yl]-1-methyl-1H-1,2,3-triazole-5-carboxamide | 2,3,5-trichlorophenyl | LCMS Rt = 3.62 min MS m/z 397 [MH]+ | Method C, using 3-(2,3,5-trichlorophenyl)pyridine-2,6-diamine (Preparation 6) and 1 equivalent acid chloride. Stirred at 60° C. for 1 hour. Purified by preparative HPLC. |
| 85 N-{6-Amino-5-[2-(trifluoromethoxy)phenyl]-pyridin-2-yl}-1-methyl-1H-1,2,3-triazole-5-carboxamide | 2-(trifluoromethoxy)phenyl | LCMS Rt = 3.44 min MZ m/z 379 [MH]+ | Method C, using 3-[2-(trifluoromethoxy)phenyl]pyridine-2,6-diamine (Preparation 2) and 1 equivalent acid chloride. Stirred at 60° C. for 1 hour. Purified by preparative HPLC. |
| 86 N-[6-Amino-5-(2-chloro-5-fluorophenyl)pyridin-2-yl]-1-methyl-1H-1,2,3-triazole-5-carboxamide | 2-chloro-5-fluorophenyl | LCMS Rt = 3.17 min MS m/z 345 [M]− | Method C, using 3-(2-chloro-5-fluorophenyl)pyridine-2,6-diamine (Preparation 3) and 1 equivalent acid chloride. Stirred at 60° C. for 1 hour. Further 1 equivalent acid chloride added and stirred for a further 1 hour at 60° C. Purified by preparative HPLC. |
| 87 N-[6-Amino-5-(2,5-dichloro-3-methoxyphenyl)pyridin-2-yl]-1-methyl-1H-1,2,3-triazole-5-carboxamide | 2,5-dichloro-3-methoxyphenyl | LCMS Rt = 2.02 min MS m/z 393 [MH]+ $^1$HNMR (CDCl$_3$): 3.73 (s, 3H), 4.23 (s, 3H) 6.04 (d, 1H), 6.80 (d, 1H), 7.22 (d, 1H) 7.61 (m, 1H) 7.98 (s, 1H), 8.53 (br s, 3H) | Method C, using 3-(2,5-dichloro-3-methoxyphenyl)pyridine-2,6-diamine (Preparation 4) and 1 equivalent acid chloride. Stirred at 60° C. for 1 hour. Further 1 equivalent acid chloride added and stirred for a further 1 hour at 60° C. Purified by silica gel column chromatography eluting with 100:0 to 0:100 pentane:ethyl acetate. |

The following examples of the general formula:

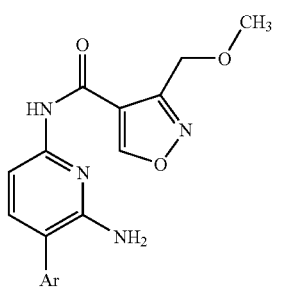

were prepared by methods analogous to Method A, as described for Example 1 above, using an acid chloride prepared from a mixture of 3-(methoxymethyl)isoxazole-4-carboxylic acid and 3-(methoxymethyl)isoxazole-5-carboxylic acid (Preparation 37). Unless otherwise noted, preparation details are as described for the method referred to.

The following examples of the general formula:

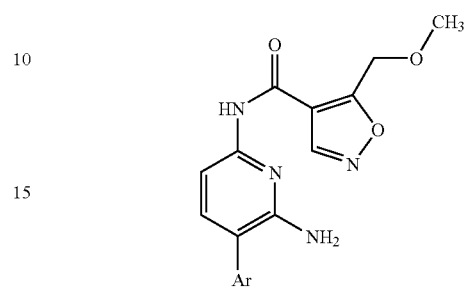

were prepared by methods analogous to Method A, as described for Example 1 above, using an acid chloride prepared from 5-(methoxymethyl)isoxazole-4-carboxylic acid (Preparation 41). Unless otherwise noted, preparation details are as described for the method referred to.

| Example No. Name | Ar | Data | Preparation Information |
|---|---|---|---|
| 88 N-{6-Amino-5-[2-(trifluoromethoxy)phenyl]-pyridin-2-yl}-3-(methoxymethyl)isoxazole-4-carboxamide | 2-(trifluoromethoxy)-phenyl | LCMS Rt = 3.17 min MS m/z 409 [MH]+ $^1$HNMR (CDCl$_3$): 3.66 (s, 3H), 4.30 (br s, 2H), 4.83 (s, 2H), 7.42 (m, 5H), 7.75 (d, 1H), 9.07 (s, 1H), 10.18 (br s, 1H) | Using 3-[2-(trifluoromethoxy)phenyl]pyridine-2,6-diamine (Preparation 2), 3.3 equivalents lutidine and 1.1 equivalents acid chloride. Purified by silica gel column chromatography eluting with 70:30 to 50:50 heptane:ethyl acetate. |
| 89 N-[6-Amino-5-(2-chlorophenyl)pyridin-2-yl]-3-(methoxymethyl)isoxazole-4-carboxamide | 2-chlorophenyl | LCMS Rt = 3.03 min MS m/z 359 [MH]+ $^1$HNMR (CDCl$_3$): 3.66 (s, 3H), 4.29 (br s, 2H), 4.83 (s, 2H), 7.36 (m, 4H), 7.52 (m, 1H), 7.75 (d, 1H), 9.07 (s, 1H), 10.17 (br s, 1H) | Using 3-(2-chlorophenyl)pyridine-2,6-diamine (Preparation 5), 3.4 equivalents lutidine and 1.12 equivalents acid chloride. Purified by silica gel column chromatography eluting with 65:35 to 55:45 heptane:ethyl acetate. |
| 90 N-[6-Amino-5-(2-chloro-5-fluorophenyl)pyridin-2-yl]-3-(methoxymethyl)isoxazole-4-carboxamide | 2-chloro-5-fluorophenyl | LCMS Rt = 3.18 min MS m/z 377 [MH]+ $^1$HNMR (CDCl$_3$): 3.66 (s, 3H), 4.31 (br s, 2H), 4.83 (s, 2H), 7.07 (m, 2H), 7.40 (d, 1H), 7.49 (m, 1H), 7.76 (d, 1H), 9.07 (s, 1H), 10.20 (br s, 1H) | Using 3-(2-chloro-5-fluorophenyl)pyridine-2,6-diamine (Preparation 3), 3.1 equivalents lutidine and 1 equivalent acid chloride. Purified by silica gel column chromatography eluting with 65:35 to 55:45 heptane:ethyl acetate. |

| Example No. Name | Ar | Data | Preparation Information |
|---|---|---|---|
| 91 N-[6-Amino-5-(2-chlorophenyl)pyridin-2-yl]-5-(methoxymethyl)isoxazole-4-carboxamide | 2-chlorophenyl | LCMS Rt = 3.10 MS m/z 359 [MH]+ $^1$HNMR (CDCl$_3$): 3.67 (s, 3H), 4.29 (br s, 2H), 4.91 (s, 2H), 7.34-7.41 (m, 4H), 7.53 (m, 1H), 7.74 (d, 1H), 8.73 (s, 1H), 9.91 (br s, 1H) | Using 3-(2-chlorophenyl)pyridine-2,6-diamine (Preparation 5), 1.2 equivalents lutidine and 1.1 equivalents acid chloride. Stirred for 18 hours. Further 0.2 equivalents acid chloride added and stirred for 2 hours. Purified by trituration with ethyl acetate. |
| 92 N-[6-Amino-5-(2-chloro-5-fluorophenyl)pyridin-2-yl]-5-(methoxymethyl)isoxazole-4-carboxamide | 2-chloro-5-fluorophenyl | LCMS Rt = 3.53 min MS m/z 377 [MH]+ | Using 3-(2-chloro-5-fluorophenyl)pyridine-2,6-diamine (Preparation 3), 1.2 equivalents lutidine and 1.1 equivalents acid chloride. Stirred for 18 hours. Further 0.151 equivalents acid chloride added and stirred for a further 18 hours. |
| 93 N-{6-Amino-5-[2-(trifluoromethoxy)phenyl]-pyridin-2-yl}-5-(methoxymethyl)isoxazole-4-carboxamide | 2-(trifluoromethoxy)-phenyl | LCMS Rt = 3.61 min MS m/z 409 [MH]+ | Using 3-[2-(trifluoromethoxy)phenyl]pyridine-2,6-diamine (Preparation 2), 1.2 equivalents lutidine and 1.1 equivalents acid chloride. Stirred for 18 hours. Further 0.175 equivalents acid chloride added and stirred for a further 18 hours. |

The following examples of the general formula:

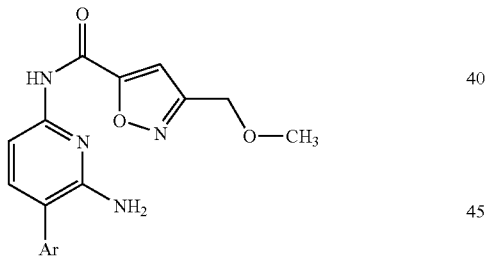

were prepared by methods analogous to Method A, as described for Examples 1 above, using an acid chloride prepared from a mixture of 3-(methoxymethyl)isoxazole-4-carboxylic acid and 3-(methoxymethyl)isoxazole-5-carboxylic acid (Preparation 37). Unless otherwise noted, preparation details are as described for the method referred to.

| Example No. Name | Ar | Data | Preparation Information |
|---|---|---|---|
| 94 N-{6-Amino-5-[2-(trifluoromethoxyl)phenyl]-pyridin-2-yl}-3-(methoxymethyl)isoxazole-5- | 2-(trifluoromethoxyl)-phenyl | LCMS Rt = 3.12 min MS m/z 409 [MH]+ $^1$HNMR (CDCl$_3$): 3.44 (s, 3H), 4.37 (br s, 2H), 4.61 (s, 2H), | Using 3-[2-(trifluoromethoxy)phenyl]pyridine-2,6-diamine (Preparation 2), 3.3 equivalents lutidine and 1.1 equivalents acid chloride. Purified by silica |

| Example No. Name | Ar | Data | Preparation Information |
|---|---|---|---|
| carboxamide | | 7.09 (s, 1H), 7.43 (m, 5H), 7.73 (d, 1H), 8.61 (br s, 1H) | gel column chromatography eluting with 70:30 to 50:50 heptane:ethyl acetate. |
| 95 N-[6-Amino-5-(2-chlorophenyl)pyridin-2-yl]-3-(methoxymethyl)isoxazole-5-carboxamide | 2-chlorophenyl | LCMS Rt = 2.97 min MS m/z 359 [MH]+ $^1$HNMR (CDCl$_3$): 3.44 (s, 3H), 4.36 (br s, 2H), 4.61 (s, 2H), 7.09 (s, 1H), 7.37 (m, 3H), 7.43 (d, 1H), 7.52 (m, 1H), 7.73 (d, 1H), 8.62 (br s, 1H) | Using 3-(2-chlorophenyl)pyridine-2,6-diamine (Preparation 5), 3.4 equivalents lutidine and 1.12 equivalents acid chloride. Purified by silica gel column chromatography eluting with 65:35 to 55:45 heptane:ethyl acetate. |
| 96 N-[6-Amino-5-(2-chloro-5-fluorophenyl)pyridin-2-yl]-3-(methoxymethyl)isoxazole-5-carboxamide | 2-chloro-5-fluorophenyl | LCMS Rt = 3.05 min MS m/z 377 [MH]+ $^1$HNMR (CDCl$_3$): 3.44 (s, 3H), 4.37 (br s, 2H), 4.61 (s, 2H), 7.09 (s, 3H), 7.43 (d, 1H), 7.47 (m, 1H), 7.74 (d, 1H), 8.63 (br s, 1H) | Using 3-(2-chloro-5-fluorophenyl)pyridine-2,6-diamine (Preparation 3), 3.1 equivalents lutidine and 1 equivalent acid chloride. Purified by silica gel column chromatography eluting with 65:35 to 55:45 heptane:ethyl acetate. |

The following examples of the general formula:

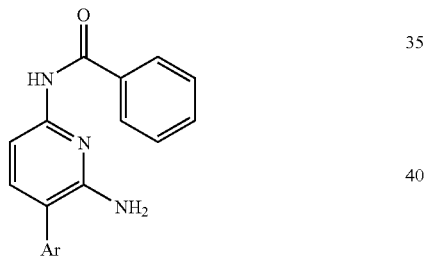

were prepared by methods analogous to Methods A and C, as described for Examples 1 and 3 above. Unless otherwise noted, preparation details are as described for the method referred to.

| Example No. Name | Ar | Data | Preparation Information |
|---|---|---|---|
| 97 N-[6-Amino-5-(2,5-dichlorophenyl)pyridin-2-yl]benzamide | 2,5-dichlorophenyl | LCMS Rt = 2.84 min MS m/z 359 [MH]+ | Method A, using 3-(2,5-dichlorophenyl)pyridine-2,6-diamine (Preparation 7), 1.1 equivalents lutidine and 1.1 equivalents benzoyl chloride. Stirred for 72 hours. |
| 98 N-[6-Amino-5-(2-chlorophenyl)pyridin-2-yl]benzamide | 2-chlorophenyl | LCMS Rt = 3.43 min MS m/z 324 [MH]+ | Method C, using 3-(2-chlorophenyl)pyridine-2,6-diamine (Preparation 5) and 1.2 equivalents benzoyl chloride. Stirred for 18 hours. Further 0.3 equivalents benzoyl chloride added and stirred |

| Example No. Name | Ar | Data | Preparation Information |
|---|---|---|---|
| | | | for a further 72 hours. Purified by preparative HPLC. |
| 99 N-{6-Amino-5-[2-(trifluoromethoxy)-phenyl]pyridin-2-yl}benzamide | 2-(trifluoromethoxy)-phenyl | LCMS Rt = 3.35 min MS m/z 374 [MH]+ | Method C, using 3-[2-(trifluoromethoxy)-phenyl]pyridine-2,6-diamine (Preparation 2) and 1.2 equivalents benzoyl chloride. Stirred for 18 hours. Purified by preparative HPLC. |

The following examples of the general formula:

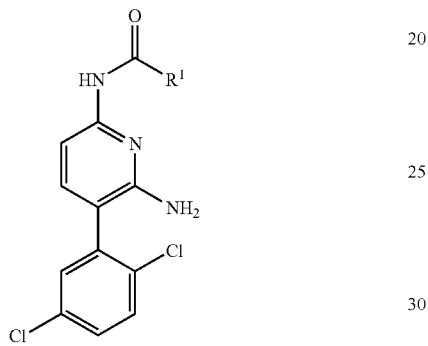

were prepared by methods analogous to Method A, as described above for Example 1, using 3-(2,5-dichlorophenyl) pyridine-2,6-diamine (Preparation 7) and the appropriate acid chloride. Unless otherwise noted, preparation details are as described for the method referred to.

| Example No. Name | R¹ | Data | Preparation Information |
|---|---|---|---|
| 100 N-[6-Amino-5-(2,5-dichlorophenyl)pyridin-2-yl]-4-chlorobenzamide | 4-chlorophenyl | LCMS Rt = 3.02 min MS m/z 392 [MH]+ | Using 1 equivalent 4-chlorobenzoyl chloride. |
| 101 N-[6-Amino-5-(2,5-dichlorophenyl)pyridin-2-yl]-2-chlorobenzamide | 2-chlorophenyl | LCMS Rt = 2.78 min MS m/z 392 [MH]+ | Using 1.1 equivalents lutidine and 1.1 equivalents 2-chlorobenzoyl chloride. Stirred for 72 hours. |
| 102 N-[6-Amino-5-(2,5-dichlorophenyl)pyridin-2-yl]-3-methoxybenzamide | 3-methoxyphenyl | LCMS Rt = 2.88 min MS m/z 389 [MH]+ | Using 1.1 equivalents lutidine and 1.1 equivalents 3-methoxybenzoyl chloride. Stirred for 72 hours. |
| 103 N-[6-Amino-5-(2,5-dichlorophenyl)pyridin-2-yl]-3,4-dimethoxybenzamide | 3,4-dimethoxyphenyl | LCMS Rt = 3.33 min MS m/z 418 [MH]+ | Using 1.1 equivalents lutidine and 1.1 equivalents acid chloride prepared from 3,4-dimethoxybenzoic acid. Stirred for 72 hours. |
| 104 N-[6-Amino-5-(2,5-dichlorophenyl)pyridin-2-yl]-3,5- | 3,5-dimethoxyphenyl | LCMS Rt = 3.48 min MS m/z 416 [M]− | Using 1.1 equivalents lutidine and 1.1 equivalents 3,5-dimethoxybenzoyl chloride. Stirred for 72 |

| Example No. Name | R¹ | Data | Preparation Information |
|---|---|---|---|
| dimethoxybenzamide 105 N-[6-Amino-5-(2,5-dichlorophenyl)pyridin-2-yl]-2,4-dimethoxybenzamide | 2,4-dimethoxyphenyl | LCMS Rt = 6.34 min MS m/z 418 [MH]+ | hours. Using 1.1 equivalents lutidine and 1.1 equivalents acid chloride prepared from 2,4-dimethoxybenzoic acid. Stirred for 72 hours. Purified by preparative HPLC. |

The following examples of the general formula:

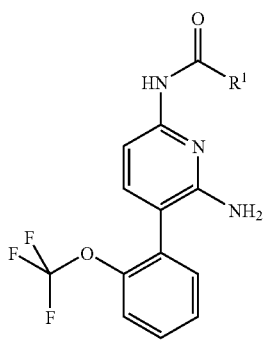

were prepared by methods analogous to Method A, as described above for Example 1, using 3-[2-(trifluoromethoxy)phenyl]pyridine-2,6-diamine (Preparation 2) and the appropriate acid chloride. Unless otherwise noted, preparation details are as described for the method referred to.

| Example No. Name | R¹ | Data | Preparation Information |
|---|---|---|---|
| 106 N-{6-Amino-5-[2-(trifluoromethoxy)-phenyl]pyridin-2-yl}-3-cyanobenzamide | 3-cyanophenyl | LCMS Rt = 3.50 min MS m/z 399 [MH]+ | Using 3-cyanobenzoyl chloride. |
| 107 N-{6-Amino-5-[2-(trifluoromethoxy)-phenyl]pyridin-2-yl}-2-cyanobenzamide | 2-cyanophenyl | LCMS Rt = 3.82 min MS m/z 399 [MH]+ | Using 2-cyanobenzoyl chloride and stirred for 72 hours. |

EXAMPLE 108

N-{6-Amino-5-[2-(trifluoromethoxy)phenyl]pyridin-2-yl}-3-methyl-1H-pyrazole-4-carboxamide

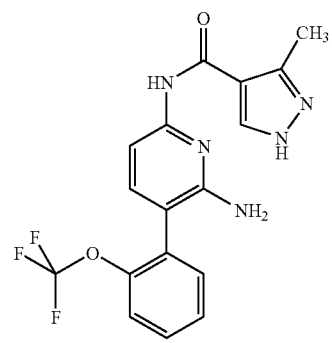

A mixture of N-{6-amino-5-[2-(trifluoromethoxy)phenyl]pyridin-2-yl}-3-methyl-1-{[2-(trimethylsilyl)ethoxy]methyl}-1H-pyrazole-4-carboxamide and N-{6-amino-5-[2-(trifluoromethoxy)phenyl]pyridin-2-yl}-3-methyl-2-{[2-(trimethylsilyl)ethoxy]methyl}-1H-pyrazole-4-carboxamide (Preparation 18 as a mixture of regioisomers, 0.050 g, 0.1 mmol) was stirred in methanol (1 ml) and water (0.5 ml). To this was added HCl in 1,4-dioxane (1 ml). The reaction was stirred at room temperature for 18 hours. A further 1 ml of HCl in 1,4-dioxane was added and the reaction stirred for a further 72 hours at room temperature before concentrating in vacuo. The residue was partitioned between ethyl acetate and water. The organic extract was dried over MgSO₄ and concentrated in vacuo to yield a gum. The gum was purified by trituration with diethyl ether to afford the title compound as a white solid (0.012 g, 32% yield).

¹HNMR ($d_4$-$CD_3OD$): 2.6 (s, 3H), 6.7 (d, 1H), 7.5-7.7 (m, 4H), 7.8 (d, 2H), 8.3 (br s 1H)

LCMS Rt=2.46 min

MS m/z 378 [MH]+

EXAMPLE 109

N-[6-amino-5-(5-fluoro-2-isopropoxyphenyl)pyridin-2-yl]-1-methyl-1H-pyrazole-5-carboxamide

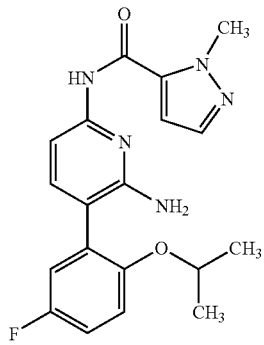

Method F

N-(6-amino-5-iodopyridin-2-yl)-1-methyl-1H-pyrazole-5-carboxamide (Preparation 16, 0.050 g, 0.15 mmol) was combined with potassium carbonate (0.060 g, 0.44 mmol), tert-butylammonium bromide (0.047 g, 0.15 mmol) and 5-fluoro-2-isopropoxyphenylboronic acid (0.038 g, 0.19 mmol) in water (1 ml) and methanol (1 ml). The reaction vessel was purged with nitrogen before the addition of palladium acetate (0.0007 g, 0.003 mmol). The reaction was sealed and heated in a Biotage microwave for 10 minutes at 130° C. The reaction was diluted with dichloromethane (5 ml), filtered through a phase separation cartridge and concentrated in vacuo. The residue was purified by preparative HPLC to afford the title compound.

MS m/z 370 [MH]+

$^1$HNMR (d$_4$-MeOD): 1.18 (d, 6H), 4.17 (s, 3H), 4.41 (m, 1H), 7.00 (m, 2H), 7.70 (m, 2H), 7.39 (m, 1H), 7.50-7.52 (m, 2H).

EXAMPLE 110

N-{6-amino-5-[5-ethoxy-2-(trifluoromethoxy)phenyl]pyridin-2-yl}-1-methyl-1H-pyrazole-5-carboxamide

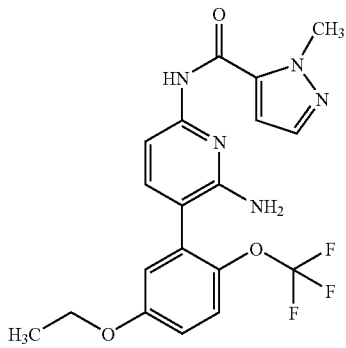

Method G

To a suspension of N-(6-amino-5-iodopyridin-2-yl)-1-methyl-1H-pyrazole-5-carboxamide (Preparation 16, 0.050 g, 0.15 mmol) in isopropanol (2 ml) and water (2 ml) was added 5-ethoxy-2-(trifluoromethoxy)phenylboronic acid (preparation 86, 0.073 g, 0.292 mmol, potassium carbonate (0.072 g, 0.526 mmol) and palladium dibenzylideneacetone (0.0035 g, 0.006 mmol). The reaction was stirred for 5 minutes under nitrogen before the addition of tri-tert-butylphosphine (1M solution in toluene, 0.073 ml, 0.73 mmol). The reaction was heated in a small, sealed, reaction vial (Reacti-vial™), at 80° C. for 4 hours before cooling to room temperature and concentrating in vacuo. The residue was partitioned between dichloromethane (5 ml) and water (5 ml), filtered through a phase separation cartridge and concentrated in vacuo. The residue was purified by preparative HPLC to afford the title compound.

LCMS Rt=3.44 min

MS m/z 422 [MH]+

The following examples of the general formula:

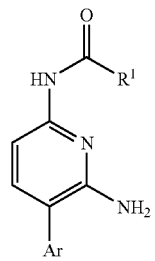

were prepared by methods analogous to Methods A, B, E, F and G as described above for Examples 1, 2, 19, 109 and 110 using the appropriate boronic acid or ester and the appropriate acid chloride. Unless otherwise noted, preparation details are as described for the method referred to.

| Eg. No. | Name R$^1$ Ar | Data | Preparation Information |
|---|---|---|---|
| 111 | N-[6-amino-5-(2-chlorophenyl)pyridin-2- | LCMS (2 min) Rt = 1.61 min MS m/z | Method A using 3-(2-chlorophenyl)pyridine-2,6-diamine (Preparation 5), 3 |

-continued

| Eg. No. | Name R¹ Ar | Data | Preparation Information |
|---|---|---|---|
| | yl]-3-(trifluoromethyl)isoxazole-4-carboxamide<br>R¹ = 3-(trifluoromethyl)isoxazole-4-carboxamide<br>Ar = 2-chlorophenyl | 383/385 [MH]+ | equivalents of lutidine and 0.9 equivalents of acid chloride prepared from 3-trifluoromethyl-isoxazole-4-carboxylic acid (Preparation 48). No purification, clean enough from crude. |
| 112 | N-{6-amino-5-[2-(trifluoromethoxy)-phenyl]pyridin-2-yl}-3-(trifluoromethyl)isoxazole-4-carboxamide<br>R¹ = 3-(trifluoromethyl)isoxazole-4-carboxamide<br>Ar = 2-trifluoromethoxyphenyl | LCMS (2 min)<br>Rt = 1.66 min<br>MS m/z<br>431 [MH]+ | Method A using 3-(2-trifluoromethoxyphenyl)pyridine-2,6-diamine (Preparation 2), 3.6 equivalents of lutidine and 1.1 equivalents of acid chloride (1M solution in acetonitrile) prepared from 3-trifluoromethyl-isoxazole-4-carboxylic acid (Preparation 48). |
| 113 | N-[6-amino-5-(2-chloro-5-methoxyphenyl)-pyridin-2-yl]-3-(trifluoromethyl)isoxazole-4-carboxamide<br>R¹ = 3-(trifluoromethyl)isoxazole-4-carboxamide<br>Ar = 2-chloro-5-methoxyphenyl | LCMS (2 min)<br>Rt = 1.63 min<br>MS m/z<br>413 [MH]+ | Method A using 3-(2-chloro-5-methoxyphenyl)pyridine-2,6-diamine (Preparation 1), 3.6 equivalents of lutidine and 1.1 equivalents of acid chloride (1M solution in acetonitrile) prepared from 3-trifluoromethyl-isoxazole-4-carboxylic acid (Preparation 48). |
| 114 | N-[6-amino-5-(2-chloro-5-fluorophenyl)pyridin-2-yl]-3-(trifluoromethyl)isoxazole-4-carboxamide<br>R¹ = 3-(trifluoromethyl)isoxazole-4-carboxamide<br>Ar = 2-chloro-5-fluoro phenyl | LCMS (2 min)<br>Rt = 1.64 min<br>MS m/z<br>401/403 [MH]+<br>¹HNMR (CDCl₃): 4.37 (br s, 2H), 7.03-7.09 (m, 2H), 7.40 (d, 1H), 7.44-7.49 (m, 1H), 7.69 (d, 1H), 8.47 (br s, 1H), 9.11 (s, 1H). | Method A using 3-(2-chloro-5-fluorophenyl)pyridine-2,6-diamine (Preparation 3), 3.7 equivalents of lutidine and 1.1 equivalents of acid chloride (1M solution in acetonitrile) prepared from 3-trifluoromethyl-isoxazole-4-carboxylic acid (Preparation 48). Purified by fractionlynx ™ to give title compound as a yellow solid (3.7 mg, 4%). |
| 115 | N-{6-amino-5-[5-fluoro-2-(trifluoromethoxy)phenyl]-pyridin-2-yl}-3-methylisoxazole-4-carboxamide<br>R¹ = 3-methylisoxazole-4-carboxamide<br>Ar = 2-trifluoromethoxy-5-fluoro phenyl | LCMS: Rt = 3.29 min<br>MS m/z<br>397 [MH]+ | Method B using [2-(trifluoromethoxy)-5-fluoro-phenyl]boronic acid (Preparation 50), 1 equivalent of cesium carbonate, 0.1 equivalent of palladium tetrakis(triphenylphosphine) and 1 equivalent N-(6-amino-5-iodopyridin-2-yl)-3-methylisoxazole-4-carboxamide (Preparation 15). |
| 116 | N-{6-amino-5-[5-fluoro-2-(trifluoromethoxy)phenyl]-pyridin-2-yl}-1-methyl-1H-pyrazole-5-carboxamide<br>R¹ = 1-methyl-1H-pyrazole-5-carboxamide<br>Ar = 2-trifluoromethoxy-5-fluoro phenyl | LCMS: Rt = 3.35 min<br>MS m/z<br>395 [MH]+ | Method B using [2-(trifluoromethoxy)-5-fluoro-phenyl]boronic acid (Preparation 50), 1 equivalent of cesium carbonate, 0.1 equivalent of palladium tetrakis(triphenylphosphine) and 1 equivalent of N-(6-amino-5-iodopyridin-2-yl)-1-methyl-1H-pyrazole-5-carboxamide (Preparation 16). |

-continued

| Eg. No. | Name<br>R¹<br>Ar | Data | Preparation Information |
|---|---|---|---|
| 117 | N-{6-amino-5-[2-ethylphenyl]pyridin-2-yl}-1-methyl-1H-pyrazole-5-carboxamide<br>R¹ = 1-methyl-1H-pyrazole-5-carboxamide<br>Ar = 2-ethylphenyl | LCMS (2 min)<br>Rt = 1.33 min<br>MS m/z<br>323 [MH]+ | Method B using 1.43 equivalents of 2-ethyl phenylboronic acid, 1.31 equivalents of cesium carbonate, 0.11 equivalents of palladium tetrakis-(triphenylphosphine) and 1 equivalent of N-(6-amino-5-iodopyridin-2-yl)-1-methyl-1H-pyrazole-5-carboxamide (Preparation 16). |
| 118 | N-{6-amino-5-[4-ethylphenyl]pyridin-2-yl}-1-methyl-1H-pyrazole-5-carboxamide<br>R¹ = 1-methyl-1H-pyrazole-5-carboxamide<br>Ar = 4-ethylphenyl | LCMS (2 min)<br>Rt = 1.38 min<br>MS m/z<br>323 [MH]+ | Method B using 1.43 equivalents of 4-ethyl phenylboronic acid, 1.31 equivalents of cesium carbonate, 0.10 equivalents of palladium tetrakis-(triphenylphosphine) and 1 equivalent of N-(6-amino-5-iodopyridin-2-yl)-1-methyl-1H-pyrazole-5-carboxamide (Preparation 16). |
| 119 | N-{6-amino-5-[2-(2,2,2-trifluoroethoxy)phenyl]-pyridin-2-yl}-1-methyl-1H-pyrazole-5-carboxamide<br>R¹ = 1-methyl-1H-pyrazole-5-carboxamide<br>Ar = 2-(2,2,2-trifluoroethoxy)phenyl | LCMS (2 min)<br>Rt = 1.31 min<br>MS m/z<br>392 [MH]+ | Method B using 1.4 equivalents of 2-(2,2,2-trifluoroethoxy)phenyl boronic acid, 1.3 equivalents of cesium carbonate, 0.09 equivalents of palladium tetrakis-(triphenylphosphine) and 1equivalent of N-(6-amino-5-iodopyridin-2-yl)-1-methyl-1H-pyrazole-5-carboxamide (Preparation 16). Purified by HPLC. |
| 120 | N-{6-amino-5-[4-(trifluoromethoxy)phenyl]-pyridin-2-yl}-1-methyl-1H-pyrazole-5-carboxamide<br>R¹ = 1-methyl-1H-pyrazole-5-carboxamide<br>Ar = 4-(trifluoromethoxy)phenyl | LCMS (2 min)<br>Rt = 1.47 min<br>MS m/z<br>378 [MH]+ | Method B using 1.5 equivalents of 4-(trifluoromethoxy)phenyl boronic acid, 1.3 equivalents of cesium carbonate, 0.09 equivalents of palladium tetrakis-(triphenylphosphine) and 1 equivalent of N-(6-amino-5-iodopyridin-2-yl)-1-methyl-1H-pyrazole-5-carboxamide (Preparation 16). Purified by HPLC. |
| 121 | N-{6-amino-5-[3-fluoro-4-(trifluoromethoxy)phenyl]-pyridin-2-yl}-1-methyl-1H-pyrazole-5-carboxamide<br>R¹ = 1-methyl-1H-pyrazole-5-carboxamide<br>Ar = 3-fluoro-4-(trifluoromethoxy)phenyl | LCMS (2 min)<br>Rt = 1.53 min<br>MS m/z<br>395 [MH]+ | Method B using 1.5 equivalents of 3-fluoro-4-(trifluoromethoxy)phenyl boronic acid, 1.3 equivalents of cesium carbonate, 0.09 equivalents of palladium tetrakis-(triphenylphosphine) and 1 equivalent of N-(6-amino-5-iodopyridin-2-yl)-1-methyl-1H-pyrazole-5-carboxamide (Preparation 16). |
| 122 | N-{6-amino-5-[4-(2,2,2-trifluoroethoxy)phenyl]-pyridin-2-yl}-1-methyl-1H-pyrazole-5-carboxamide<br>R¹ = 1-methyl-1H-pyrazole-5-carboxamide<br>Ar = 4-(2,2,2-trifluoroethoxy)phenyl | LCMS (2 min)<br>Rt = 1.39 min<br>MS m/z<br>392 [MH]+ | Method B using 1.5 equivalents of 4-(2,2,2-trifluoroethoxy)phenyl boronic acid, 1.3 equivalents of cesium carbonate, 0.09 equivalents of palladium tetrakis-(triphenylphosphine) and 1 equivalent of N-(6-amino-5-iodopyridin-2-yl)-1-methyl-1H-pyrazole-5-carboxamide (Preparation 16). |
| 123 | N-{6-amino-5-(5-fluoro-2-methoxyphenyl)pyridin-2-yl}-3-methylisoxazole-4-carboxamide | LCMS (2 min)<br>Rt = 1.30 min<br>MS m/z<br>343 [MH]+ | Method B using 1.3 equivalents of 5-fluoro-2-methoxyphenyl boronic acid, 1 equivalent of cesium carbonate and 1 equivalent of N-(6-amino-5-iodopyridin-2- |

| Eg. No. | Name<br>R[1]<br>Ar | Data | Preparation Information |
|---|---|---|---|
| | R[1] = 3-methylisoxazole-4-carboxamide<br>Ar = 5-fluoro-2-methoxyphenyl | | yl)-3-methyl-isoxazole-4-carboxamide (Preparation 15). All of the reagents were heated to 80° C., in a round bottomed flask, with stirring, prior to adding the 0.08 equivalents of palladium tetrakis-(triphenylphosphine). Stirred at this temperature for 13 hours before work-up. |
| 124 | N-{6-amino-5-[2-chloro-3-(trifluoromethyl)phenyl]-pyridin-2-yl}-3-methylisoxazole-4-carboxamide<br>R[1] = 3-methylisoxazole-4-carboxamide<br>Ar = 2-chloro-3-(trifluoromethyl)phenyl | LCMS (2 min)<br>Rt = 1.53 min<br>MS m/z<br>398 [MH]+ | Method B using 1.3 equivalents of 2-chloro-3-(trifluoromethyl)phenyl boronic acid, 1 equivalent of cesium carbonate and 1 equivalent of N-(6-amino-5-iodopyridin-2-yl)-3-methyl-isoxazole-4-carboxamide (Preparation 15). All of the reagents were heated to 80° C., in a round bottomed flask, with stirring, prior to adding the 0.08 equivalents of palladium tetrakis-(triphenylphosphine). Stirred at this temperature for 13 hours before work-up. |
| 125 | N-{6-amino-5-(2,3-dimethoxyphenyl)pyridin-2-yl}-3-methylisoxazole-4-carboxamide<br>R[1] = 1-methyl-1H-pyrazole-5-carboxamide<br>Ar = 2,3-dimethoxyphenyl | LCMS<br>Rt = 2.52 min<br>MS m/z<br>354 [MH]+ | Method B using 2 equivalents of 2,3-dimethoxyphenyl boronic acid, 1.1 equivalents of cesium carbonate, 0.10 equivalents of palladium tetrakis-(triphenylphosphine) and 1 equivalent of N-(6-amino-5-iodopyridin-2-yl)-1-methyl-1H-pyrazole-5-carboxamide (Preparation 16). Heated to 75° C. |
| 126 | N-{6-amino-5-[2-(methoxymethyl)phenyl]-pyridin-2-yl}-1-methyl-1H-pyrazole-5-carboxamide<br>R[1] = 1-methyl-1H-pyrazole-5-carboxamide<br>Ar = 2-(methoxymethyl)phenyl | LCMS (2 min)<br>Rt = 1.19 min<br>MS m/z<br>339 [MH]+ | Method B using 1.55 equivalents of 2-(methoxymethyl)phenyl boronic acid, 1.31 equivalents of cesium carbonate, 0.09 equivalents of palladium tetrakis-(triphenylphosphine) and 1 equivalent of N-(6-amino-5-iodopyridin-2-yl)-1-methyl-1H-pyrazole-5-carboxamide (Preparation 16). |
| 127 | N-{6-amino-5-[4-(methoxymethyl)phenyl]-pyridin-2-yl}-1-methyl-1H-pyrazole-5-carboxamide<br>R[1] = 1-methyl-1H-pyrazole-5-carboxamide<br>Ar = 4-(methoxymethyl)phenyl | LCMS (2 min)<br>Rt = 1.21 min<br>MS m/z<br>339 [MH]+ | Method B using 1.55 equivalents of 4-(methoxymethyl)phenyl boronic acid, 1.31 equivalents of cesium carbonate, 0.09 equivalents of palladium tetrakis-(triphenylphosphine) and 1 equivalent of N-(6-amino-5-iodopyridin-2-yl)-1-methyl-1H-pyrazole-5-carboxamide (Preparation 16). |
| 128 | N-[6-amino-5-(5-fluoro-2-hydroxyphenyl)pyridin-2-yl]-3-methylisoxazole-4-carboxamide<br>R[1] = 3-methylisoxazole-4-carboxamide<br>Ar = 5-fluoro-2-hydroxyphenyl | LCMS (2 min)<br>Rt = 1.15 min<br>MS m/z<br>329 [MH]+ | Method B using 1.3 equivalents of 5-fluoro-2-hydroxyphenyl boronic acid, 1 equivalent of cesium carbonate and 1 equivalent of N-(6-Amino-5-iodopyridin-2-yl)-3-methyl-isoxazole-4-carboxamide (Preparation 15). All of the reagents were heated to 80° C., in a round bottomed flask, with stirring, prior to adding the 0.08 equivalents of palladium tetrakis-(triphenylphosphine). Stirred at this temperature for 13 hours before work-up. |

| Eg. No. | Name<br>R¹<br>Ar | Data | Preparation Information |
|---|---|---|---|
| 129 | N-{6-amino-5-[2-(methoxymethyl)phenyl]-pyridin-2-yl}-3-methylisoxazole-4-carboxamide<br>R¹ = 3-methylisoxazole-4-carboxamide<br>Ar = 2-(methoxymethyl)phenyl | LCMS (2 min)<br>Rt = 1.22 min<br>MS m/z<br>339 [MH]+ | Method B using 1.5 equivalents of 2-(methoxymethyl)phenyl boronic acid, 1 equivalent of cesium carbonate, 0.08 equivalents of palladium tetrakis-(triphenylphosphine) and 1 equivalent of N-(6-Amino-5-iodopyridin-2-yl)-3-methyl-isoxazole-4-carboxamide (Preparation 15). Purified by column chromatography on silica gel eluting with heptane:ethyl acetate 1:1. |
| 130 | N-[6-amino-5-(2-ethoxyphenyl)pyridin-2-yl]-1-methyl-1H-pyrazole-5-carboxamide<br>R¹ = 1-methyl-1H-pyrazole-5-carboxamide<br>Ar = 2-ethoxyphenyl | LCMS (2 min)<br>Rt = 1.28 min<br>MS m/z<br>338 [MH]+ | Method B using 2 equivalents of 2-ethoxyphenyl boronic acid, 1.1 equivalents of cesium carbonate, 0.10 equivalents of palladium tetrakis-(triphenylphosphine) and 1 equivalent of N-(6-amino-5-iodopyridin-2-yl)-1-methyl-1H-pyrazole-5-carboxamide (Preparation 16). Heated to 75° C. |
| 131 | N-[6-amino-5-(2-isobutoxyphenyl)pyridin-2-yl]-1-methyl-1H-pyrazole-5-carboxamide<br>R¹ = 1-methyl-1H-pyrazole-5-carboxamide<br>Ar = 2-isobutoxyphenyl | LCMS (2 min)<br>Rt = 1.41 min<br>MS m/z<br>366 [MH]+ | Method B using 2 equivalents of 2-isobutoxyphenyl boronic acid, 1.1 equivalents of cesium carbonate, 0.10 equivalents of palladium tetrakis-(triphenylphosphine) and 1 equivalent of N-(6-amino-5-iodopyridin-2-yl)-1-methyl-1H-pyrazole-5-carboxamide (Preparation 16). Heated to 75° C. |
| 132 | N-[6-amino-5-(2-ethoxy-5-fluorophenyl)-pyridin-2-yl]-1-methyl-1H-pyrazole-5-carboxamide<br>R¹ = 1-methyl-1H-pyrazole-5-carboxamide<br>Ar = 2-ethoxy-5-fluorophenyl | LCMS (2 min)<br>Rt = 2.80 min<br>MS m/z<br>356 [MH]+<br>¹HNMR ($d_4$-$CD_3OD$):<br>1.24 (t, 3H), 4.03 (q, 2H), 4.17 (d, 3H), 6.97-7.00 (m, 2H), 7.06-7.08 (m, 2H), 7.39 (d, 1H), 7.51 (d, 1H), 7.52-7.53 (m, 1H). | Method B using 2 equivalents of 2-isobutoxyphenyl boronic acid, 1.1 equivalents of cesium carbonate, 0.10 equivalents of palladium tetrakis-(triphenylphosphine) and 1 equivalent of N-(6-amino-5-iodopyridin-2-yl)-1-methyl-1H-pyrazole-5-carboxamide (Preparation 16). Heated to 75° C., Purified by column chromatography on silica gel eluting with heptane:ethyl acetate 7:3. |
| 133 | N-[6-amino-5-(2,3-dimethoxyphenyl)-pyridin-2-yl]-3-methylisoxazole-4-carboxamide<br>R¹ = 3-methylisoxazole-4-carboxamide<br>Ar = 2,3-dimethoxyphenyl | LCMS<br>Rt = 3.00 min<br>MS m/z<br>355 [MH]+ | Method B using 1.5 equivalents of 2,3-dimethoxyphenyl boronic acid, 1.5 equivalents of cesium carbonate, 0.08 equivalents of palladium tetrakis-(triphenylphosphine) and 1 equivalent of N-(6-Amino-5-iodopyridin-2-yl)-3-methyl-isoxazole-4-carboxamide (Preparation 15). |
| 134 | N-{6-amino-5-[2-(2,2,2-trifluoroethoxy)phenyl]-pyridin-2-yl}-3-methylisoxazole-4-carboxamide<br>R¹ = 3-methylisoxazole-4-carboxamide<br>Ar = 2-(2,2,2- | LCMS (2 min)<br>Rt = 2.82 min<br>MS m/z<br>393 [MH]+<br>¹HNMR ($d_6$-DMSO):<br>2.40 (s, 3H), 4.70 (q, 2H), 5.20 (br s, 2H),<br>7.10-7.50 (m, 6H), 9.60 (s, | Method B using 1.5 equivalents of 2-(2,2,2-trifluoroethoxy)phenyl boronic acid 1.5 equivalents of cesium carbonate, 0.08 equivalents of palladium tetrakis-(triphenylphosphine) and 1 equivalent of N-(6-Amino-5-iodopyridin-2-yl)-3-methyl-isoxazole-4-carboxamide |

| Eg. No. | Name R¹ Ar | Data | Preparation Information |
|---|---|---|---|
| | trifluoroethoxy)phenyl | 1H), 10.40 (br s, 1H). | (Preparation 15). Purified by column chromatography on silica gel eluting with heptane:ethyl acetate 1:1. |
| 135 | N-[6-amino-5-(2-ethoxy-5-fluorophenyl)-pyridin-2-yl]-3-methylisoxazole-4-carboxamide<br>R¹ = 3-methylisoxazole-4-carboxamide<br>Ar = 2-ethoxy-5-fluorophenyl | LCMS (2 min) Rt = 2.86 min MS m/z 357 [MH]+ ¹HNMR (d₆-DMSO): 1.21 (t, 3H), 2.50 (s, 3H), 4.01 (q, 2H), 6.96-6.99 (m, 1H), 7.05-7.07 (m, 2H), 7.36 (d, 1H), 7.45 (d, 1H), 9.19 (s, 1H). | Method B using 2 equivalents of 2-ethoxy-5-fluorophenyl boronic acid, 1.2 equivalents of cesium carbonate and 1 equivalent of N-(6-Amino-5-iodopyridin-2-yl)-3-methyl-isoxazole-4-carboxamide (Preparation 15). All of the reagents were rapidly heated to 75° C., in a round bottomed flask, with stirring, prior to adding 0.083 equivalents of palladium tetrakis-(triphenylphosphine). Stirred at this temperature for 6 hours before work-up. Purified by column chromatography, eluting with heptane:ethyl acetate 9:1. |
| 136 | N-[6-amino-5-(5-fluoro-2-propoxyphenyl)-pyridin-2-yl]-1-methyl-1H-pyrazole-5-carboxamide<br>R¹ = 1-methyl-1H-pyrazole-5-carboxamide<br>Ar = 5-fluoro-2-propoxyphenyl | LCMS (2 min) Rt = 1.54 min MS m/z 370 [MH]+ | Method A, using 3-(2-propoxy-5-fluorophenyl)-pyridine-2,6-diamine (Preparation 51), 1.5 equivalents of lutidine and 1.15 equivalents acid chloride prepared from 1-methyl-1H-pyrazole-5-carboxylic acid. |
| 137 | N-{6-amino-5-[5-methyl-2-(trifluoromethoxy)phenyl]-pyridin-2-yl}-1-methyl-1H-pyrazole-5-carboxamide<br>R¹ = 1-methyl-1H-pyrazole-5-carboxamide<br>Ar = 5-methyl-2-(trifluoromethoxy)phenyl | LCMS Rt = 3.03 min MS m/z 392 [MH]+ ¹HNMR (CDCl₃): 2.13 (br s, 1H), 2.37 (s, 3H), 4.21 (s, 3H), 4.36 (br s, 2H), 6.72 (d, 1H), 7.17-7.25 (m, 3H), 7.37 (d, 2H), 7.48 (d, 1H), 7.68 (d, 1H), 8.23 (s, 1H). | Method B using 2 equivalents of 5-methyl-2-(trifluoromethoxy)phenyl boronic acid, 1.2 equivalents of cesium carbonate, 0.083 equivalents of palladium tetrakis-(triphenylphosphine) and 1 equivalent of N-(6-amino-5-iodopyridin-2-yl)-1-methyl-1H-pyrazole-5-carboxamide (Preparation 16). Heated to 75° C. for 6 hours before work-up. Purified by column chromatography, eluting with heptane:ethyl acetate 85:15 to 0:100. |
| 138 | N-{6-amino-5-[2-chloro-5-(methoxymethyl)phenyl]-pyridin-2-yl}-3-methylisoxazole-4-carboxamide<br>R¹ = 3-methylisoxazole-4-carboxamide<br>Ar = 2-chloro-5-(methoxymethyl)phenyl | LCMS Rt = 3.02-3.07 min MS m/z 373 [MH]+ | Method B using 4 equivalents of 2-(2-Chloro-5-methoxymethylphenyl)-4,4,5,5-tetramethyl-[1,3,2]-dioxaborolane (Preparation 54), 1.1 equivalents of cesium carbonate, 0.083 equivalents of palladium tetrakis-(triphenylphosphine) and 1 equivalent of N-(6-Amino-5-iodopyridin-2-yl)-3-methyl-isoxazole-4-carboxamide (Preparation 15). Stirred at this temperature for 6 hours before work-up. |
| 139 | N-{6-amino-5-[2-(2,2,2-trifluoroethyl)phenyl]-pyridin-2-yl}-1-methyl-1H-pyrazole-5-carboxamide<br>R¹ = 1-methyl-1H- | ¹HNMR (d₄-CD₃OD): 3.30-3.50 (m, 2H), 4.17 (s, 3H), 6.98 (d, 1H), 7.26 (d, 1H), 7.31 (d, 1H), 7.42-7.46 (m, | Method F using 4,4,5,5-Tetramethyl-2-[2-(2,2,2-trifluoroethyl)-phenyl]-[1,3,2]-dioxaborolane (Preparation 58) and N-(6-amino-5-iodopyridine-2-yl)-1-methyl-1H-pyrazole-5-carboxamide (Preparation 16). |

| Eg. No. | Name R¹ Ar | Data | Preparation Information |
|---|---|---|---|
| | pyrazole-5-carboxamide Ar = 2-(2,2,2-trifluoroethyl)phenyl | 2H), 7.50-7.56 (m, 4H). | |
| 140 | N-{6-amino-5-[5-methoxy-2-(trifluoromethoxy)phenyl]-pyridin-2-yl}-1-methyl-1H-pyrazole-5-carboxamide R¹ = 1-methyl-1H-pyrazole-5-carboxamide Ar = 5-methoxy-2-(trifluoromethoxy)phenyl | LCMS Rt = 3.94 min MS m/z 408 [MH]+ | Method E using 1.5 equivalents of 5-methoxy-2-(trifluoromethoxy)phenyl boronic acid (Preparation 60) and N-(6-amino-5-iodopyridine-2-yl)-1-methyl-1H-pyrazole-5-carboxamide (Preparation 16). Heated at 100° C. for 10 minutes |
| 141 | N-{6-amino-5-[2-chloro-5-(methoxymethyl)phenyl]-pyridin-2-yl}-1-methyl-1H-pyrazole-5-carboxamide R¹ = 1-methyl-1H-pyrazole-5-carboxamide Ar = 2-chloro-5-(methoxymethyl)phenyl | LCMS Rt = 2.83 min MS m/z 372 [MH]+ ¹HNMR (CDCl₃): 3.41 (s, 3H), 4.22 (s, 3H), 4.28 (s, 2H), 4.44 (s, 2H), 6.68 (d, 1H), 7.29-7.32 (m, 2H), 7.39 (d, 1H), 7.46-7.50 (m, 2H), 7.68 (d, 1H), 8.07 (s, 1H). | Method E using 3.4 equivalents of 2-(2-Chloro-5-methoxymethylphenyl)-4,4,5,5-tetramethyl-[1,3,2]-dioxaborolane (Preparation 54) and N-(6-amino-5-iodopyridine-2-yl)-1-methyl-1H-pyrazole-5-carboxamide (Preparation 16). Heated at 100° C. for 10 minutes. Purified by column chromatography, ISCO ™ system (4 g, silica cartridge) eluting with heptane:ethyl acetate 5:1 to 1:1. |
| 142 | N-[6-amino-5-(2-chloro-5-methoxyphenyl)pyridin-2-yl]-1-isopropyl-1H-pyrazole-5-carboxamide R¹ = 1-isopropyl-1H-pyrazole-5-carboxamide Ar = 2-chloro-5-methoxyphenyl | LCMS Rt = 3.24 min MS m/z 386 [MH]+ | Method E using 1 equivalent of 2-chloro-5-methoxyphenyl boronic acid and N-(6-amino-5-iodopyridine-2-yl)-1-isopropyl-1H-pyrazole-5-carboxamide (Preparation 61). Heated at 100° C. for 10 minutes. |
| 143 | N-{6-amino-5-[2-(cyclopropylmethoxy)phenyl]pyridin-2-yl}-1-methyl-1H-pyrazole-5-carboxamide R¹ = 1-methyl-1H-pyrazole-5-carboxamide Ar = 2-(cyclopropylmethoxy)phenyl | LCMS Rt = 2.84 min MS m/z 364 [MH]+ | Method E using 2 equivalents of 2-(cyclopropylmethoxy) phenyl boronic acid and N-(6-amino-5-iodopyridine-2-yl)-1-methyl-1H-pyrazole-5-carboxamide (Preparation 16). Heated at 100° C. for 10 minutes. |
| 144 | N-[6-amino-5-(2-butoxy-5-fluorophenyl)pyridin-2-yl]-1-methyl-1H-pyrazole-5-carboxamide R¹ = 1-methyl-1H-pyrazole-5-carboxamide Ar = 2-butoxy-5-fluorophenyl | LCMS Rt = 3.14 min MS m/z 384 [MH]+ | Method E using 2 equivalents of 2-butoxy-5-fluorophenyl boronic acid and N-(6-amino-5-iodopyridine-2-yl)-1-methyl-1H-pyrazole-5-carboxamide (Preparation 16). Heated at 100° C. for 10 minutes. |
| 145 | N-[6-amino-5-(5-fluoro-2-isopropoxyphenyl)pyridin-2-yl]-3-methylisoxazole-4-carboxamide R¹ = 3-methylisoxazole-4- | LCMS Rt = 2.99 min MS m/z 371 [MH]+ ¹HNMR (d₄-CD₃OD): 1.19 (dd, 6H), 3.51 (s, 3H), | Method F using 1.5 equivalents of 5-fluoro-2-isopropoxyphenyl boronic acid, 1.2 equivalents of tert-butyl ammonium bromide, 0.05 equivalents of palladium acetate and 1 equivalent of N-(6-amino-5-iodopyridin-2-yl)-3- |

| Eg. No. | Name<br>R¹<br>Ar | Data | Preparation Information |
|---|---|---|---|
| | carboxamide<br>Ar = 5-fluoro-2-isopropoxyphenyl | 4.37-4.43 (m, 1H),<br>6.96-7.01 (m, 1H),<br>7.05-7.09 (m,<br>2H), 7.38 (dd,<br>1H), 7.47 (dd,<br>1H), 9.20 (s,<br>1H). | methyl-isoxazole-4-carboxamide (Preparation 15). Heated for 10 minutes at 80° C. Purified by fractionlynx ™ HPLC. |
| 146 | N-{6-amino-5-[2-(2,2,2-trifluoroethyl)phenyl]-pyridin-2-yl}-3-methylisoxazole-4-carboxamide<br>R¹ = 3-methylisoxazole-4-carboxamide<br>Ar = 2-(2,2,2-trifluoroethyl)phenyl | LCMS<br>Rt = 2.96 min<br>MS m/z<br>377 [MH]+<br>¹HNMR (d₄-CD₃OD):<br>2.50 (s, 3H),<br>3.33-3.50 (m,<br>2H),<br>7.26-7.29 (m, 1H),<br>7.31 (d, 1H),<br>7.42-7.46 (m, 2H),<br>7.47 (d,<br>1H),<br>7.50-7.52 (m, 1H), 9.20 (s,<br>1H). | Method F using 1.4 equivalents of 4,4,5,5-tetramethyl-2-[2-(2,2,2-trifluoroethyl)-phenyl]-[1,3,2]-dioxaborolane (Preparation 58), 1.1 equivalents of tert-butyl ammonium bromide, 0.02 equivalents of palladium acetate and 1 equivalent of N-(6-amino-5-iodopyridin-2-yl)-3-methyl-isoxazole-4-carboxamide (Preparation 15). Heated for 240 minutes at 120° C. Purified by fractionlynx ™ HPLC. |
| 147 | N-{6-amino-5-[5-fluoro-2-(2-methoxyethoxy)phenyl]-pyridin-2-yl}-1-methyl-1H-pyrazole-5-carboxamide<br>R¹ = 1-methyl-1H-pyrazole-5-carboxamide<br>Ar = 5-fluoro-2-(2-methoxyethoxy)phenyl | LCMS (2 min)<br>Rt = 1.24 min<br>MS m/z<br>386 [MH]+<br>¹HNMR (d₄-CD₃OD):<br>3.24 (s, 3H), 3.60 (t,<br>2H), 4.09 (t,<br>2H), 4.15 (s,<br>3H),<br>6.84-6.89 (m, 2H),<br>7.04-7.07 (m, 2H),<br>7.38 (d, 1H),<br>7.47-750 (m,<br>2H). | Method F using 1.3 equivalents of 2-[5-fluoro-2-(2-methoxyethoxy)-phenyl]-4,4,5,5-tetramethyl-[1,3,2]-dioxaborolane (Preparation 63), and 1 equivalent of N-(6-amino-5-iodopyridine-2-yl)-1-methyl-1H-pyrazole-5-carboxamide (Preparation 16). Heated for 10 minutes at 130° C. |
| 148 | N-{6-amino-5-[5-methoxy-2-(trifluoromethoxy)phenyl]-pyridin-2-yl}-3-methylisoxazole-4-carboxamide<br>R¹ = 3-methylisoxazole-4-carboxamide<br>Ar = 5-methoxy-2-(trifluoromethoxy)phenyl | LCMS<br>Rt = 2.45 min<br>MS m/z<br>409 [MH]+ | Method E using 1.5 equivalents of 5-methoxy-2-(trifluoromethoxy)phenyl boronic acid (Preparation 60), 0.01 equivalents of palladium tetrakis(triphenylphosphine) and N-(6-amino-5-iodopyridin-2-yl)-3-methyl-isoxazole-4-carboxamide (Preparation 15). Heated at 100° C. for 10 minutes. |
| 149 | N-{6-amino-5-[2-(2-methoxyethoxy)phenyl]-pyridin-2-yl}-3-methylisoxazole-4-carboxamide<br>R¹ = 3-methylisoxazole-4-carboxamide<br>Ar = 2-(2-methoxyethoxy)phenyl | LCMS Rt = 3.12 min<br>MS m/z<br>369/370 [MH]+ | Method G using 2.1 equivalents of 2-[2-(2-methoxyethoxy)-phenyl]-4,4,5,5-tetramethyl-[1,3,2]-dioxaborolane (Preparation 65), 0.5 equivalents of tri-tert-butylphosphine and 1 equivalent of N-(6-amino-5-iodopyridin-2-yl)-3-methyl-isoxazole-4-carboxamide (Preparation 15). |
| 150 | N-[6-amino-5-(2-chloro-5-ethoxyphenyl)pyridin-2-yl]-1-methyl-1H-pyrazole-5-carboxamide<br>R¹ = 1-methyl-1H-pyrazole-5-carboxamide<br>Ar = 2-chloro-5-ethoxyphenyl | LCMS<br>Rt = 3.06 min<br>MS m/z<br>372 [MH]+ | Method E using 1.2 equivalents of 2-chloro-5-ethoxyphenyl boronic acid and 1 equivalent of N-(6-amino-5-iodopyridine-2-yl)-1-methyl-1H-pyrazole-5-carboxamide (Preparation 16). Heated at 100° C. for 20 minutes. |
| 151 | N-{6-amino-5-[2-chloro-5-(2-methoxyethoxy)phenyl]-pyridin-2-yl}-1-methyl-1H- | LCMS<br>Rt = 2.83 min<br>MS m/z<br>402 [MH]+ | Method E using 2.1 equivalents of 2-[2-chloro-5-(2-methoxyethyoxy)-phenyl]-4,4,5,5-tetramethyl-[1,3,2]-dioxaborolane (Preparation |

| Eg. No. | Name<br>R¹<br>Ar | Data | Preparation Information |
|---|---|---|---|
| | pyrazole-5-carboxamide<br>R¹ = 1-methyl-1H-pyrazole-5-carboxamide<br>Ar = 2-chloro-5-(2-methoxyethoxy)phenyl | | 67) and 1 equivalent of N-(6-amino-5-iodopyridine-2-yl)-1-methyl-1H-pyrazole-5-carboxamide (Preparation 16). Heated at 100° C. for 20 minutes. |
| 152 | N-{6-amino-5-[5-fluoro-2-(3-methoxypropoxy)phenyl]-pyridin-2-yl}-3-methylisoxazole-4-carboxamide<br>R¹ = 3-methylisoxazole-4-carboxamide<br>Ar = 5-fluoro-2-(3-methoxypropoxy)phenyl | LCMS (2 min)<br>Rt = 1.38 min<br>MS m/z<br>401 [MH]+ | Method A using 3-[5-fluoro-2-(3-methoxypropoxy)-phenyl]-pyridine-2,6-diamine (Preparation 70), 1.5 equivalents of lutidine and 1.2 equivalents of acid chloride (1M solution in acetonitrile) prepared from 3-methyl-isoxazole-4-carboxylic acid. |
| 153 | N-{6-amino-5-[5-fluoro-2-(3-methoxypropoxy)phenyl]-pyridin-2-yl}-3-methylisoxazole-4-carboxamide<br>R¹ = 1-methyl-1H-pyrazole-5-carboxamide<br>Ar = 5-fluoro-2-(3-methoxypropoxy)phenyl | LCMS (2 min)<br>Rt = 1.35 min<br>MS m/z<br>400 [MH]+ | Method A using 3-[5-fluoro-2-(3-methoxypropoxy)-phenyl]-pyridine-2,6-diamine (Preparation 70), 1.5 equivalents of lutidine and 1.15 equivalents of acid chloride (1M solution in acetonitrile) prepared from 1-methyl-1H-pyrazole-5-carboxylic acid. |
| 154 | N-[6-amino-5-(2-chloro-5-ethoxyphenyl)pyridin-2-yl]-3-methylisoxazole-4-carboxamide<br>R¹ = 3-methylisoxazole-4-carboxamide<br>Ar = 2-chloro-5-ethoxyphenyl | LCMS<br>Rt = 3.13 min<br>MS m/z<br>373 [MH]+ | Method B using 1.1 equivalents of 2-chloro-5-ethoxyphenyl boronic acid, 1.5 equivalents of cesium carbonate, 0.10 equivalents of palladium tetrakis-(triphenylphosphine) and 1 equivalent of N-(6-amino-5-iodopyridin-2-yl)-3-methyl-isoxazole-4-carboxamide (Preparation 15). |
| 155 | N-{6-amino-5-[2-(2-methoxyethoxy)phenyl]-pyridin-2-yl}-1-methyl-1H-pyrazole-5-carboxamide<br>R¹ = 1-methyl-1H-pyrazole-5-carboxamide<br>Ar = 2-(2-methoxyethoxy)phenyl | LCMS<br>Rt = 2.42 min<br>MS m/z<br>368 [MH]+ | Method B using 1.1 equivalents of 2-[2-(2-methoxyethoxy)-phenyl]-4,4,5,5-tetramethyl-[1,3,2]-dioxaborolane (Preparation 65), 3.0 equivalents of potassium carbonate, 0.05 equivalents of palladium tetrakis-(triphenylphosphine) and 1 equivalent of N-(6-amino-5-iodopyridine-2-yl)-1-methyl-1H-pyrazole-5-carboxamide (Preparation 16). Reagents were heated to 80° C. in a round bottom flask for 4 hours. |
| 156 | N-{6-amino-5-[2-(3-methoxypropoxy)phenyl]-pyridin-2-yl}-3-methylisoxazole-4-carboxamide<br>R¹ = 3-methylisoxazole-4-carboxamide<br>Ar = 2-(3-methoxypropoxy)phenyl | LCMS (2 min)<br>Rt = 1.28 min<br>MS m/z<br>383 [MH]+ | Method A using 3-[2-(3-methoxypropoxy)-phenyl]-pyridine-2,6-diamine (Preparation 73), 1.5 equivalents of lutidine and 1.2 equivalents of acid chloride (0.5M solution in acetonitrile) prepared from 3-methylisoxazole-4-carboxylic acid. |
| 157 | N-{6-amino-5-[2-(3-methoxypropoxy)phenyl]-pyridin-2-yl}-1-methyl-1H-pyrazole-5-carboxamide<br>R¹ = 1-methyl-1H- | LCMS (2 min)<br>Rt = 1.26 min<br>MS m/z<br>382 [MH]+ | Method A using 3-[2-(3-methoxypropoxy)-phenyl]-pyridine-2,6-diamine (Preparation 73), 1.5 equivalents of lutidine and 1.15 equivalents of acid chloride (0.5M solution in |

-continued

| Eg. No. | Name<br>R[1]<br>Ar | Data | Preparation Information |
|---|---|---|---|
| | pyrazole-5-carboxamide<br>Ar = 2-(3-methoxypropoxy)phenyl | | acetonitrile) prepared from 1-methyl-1H-pyrazole-5-carboxylic acid. |
| 158 | N-{6-amino-5-[5-fluoro-2-(2-methoxypropoxy)phenyl]-pyridin-2-yl}-1-methyl-1H-pyrazole-5-carboxamide<br>R[1] = 1-methyl-1H-pyrazole-5-carboxamide<br>Ar = 5-fluoro-2-(2-methoxypropoxy)phenyl | LCMS<br>Rt = 2.74 min<br>MS m/z<br>400 [MH]+ | Method B using 3 equivalents of 2-[5-fluoro-2-(2-methoxypropoxy)-phenyl]-4,4,5,5-tetramethyl-[1,3,2]-dioxaborolane (Preparation 76), 1.2 equivalents of cesium carbonate, 0.08 equivalents of palladium tetrakis-(triphenylphosphine) and 1 equivalent of N-(6-amino-5-iodopyridine-2-yl)-1-methyl-1H-pyrazole-5-carboxamide (Preparation 16). Reagents were heated to 80° C. in a round bottom flask for 4 hours. |
| 159 | N-{6-amino-5-[5-fluoro-2-(2-methoxypropoxy)phenyl]-pyridin-2-yl}-3-methylisoxazole-4-carboxamide<br>R[1] = 3-methylisoxazole-4-carboxamide<br>Ar = 5-fluoro-2-(2-methoxypropoxy)phenyl | LCMS<br>Rt = 2.85 min<br>MS m/z<br>401 [MH]+ | Method G using 3 equivalents of 2-[5-fluoro-2-(2-methoxypropoxy)-phenyl]-4,4,5,5-tetramethyl-[1,3,2]-dioxaborolane (Preparation 76), 0.2 equivalents of tri-tert-butylphosphine and 1 equivalent of N-(6-amino-5-iodopyridin-2-yl)-3-methyl-isoxazole-4-carboxamide (Preparation 15). |
| 160 | N-{6-amino-5-[2-(2-methoxypropoxy)phenyl]-pyridin-2-yl}-1-methyl-1H-pyrazole-5-carboxamide<br>R[1] = 1-methyl-1H-pyrazole-5-carboxamide<br>Ar = 2-(2-methoxypropoxy)phenyl | LCMS (2 min)<br>Rt = 1.25 min<br>MS m/z<br>382 [MH]+ | Method B using 3 equivalents of 2-[2-(2-methoxypropoxy)-phenyl]-4,4,5,5-tetramethyl-[1,3,2]-dioxaborolane (Preparation 78), 1.2 equivalents of cesium carbonate, 0.08 equivalents of palladium tetrakis-(triphenylphosphine) and 1 equivalent of N-(6-amino-5-iodopyridine-2-yl)-1-methyl-1H-pyrazole-5-carboxamide (Preparation 16). |
| 161 | N-{6-amino-5-[2-(2-methoxypropoxy)phenyl]-pyridin-2-yl}-3-methylisoxazole-4-carboxamide<br>R[1] = 3-methylisoxazole-4-carboxamide<br>Ar = 2-(2-methoxypropoxy)phenyl | LCMS<br>Rt = 2.65 min<br>MS m/z<br>383 [MH]+ | Method G using 3 equivalents of 2-[2-(2-methoxypropoxy)-phenyl]-4,4,5,5-tetramethyl-[1,3,2]-dioxaborolane (Preparation 78), 0.2 equivalents of tri-tert-butylphosphine and 1 equivalent of N-(6-amino-5-iodopyridin-2-yl)-3-methyl-isoxazole-4-carboxamide (Preparation 15). |
| 162 | N-[6-amino-5-(5-fluoro-2-propoxyphenyl)pyridin-2-yl]-3-methylisoxazole-4-carboxamide<br>R[1] = 3-methylisoxazole-4-carboxamide<br>Ar = 5-fluoro-2-propoxyphenyl | LCMS (2 min)<br>Rt = 1.49 min<br>MS m/z<br>371 [MH]+ | Method A, using 3-(2-propoxy-5-fluorophenyl)-pyridine-2,6-diamine (Preparation 51), 1.5 equivalents of lutidine and 1.15 equivalents acid chloride prepared from 3-methylisoxazole-4-carboxylic acid. |
| 163 | N-{6-amino-5-[5-chloro-2-(2,2,2-trifluoroethoxy)phenyl]-pyridin-2-yl}-3-methylisoxazole-4-carboxamide<br>R[1] = 3-methylisoxazole-4-carboxamide | LCMS<br>Rt = 3.27 min<br>MS m/z<br>427 [MH]+<br>$^1$HNMR<br>(CDCl$_3$):<br>2.57 (s, 3H), 4.24 (q, 2H), 4.37 (s, 2H), 6.95 (d, | Method B using 1.5 equivalents of 2-[5-chloro-2-(2,2,2-trifluoroethoxy)-phenyl]-4,4,5,5-tetramethyl-[1,3,2]-dioxaborolane (Preparation 80), 2 equivalents of cesium carbonate, 0.10 equivalents of palladium tetrakis-(triphenylphosphine) and 1 |

-continued

| Eg. No. | Name<br>R¹<br>Ar | Data | Preparation Information |
|---|---|---|---|
| | Ar = 5-chloro-2-(2,2,2-trifluoroethoxy)phenyl | 1H),<br>7.29-7.34 (m, 2H),<br>7.40 (d, 1H), 7.63 (d, 1H), 7.85 (s, 1H), 8.79 (s, 1H). | equivalent of N-(6-amino-5-iodopyridin-2-yl)-3-methyl-isoxazole-4-carboxamide (Preparation 15). Heated to 80° C. for 1.25 hours in a round bottom flask. Purified by column chromatography on silica gel eluting with dichloromethane:methanol 100:0 to 98:2. |
| 164 | N-{6-amino-5-[5-chloro-2-(2,2,2-trifluoroethoxy)phenyl]-pyridin-2-yl}-1-methyl-1H-pyrazole-5-carboxamide<br>R¹ = 1-methyl-1H-pyrazole-5-carboxamide<br>Ar = 5-chloro-2-(2,2,2-trifluoroethoxy)phenyl | LCMS<br>Rt = 3.18 min<br>MS m/z<br>426 [MH]+<br>¹HNMR (CDCl₃):<br>4.22 (s, 3H), 4.24 (q, 2H), 4.38 (s, 2H), 6.68 (d, 1H), 6.95 (d, 1H),<br>7.30-7.34 (m, 2H),<br>7.41 (d, 1H), 7.49 (d, 1H), 7.68 (d, 1H), 8.05 (s, 1H). | Method B using 2.5 equivalents of 2-[5-chloro-2-(2,2,2-trifluoroethoxy)-phenyl]-4,4,5,5-tetramethyl-[1,3,2]-dioxaborolane (Preparation 80), 2 equivalents of cesium carbonate, 0.08 equivalents of palladium tetrakis-(triphenylphosphine) and 1 equivalent of N-(6-amino-5-iodopyridine-2-yl)-1-methyl-1H-pyrazole-5-carboxamide (Preparation 16). Reagents were heated to 80° C. for 2 hours in a round bottom flask. Purified by column chromatography on silica gel eluting with dichloromethane:methanol 100:0 to 99:1. |
| 165 | N-{6-amino-5-[5-fluoro-2-(2,2,2-trifluoroethoxy)phenyl]-pyridin-2-yl}-1-methyl-1H-pyrazole-5-carboxamide<br>R¹ = 1-methyl-1H-pyrazole-5-carboxamide<br>Ar = 5-fluoro-2-(2,2,2-trifluoroethoxy)phenyl | LCMS (2 min)<br>Rt = 1.44 min<br>MS m/z<br>410 [MH]+<br>¹HNMR (CDCl₃):<br>4.21 (q, 2H), 4.24 (s, 3H), 4.43 (s, 2H), 6.69 (d, 1H),<br>7.00-7.10 (m, 3H),<br>7.44 (d, 1H), 7.51 (d, 1H), 7.70 (d, 1H), 8.07 (s, 1H). | Method B using 2.5 equivalents of 2-[5-fluoro-2-(2,2,2-trifluoroethoxy)-phenyl]-4,4,5,5-tetramethyl-[1,3,2]-dioxaborolane (Preparation 82), 2 equivalents of cesium carbonate, 0.08 equivalents of palladium tetrakis-(triphenylphosphine) and 1 equivalent of N-(6-amino-5-iodopyridine-2-yl)-1-methyl-1H-pyrazole-5-carboxamide (Preparation 16). Purified by column chromatography on silica gel eluting with dichloromethane:methanol 100:0 to 99:1. |
| 166 | N-{6-amino-5-[5-fluoro-2-(2,2,2-trifluoroethoxy)phenyl]-pyridin-2-yl}-3-methylisoxazole-4-carboxamide<br>R¹ = 3-methylisoxazole-4-carboxamide<br>Ar = 5-fluoro-2-(2,2,2-trifluoroethoxy)phenyl | LCMS (2 min)<br>Rt = 1.47 min<br>MS m/z<br>411 [MH]+<br>¹HNMR (CDCl₃):<br>2.59 (s, 3H), 4.21 (q, 2H), 4.42 (s, 2H),<br>6.99-7.10 (m, 3H),<br>7.42 (d, 1H), 7.65 (d, 1H), 7.89 (s, 1H), 8.81 (s, 1H). | Method B using 2.5 equivalents of 2-[5-fluoro-2-(2,2,2-trifluoroethoxy)-phenyl]-4,4,5,5-tetramethyl-[1,3,2]-dioxaborolane (Preparation 82), 2 equivalents of cesium carbonate, 0.08 equivalents of palladium tetrakis-(triphenylphosphine) and 1 equivalent of N-(6-amino-5-iodopyridin-2-yl)-3-methyl-isoxazole-4-carboxamide (Preparation 15). Purified by column chromatography on silica gel eluting with dichloromethane:methanol 100:0 to 98:2. |
| 167 | N-{6-amino-5-[5-fluoro-2-(tetrahydrofuran-3-yloxy)phenyl]pyridin-2-yl}-3-methylisoxazole-4-carboxamide<br>R¹ = 3-methylisoxazole-4-carboxamide | LCMS (6 min)<br>Rt = 2.60 min<br>MS m/z<br>399 [MH]+ | Method B using 3 equivalents of 2-[5-fluoro-2-(tetrahydrofuran-3-yloxy)-phenyl]-4,4,5,5-tetramethyl-[1,3,2]-dioxaborolane (Preparation 84), 1.1 equivalents of cesium carbonate, 0.08 equivalents of palladium tetrakis-(triphenylphosphine) and 1 |

| Eg. No. | Name<br>R[1]<br>Ar | Data | Preparation Information |
|---|---|---|---|
| | Ar = 5-fluoro-2-(tetrahydrofuran-3-yloxy)phenyl | | equivalent of N-(6-amino-5-iodopyridin-2-yl)-3-methyl-isoxazole-4-carboxamide (Preparation 15). |
| 168 | N-{6-amino-5-[5-fluoro-2-(tetrahydrofuran-3-yloxy)phenyl]pyridin-2-yl}-1-methyl-1H-pyrazole-5-carboxamide<br>R[1] = 1-methyl-1H-pyrazole-5-carboxamide<br>Ar = 5-fluoro-2-(tetrahydrofuran-3-yloxy)phenyl | LCMS<br>Rt = 2.59 min<br>MS m/z<br>398 [MH]+<br>$^1$HNMR (CDCl$_3$):<br>2.00-2.07 (m, 2H), 3.76-3.81 (m, 4H), 4.21 (s, 3H), 4.95 (br s, 2H), 4.76-4.80 (m, 1H), 6.68 (d, 1H), 6.84-6.87 (m, 1H), 6.98-7.03 (m, 2H), 7.40 (d, 1H), 7.48 (d, 1H), 7.65 (d, 1H), 8.08 (br s, 1H). | Method G using 2.2 equivalents of 2-[5-fluoro-2-(tetrahydrofuran-3-yloxy)-phenyl]-4,4,5,5-tetramethyl-[1,3,2]-dioxaborolane (Preparation 84), 1.1 equivalents of sodium carbonate, 0.03 equivalents of palladium dibenylidene-acetone, 0.2 equivatents of tri-tert-butylphosphine and 1 equivalent of N-(6-amino-5-iodopyridine-2-yl)-1-methyl-1H-pyrazole-5-carboxamide (Preparation 16). |
| 169 | N-{6-amino-5-[5-fluoro-2-(2-methoxyethoxy)phenyl]-pyridin-2-yl}-3-methylisoxazole-4-carboxamide<br>R[1] = 3-methylisoxazole-4-carboxamide<br>Ar = 5-fluoro-2-(2-methoxyethoxy)phenyl | LCMS<br>Rt = 2.71 min<br>MS m/z<br>387 [MH]+ | Method B using 1.33 equivalents of 2-[5-fluoro-2-(2-methoxyethoxy)-phenyl]-4,4,5,5-tetramethyl-[1,3,2]-dioxaborolane (Preparation 63) in dioxane with 0.02 equivalents of [1,3-Bis(2,6-Diisopropylphenyl)imidazol-2-ylidene](3-chloropyridyl)-palladium(II) dichloride, 2.24 equivalents of potassium carbonate and 1 equivalent of N-(6-amino-5-iodopyridin-2-yl)-3-methyl-isoxazole-4-carboxamide (Preparation 15). Heated to 80° C. in a round bottom flask for 1 hour. |
| 170 | N-{6-amino-5-[2-chloro-5-(2-methoxyethoxy)phenyl]-pyridin-2-yl}-3-methylisoxazole-4-carboxamide<br>R[1] = 3-methylisoxazole-4-carboxamide<br>Ar = 2-chloro-5-(2-methoxyethoxy)phenyl | LCMS<br>Rt = 2.71 min<br>MS m/z<br>404 [MH]+ | Method B using 1.9 equivalents of 2-[2-chloro-5-(2-methoxyethyoxy)-phenyl]-4,4,5,5-tetramethyl-[1,3,2]-dioxaborolane (Preparation 67), 1.5 equivalents of cesium carbonate, 0.1 equivalents of palladium tetrakis-(triphenylphosphine) and 1 equivalent of N-(6-amino-5-iodopyridin-2-yl)-3-methyl-isoxazole-4-carboxamide (Preparation 15). Heated to 50° C. for 4 hours. |
| 171 | N-{6-amino-5-[5-ethoxy-2-(trifluoromethoxy)phenyl]-pyridin-2-yl}-3-methylisoxazole-4-carboxamide<br>R[1] = 3-methylisoxazole-4-carboxamide<br>Ar = 5-ethoxy-2-(trifluoromethoxy)phenyl | LCMS<br>Rt = 3.18 min<br>MS m/z<br>423 [MH]+ | Method B using 2 equivalents of 5-ethoxy-2-trifluoro-methoxyphenyl boronic acid (Preparation 86) 2 equivalents of cesium carbonate, 0.1 equivalents of palladium tetrakis-(triphenyl-phosphine)and 1 equivalent of N-(6-amino-5-iodopyridin-2-yl)-3-methyl-isoxazole-4-carboxamide (Preparation 15). Heated to 50° C. for 2 hours. |
| 172 | N-{6-amino-5-[2-(cyclopropyloxy)-5-fluorophenyl]pyridin-2-yl}-1-methyl-1H-pyrazole-5-carboxamide | $^1$HNMR (CDCl$_3$):<br>0.69-0.75 (m, 4H), 3.69-3.74 (m, 1H), 4.23 (s, | Method B using 1.3 equivalents of 2-(2-cyclopropoxy-5-fluorophenyl)-4,4,5,5-tetramethyl-[1,3,2]-dioxaborolane (Preparation |

| Eg. No. | Name R¹ Ar | Data | Preparation Information |
|---|---|---|---|
| | carboxamide R¹ = 1-methyl-1H-pyrazole-5-carboxamide Ar = 2-(cyclopropyloxy)-5-fluorophenyl | 3H), 4.39 (br s, 2H), 4.76-4.80 (m, 1H), 6.68 (d, 1H), 6.98 (dd, 1H), 7.05 (dt, 1H), 7.28 (dd, 1H), 7.39 (d, 1H), 7.50 (d, 1H), 7.66 (d, 1H), 8.09 (br s, 1H). | 90), 2 equivalents of cesium carbonate, 0.05 equivalents of palladium tetrakis-(triphenylphosphine) and 1 equivalent of N-(6-amino-5-iodopyridine-2-yl)-1-methyl-1H-pyrazole-5-carboxamide (Preparation 16). Purified by column chromatography on silica gel eluting with dichloromethane:methanol 100:0 to 99:1. |
| 173 | N-{6-amino-5-[2-(cyclopropyloxy)-5-fluorophenyl]pyridin-2-yl}-3-methylisoxazole-4-carboxamide R¹ = 3-methylisoxazole-4-carboxamide Ar = 2-(cyclopropyloxy)-5-fluorophenyl | LCMS Rt = 3.08 min MS m/z 369 [MH]+ | Method B using 1.3 equivalents of 2-(2-cyclopropoxy-5-fluorophenyl)-4,4,5,5-tetramethyl-[1,3,2]-dioxaborolane (Preparation 90), 2 equivalents of cesium carbonate, 0.1 equivalents of palladium tetrakis-(triphenylphosphine) and 1 equivalent of N-(6-amino-5-iodopyridin-2-yl)-3-methyl-isoxazole-4-carboxamide (Preparation 15). |
| 174 | N-[6-amino-5-(2-chloro-5-hydroxyphenyl)-pyridin-2-yl]-1-methyl-1H-pyrazole-5-carboxamide R¹ = 1-methyl-1H-pyrazole-5-carboxamide Ar = 2-chloro-5-hydroxyphenyl | LCMS Rt = 2.39 min MS m/z 344 [MH]+ ¹HNMR (d₆-DMSO): 3.31 (s, 3H), 5.29 (s, 1H), 6.72 (d, 1H), 6.79 (dd, 1H), 7.22 (d, 1H), 7.28 (d, 1H), 7.34 (d, 1H), 7.39 (d, 1H), 7.50 (d, 1H), 9.77 (s, 1H), 10.28 (s, 1H). | Method G using 2 equivalents of 2-chloro-5-hydroxyphenyl boronic acid, 4 equivalents of sodium carbonate and 1 equivalent of N-(6-amino-5-iodopyridin-2-yl)-3-methyl-isoxazole-4-carboxamide (Preparation 15) in ethanol:water 1 ml:1 ml. Solid residue was collected by filtration. |

EXAMPLE 175

N-[6-amino-5-(2-chloro-5-hydroxyphenyl)pyridin-2-yl]-3-methylisoxazole-4-carboxamide

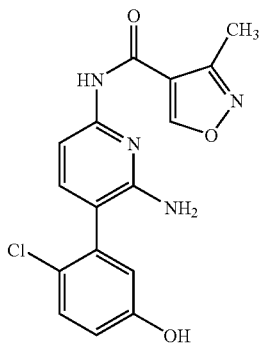

Method H

To a cooled solution of N-[6-amino-5-(2-chloro-5-methoxyphenyl)pyridin-2-yl]-3-methylisoxazole-4-carboxamide (Example 24, 0.087 g, 0.24 mmol) in dichloromethane (2 ml) was added a 1M solution of boron tribromide (0.25 ml, 0.25 mmol) in dichloromethane. The reaction was warmed to room temperature and stirred for 1 hour. A further 0.2 ml boron tribromide (0.2 mmol) was added and the reaction stirred for a further 3 hours at room temperature before concentrating in vacuo and quenching with methanol (5 ml). The reaction was then concentrated in vacuo before partitioning between dichloromethane (10 ml) and a saturated aqueous solution of NaHCO₃ (10 ml). The organic layer was dried over MgSO₄ and concentrated in vacuo. The residue was purified by silica gel column chromatography eluting with 50:50 ethyl acetate:heptane to afford the title compound as a white solid (0.036 g, 42% yield).

MS m/z 345 [MH]+

¹HNMR (d₆-DMSO): 2.43 (s, 3H), 5.23 (br s, 2H), 6.96 (d, 1H), 7.14 (d, 1H), 7.22 (d, 1H), 7.33 (d, 1H), 7.43 (d, 1H), 9.57 (s, 1H), 9.93 (s, 1H), 10.40 (br s, 1H)

The following examples of the general formula:

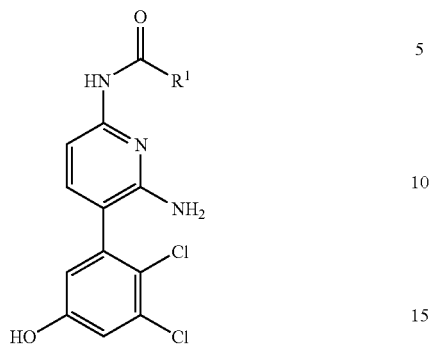

were prepared by methods analogous to Method H as described above for example 175. Unless otherwise noted, preparation details are as described for the method referred to.

| Example No. | Name R$^1$ | Data | Preparation Information |
|---|---|---|---|
| 176 | N-[6-amino-5-(2,3-dichloro-5-hydroxyphenyl)pyridine-2-yl]-3-methylisoxazole-4-carboxamide<br>R$^1$ = 3-methylisoxazole-4-carboxamide | LCMS (2 min)<br>Rt = 1.39 min<br>MS m/z<br>379/381 [MH]+ | Using N-[6-Amino-5-(2,3-dichloro-5-methoxyphenyl)pyridin-2-yl]-3-methylisoxazole-4-carboxamide (example 29), 2 equivalents of boron tribromide and stirring for 24 hours followed by a further addition of 2 equivalents of boron tribromide and stirring for 24 hours. Purified using column chromatography (dichloromethane:methanol 95:5). |
| 177 | N-[6-amino-5-(2,3-dichloro-5-hydroxyphenyl)pyridine-yl]-1-methyl-1Hpyrazole-5-carboxamide<br>R$^1$ = 1-methyl-1H-pyrazole-5-carboxamide | LCMS<br>Rt = 3.05 min<br>MS m/z<br>378/380 [MH]+ | Using N-[6-Amino-5-(2,3-dichloro-5-methoxyphenyl)pyridin-2-2-yl]-1-methyl-1H-pyrazole-5-carboxamide (example 7), 3 equivalents of boron tribromide and stirring for 3.5 hours followed by a further addition of 3 equivalents of boron tribromide and stirring for 3 hours. Reaction partitioned between dichloromethane (10 ml) and a saturated aqueous solution of NaHCO$_3$ (10 ml) and separated using a phase separation cartridge. Some solid precipitated, was collected and purified using preparative HPLC. |

The following examples may be prepared by processes analogous to those described above.

| Example No. Name | R¹ | Ar |
|---|---|---|
| 178<br>N-{6-amino-5-[5-fluoro-2-(trifluoromethoxy)phenyl]pyridin-2-yl}-3-(trifluoromethyl)isoxazole-4-carboxamide | (trifluoromethyl-substituted isoxazole structure) | (5-fluoro-2-(trifluoromethoxy)phenyl structure) |
| 179<br>N-{6-amino-5-[5-fluoro-2-(trifluoromethyl)phenyl]pyridin-2-yl}-3-(trifluoromethyl)isoxazole-4-carboxamide | (trifluoromethyl-substituted isoxazole structure) | (5-fluoro-2-(trifluoromethyl)phenyl structure) |

EXAMPLE 180

Crystalline Form of N-{6-Amino-5-[2-(trifluoromethoxy)phenyl]pyridin-2-yl}-3-methylisoxazole-4-carboxamide N-{6-Amino-5-[2-(trifluoromethoxy)phenyl]pyridin-2-yl}-3-methylisoxazole-4-carboxamide, prepared by the process described in Example 43b), was obtained in crystalline form and was characterised by the following techniques:
1. Differential scanning calorimetry (DSC)
2. Powder X-ray diffraction (PXRD)
3. FT-IR
4. FT-Raman The experimental conditions used are described hereinbelow.

DSC

A sample of N-{6-amino-5-[2-(trifluoromethoxy)phenyl]pyridin-2-yl}-3-methylisoxazole-4-carboxamide was heated from 20 to 300° C. at 20° C. per minute using a TA Instruments Q1000 DSC in aluminium pans with lids, with a nitrogen purge gas.

PXRD

The powder X-ray diffraction pattern was determined using a Bruker-AXS Ltd. D4 powder X-ray diffractometer fitted with an automatic sample changer, a theta-theta goniometer, automatic beam divergence slit, and a PSD Vantec-1 detector. The sample was prepared for analysis by mounting on a low background silicon wafer specimen mount. The specimen was rotated whilst being irradiated with copper K-alpha$_1$ X-rays (wavelength=1.5418 Ångstroms) with the X-ray tube operated at 40 kV/40 mA. The analyses were performed with the goniometer running in continuous mode set for a 0.2 second count per 0.018° step over a two theta range of 2° to 50°. The peaks obtained were aligned against a silicon reference standard. The peaks were selected using Bruker-AXS Ltd. Evaluation software with a threshold of 1 and a peak width of 0.30 two theta. The data were collected at 21° C.

As will be appreciated by the skilled person, the relative intensities of the various peaks within Table 1 given below may vary due to a number of factors such as for example orientation effects of crystals in the X-ray beam or the purity of the material being analysed or the degree of crystallinity of the sample. The peak positions may also shift for variations in sample height but the peak positions will remain substantially as defined in the given Table.

The skilled person will also appreciate that measurements using a different wavelength will result in different shifts according to the Bragg equation—$n\lambda=2d \sin \theta$.

Such further PXRD patterns generated by use of alternative wavelengths are considered to be alternative representations of the PXRD patterns of the crystalline materials of the present invention and as such are within the scope of the present invention.

FT-IR

The IR spectrum was acquired using a ThermoNicolet Avatar 360 FTIR spectrometer equipped with a Smart Golden Gate™ single reflection ATR accessory (diamond ATR crystal with zinc selenide optics) and d-TGS KBr detector. The spectrum was collected at 2 cm$^{-1}$ resolution and a co-addition of 128 scans. Happ-Genzel apodisation was used. Because the FT-IR spectrum was recorded using single reflection ATR, no sample preparation was required. Using ATR FT-IR will cause the relative intensities of infrared bands to differ from those seen in an absorbance FT-IR spectrum using KBr disc or nujol mull sample preparations. Due to the nature of ATR FT-IR, the bands at lower wavenumber are more intense than those at higher wavenumber. Experimental error, unless otherwise noted, was ±2 cm$^{-1}$. Peaks were picked using ThermoNicolet Omnic 6.1a software. Intensity assignments are relative to the major band in the spectrum so they are not based on absolute values measured from the baseline. When assessing split peaks, the intensity value was taken from the baseline but again the intensity was assigned relative to the strongest band in the spectrum.

FT-Raman

The Raman spectrum was collected using a Bruker Vertex 70 FT-IR spectrometer with a Ram II FT-Raman module equipped with a 1064 nm NdYAG laser and LN-Germanium detector. All spectra were recorded using 2 cm$^{-1}$ resolution and Blackman-Harris 4-term apodisation, 350 mW laser power and 2048 scans. The sample was measured directly from its glass vial and exposed to the laser radiation. The data is presented as intensity as a function of Raman shift and is corrected for instrument response and frequency dependent scattering using a white light spectrum from a reference lamp using the Bruker Raman Correct function (Bruker software—

OPUS 6.0). Experimental error, unless otherwise noted, was ±2 cm⁻¹. Peaks were picked using ThermoNicolet Omnic 6.1a software. Intensity assignments are relative to the major band in the spectrum so they are not based on absolute values measured from the baseline. When assessing split peaks, the intensity value was taken from the baseline but again the intensity was assigned relative to the strongest band in the spectrum.

Characterisation Data

A sample of 2.189 mg was analysed by DSC as described above. The DSC thermogram is shown in FIG. 1. The material shows a sharp endothermic peak at 158° C.±2° C. The peak at 158° C.±2° C. is due to the melt of N-{6-amino-5-[2-(trifluoromethoxy)phenyl]pyridin-2-yl}-3-methylisoxazole-4-carboxamide.

Figure 2:
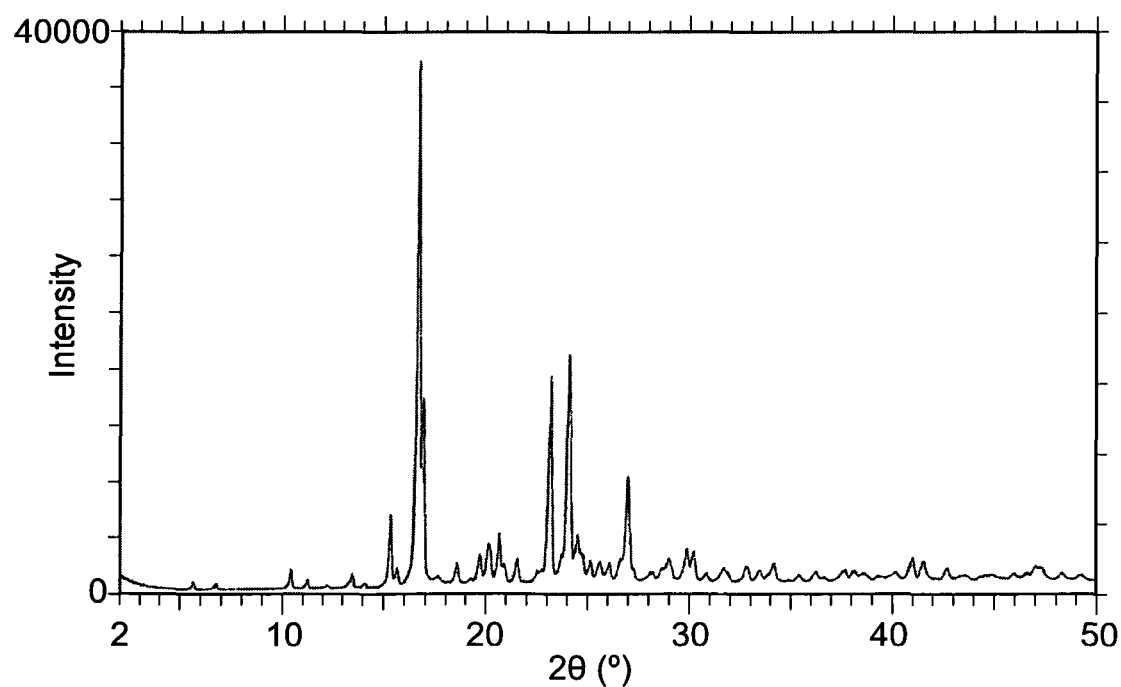
FIG. 2 shows a PXRD pattern for a crystalline form of N-{6-amino-5-[2-(trifluoromethoxy)phenyl]pyridin-2-yl}-3-methylisoxazole-4-carboxamide.

The PXRD pattern for N-{6-amino-5-[2-(trifluoromethoxy)phenyl]pyridin-2-yl}-3-methylisoxazole-4-carboxamide is shown in FIG. 2. The main characteristic peaks, with a relative intensity greater than 4%, are given in Table 1. The 5 unique, most intense peaks for N-{6-amino-5-[2-(trifluoromethoxy)phenyl]pyridin-2-yl}-3-methylisoxazole-4-carboxamide are Angle 2-Theta (degrees): 16.6, 16.8, 23.1, 24.1 and 27.0. The error associated with these peaks is ±0.1 degrees two theta.

Figure 3A:
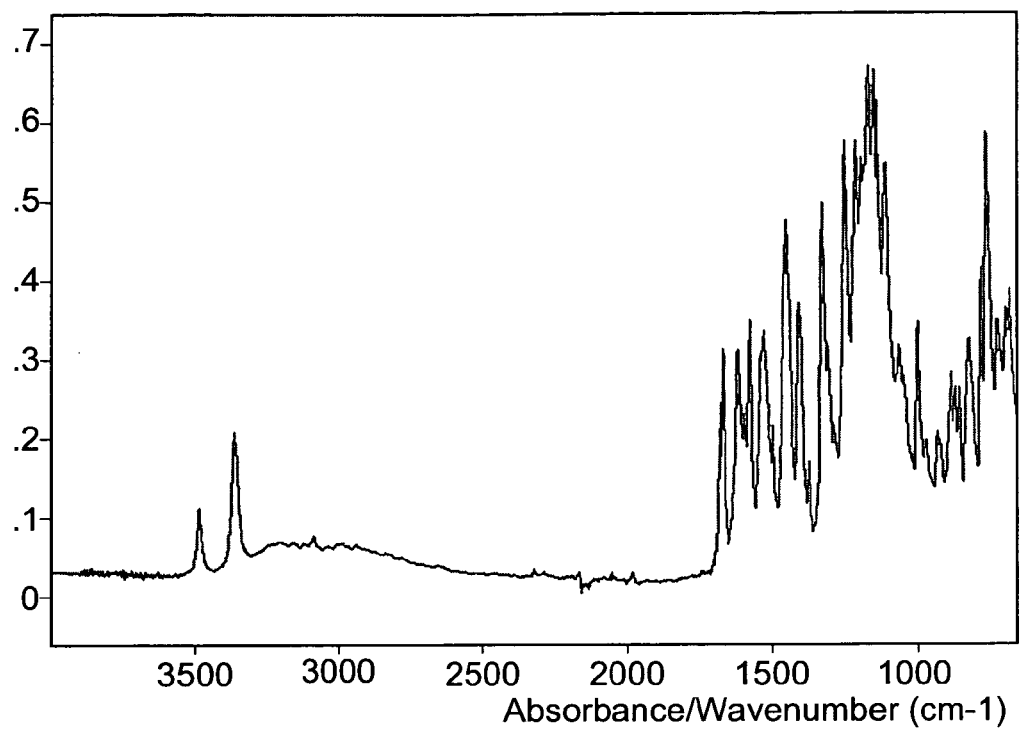
FIG. 3 shows an FT-IR spectrum for a crystalline form of N-{6-amino-5-[2-(trifluoromethoxy)phenyl]pyridin-2-yl}-3-methylisoxazole-4-carboxamide.
Figure 3B:
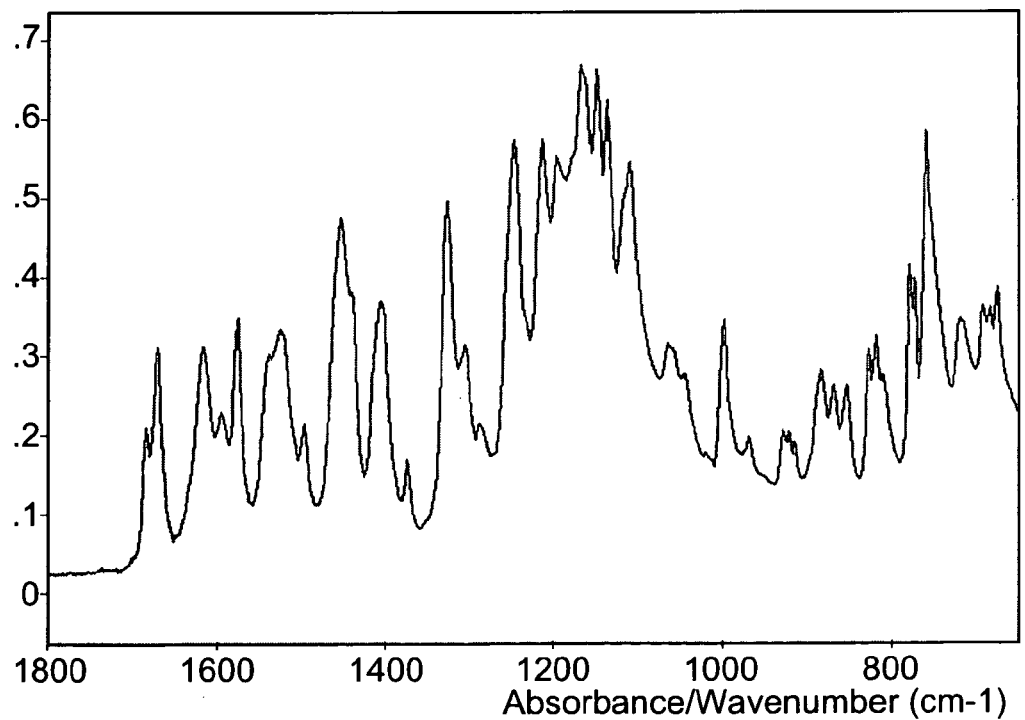
Figure 4A:
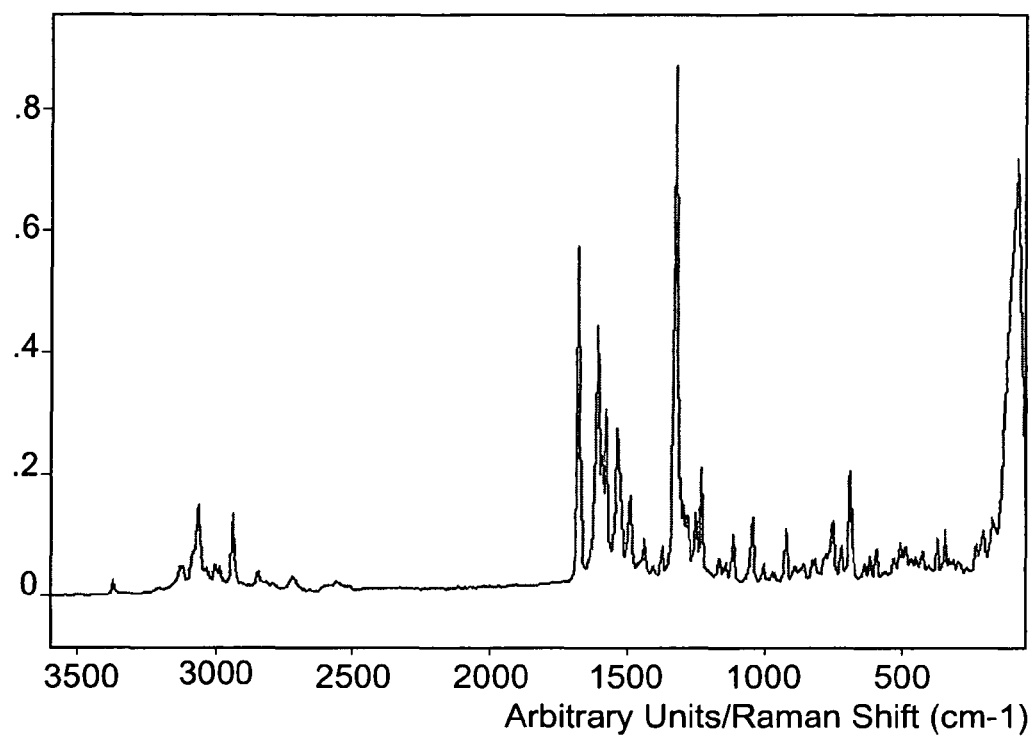
FIG. 4 shows an FT-Raman spectrum for a crystalline form of N-{6-amino-5-[2-(trifluoromethoxy)phenyl]pyridin-2-yl}-3-methylisoxazole-4-carboxamide.
Figure 4B:
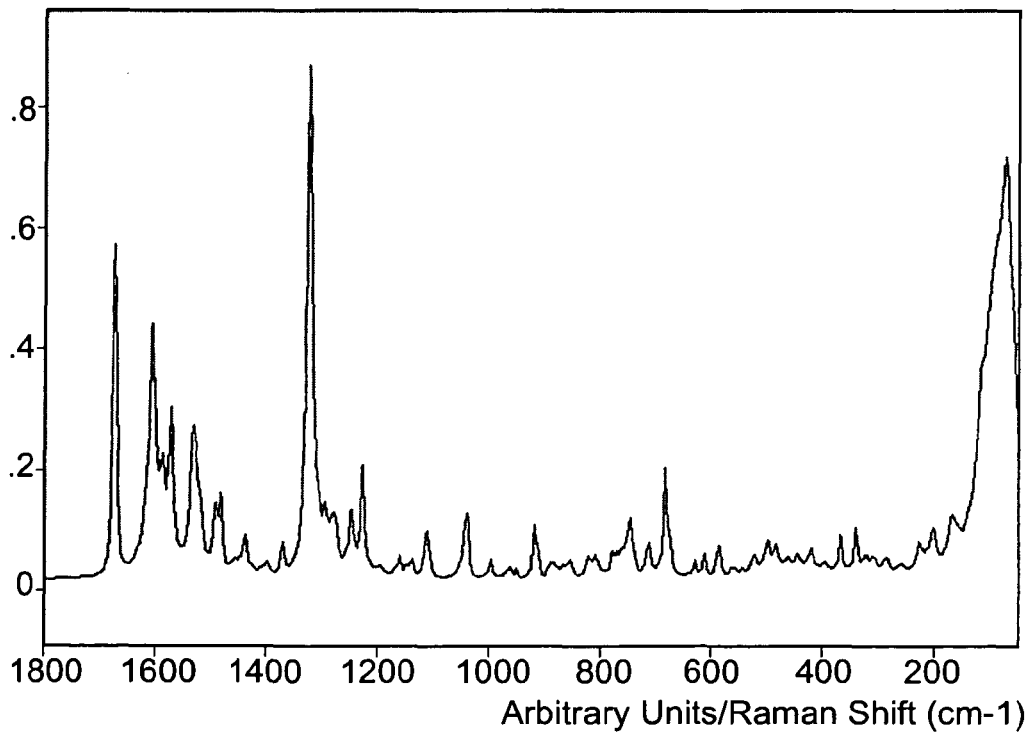

The FT-IR peaks are shown in Table 2. The FT-IR spectrum is shown in FIG. 3. The FT-Raman peaks are shown in Table 3. The FT-Raman spectrum is shown in FIG. 4.

TABLE 1

Characteristic PXRD Peaks for N-{6-amino-5-[2-(trifluoromethoxy)phenyl]pyridin-2-yl}-3-methylisoxazole-4-carboxamide

| Angle 2-Theta (degrees) | Relative Intensity % |
| --- | --- |
| 10.4 | 4.2 |
| 15.3 | 14.5 |
| 15.6 | 4.4 |
| 16.6 | 100.0 |
| 16.8 | 36.1 |
| 18.5 | 5.3 |
| 19.7 | 6.9 |
| 20.1 | 9.0 |
| 20.6 | 10.8 |
| 20.8 | 5.1 |
| 21.5 | 6.3 |
| 22.7 | 4.2 |
| 23.1 | 40.6 |
| 23.7 | 6.5 |
| 24.1 | 44.8 |
| 24.5 | 10.7 |
| 24.7 | 7.1 |
| 25.1 | 5.8 |
| 25.6 | 5.7 |
| 26.1 | 5.4 |
| 26.6 | 6.2 |
| 27.0 | 21.8 |
| 27.3 | 4.3 |
| 28.7 | 4.4 |
| 29.0 | 6.2 |
| 29.9 | 8.1 |
| 30.2 | 7.5 |
| 31.7 | 4.4 |
| 32.8 | 4.8 |
| 33.5 | 4.0 |
| 34.2 | 5.2 |
| 37.7 | 4.1 |
| 41.0 | 6.4 |
| 41.5 | 5.7 |
| 47.0 | 4.9 |
| 47.3 | 4.8 |

TABLE 2

FT IR Peak table for N-{6-amino-5-[2-(trifluoromethoxy)phenyl]pyridin-2-yl}-3-methylisoxazole-4-carboxamide
FT IR Absorption band frequencies (cm⁻¹)
(w: weak, m: medium, s: strong)

| |
| --- |
| 3489 w |
| 3365 m |
| 3092 w |
| 2991 w |
| 1684 m |
| 1671 m |
| 1618 m |
| 1595 m |
| 1577 s |
| 1526 m |
| 1497 m |
| 1453 s |
| 1406 s |
| 1374 w |
| 1326 s |
| 1305 m |
| 1287 m |
| 1246 s |
| 1214 s |
| 1196 s |
| 1167 s |
| 1148 s |
| 1136 s |
| 1109 s |
| 1064 m |
| 1045 m |
| 998 s |
| 969 m |
| 928 m |
| 921 m |
| 914 m |
| 884 m |
| 868 m |
| 853 m |
| 827 m |
| 819 m |
| 811 m |
| 779 s |
| 773 s |
| 760 s |
| 720 s |
| 692 s |
| 683 s |
| 675 s |

Experimental error is ±2 cm⁻¹.

TABLE 3

FT Raman Peak table for N-{6-amino-5-[2-(trifluoromethoxy)phenyl]pyridin-2-yl}-3-methylisoxazole-4-carboxamide
FT Raman Absorption bands (cm⁻¹)
(w: weak, m: medium, s: strong, vs: very strong)

| |
| --- |
| 3373 w |
| 3126 w |
| 3084 w |
| 3069 m |
| 3007 w |
| 2990 w |
| 2941 m |
| 2847 w |
| 2717 w |
| 2558 w |
| 1679 vs |
| 1612 vs |
| 1606 s |
| 1593 s |
| 1578 s |
| 1537 s |
| 1497 m |

TABLE 3-continued

FT Raman Peak table for N-{6-amino-5-[2-(trifluoromethoxy)phenyl]pyridin-2-yl}-3-methylisoxazole-4-carboxamide
FT Raman Absorption bands (cm$^{-1}$)
(w: weak, m: medium, s: strong, vs: very strong)

| |
|---|
| 1488 m |
| 1442 w |
| 1402 w |
| 1375 w |
| 1328 vs |
| 1297 m |
| 1282 m |
| 1251 m |
| 1231 m |
| 1165 w |
| 1141 w |
| 1116 w |
| 1044 m |
| 1000 w |
| 967 w |
| 956 w |
| 921 m |
| 915 w |
| 885 w |
| 857 w |
| 826 w |
| 812 w |
| 780 w |
| 774 w |
| 749 m |
| 717 w |
| 686 m |
| 633 w |
| 615 w |
| 590 w |
| 560 w |
| 527 w |
| 501 w |
| 486 w |
| 465 w |
| 447 w |
| 423 w |
| 397 w |
| 370 w |
| 342 m |
| 324 w |
| 310 w |
| 288 w |
| 261 w |
| 230 w |
| 205 m |
| 170 m |
| 75 vs |

Experimental error is ±2 cm$^{-1}$

The following Preparations illustrate the preparation of certain intermediates used to prepare the above Examples.

Preparation 1

3-(2-Chloro-5-methoxyphenyl)pyridine-2,6-diamine

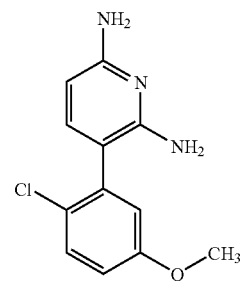

1a) Method I

To a suspension of 3-iodopyridine-2,6-diamine (Preparation 44, 2 g, 8.51 mmol) in 1,4-dioxane (10 ml) and water (5 ml) was added 2-chloro-5-methoxyphenyl boronic acid (0.793 g, 4.25 mmol), cesium carbonate (2.77 g, 8.51 mmol) and palladium tetrakis(triphenylphosphine) (0.123 g, 0.0125 mmol). The reaction was purged with nitrogen and heated at 80° C. for 20 minutes. Three further portions of palladium tetrakis(triphenylphosphine) (0.123 g, 0.0125 mmol) and 2-chloro-5-methoxyphenyl boronic acid (0.793 g, 4.25 mmol) were added at 20 minute intervals. The reaction was heated at 80° C. for 18 hours before concentrating in vacuo. The residue was taken up in ethyl acetate (20 ml) and washed with a saturated aqueous solution of brine (20 ml) before drying over Na$_2$SO$_4$ and concentrating in vacuo. The residue was purified by silica gel column chromatography, eluting with 50:50 to 100:0 ethyl acetate:pentane to afford the title compound as a brown foam (1.157 g, 55% yield).

MS m/z 250 [MH]+

$^1$HNMR (CDCl$_3$): 3.79 (s, 3H), 4.23 (br s, 2H), 4.32 (br s, 2H), 6.00 (d, 1H), 6.86 (m, 2H), 7.14 (d, 1H), 7.38 (d, 1H)

1b) 3-(2-Chloro-5-methoxyphenyl)pyridine-2,6-diamine can also be prepared according to the following method:

To 3-iodopyridine-2,6-diamine (Preparation 44, 3.0 g, 12.8 mmol), 5-methoxy-2-chlorophenylboronic acid (2.62 g, 14.0 mmol), sodium carbonate (1.49 g, 14.0 mmol), ethanol (15 ml), water (15 ml) and tris(dibenzylideneacetone)dipalladium (0) (175 mg, 0.19 mmol) at ambient temperature under a nitrogen atmosphere was added tri-tertbutylphosphine (1M in toluene, 0.574 ml, 0.574 mmol). The brown mixture was heated to reflux and maintained until reaction completion by HPLC. The reaction was cooled to ambient and the ethanol removed by vacuum distillation. 2-methyltetrahydrofuran (30 ml) was then added and the biphasic mixture filtered over Arbocel™, extracted with saturated aqueous sodiumhydrogencarbonate (20 ml) and separated. The organic layer was extracted five times with 10% w/v citric acid (20 ml), then to the combined aqueous layers was added 2-methyltetrahydrofuran (30 ml) then 5M sodium hydroxide until obtaining a pH>10. The layers were separated and the upper organic layer was concentrated to dryness in vacuo obtaining product as a beige solid 2.90 g (91% yield).

Preparation 2

3-[2-(Trifluoromethoxy)phenyl]pyridine-2,6-diamine

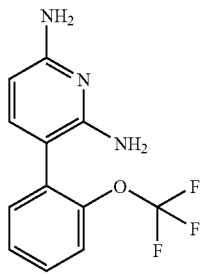

2a) A suspension of 3-iodopyridine-2,6-diamine in 1,4-dioxane (4 ml) and water (2 ml) was treated as for method I, preparation 1, in a small, sealed, reaction vial (Reacti-vial T™), using 1.4 equivalents 2-(trifluoromethoxy)phenyl boronic acid, 1 equivalent cesium carbonate and 0.07 equivalents palladium tetrakis(triphenylphosphine). The catalyst was added at 75° C. and the reaction stirred for 5 hours. Further 0.035 equivalents of catalyst, 0.6 equivalents of boronic acid and 0.6 equivalents cesium carbonate were added and stirred for 1.5 hours.

LCMS Rt=1.58 min
MS m/z 270 [MH]+
$^1$HNMR (d$_6$-DMSO): 4.87 (br s, 2H), 5.55 (br s, 2H), 5.78 (m, 2H), 6.92 (d, 1H), 7.33-7.64 (m, 3H)

2b) 3-[2-(Trifluoromethoxy)phenyl]pyridine-2,6-diamine can also be prepared according to the following method:

To a suspension of 3-iodopyridine-2,6-diamine (5 g, 21 mmol), 2-(trifluoromethoxy)phenyl boronic acid (4.82 g, 23 mmol) and sodium carbonate (2.48 g, 23 mmol) in ethanol (25 ml) and water (25 ml) was added tris(dibenzylideneacetone) dipalladium (0.292 g, 0.319 mmol) followed by tri-tert-butylphosphine (1M solution in toluene, 0.957 ml, 0.957 mmol). The reaction was heated to 78° C. for 16 hours before cooling to room temperature and addition of isopropylacetate (50 ml). The bi-phasic mixture was filtered through Arbocel™ and the filter cake washed with isopropylacetate (2×25 ml). The layers were separated and the organic phase washed with half saturated aqueous sodium hydrogen carbonate solution (50 ml) and water (2×25 ml) before concentration in vacuo. Toluene (2×25 ml) was added during the concentration process and evaporation continued to dryness. The crude residue was purified using silica gel column chromatography (Biotage™) eluting with isopropanol:toluene 5:95 to furnish the title compound as a solid, 90%.

The following Preparations of the general formula:

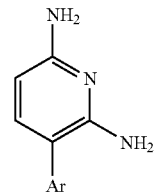

were prepared by methods analogous to Method I, as described for Preparation 1 above. Unless otherwise noted, preparation details are as described for the method referred to.

| Preparation No. Name | Ar | Data | Preparation Information |
|---|---|---|---|
| 3<br>3-(2-Chloro-5-fluorophenyl)pyridine-2,6-diamine | 2-chloro-5-fluorophenyl | LCMS Rt = 1.77 min<br>MS m/z<br>238 [MH]+<br>$^1$HNMR (CDCl$_3$):<br>4.15 (br s, 2H),<br>4.25 (br s, 2H),<br>6.00 (d, 1H),<br>6.98-7.20 (m, 3H), 7.45 (m, 1H) | Using 1.3 equivalents 2-chloro-5-fluorophenyl boronic acid and 0.08 equivalents palladium tetrakis(triphenylphosphine). Catalyst added at 80° C. Purified by trituration with diethyl ether. |
| 4<br>3-(2,5-Dichloro-3-methoxyphenyl)-pyridine-2,6-diamine | 2,5-dichloro-3-methoxyphenyl | LCMS Rt = 1.94 min<br>MS m/z<br>284 [MH]+<br>$^1$HNMR (d$_6$-DMSO):<br>3.88 (s, 3H), 4.95 (s, 2H), 5.54 (s, 2H), 5.76 (d, 1H), 6.88 (d, 2H), 7.14 (s, 1H) | Performed in a small, sealed, reaction vial (Reacti-vial ™) using 2 equivalents 2-(2,5-dichloro-3-methoxy-phenyl)-4,4,5,5-tetramethyl-[1,3,2]dioxaborolane (Preparation 26) and 0.07 equivalents palladium tetrakis(triphenylphosphine). Purified by trituration in diethyl ether:heptane. |
| 5<br>3-(2-Chlorophenyl)pyridine-2,6-diamine | 2-chlorophenyl | LCMS Rt = 1.68 min<br>MS m/z<br>220 [MH]+<br>$^1$HNMR (CDCl$_3$):<br>4.15 (br s, 2H),<br>4.25 (br s, 2H),<br>5.99 (d, 1H),<br>7.12 (d, 1H),<br>7.22-7.37 (m, 3H), 7.49 (d, 1H) | Using 1.2 equivalents 2-chlorophenyl boronic acid and 0.08 equivalents palladium tetrakis(triphenylphosphine). Catalyst added at 80° C. Purified by silica gel column chromatography, eluting with 80:20 to 100:0 ethyl acetate:heptane. |

-continued

| Preparation No. Name | Ar | Data | Preparation Information |
|---|---|---|---|
| 6<br>3-(2,3,5-Trichlorophenyl)-pyridine-2,6-diamine | 2,3,5-trichlorophenyl | MS m/z 289 [MH]+<br>$^1$HNMR (d$_6$-DMSO): 5.15 (br s, 2H), 5.61 (br s, 2H), 5.75 (d, 1H), 6.91 (d, 1H), 7.28 (s, 1H), 7.72 (s, 1H) | Using 2,3,5-trichlorophenyl boronic acid, 1.5 equivalents cesium carbonate and 0.1 equivalents palladium tetrakis(triphenylphosphine). Catalyst added at 75° C. Reaction stirred for 22 hours at 75° C. Further 0.003 equivalents palladium tetrakis(triphenylphosphine) added and stirred at 75° C. for 18 hours. Purified by recrystallisation from toluene. |
| 7<br>3-(2,5-Dichlorophenyl)-pyridine-2,6-diamine | 2,5-dichlorophenyl | MS m/z 254 [MH]+<br>$^1$HNMR (CDCl$_3$): 4.23 (br s, 2H), 4.34 (br s, 2H), 6.00 (d, 1H), 7.13 (d, 1H), 7.25 (m, 1H), 7.33 (s, 1H), 7.43 (d, 1H) | Using 2,5-dichlorophenyl boronic acid. |
| 8<br>3-(2,3-Dichloro-5-methoxyphenyl)-pyridine-2,6-diamine | 2,3-dichloro-5-methoxyphenyl | LCMS Rt = 0.53 min MS m/z 284 [MH]+<br>$^1$HNMR (d$_6$-DMSO): 3.8 (s, 3H), 5.0 (br s, 2H), 5.55 (br s 2H), 5.75 (d, 1H), 6.8 (d, 1H), 6.9 (d, 1H), 7.2 (d, 1H) | Using 1.35 equivalents 2-(2,3-dichloro-5-methoxy-phenyl)-4,4,5,5-tetramethyl-[1,3,2]dioxaborolane (Preparation 24) and 0.08 equivalents palladium tetrakis(triphenylphosphine). Stirred for 3 hours. |
| 9<br>3-(3,5-Dichlorophenyl)-pyridine-2,6-diamine | 3,5-dichlorophenyl | MS m/z 254 [MH]+<br>$^1$HNMR (d$_6$-DMSO): 5.3 (br s, 2H), 5.65 (br s, 2H), 5.8 (d, 1H), 7.1 (d, 1H), 7.4 (m, 3H) | Using 3,5-dichlorophenyl boronic acid, 2.3 equivalents cesium carbonate and 0.1 equivalents palladium tetrakis(triphenylphosphine). Reaction stirred at 80° C. for 2 hours. Purified by silica gel column chromatography, eluting with 50:50 to 65:35 ethyl acetate:heptane |
| 10<br>3-(2,4-Dichlorophenyl)-pyridine-2,6-diamine | 2,4-dichlorophenyl | LCMS Rt = 5.88 min MS m/z 254 [MH]+<br>$^1$HNMR (d$_6$-DMSO): 5.00 (br s, 2H), 5.59 (brs, 2H), 5.77 (d, 1H), 6.90 (d, 1H), 7.31 (d, 1H), 7.63 (d, 1H), 7.64 (d, 1H) | Using 1.5 equivalents 2,4-dichlorophenyl boronic acid, 1.2 equivalents of cesium carbonate and 0.01 equivalents palladium tetrakis(triphenylphosphine). Reaction stirred at 80° C. for 16 hours. |
| 11<br>3-[2-Chloro-5-(trifluoromethoxy)-phenyl]pyridine-2,6-diamine | 2-chloro-5-(trifluoromethoxy)-phenyl | LCMS Rt = 1.04 min MS m/z 304 [MH]+<br>$^1$HNMR (CDCl$_3$): 4.18 (br s, 2H), 4.33 (br s, 2H), 6.02 (d, 1H), 7.13 (m, 2H), 7.23 (m, 1H), 7.52 (d, 1H) Structure was confirmed by gHSQC (Homonuclear Single Quantum Coherence) NMR techniques. | Using 1.5 equivalents 2-chloro-5-(trifluoromethoxy)phenyl boronic acid, 1.08 equivalents cesium carbonate and 0.08 equivalents palladium tetrakis(triphenylphosphine). Stirred for 2 hours. Purified by silica gel column chromatography eluting with 60:40 to 20:80 heptane:ethyl acetate, followed by trituration with t-butyl methyl ether. |

-continued

| Preparation No. Name | Ar | Data | Preparation Information |
|---|---|---|---|
| 12 3-[5-Chloro-2-(trifluoromethoxy)-phenyl]pyridine-2,6-diamine | 5-chloro-2-(trifluoromethoxy)-phenyl | $^1$HNMR (CDCl$_3$): 4.21 (br s, 2H), 4.33 (br s, 2H), 6.00 (d, 1H), 7.11 (d, 1H), 7.30-7.33 (m, 2H), 7.41 (s, 1H) | Performed in a small, sealed, reaction vial (Reacti-vial ™), using 2.44 equivalents of a mixture of 5-chloro-2-(trifluoromethoxy)phenylboronic acid and its corresponding regioisomer, 2-chloro-5-(trifluoromethoxy)phenylboronic acid (preparation 35), 1.1 equivalents cesium carbonate and 0.08 equivalents palladium tetrakis(triphenylphosphine). Catalyst added at 75° C. Stirred for 4.5 hours. Purified by silica gel column chromatography eluting with 70:30 to 40:60 heptane:ethyl acetate. Regioisomers separated. |
| 13 3-[2-Fluoro-5-(trifluoromethoxy)-phenyl]pyridine-2,6-diamine | 2-fluoro-5-(trifluoromethoxy)-phenyl | $^1$HNMR (d$_6$-DMSO): 5.18 (br s, 2H), 5.67 (br s, 2H), 5.81 (d, 1H), 7.02 (d, 1H), 7.29-7.37 (m, 3H) Structure was confirmed by gHSQC (Homonuclear Single Quantum Coherence) NMR techniques. | Using 2.6 equivalents 2-fluoro-5-(trifluoromethoxy)phenyl boronic acid (Preparation 36), 1.1 equivalents cesium carbonate and 0.078 equivalents palladium tetrakis(triphenylphosphine). Catalyst added at 75° C. Stirred for 4 hours. Purified by silica gel column chromatography eluting with 65:35 to 25:75 heptane:ethyl acetate. |

Preparation 14

3-(2,3-Dichlorophenyl)pyridine-2,6-diamine

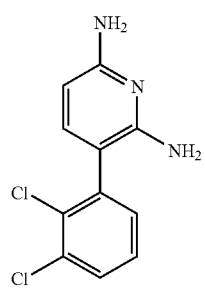

To a suspension of 3-bromopyridine-2,6-diamine (0.376 g, 2.00 mmol) in 1,4-dioxane (12 ml) and water (6 ml) was added 2,3-dichlorophenyl boronic acid (0.573 g, 3.00 mmol), potassium carbonate (0.552 g, 4.00 mmol) and palladium tetrakis(triphenylphosphine) (0.115 g, 0.01 mmol). The reaction was purged with nitrogen and heated at 80° C. for 18 hours. Further palladium tetrakis(triphenylphosphine) (0.115 g, 0.01 mmol) and 2,3-dichlorophenyl boronic acid (0.573 g, 3.00 mmol) were added and the reaction heated at 80° C. for a further 18 hours before concentrating in vacuo. The residue was taken up in ethyl acetate (20 ml) and washed with a saturated aqueous solution of K$_2$CO$_3$ before drying over MgSO$_4$ and concentrating in vacuo. The residue was purified by silica gel column chromatography, eluting with 99:1 dichloromethane:methanol, then recrystallised from toluene to afford the title compound (0.180 g, 35% yield).

MP 170-172° C.

LCMS Rt=0.97 min

MS m/z 254 [MH]+

$^1$HNMR (d$_6$-DMSO): 5.00 (br s, 2H), 5.60 (br s, 2H), 5.75 (d, 1H), 6.90 (d, 1H), 7.23 (d, 1H), 7.35 (t, 1H), 7.55 (d, 1H)

Preparation 15

N-(6-Amino-5-iodopyridin-2-yl)-3-methylisoxazole-4-carboxamide

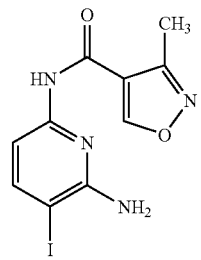

Method J

To a suspension of 3-methylisoxazole-4-carboxylic acid (0.400 g, 3.15 mmol) in thionyl chloride (15 ml, 3.15 mmol) was added two drops dimethylformamide. The reaction was

117 left to stir at room temperature for 20 hours. The reaction was then concentrated in vacuo and azeotroped with dichloromethane (10 ml). The residue was dissolved in $CH_3CN$ to make a 0.25 M solution. 7.12 ml of the 0.25 M solution of acid chloride (1.78 mmol) in $CH_3CN$ was added to a cooled solution of 3-iodo-pyridine-2,6-diamine (Preparation 44, 0.380 g, 1.62 mmol) and lutidine (0.272 ml, 2.43 mmol) in $CH_3CN$ (20 ml). The reaction was warmed to room temperature and stirred for 24 hours before concentrating in vacuo. The residue was taken up in ethyl acetate and washed with water before drying over $Na_2SO_4$ and concentrating in vacuo. The residue was triturated with dichloromethane to afford the title compound (0.258 g, 46% yield).

$^1$HNMR ($d_6$-DMSO): 2.39 (s, 3H), 5.83 (br s, 2H), 7.15 (d, 1H), 7.85 (d, 1H), 9.52 (s, 1H), 10.43 (s, 1H)

The structure was confirmed by NOESY (Nuclear Overhauser Effect) NMR techniques.

The following Preparations of the general formula:

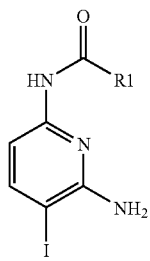

were prepared by methods analogous to Method J, as described for Preparation 15 above. Unless otherwise noted, preparation details are as described for the method referred to.

118

Preparation 18

N-{6-Amino-5-[2-(trifluoromethoxy)phenyl]pyridine-2-yl}-methyl-1-{[2-(trimethylsilyl)ethoxy]methyl}-1H-pyrazole-4-carboxamide and N-{6-Amino-5-[2-(trifluoromethoxy)phenyl]pyridine-2-yl}-3-methyl-2-{[2-(trimethylsilyl)ethoxy]methyl}-1H-pyrazole-4-carboxamide

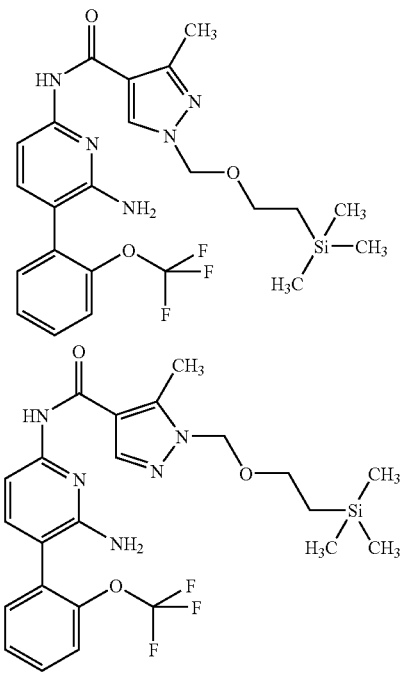

Oxalyl chloride (0.120 ml, 1.37 mmol) was added to a solution of 3-methyl-1-{[2-(trimethylsilyl)ethoxy]methyl}-1H-pyrazole-4-carboxylic acid and 3-methyl-2-{[2-(trimethylsilyl)ethoxy]methyl}-1H-pyrazole-4-carboxylic acid (Preparation 19 as a mixture of regioisomers, 0.320 g, 1.25

| Preparation No. Name | R1 | Data | Preparation Information |
|---|---|---|---|
| 16 N-(6-Amino-5-iodopyridin-2-yl)-1-methyl-1H-pyrazole-5-carboxamide | 1-methyl-1H-pyrazol-5-yl | $^1$HNMR ($d_6$-DMSO): 4.06 (s, 3H), 5.84 (br s, 2H), 7.15 (d, 1H), 7.19 (s, 1H), 7.48 (s, 1H), 7.89 (d, 1H), 10.32 (br s, 1H) | Using 1.75 equivalents lutidine and 1.4 equivalents acid chloride prepared from 1-methyl-1H-pyrazole-5-carboxylic acid. |
| 17 N-(6-Amino-5-iodopyridin-2-yl)-1-ethyl-1H-pyrazole-5-carboxamide | 1-ethyl-1H-pyrazol-5-yl | LCMS Rt = 1.03 min MS m/z 358 [MH]+ $^1$HNMR ($d_6$-DMSO): 1.31 (t, 3H), 4.50 (q, 2H), 5.84 (br s, 2H), 7.12 (d, 1H), 7.18 (s, 1H), 7.50 (s, 1H), 7.86 (d, 1H), 10.31 (br s, 1H) | Method G, using 1.75 equivalents lutidine and 1 equivalent acid chloride prepared from 1-ethyl-1H-pyrazole-5-carboxylic acid. Acid chloride prepared using oxalyl chloride at room temperature for 7 hours. Purified by silica gel column chromatography eluting with 65:35 to 60:30 heptane:ethyl acetate. | mmol) in dichloromethane (5 ml). One drop dimethylformamide was added and the reaction left to stir at room temperature for 3 hours. The reaction was concentrated in vacuo and azeotroped with dichloromethane. The residue was dissolved in 1.67 ml CH$_3$CN to make a 1M solution. 0.1 ml of the 1M solution of acid chloride (1.1 mmol) was added to a solution of 3-[2-(trifluoromethoxy)phenyl]pyridine-2,6-diamine (Preparation 2, 0.2 g, 0.743 mmol) and lutidine (0.133 ml, 1.19 mmol) in CH$_3$CN (10 ml). The reaction was stirred at room temperature for 18 hours then concentrated in vacuo and partitioned between dichloromethane and water. The layers were separated using a phase separation cartridge, and the organic layer concentrated in vacuo. The residue was purified using silica gel column chromatography eluting with 66:33 ethyl acetate:heptane to afford the title compounds as a mixture of N1 and N2 regioisomers (0.1 g, 27% yield).

Regioisomers were not separated.
LCMS Rt=1.71-1.74 (two peaks, one for each regioisomer)
MS m/z 508 [MH]+
$^1$HNMR (d$_6$-DMSO): 0.0 (d, 9H), 0.84 (m, 2H), 2.41 (s, 1.6H), 2.60 (s, 1.4H), 3.60 (m, 2H), 5.31 (br s, 2H), 5.37 (s, 1.1H), 5.47 (s, 0.9H), 7.30 (m, 1H), 7.4-7.6 (m, 5H), 8.28 (s, 0.4H), 8.70 (s, 0.6H), 9.87 (s, 0.4H 1), 9.92 (s, 0.6H)

Preparation 19

3-Methyl-1-{[2-(trimethylsilyl)ethoxy]methyl}-1H-pyrazole-4-carboxylic acid and 3-methyl-2{[2-(trimethylsilyl)ethoxy]methyl}-1H-pyrazole-4-carboxylic acid

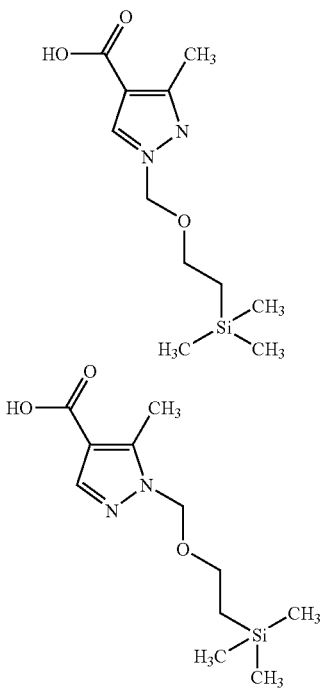

To a solution of ethyl 3-methyl-1-{[2-(trimethylsilyl)ethoxy]methyl}-1H-pyrazole-4-carboxylate and ethyl 3-methyl-2-{[2-(trimethylsilyl)ethoxy]methyl}-1H-pyrazole-4-carboxylate (Preparation 20 as a mixture of regioisomers, 0.526 g, 1.85 mmol) in methanol (10 ml) and water (5 ml) was added lithium hydroxide (0.233 g, 5.55 mmol). The reaction was stirred at room temperature for 18 hours before concentrating in vacuo. The oily residue was acidified with 2N aqueous HCl and immediately extracted into ethyl acetate. The organic extract was dried over MgSO$_4$ and concentrated in vacuo to afford the title compounds as a mixture of N1 and N2 regioisomers (0.320 g, 68% yield). Regioisomers were not separated.

MS m/z 255 [MH]+
$^1$HNMR (d$_6$-DMSO): 0.01 (s, 9H), 0.87 (t, 2H), 2.37 (s, 1.5H), 2.55 (s, 1.5H), 3.3 (br s, 1H), 3.57 (m, 2H), 5.37 (s, 1H), 5.48 (s, 1H), 7.80 (s, 0.5H), 8.33 (s, 0.5H)

Preparation 20

Ethyl 3-methyl-1-{[2-(trimethylsilyl)ethoxy]methyl}-1H-pyrazole-4-carboxylate and ethyl 3-methyl-2-{[2-(trimethylsilyl)ethoxy]methyl}-1H-pyrazole-4-carboxylate

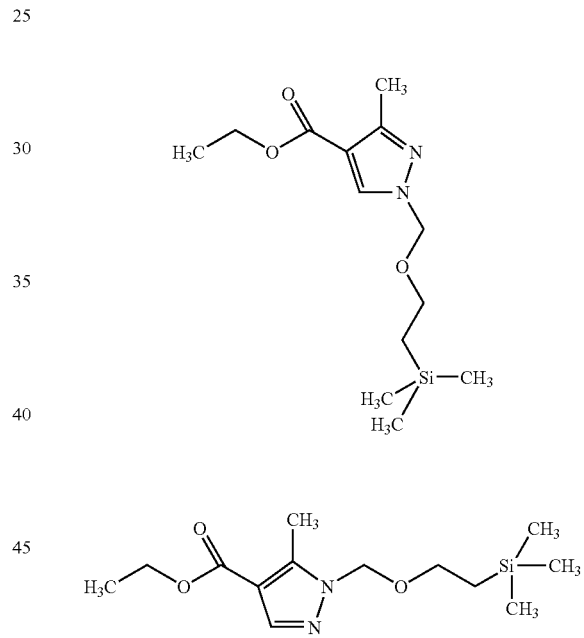

To a solution of ethyl 3-methyl-1H-pyrazole-4-carboxylate (Preparation 21, 1 g, 6.48 mmol) in tetrahydrofuran (THF, 10 ml) was added sodium hydride (0.285 g, 7.14 mmol) and the reaction stirred for 10 minutes. 2-(Trimethylsilyl)ethoxymethyl chloride was added (1.190 g, 7.14 mmol) and the reaction stirred at room temperature for 18 hours. The reaction was quenched with water (20 ml) and extracted with ethyl acetate. The organic extract was dried over MgSO$_4$ and concentrated in vacuo to afford the title compounds as a mixture of N1 and N2 regioisomers (1.57 g, 85% yield).

Regioisomers were not separated.
$^1$HNMR (d$_6$-DMSO): 0.01 (s, 9H), 0.89 (t, 2H), 1.23 (m, 3H), 2.40 (s, 2H), 2.56 (s, 1H), 3.58 (m, 2H), 4.24 (m, 2H), 5.40 (s, 1H), 5.51 (s, 1H), 7.87 (s, 0.5H), 8.43 (s, 0.5H)

Preparation 21

Ethyl 3-methyl-1H-pyrazole-4-carboxylate

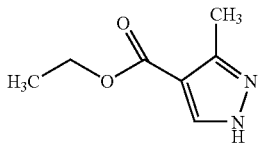

To a solution of 3-methyl-1H-pyrazole-4-carboxylic acid (2.986 g, 23.68 mmol) in ethanol (20 ml) was added concentrated sulphuric acid (1 ml). The reaction was heated at reflux for 6 hours, cooled to room temperature, and then poured into a saturated aqueous solution of NaHCO$_3$. The mixture was extracted with dichloromethane (3×50 ml) then the combined organic extracts dried over MgSO$_4$ and concentrated in vacuo. The product crystallised on standing (2.105 g, 58% yield).

MS m/z 155 [MH]+
$^1$HNMR (CDCl$_3$): 1.36 (t, 3H), 2.59 (s, 3H), 4.32 (q, 2H), 8.00 (s, 1H), 9.22 (br s, 1H)

Preparation 22

1-Bromo-3-chloro-5-methoxybenzene

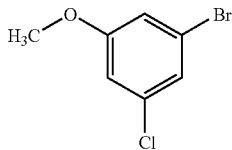

To a solution of 1-bromo-3-chloro-5-fluorobenzene (25 g, 120 mmol) in methanol (800 ml) was added sodium methoxide (64 g, 1180 mmol). The reaction was heated to reflux for 9 days. The reaction was then concentrated in vacuo to one fifth of the volume (150 ml), cooled. and water (1000 ml) added. The mixture was extracted with diethyl ether (3×150 ml). The combined organic extracts were washed with brine (2×100 ml), dried over Na$_2$SO$_4$ and evaporated to afford the title compound (24.6 g).

$^1$HNMR (CDCl$_3$): 3.80 (s, 3H), 6.84 (s, 1H), 6.96 (s, 1H), 7.10 (s, 1H)
GCMS Rt=3.86 min
MS m/z 222 [MH]+

Preparation 23

1-Bromo-2,3-dichloro-5-methoxybenzene

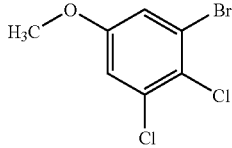

1-Bromo-3-chloro-5-methoxybenzene (Preparation 22, 6.0 g, 27 mmol) and trichloroisocyanuric acid (2.3 g, 9.9 mmol) were stirred in dimethylformamide (100 ml) at 50° C. for 3 hours. N-Heptane was added and the mixture filtered to remove insoluble impurities. The mixture was then concentrated in vacuo and the residue purified by silica gel column chromatography, eluting with 90:10 heptane:ethyl acetate to afford the title compound as a white solid (5.0 g).

$^1$HNMR (CDCl$_3$): 3.80 (s, 3H), 7.00 (s, 1H), 7.20 (s, 1H)
GCMS Rt=4.60 min
MS m/z 256 [MH]+

Preparation 24

2, (2,3-Dichloro-5-methoxy-phenyl)-4,4,5,5-tetramethyl-[1,3,2]dioxaborolane

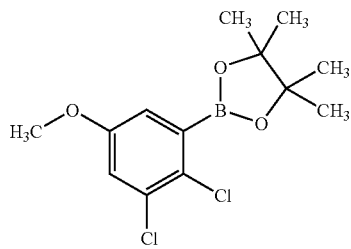

1-Bromo-2,3-dichloro-5-methoxybenzene (Preparation 23, 1.3 g, 5.1 mmol), bis(pinacolato)diboron (1.4 g, 5.6 mmol), potassium acetate (1.5 g, 15 mmol) and 1,1'-[bis(diphenylphosphino)ferrocene]dichloropalladium (II) (0.37 g, 0.51 mmol) were combined and stirred in dimethylsulfoxide (10 ml) for 5 hours at 83° C. in a sealed vessel. The mixture was then poured onto ice and extracted with diethyl ether. The organic extract was dried and evaporated. The residue was stirred in n-heptane, filtered and evaporated. This reaction was performed three times and the crude material combined for purification by silica gel column chromatography, eluting with 90:10 heptane:ethyl acetate to afford the title compound as a yellow oil (3.1 g).

$^1$HNMR (CDCl$_3$): 1.40 (s, 12H), 3.80 (s, 3H), 7.08 (s, 1H), 7.10 (s, 1H)
GCMS Rt=5.78 min
MS m/z 304 [MH]+

Preparation 25

1-Bromo-2,5-dichloro-3-methoxybenzene

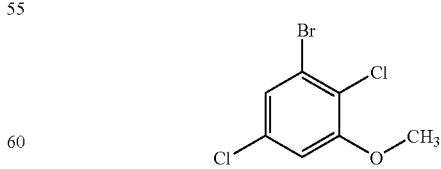

1-Bromo-2,5-dichloro-3-fluorobenzene (40 g, 160 mmol) and sodium methoxide (44.3 g, 820 mmol) were stirred in methanol (500 ml) at reflux for 16 hours. The reaction was cooled to ambient temperature then quenched with water (500 ml). The mixture was extracted with diethyl ether (3×300 ml), dried over Na$_2$SO$_4$ and evaporated to afford the title compound as a white solid (40 g).

$^1$HNMR (CDCl$_3$): 3.90 (s, 3H), 6.86 (d, 1H), 7.26 (d, 1H)
GCMS Rt=4.58 min
MS m/z 256 [MH]+

Preparation 26

2-(2,5-Dichloro-3-methoxy-phenyl)-4,4,5,5-tetramethyl-[1,3,2]dioxaborolane

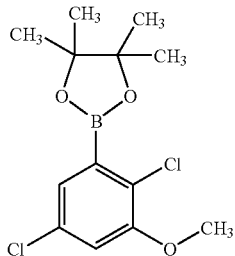

1-Bromo-2,5-dichloro-3-methoxybenzene (Preparation 25, 10 g, 39 mmol), bis(pinacolato)diboron (10.9 g, 43 mmol), potassium acetate (11.5 g, 117 mmol) and 1,1'-[bis(diphenylphosphino)ferrocene]dichloropalladium (II) (2.8 g, 4.0 mmol) were combined and stirred in dimethylsulfoxide (100 ml). The reaction flask was purged with nitrogen for 5 minutes before heating to 80° C. for 16 hours. The mixture was cooled and concentrated in vacuo. The residue was partitioned between water (500 ml) and dichloromethane (3×200 ml). The organic extracts were washed with brine (300 ml), dried over Na$_2$SO$_4$ and evaporated to give a black oil. The residue was dissolved in diethyl ether (200 ml) and filtered over a plug of silica to afford a green oil. This was purified using silica gel column chromatography, eluting with 88:12 heptane:diethyl ether to afford the title compound as a white solid (5.6 g).

$^1$HNMR (CDCl$_3$): 1.40 (s, 12H), 3.89 (s, 3H), 6.98 (s, 1H), 7.20 (s, 1H)
GCMS Rt=5.75 min
MS m/z 304 [MH]+

Preparation 27

3-Bromo-5-chloro-benzene-1,2-diol

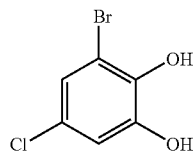

To a stirred suspension of 3-bromo-5-chloro-2-hydroxybenzaldehyde (49.5 g, 0.21 mol) in 0.5N aqueous NaOH (500 ml, 250 mmol) at 40° C. was added dropwise hydrogen peroxide (21.4 g of a 35% aqueous solution, 220 mmol) over 15 minutes and the resultant mixture stirred for 16 hours. The mixture was cooled to room temperature, diluted with 1N aqueous NaOH (200 ml) and washed with diethyl ether (3×300 ml). The aqueous layer was acidified with concentrated HCl to pH 2 and extracted with diethyl ether (3×200 ml). The organic extracts were combined, washed with brine, dried over Na$_2$SO$_4$, filtered and concentrated in vacuo to afford the title compound as a red/brown solid (46.0 g, 99% yield).

1 HNMR (CDCl$_3$): 5.40 (s, 1H), 5.55 (br s, 1H), 6.88 (d, 1H), 7.05 (d, 1H)
MS m/z 224 [MH]+
MP 71-73° C.

Preparation 28

5-Bromo-7-chloro-2,3-dihydro-benzo[1,4]dioxine

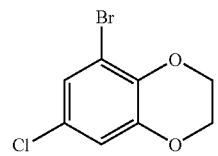

To a solution of 1,2-dibromoethane (1.44 ml, 16 mmol) and tetrabutylammonium bromide (96 mg, 2.5 mol %) in water (8 ml) at reflux under nitrogen was added a mixture of 3-bromo-5-chloro-benzene-1,2-diol (Preparation 27, 2.68 g, 12 mmol) and NaOH (1.06 g, 26.2 mmol) in water (10 ml) over 4 hours, and the resultant mixture stirred overnight. The reaction mixture was cooled to room temperature and diluted with water (100 ml). The mixture was extracted with diethyl ether (3×100 ml), and the combined organic extracts were concentrated in vacuo. Purification by flash chromatography, eluting with 90:10 pentane:dichloromethane, afforded the title compound as a yellow oil which crystallised upon standing to a yellow solid (1.78 g, 60% yield).

$^1$HNMR (CDCl$_3$): 4.27 (t, 2H), 4.35 (t, 2H), 6.86 (d, 1H), 7.10 (d, 1H)
MP 56.5-58.0° C.

Preparation 29

(7-Chloro-2,3-dihydro-1,4-benzodioxin-5-yl)boronic acid

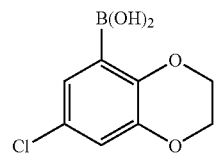

To a stirred solution of 5-bromo-7-chloro-2,3-dihydrobenzo[1,4]dioxine (Preparation 28, 1.5 g, 6 mmol) in dry Et$_2$O (45 ml) under nitrogen at −70° C. was added n-butyl lithium (2.63 ml of a 2.5M solution in hexane, 6.6 mmol) and the resultant mixture stirred for 1 hour. Trimethyl borate (0.92 ml, 8 mmol) was then added and the mixture stirred at room temperature overnight. Saturated aqueous NH$_4$Cl was added (60 ml) and the aqueous layer extracted with diethyl ether (3×100 ml). The combined organic extracts were concentrated in vacuo. The residue was taken up in 1M aqueous NaOH and washed with diethyl ether (100 ml). The aqueous layer was then acidified with 2N aqueous HCl (pH 2) and extracted with diethyl ether (3×100 ml). The organic extracts were combined, dried over MgSO$_4$, filtered and concentrated in vacuo to afford the title compound as a white solid (1.12 g, 87% yield).

$^1$HNMR (CDCl$_3$): 4.30 (t, 2H), 4.37 (t, 2H), 5.62 (2H, s), 6.99 (d, 1H), 7.37 (d, 1H) MP 125-127° C.

Preparation 30

2-[2-(Difluoromethoxy)phenyl]-4,4,5,5-tetramethyl-1,3,2-dioxaborolane

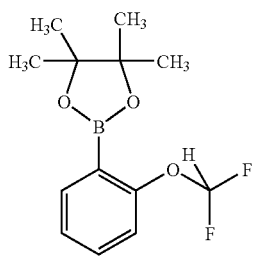

1-Bromo-2-difluoromethoxybenzene (0.5 g, 2 mmol), bis(pinacolato)diboron (0.854 g, 3.36 mmol), potassium acetate (0.88 g, 8.97 mmol) and 1,1'-[bis(diphenylphosphino)ferrocene]dichloropalladium (II) (0.0916 g, 0.112 mmol) were combined and stirred in dimethylformamide (12 ml). The reaction flask was purged with nitrogen for 5 minutes before heating to 70° C. for 18 hours. The mixture was cooled and concentrated in vacuo. The residue was partitioned between ethyl acetate and a saturated aqueous solution of brine before drying over Na$_2$SO$_4$ and concentrating in vacuo to afford the crude title compound (1.15 g).

MS m/z 271 [MH]+

Preparation 31

2-[2-(Difluoromethyl)phenyl]-4,4,5,5-tetramethyl-1,3,2-dioxaborolane

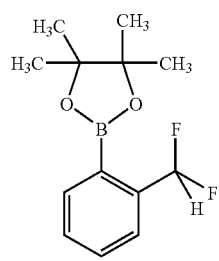

1-Bromo-2-difluoromethylbenzene (2.5 g, 12 mmol), bis(pinacolato)diboron (3.47 g, 13.6 mmol), potassium acetate (3.56 g, 36.2 mmol) and 1,1'-[bis(diphenylphosphino)ferrocene]dichloropalladium (II) (0.884 g, 121 mmol) were combined and stirred in dimethylsulphoxide (25 ml). The reaction flask was purged with nitrogen for 5 minutes before heating to 80° C. for 10 hours. The mixture was cooled and partitioned between diethyl ether and water. Insoluble material was removed by filtration then the organic extract dried over MgSO$_4$ and concentrating in vacuo to afford the crude title compound. The structure was proven at next stage in the synthesis.

Preparation 32

1-Methyl-1H-1,2,3-triazole

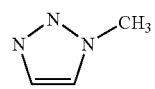

Sodium methoxide, prepared from sodium (1.8 g, 79.8 mmol) and methanol (30 ml) was added to a cooled solution of 1H-1,2,3-triazole (5 g, 72.5 mmol) and stirred at 0° C. for 30 minutes. Iodomethane (5 ml, 79.8 mmol) was then added dropwise and the reaction warmed to room temperature and stirred for 24 hours. The reaction was concentrated in vacuo and the residue partitioned between dichloromethane and 1M aqueous NaOH. The organic extract was dried over MgSO$_4$ and concentrated in vacuo to afford the title compound as a yellow oil (2.5 g, 42% yield).

$^1$HNMR (CDCl$_3$): 4.11 (s, 3H), 7.53 (s, 1H), 7.69 (s, 1H)

Preparation 33

1-Methyl-1H-1,2,3-triazole-5-carbaldehyde

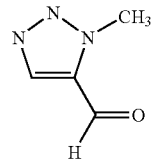

To a solution of 1-methyl-1H-1,2,3-triazole (Preparation 32, 0.1 g, 1.2 mmol) in tetrahydrofuran (THF, 10 ml) at −78° C. was added dropwise 1.6 M n-butyl lithium (0.9 ml, 1.4 mmol), maintaining the temperature below −60° C. The reaction was stirred at −78° C. for 30 minutes, then dimethylformamide (0.14 ml, 1.8 mmol) was added. The reaction was warmed to room temperature and stirred for 1 hour. The reaction was quenched with water and extracted with ethyl acetate (3×10 ml). The combined organic extracts were washed with water (3×10 ml), dried over MgSO$_4$ and concentrated in vacuo. The residue was purified by silica gel column chromatography, eluting with 95:5 to 100:0 dichloromethane:methanol, to afford the title compound as a yellow oil (0.04 g, 30% yield).

$^1$HNMR (CDCl$_3$): 4.10 (s, 3H), 7.88 (s, 1H), 9.55 (s, 1H)

Preparation 34

1-Methyl-1H-1,2,3-triazole-5-carboxylic acid

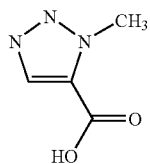

To a solution of 1-methyl-1H-1,2,3-triazole-5-carbaldehyde (Preparation 33, 5 g, 45 mmol) and sodium hydroxide (8.59 g, 215 mmol) in water (120 ml) at 15° C. was added dropwise a solution of potassium permanganate (5.83 g, 36.9 mmol) in water (120 ml). The reaction was stirred at room temperature for 30 minutes and then heated to reflux for 1 hour. The reaction was filtered and the filtrate acidified to pH 3 with concentrated HCl before extracting with ethyl acetate (3×100 ml). The combined organic extracts were washed with saturated aqueous brine, dried over $Na_2SO_4$ and concentrated in vacuo to afford the title compound.
LCMS Rt=1.72 min
MS m/z 128 [MH]+
$^1$HNMR ($d_4$-$CD_3OD$): 4.31 (s, 3H), 8.14 (s, 1H)

Preparation 35

[5-chloro-2-(trifluoromethoxy)phenyl]boronic acid

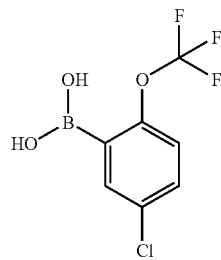

Boron trifluoride etherate (0.415 ml, 3.56 mmol) and trimethyl borate (0.794 ml, 7.12 mmol) were stirred in diethyl ether (10 ml) for 10 minutes to form dimethoxyfluoroborane in situ.
To a solution of the 4-chloro(trifluoromethoxy)benzene (2.0 g, 10.18 mmol) in dry tetrahydrofuran (THF, 30 ml) at −78° C., was added ethylenediaminetetraacetic acid (EDTA, 1.24 g, 10.7 mmol) followed by a 1.3 M solution of sec-butyllithium in cyclohexane (7.63 ml, 10.7 mmol) and the reaction stirred for 2 hours under nitrogen. To this reaction mixture at −78° C., was then added dropwise the preformed dimethoxyfluoroborane mixture. The reaction was stirred at −78° C. for 30 minutes, warmed to room temperature for 30 minutes, and then quenched with water (10 ml). The reaction mixture was extracted with diethyl ether (4×50 ml). The combined organic extracts were dried over $MgSO_4$ and concentrated in vacuo. To purify, the residue was dissolved in diethyl ether (10 ml) and washed with an aqueous solution of 10% NaOH (50 ml). The aqueous layer was acidified and extracted with ethyl acetate (3×40 ml). The combined ethyl acetate extracts were dried over $MgSO_4$ and concentrated in vacuo to afford a mixture of the title compound and its corresponding regioisomer as a white solid (0.862 g).
LCMS Rt=1.42 min
MS mm/z 239 [M]−

Preparation 36

[2-Fluoro-5-(trifluoromethoxy)phenyl]boronic acid

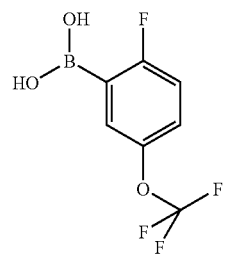

Boron trifluoride etherate (0.453 ml, 3.89 mmol) and trimethyl borate (0.867 ml, 7.77 mmol) were stirred in anhydrous tetrahydrofuran (THF, 10 ml) for 10 minutes to form dimethoxyfluoroborane in situ.
To a solution of the 4-fluoro(trifluoromethoxy)benzene (2.0 g, 11.1 mmol) in dry THF (30 ml) at −78° C., was added ethylenediaminetetraacetic acid (EDTA, 1.36 g, 11.7 mmol) followed by a 1.4 M solution of sec-butyllithium in cyclohexane (8.33 ml, 11.7 mmol) and the reaction stirred for 2 hours under nitrogen. To this reaction mixture at −78° C., was then added dropwise the preformed dimethoxyfluoroborane mixture. The reaction was stirred at −78° C. for 30 minutes, warmed to room temperature for 30 minutes, and then quenched with water (10 ml). The volume of the reaction mixture was reduced in vacuo, then the residue dissolved in diethyl ether (10 ml) and washed with an aqueous solution of 10% NaOH (50 ml). The aqueous layer was acidified and extracted with ethyl acetate (3×40 ml). The combined ethyl acetate extracts were dried over $MgSO_4$ and concentrated in vacuo to afford the title compound as a single regioisomer (1.51 g).
LCMS Rt=1.38 min
MS m/z 223 [M]−

Preparation 37

3-(Methoxymethyl)isoxazole-4-carboxylic acid and
3-(Methoxymethyl)isoxazole-5-carboxylic acid

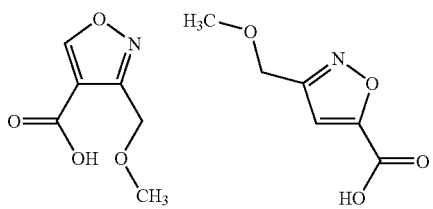

To a solution of 3-(methoxymethyl)isoxazole-4-carboxylic acid methyl ester and 3-(methoxymethyl)isoxazole-5-carboxylic acid methyl ester prepared as a mixture of isoxazole regioisomers (Preparation 38, 2.0 g, 2.3 mmol) in 1,4-dioxane (20 ml) was added an aqueous solution of sodium hydroxide (0.5 g, 12.5 mmol in 5 ml water) and the reaction stirred vigorously at room temperature for 1 hour. The reaction was concentrated in vacuo, and the residue partitioned between t-butylmethyl ether (80 ml) and water (30 ml). The aqueous layer was separated and acidified with concentrated hydrochloric acid before extracting with t-butylmethyl ether. The organic layer was then dried over $Na_2SO_4$ and concentrated in vacuo to afford a 1:5 mixture of regioisomers. The solid was dissolved in warm t-butylmethyl ether (10 ml) and heptane (10 ml) added. The re-cyrstallisation liquors were concentrated in vacuo to afford a mixture of isoxazole regioisomers, enriched with the desired product to give a 1:3 ratio (0.3 g, 16% yield)

$^1$HNMR ($CDCl_3$): 3.36 (s, 2.25H), 3.45 (s, 0.75H), 4.55 (s, 1.5H), 4.75 (s, 0.5H), 7.04 (s, 0.75H), 8.96 (s, 0.25H)

Preparation 38

3-(Methoxymethyl)isoxazole-4-carboxylic acid methyl ester and
3-(Methoxymethyl)isoxazole-5-carboxylic acid methyl ester

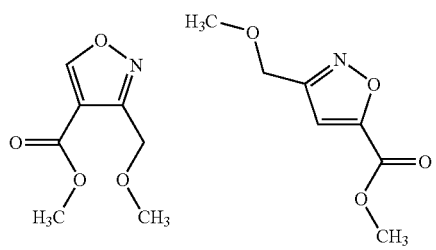

To a cooled solution of N-hydroxy-2-methoxyethanimidoyl chloride (Preparation 39, 2.0 g, 16.19 mmol) and methyl propiolate (3 ml, 33.0 mmol) in toluene (20 ml) was added dropwise diisopropylethylamine (3 ml, 17.0 mmol). The reaction was stirred at room temperature for 1 hour. t-Butylmethyl ether (50 ml) and water (50 ml) were added to the mixture and the pH of the aqueous layer adjusted to pH 1-2 with 2M hydrochloric acid. The organic layer was dried over $Na_2SO_4$ and concentrated in vacuo to afford the title compounds as an inseparable mixture of isoxazole regioisomers (2.0 g, 72% yield).

$^1$HNMR ($CDCl_3$): 3.41 (s, 2.55H), 3.48 (s, 0.45H), 3.89 (s, 2.55H), 3.98 (s, 0.45H), 4.59 (s, 1.7H), 4.79 (s, 0.3H), 7.06 (s, 0.84H), 8.90 (s, 0.15H)

Preparation 39

N-Hydroxy-2-methoxyethanimidoyl chloride

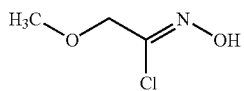

To a cooled solution of methoxyacetaldehyde oxime (Preparation 40, 1.5 g, 16.84 mmol) in dimethylformamide (7 ml) was added N-chlorosuccinimide (2.3 g, 17.22 mmol) and the reaction was stirred at room temperature for 1 hour. The reaction was concentrated in vacuo and the residue partitioned between t-butylmethyl ether (100 ml) and water (50 ml). The organic layer was dried over $Na_2SO_4$ and concentrated in vacuo, to afford the title compound as a colourless oil (2.0 g, 96% yield)

$^1$HNMR ($CDCl_3$): 3.4 (s, 3H), 4.2 (s, 2H), 8.61 (br s, 1H)

Preparation 40

Methoxyacetaldehyde Oxime

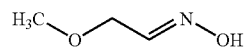

To a solution of methoxyacetaldehyde dimethylacetal (5 g, 41.63 mmol) in methanol (20 ml) was added a solution of hydroxylamine hydrochloride (2.9 g, 41.73 mmol) in water (10 ml). The reaction was stirred at room temperature for 18 hours. To the reaction was then added an aqueous solution of sodium hydroxide (1.67 g, 41.6 mmol in 10 ml water) and stirred for 3 hours at room temperature. The methanol was removed in vacuo and the mixture acidified with concentrated hydrochloric acid to pH 5-6, before extracting with t-butylmethyl ether, drying over $Na_2SO_4$ and concentrating in vacuo to afford the title compound as a 1.5:1 mixture of E/Z isomers (2.64 g, 71% yield).

$^1$HNMR ($CDCl_3$): 3.4 (m, 3H), 4.05 (d, 1.2H), 4.3 (d, 0.8H), 6.9 (t, 0.4H), 7.5 (t, 0.6H), 8.55 (br s, 0.6H), 8.85 (br s, 0.4H)

Preparation 41

5-(Methoxymethyl)isoxazole-4-carboxylic acid

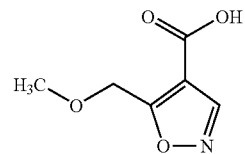

Methyl 5-(methoxymethyl)isoxazole-4-carboxylate (Preparation 42, 1.8 g, 11 mmol) was stirred in a 1:1:1 mixture of concentrated hydrochloric acid (2 ml), acetic acid (2 ml) and water (2 ml) at reflux for 6 hours. Acetone (6 ml) was added and the mixture concentrated in vacuo. The solid residue was triturated with ethyl acetate and the filtrate concentrated in vacuo to afford the title compound as an off white solid (1.4 g, 85% yield).

LCMS Rt=0.86 min

MS m/z 157 [MH]+

$^1$HNMR ($CDCl_3$): 3.52 (s, 3H), 4.91 (s, 2H), 8.61 (s, 1H)

Preparation 42

Methyl 5-(methoxymethyl)isoxazole-4-carboxylate

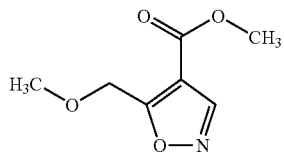

To a solution of methyl 2-[(dimethylamino)methylene]-4-methoxy-3-oxobutanoate (Preparation 43, 5.2 g, 26 mmol) in methanol (55 ml) was added hydroxylamine hydrochloride (1.8 g, 25.8 mmol) and the reaction stirred at reflux for 7 hours. The reaction was concentrated in vacuo. The solid residue was purified by trituration with ethyl acetate to afford the title compound as a solid (3.6 g, 18% yield).

$^1$HNMR (CDCl$_3$): 3.48 (s, 3H), 3.89 (s, 3H), 4.87 (s, 2H), 8.53 (s, 1H)
LCMS Rt=1.06 min
MS m/z 172 [MH]+

Preparation 43

Methyl 2-[(dimethylamino)methylene]-4-methoxy-3-oxobutanoate

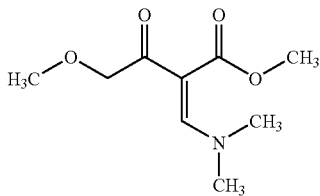

Methyl-4-methoxyacetoacetate (9 ml, 70 mmol) was added to dimethylformamide dimethylacetal (18.8 ml, 139 mmol) and the reaction stirred at 90° C. for 2 hours before cooling to room temperature and stirring for 18 hours. The reaction was concentrated in vacuo and purified by silica gel column chromatography, eluting with 70:30 to 100:0 ethyl acetate:heptane to afford the title compound as an oil (7.68 g, 50% yield).

$^1$HNMR (CDCl$_3$): 2.87 (br s, 3H), 3.25 (br s, 3H), 3.39 (s, 3H), 3.72 (s, 3H), 4.37 (s, 2H), 7.74 (s, 1H)

Preparation 44

3-Iodo-pyridine-2,6-diamine

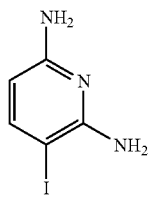

44a) To a solution of 2,6-diaminopyridine (20 g, 0.18 mol) in 2-methyl-tetrahydrofuran (400 ml) was added potassium carbonate (25.3 g, 0.18 mol). To this suspension was added a solution of iodine (46.6 g, 0.18 mol) in 2-methyl-tetrahydrofuran (100 ml) dropwise over 1 hour. The reaction was stirred for 2 hours at room temperature. The reaction was filtered through a pad of celite, and the filtrate collected and washed with water (200 ml) and saturated aqueous sodium thiosulphate solution. The organic layer was dried over sodium sulphate and concentrated in vacuo azeotroping with dichloromethane to afford a light brown solid. The solid was stirred in methanol (500 ml) for 15 minutes. The suspension was filtered and the filtrate collected and concentrated in vacuo. The residue was stirred with methanol (50 ml) for another 15 minutes. The solid was collected by filtration and dried to furnish 14.3 g of an off-white solid. The filtrate was concentrated in vacuo and again stirred with methanol (15 ml). The resulting solid was filtered to furnish 12.2 g solid. These two batches were combined to afford 26.5 g of the title compound (62%).

$^1$HNMR (d$_6$-DMSO): 5.42 (s, 2H), 5.56 (d, 2H), 5.65 (s, 2H), 7.36 (d, 1H).

44b) 3-Iodo-pyridine-2,6-diamine can also be prepared according to the following method: To a solution of industrial methylated spirit (3-5% methanol in ethanol, 200 ml) and triethylamine (25.4 ml, 183 mmol) was added 2,6-diaminopyridine (20 g, 183 mmol) and the contents stirred for 30 min to obtain a solution. A solution of iodine (46.5 g, 183 mmol) in industrial methylated spirit (300 ml) was then added dropwise over 2.5-3.5 hours, maintaining the temperature at 25° C. and the reaction allowed to stir for a further 2 hours. A 10% w/v aqueous solution of sodium thiosulfate (20 g in 200 ml water) was added and the reaction allowed to stir for 1.5 hours. The suspension was filtered and the organic concentrated at 40° C. in vacuo with the addition of water to maintain a volume between 10 ml/g and 25 ml/g until all the ethanol was removed and a beige suspension resulted. The suspension was filtered and dried to furnish the title compound (55%).

Preparation 45

Trifluoro-acetaldehyde oxime

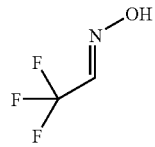

To a solution of trifluoroacetaldehydemethyl hemiacetal (10 g, 77 mmol) and hydroxylamine hydrochloride (5.50 g, 79 mmol) in methanol (15 ml) and water (35 ml) at 0° C. was slowly added sodium hydroxide (50% aqueous solution) (18 ml). The reaction mixture was then allowed to warm to room temperature with stirring over 16 hours. Heptane (50 ml) was added and the layers separated. The aqueous layer was then acidified by addition of hydrochloric acid (6M aqueous solution) (30 ml) then extracted with diethyl ether (2×100 ml). The organic extracts were combined and dried over anhydrous Na$_2$SO$_4$ (s), filtered and evaporated at atmospheric pressure to afford the crude title compound as a 1:2 etherate, as a colourless oil (16.77 g, containing 7.5 g of oxime, 86.3%). Material was taken on without further purification.

$^1$HNMR (CDCl$_3$): 7.45-7.50 (m, 1H), 9.58 (s, 1H).

Preparation 46

(1Z)-2,2,2-trifluoro-N-hydroxyethanimidoyl bromide

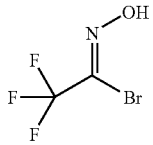

To an ice cooled solution of trifluoro-acetaldehyde oxime (Preparation 45, 16.77 g of a 2:1 etherate containing 7.5 g, 66.3 mmol of the oxime) in anhydrous N,N-dimethylformamide (10 ml) was added a solution of N-bromosuccinimide (12 g, 67 mmol) in anhydrous N,N-dimethylformamide (20 ml), drop-wise, over a period of 45 minutes. The reaction mixture was then warmed to room temperature with stirring over 4 hours. Diethyl ether (150 ml) and water (100 ml) were added and the layers separated. The organic layer was dried over anhydrous $Na_2SO_4$ (s), filtered and evaporated at atmospheric pressure to afford the crude title compound as a 1:1.5 etherate, as a yellow oil (17.4 g, containing 12.0 g of oxime, 94%). Material was taken on without further purification.

$^1$HNMR ($CDCl_3$): 8.02 (s, 1H).

Preparation 47

3-Trifluoromethyl-isoxazole-4-carboxylic acid ethyl ester

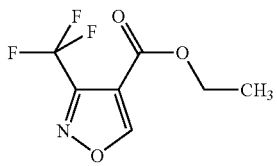

To a solution of dimethylamino acrylate (5.0 g, 35 mmol) in toluene (50 ml) was added bromo-oxime (Preparation 46, 6.0 g plus ether, 31 mmol), drop-wise, and the resultant solution was stirred for three hours at room temperature. The reaction mixture was evaporated to dryness, then t-butylmethyl ether (60 ml) and water (20 ml) were added. The layers were separated and the organic layer was washed with dilute hydrochloric acid (20 ml), then water (20 ml) and brine (10 ml). The organic fraction was then dried over anhydrous $Na_2SO_4$ (s), filtered and evaporated in vacuo to afford the title compound as an orange/brown oil (4.65 g, 72%). Material was taken on with no further purification.

$^1$HNMR ($CDCl_3$): 1.35 (t, 3H), 4.36 (q, 2H), 9.03 (s, 1H).

Preparation 48

3-Trifluoromethyl-isoxazole-4-carboxylic acid

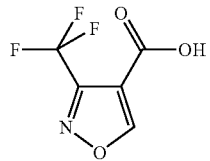

3-Trifluoromethyl-isoxazole-4-carboxylic acid ethyl ester (Preparation 47, 1.00 g, 4.78 mmol), glacial acetic acid (4 ml), concentrated hydrochloric acid (2 ml, 20 mmol) and water (2 ml, 200 mmol) were heated together with stirring at 70° C. for 2 hours. Solvents were removed by evaporation in vacuo and the residue was left to stand at room temperature for 16 hours. Water (40 ml) and t-butylmethyl ether (80 ml) was added and the layers separated. The organic layer was washed with dilute hydrochloric acid (20 ml), then dried over anhydrous $Na_2SO_4$ (s), filtered and evaporated in vacuo to afford the title compound as a brown gum (70 mg, 8%). Material was taken on with no further purification.

Preparation 49

[2-(trifluoromethoxy)-5-fluoro-1-bromo]benzene

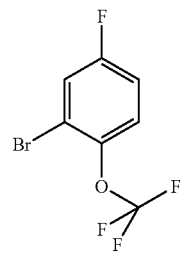

To a stirred solution of 3-bromo-4-trifluoromethoxyaniline (30 g, 0.12 mol) in hydrochloric acid (6N aqueous solution) (300 ml) was added drop-wise a solution of sodium nitrite (9.7 g, 0.14 mol) in water (30 ml) at 0° C. The resulting mixture was stirred at 0-5° C. for 1 hour until the reaction system became clear. Tetrafluoroboronic acid (40% aqueous solution) (90 ml) was then added drop-wise over 15 minutes. The resulting mixture was again stirred at 0-5° C. for 1 hour then filtered. The filter cake was washed with cold water (100 ml) and diethyl ether (100 ml), then dried in vacuo to give the hydrazinium tetrafluoroborate salt as a white solid (35 g, 84%). This solid (8.5 g, 0.024 mol) was then slowly heated to 140° C. and maintained at this temperature for 1 hour under an atmosphere of nitrogen. The reaction mixture was cooled to room temperature and distilled under reduced pressure to afford the title compound as a colourless oil (4.86 g, 78%).

$^1$HNMR ($CDCl_3$): 7.02-7.09 (m, 1H), 7.26-7.29 (m, 1H), 7.33-7.38 (m, 1H).

LCMS (30 min) Rt=6.9 min MS m/z 258 [MH+]

Preparation 50

[2-(trifluoromethoxy)-5-fluorophenyl]boronic acid

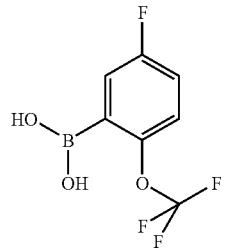

A solution of isopropylmagnesium bromide (2M solution in tetrahydrofuran) (83 ml, 0.166 mol) was added drop-wise to a stirred solution of 2-(trifluoromethoxy)-5-fluoro-1-bromobenzene (Preparation 49, 27.6 g, 0.107 mol) in anhydrous tetrahydrofuran (125 ml) at −10° C. under an atmosphere of nitrogen. The resulting mixture was stirred at room temperature for 2 hours. Triisopropyl borate (26.1 g, 0.139 mol) was then added drop-wise at −10° C. and the resulting mixture was stirred at room temperature for 16 hours. Hydrochloric acid (1N aqueous solution) (100 ml) was added drop-wise at 0° C. and the mixture stirred at room temperature for 30 minutes. Ethyl acetate (150 ml) was added and the layers were separated, the aqueous layer was further extracted with ethyl acetate (2×150 ml). The organic extracts were combined and concentrated in vacuo. The residue was dissolved in potassium hydroxide (10% aqueous solution) (50 ml) and extracted with diethyl ether (2×150 ml). The separated aqueous layer was acidified to pH~4 by addition of hydrochloric acid (1N aqueous solution) (100 ml) and extracted with ethyl acetate (3×150 ml). The combined organic extracts were dried over anhydrous $Na_2SO_4$, filtered and evaporated in vacuo to give an off white solid. Purification by preparative HPLC gave the title compound as an off white solid (5.82 g, 24%).

$^1$HNMR ($d_6$-DMSO): 7.23-7.32 (m, 3H), 7.53-7.55 (m, 1H), 8.36 (br s, 1H).

MS m/z 223 [MH]−

Preparation 51

3-(5-Fluoro-2-propoxyphenyl)-pyridine-2,6-diamine

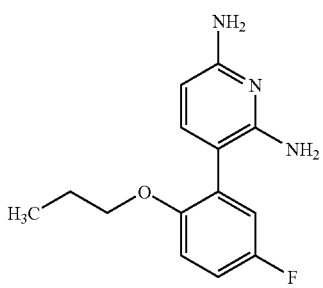

To a suspension of 3-iodopyridine-2,6-diamine (Preparation 44, 1.5 g, 6.38 mmol) in ethanol (5 ml) and water (5 ml) was added 5-fluoro-2-propoxyphenyl boronic acid (1.6 g, 8.10 mmol) and sodium carbonate (744 mg, 7.02 mmol), then the slurry was stirred for 10 minutes at room temperature under nitrogen. Palladium (0) bis(dibenzylideneacetone) (0.088 g, 0.153 mmol) and tri-tert-butyl phosphine (1M solution in toluene, 1.28 ml, 1.28 mmol) were added and the reaction was heated at 80° C. for 6 hours before concentrating in vacuo. The residue was taken up in ethyl acetate (100 ml) and washed with water (3×50 ml) then brine (50 ml) before drying over anhydrous $MgSO_4$, filtering and concentrating in vacuo. The residue was purified by column chromatography eluting with 1:9 to 8:2 ethyl acetate:heptane to afford the title compound as a yellow foam (0.591 g, 35% yield).

LCMS (2 min) Rt=0.98 min, MS m/z 262 [MH]+

$^1$HNMR ($d_6$-DMSO): 0.88 (t, 3H), 1.57-1.66 (m, 2H), 3.87 (t, 2H), 4.87 (br s, 2H), 5.50 (br s, 2H), 5.77 (d, 1H), 6.93 (dd, 1H), 6.97 (d, 1H), 7.01-7.07 (m, 2H)

Preparation 52

2-[5-Methyl-2-(trifluoromethoxy)phenyl]4,5,5-tetramethyl-1,3,2-dioxaborolane

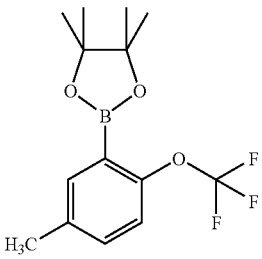

1-Bromo-5-methyl-2-trifluoromethoxybenzene (1.0 g, 3.92 mmol), bis(pinacolato)diboron (1.49 g, 5.88 mmol), potassium acetate (1.54 g, 15.7 mmol) and 1,1'-[bis(diphenylphosphino)ferrocene]dichloropalladium (II) (0.287 g, 0.392 mmol) were combined and stirred in dimethylsulphoxide (25 ml). The reaction flask was purged with nitrogen for 5 minutes before heating to 100° C. for 10 hours. The mixture was cooled and partitioned between tert-butylmethyl ether (100 ml) and water (100 ml). Insoluble material was removed by filtration then the organic extract dried over anhydrous $MgSO_4$, filtered and evaporated in vacuo to afford the crude title compound as a brown oil (895 mg, 76%). Material was taken on without further purification to next stage.

Preparation 53

2-Bromo-1-chloro-4-methoxymethyl-benzene

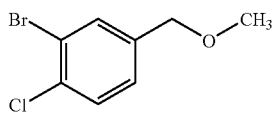

To a stirred solution of 4-chloro-3-bromophenyl-methanol (cited in Amgen patent WO03099776) (900 mg, 4.06 mmol) in 2-methyl-tetrahydrofuran (15 ml) was added potassium hydroxide (912 mg, 16.3 mmol) and the resulting suspension was stirred at room temperature for 30 minutes. Iodomethane (1.01 ml, 4.00 mmol) was then added and the reaction was stirred for 16 hours at room temperature. LCMS indicated incomplete reaction. Potassium hydroxide (912 mg, 16.3 mmol) was added and the resulting mixture stirred for 5 minutes before adding further iodomethane (4.04 ml, 16 mmol) and stirring was continued for 3 hours at room temperature. Ethyl acetate (60 ml) and saturated brine solution (30 ml) were added and the layers were separated. The organic extract was further washed with saturated brine solution (2×30 ml) then dried over anhydrous $MgSO_4$ (s), filtered and evaporated in vacuo to afford the crude title compound as a yellow oil (901 mg, 94%).

$^1$HNMR ($d_6$-DMSO): 3.40 (s, 3H), 4.21 (s, 2H), 5.50 (br s, 2H), 7.21 (dd, 1H), 7.42 (d, 1H), 7.60 (s, 1H).

Preparation 54

2-(2-Chloro-5-methoxymethylphenyl)-4,4,5,5-tetramethyl-[1,3,2]dioxaborolane

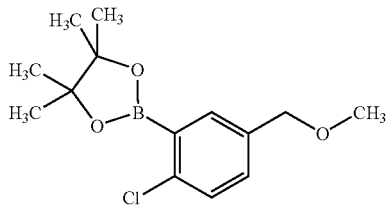

2-Bromo-1-chloro-4-methoxymethyl-benzene (Preparation 53, 901 mg, 3.83 mmol), bis(pinacolato)diboron (1.46 g, 5.74 mmol), potassium acetate (1.50 g, 15.3 mmol) and 1,1'-[bis(diphenylphosphino)-ferrocene]dichloropalladium (II) (0.280 g, 0.383 mmol) were combined and stirred in dimethylsulphoxide (10 ml). The reaction flask was purged with nitrogen for 5 minutes before heating to 100° C. for 14 hours. The mixture was cooled and partitioned between ethyl acetate (150 ml) and saturated brine solution (100 ml). Insoluble material was removed by filtration then the organic extract was dried over anhydrous $MgSO_4$, filtered and evaporated in vacuo to afford the crude title compound as a black oil (1.97 g, >100%). Material was taken on without further purification to next stage.

Preparation 55

1-(2-Bromophenyl)-2,2,2-trifluoro-ethanol

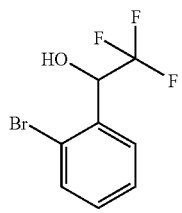

To a solution of 2-bromobenzaldehyde (27.0 g, 146.5 mmol) and trimethylsilyl-trifluoromethane (25.0 g, 175.8 mmol) in tetrahydrofuran (300 ml) was added drop-wise tetrabutylammonium fluoride (1 M in tetrahydrofuran, 5 ml, 5 mmol) at 0° C. After the addition, the mixture was stirred at room temperature for 2 hours. Further tetrabutylammonium fluoride hydrate (49.0 g, 175.8 mmol) was added and the mixture was stirred for 30 minutes. The solvent was evaporated in vacuo. The residue was dissolved in dichloromethane (200 ml) and washed with hydrochloric acid (2N aqueous solution) (4×100 ml). The organic layer was separated, washed with $Na_2CO_3$ (10% aqueous solution) (50 ml), dried over anhydrous $MgSO_4$ (s), filtered and evaporated in vacuo to afford the crude title compound as a yellow oil (45.0 g, ~100%).

$^1$HNMR ($CDCl_3$): 4.79 (br s, 1H), 5.58 (q, 1H), 7.14 (t, 1H), 7.27 (t, 1H), 7.47 (d, 1H), 7.63 (d, 1H).

Preparation 56

Imidazole-1-carbothioic acid O-[1-(2-bromophenyl)-2,2,2-trifluoroethyl]-ester

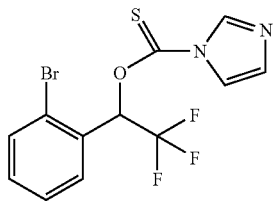

Thiophosgene (24.0 g, 210.0 mmol) was added portionwise to a vigorously stirred suspension of imidazole (57.0 g, 840.0 mmol) in 1,2-dichloroethane (500 ml) under an atmosphere of nitrogen. After the addition, the reaction mixture was stirred at room temperature for 30 minutes. 1-(2-Bromophenyl)-2,2,2-trifluoro-ethanol (Preparation 55, 46 g, crude, about 140 mmol) in 1,2-dichloroethane (100 m) was added at room temperature. After the addition, the mixture was heated at reflux for 10 minutes. The reaction mixture was cooled then the solvent was evaporated in vacuo. The crude product was purified by column chromatography on silica gel eluting with petroleum ether, then petroleum ether:ethyl acetate (10:1) to afford the title compound as a yellow oil (41.5 g, 81%).

$^1$HNMR ($CDCl_3$): 7.09 (s, 1H), 7.19 (q, 1H), 7.33 (t, 1H), 7.37 (t, 1H), 7.48 (d, 1H), 7.67 (d, 2H), 8.39 (s, 1H).

Preparation 57

1-bromo-2-(-2,2,2-trifluoroethyl)-benzene

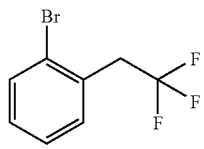

A solution of imidazole-1-carbothioic acid O-[1-(2-bromophenyl)-2,2,2-trifluoroethyl]-ester (Preparation 56, 27.0 g, 73.8 mmol) in toluene (400 ml) was heated at reflux and treated with tri-n-butyltin hydride in three portions: 22 g (75.6 mmol) at first, an additional 10 g (34.4 mmol) after 30 min, and finally 11 g (37.8 mmol) 30 min later. After the addition, the mixture was heated at reflux for another 30 min. The reaction mixture was cooled then the product was distilled at 25 Pa, 60-100° C. to afford the title compound as a colourless oil (17.0 g, 59%).

¹HNMR (CDCl₃): 3.59 (q, 2H), 7.13 (t, 1H), 7.25 (t, 1H), 7.33 (d, 1H), 7.57 (d, 1H).

Preparation 58

4,4,5,5-Tetramethyl-2-[2-(2,2,2-trifluoroethyl)-phenyl]-[1,3,2]dioxaborolane

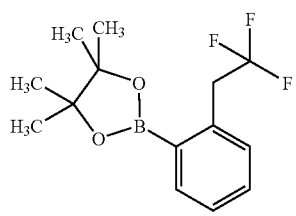

The mixture of compound 1-bromo-2-(2,2,2-trifluoroethyl)-benzene (Preparation 57, 15.0 g, crude, about 27.6 mmol), bis(pinacolato)diboron (10.5 g, 41.4 mmol), potassium acetate (8.1 g, 82.8 mmol) and 1,1'-[bis(diphenylphosphino)-ferrocene]dichloropalladium (II) (0.5 g, 0.68 mmol) in 1,4-dioxane (200 ml) was degassed for three times and heated at 80-90° C. for 14 hours. The reaction mixture was cooled then the solvent was removed in vacuo. The crude product was purified by column chromatography on silica gel eluting with petroleum ether to afford the title compound as a pale yellow oil (5.3 g, 67%).

MS m/z 304.1 [M+NH4]⁺

¹HNMR (CDCl₃): 1.37 (s, 12H), 3.86 (q, 2H), 7.33-7.37 (m, 2H), 7.43 (t, 1H), 7.88 (d, 1H).

Preparation 59

2-Bromo-4-methoxy-1-trifluoromethoxy-benzene

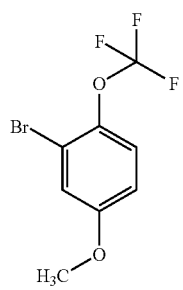

To a stirred suspension of 3-Bromo-4-trifluoromethoxy-phenol (20.0 g, 82.6 mol) and potassium carbonate (46.3 g, 330.4 mmol) in acetone (600 ml) was added drop-wise iodomethane (46.9 g, 330.4 mmol) under an atmosphere of nitrogen. The resulting mixture was stirred at reflux for 2 hours. The reaction mixture was cooled to room temperature then filtered and the filtrate was evaporated in vacuo to afford the title compound as a colourless oil (19.8 g, 93%).

¹HNMR (CDCl₃): 3.73 (s, 3H), 6.78 (dd, 1H), 7.08 (d, 1H), 7.18 (dd, 1H).

Preparation 60

5-methoxy-2-(trifluoromethoxy)-phenyl boronic acid

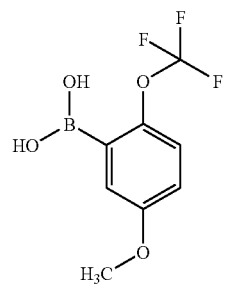

To a stirred solution of 2-Bromo-4-methoxy-1-trifluoromethoxy-benzene (Preparation 59, 19.0 g, 73.9 mmol) in anhydrous tetrahydrofuran (400 ml) was added n-butyl lithium (2.5M solution in hexanes, 44.2 ml, 110.9 mmol) while maintaining the temperature below −70° C. under an atmosphere of nitrogen. The resulting solution was stirred at −70° C. for 1 hour. Tri-isopropyl borate (20.9 g, 110.9 mmol) was added and the mixture stirred at −70° C. for an additional 2 hours. The reaction mixture was quenched with saturated ammonium chloride aqueous solution (400 ml). The resulting mixture was acidified to pH~5 by addition of hydrochloric acid (1N aqueous solution). The layers were separated and the organic layer was washed with water (200 ml) then dried over anhydrous MgSO₄ (s), filtered and evaporated in vacuo. Residue was purified by recrystallization from ethyl acetate:petroleum ether (2 ml:50 ml) to afford the title compound as a white solid (7.5 g, 43%).

¹HNMR (d₆-DMSO): 3.76 (s, 3H), 6.99 (dd, 1H), 7.06 (d, 1H), 7.18 (dd, 1H), 8.36 (s, 2H).

Preparation 61

N-(6-amino-5-iodopyridine-2-yl)-1-isopropyl-1H-pyrazole-5-carboxamide

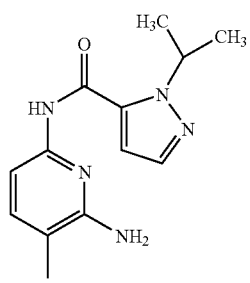

Method A using 3-Iodo-pyridine-2,6-diamine (Preparation 44), 1.6 equivalents of lutidine and 1.5 equivalents of acid chloride prepared from 2-isopropyl-2H-pyrazole-3-carboxylic acid. Purified by trituration with methanol:ethylacetate 1:2 to afford the title compound as a colourless oil (608 mg, 38%).

LCMS Rt=3.10 min, MS m/z 372 [MH]+

$^1$HNMR (CDCl$_3$): 1.50 (d, 6H), 4.80 (br s, 2H), 5.45-5.52 (m, 1H), 6.62 (s, 1H), 7.39 (d, 1H), 7.52 (d, 1H), 7.84 (d, 1H), 8.00 (br s, 1H).

Preparation 62

2-Bromo-4-fluoro-1-(2-methoxyethoxy)-benzene

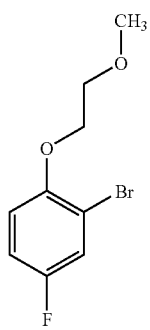

To a solution of 2-bromo-4-fluorophenol (1.2 g, 6.28 mmol) in acetonitrile (10 ml) was added potassium carbonate (2.78 g, 20 mmol) and 2-bromoethyl methyl ether (0.85 ml, 9.5 mmol). The resultant solution was heated to reflux for 16 hours. The reaction mixture was cooled then concentrated in vacuo. tert-Butyl-dimethyl ether (20 ml) and sodium hydroxide (1M aqueous solution) (10 ml) were added and the layers were separated. The organic layer was washed with saturated brine solution (10 ml) then dried over anhydrous Na$_2$SO$_4$ (s), filtered and evaporated in vacuo. Purification by column chromatography on silica gel eluting with heptane to heptane:ethyl acetate (9:1) afforded the title compound as a colourless oil (1.03 g, 66%).

$^1$HNMR (CDCl$_3$): 3.46 (s, 3H), 3.76 (t, 2H), 4.12 (t, 2H), 6.87 (dd, 1H), 6.92-6.97 (m, 1H), 7.27 (dd, 1H).

Preparation 63

2-[5-Fluoro-2-(2-methoxyethoxy)-phenyl]-4,4,5,5-tetramethyl-[1,3,2]-dioxaborolane

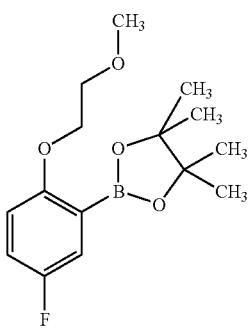

The mixture of 2-bromo-4-fluoro-1-(2-methoxyethoxy)-benzene (Preparation 62, 1.0 g, 4.01 mmol), bis(pinacolato)diboron (1.27 g, 5.02 mmol), potassium acetate (1.58 g, 16.1 mmol) and 1,1'-[bis(diphenylphosphino)-ferrocene]dichloropalladium (II) (0.29 g, 0.39 mmol) in N,N-dimethylformamide (10 ml) was degassed three times and heated at 100° C. for 14 hours. The reaction mixture was cooled then the solvent was removed in vacuo. The crude product was diluted with tert-butyl-dimethyl ether (30 ml) and filtered through Arbocel™. The filtrate was washed with water (10 ml) then saturated brine solution (10 ml) before drying over anhydrous Na$_2$SO$_4$ (s). The solution was filtered then evaporated in vacuo to give crude title compound as a dark brown oil. This was dissolved in tert-butyl-dimethyl ether:heptane (10 ml:10 ml) and was washed with sodium bicarbonate (aqueous solution) to remove residual N,N-dimethylformamide traces. This afforded the title compound as a brown oil (975 mg, 82%). Material was taken on with no further purification.

MS m/z 297 [MH]+

$^1$HNMR (CDCl$_3$): 1.31 (s, 12H), 3.44 (s, 3H), 3.74 (t, 2H), 4.05 (t, 2H), 6.78 (dd, 1H), 6.98-7.03 (m, 1H), 7.28 (dd, 1H).

Preparation 64

2-Bromo-1-(2-methoxyethoxy)-benzene

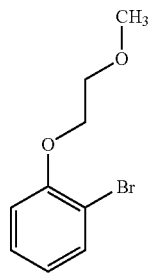

2-Bromophenol (4.03 g, 23.0 mmol) in acetonitrile (20 ml) was treated as for preparation 62 to afford crude title compound as a brown oil (2.8 g, 62%).

$^1$HNMR (CDCl$_3$): 3.47 (s, 3H), 3.78 (t, 2H), 4.14 (t, 2H), 6.82 (dt, 1H), 6.90 (dd, 1H), 7.23 (dt, 1H), 7.51 (dd, 1H).

Preparation 65

2-[2-(2-methoxyethoxy)-phenyl]-4,4,5,5-tetramethyl-[1,3,2]-dioxaborolane

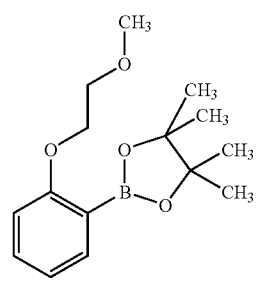

2-Bromo-1-(2-methoxyethoxy)-benzene (Preparation 64, 1.7 g, 7.36 mmol) was treated as for preparation 63 to afford the title compound as a brown oil (1.50 g, 73%). Material was taken on with no further purification.

$^1$HNMR (CDCl$_3$): 1.32 (s, 12H), 3.47 (s, 3H), 3.75 (t, 2H), 4.10 (t, 2H), 6.84 (dd, 1H), 6.93 (dt, 1H), 7.34 (dt, 1H), 7.63 (dd, 1H).

Preparation 66

2-[2-chloro-5-hydroxyphenyl]-4,4,5,5-tetramethyl-[1,3,2]-dioxaborolane

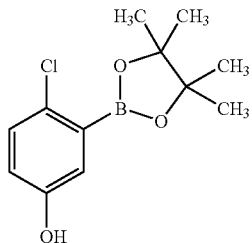

2-Chloro-5-hydroxyphenyl boronic acid (2.00 g, 11.6 mmol) and 2,3-Butanediol, 2,3-dimethyl-, hexahydrate (1.65 g, 13.9 mmol) were stirred together in tetrahydrofuran (110 ml) at room temperature for 15 hours. The solvent was removed in vacuo, and dichloromethane (20 ml) was added. This solution was washed with water (3×20 ml). The organic extract was evaporated in vacuo to afford the crude title compound as a colourless oil (2.7 g, 91%). Material was taken on without further purification.

$^1$HNMR (CDCl$_3$): 1.34 (s, 12H), 4.62 (s, 1H), 6.80 (dd, 1H), 7.11 (d, 1H), 7.19 (d, 1H).

Preparation 67

2-[2-chloro-5-(2-methoxyethoxy)-phenyl]-4,4,5,5-tetramethyl-[1,3,2]-dioxaborolane

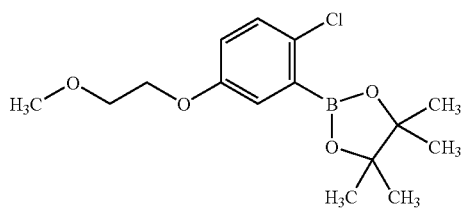

Methanesulfonic acid 2-methoxyethyl ester (70.5 mg, 0.50 mmol) and 2-[2-chloro-5-hydroxyphenyl]-4,4,5,5-tetramethyl-[1,3,2]-dioxaborolane (Preparation 66, 100 mg, 0.42 mmol) were stirred together in N,N-dimethylacetamide (4 ml). Potassium carbonate (58 mg, 0.42 mmol) was added and the resultant solution was heated to 100° C. for 10 hours. The reaction mixture was cooled then quenched with water (10 ml) and extracted with ethylacetate (10 ml). The organic layer was dried over anhydrous MgSO$_4$ (s), filtered and evaporated in vacuo to give crude title compound. Material taken on without further purification.

Preparation 68

2-Bromo-4-fluoro-1-(2-methoxypropoxy)-benzene

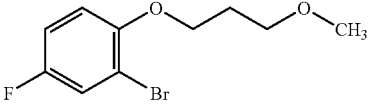

2-Bromo-4-fluorophenol (950 mg, 4.97 mmol) and 1-bromo-3-methoxypropane (1000 mg, 6.53 mmol) in acetonitrile (10 ml) was treated as for preparation 62 to afford crude title compound as a yellow oil (1.16 g, 88%).

$^1$HNMR (d$_6$-DMSO): 1.90-1.98 (m, 2H) 3.23 (s, 3H), 3.48 (t, 2H), 4.06 (t, 2H), 7.11 (dd, 1H), 7.19 (dd, 1H), 7.52 (dd, 1H).

Preparation 69

2-[4-Fluoro-2-(3-methoxypropoxy)-phenyl]-4,4,5,5-tetramethyl-[1,3,2]-dioxaborolane

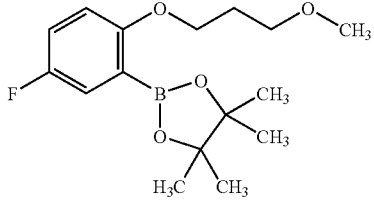

2-Bromo-4-fluoro-1-(2-methoxypropoxy)-benzene (Preparation 68, 1.15 g, 4.37 mmol) was treated as for preparation 63 to afford the title compound as a dark green oil (1.55 g, >100%). Material was taken on with no further purification.

$^1$HNMR (d$_6$-DMSO): 1.26 (s, 12H), 1.86-1.92 (m, 2H), 3.22 (s, 3H), 3.54 (t, 2H), 3.93 (t, 2H), 6.94 (dd, 1H), 7.13-7.22 (m, 2H).

Preparation 70

3-[5-Fluoro-2-(3-methoxypropoxy)-phenyl]-pyridine-2,6-diamine

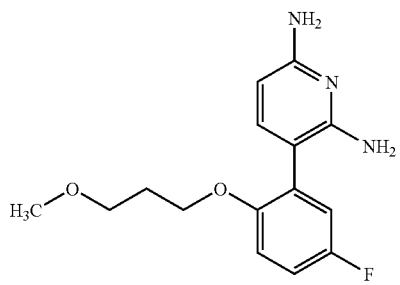

2-[4-Fluoro-2-(3-methoxypropoxy)-phenyl]-4,4,5,5-tetramethyl-[1,3,2]-dioxaborolane (Preparation 69, 581 mg, 1.87 mmol) was treated as for preparation 51 to afford the title compound as a brown oil (142 mg, 57%).

LCMS (2 min) Rt=0.92 min, MS m/z 292 [MH]+

$^1$HNMR (CDCl$_3$): 1.89-1.95 (m, 2H), 3.28 (s, 3H), 3.41 (t, 2H), 3.99 (t, 2H), 4.25 (br s, 2H), 4.36 (br s, 2H), 5.98 (d, 1H), 6.89-6.98 (m, 3H), 7.16 (d, 1H).

Preparation 71

2-Bromo-1-(2-methoxypropoxy)-benzene

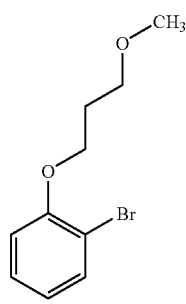

2-Bromophenol (861 mg, 4.97 mmol) and 1-bromo-3-methoxypropane (1000 mg, 6.53 mmol) in acetonitrile (10 ml) was treated as for preparation 62 to afford crude title compound as a colourless liquid (1.23 g, 101%).

$^1$HNMR (d$_6$-DMSO): 1.90-1.98 (m, 2H) 3.23 (s, 3H), 3.48 (t, 2H), 4.07 (t, 2H), 6.86 (dt, 1H), 7.09 (dd, 1H), 7.31 (dt, 1H), 7.55 (dd, 1H).

Preparation 72

2-[2-(3-methoxypropoxy)-phenyl]-4,4,5,5-tetramethyl-[1,3,2]-dioxaborolane

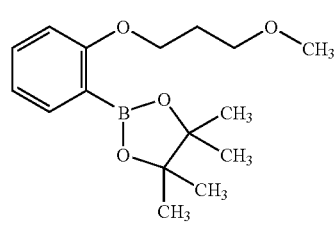

2-Bromo-1-(2-methoxypropoxy)-benzene (Preparation 71, 1.11 g, 4.53 mmol) was treated as for preparation 63 to afford the title compound as a dark green oil (1.42 g, >100%). Material was taken on with no further purification.

$^1$HNMR (d$_6$-DMSO): 1.26 (s, 12H), 1.86-1.92 (m, 2H), 3.23 (s, 3H), 3.56 (t, 2H), 3.95 (t, 2H), 6.86-6.92 (m, 2H), 7.35-7.40 (m, 1H).

Preparation 73

3-[2-(3-methoxypropoxy)-phenyl]-pyridine-2,6-diamine

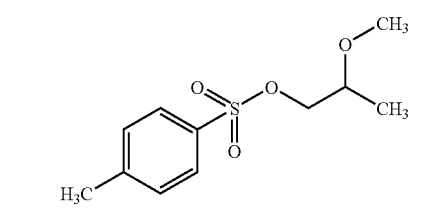

2-[2-(3-methoxypropoxy)-phenyl]-4,4,5,5-tetramethyl-[1,3,2]-dioxaborolane (Preparation 72, 684 mg, 2.34 mmol) was treated as for preparation 51 to afford the title compound as a brown solid (217 mg, 75%).

LCMS (2 min) Rt=0.90 min, MS m/z 274 [MH]+

$^1$HNMR (d$_6$-DMSO): 1.80-1.87 (m, 2H), 3.18 (s, 3H), 3.36 (t, 2H), 3.98 (t, 2H), 4.72 (s, 2H), 5.40 (s, 2H), 5.78 (d, 1H), 6.92-6.96 (m, 2H), 7.01-7.03 (m, 1H), 7.10 (dd, 1H), 7.21-7.25 (m, 1H).

Preparation 74

Toluene-4-sulfonic acid-2-methoxypropyl ether

To a stirred solution of 2-methoxy-propan-1-ol (1.70 g, 18.86 mmol) in dichloromethane (20 ml) was added 2,6-lutidine (4.38 ml, 37.9 mmol) followed by para-toluene-sulphonyl chloride (4320 mg, 22.6 mmol) portion-wise. The reaction mixture was stirred at room temperature for 72 hours. Solvents were evaporated in vacuo, then ethyl acetate (100 ml) and saturated citric acid (aqueous) (100 ml) were added. The layers were separated and the organic extract was washed with further saturated citric acid (aqueous) (2×40 ml). The organic extract was then washed with saturated sodium bicarbonate (aqueous solution) (50 ml) then dried over anhydrous MgSO4 (s), filtered and evaporated in vacuo to afford crude title compound (4.51 g, 56%). Material was taken on without further purification.

¹H-NMR (CDCl₃): 1.08 (d, 3H), 2.42 (d, 3H), 3.26 (s, 3H), 3.94 (s, 2H), 7.32 (d, 2H), 7.77 (d, 2H).

Preparation 75

2-Bromo-4-fluoro-1-(2-methoxypropoxy)-benzene

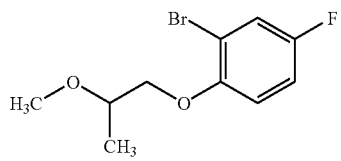

To a solution of 2-bromo-4-fluorophenol (790 mg, 4.14 mmol) in acetonitrile (12 ml) was added potassium carbonate (1.43 g, 10.3 mmol) and toluene-4-sulfonic acid-2-methoxypropyl ether (Preparation 74, 2.32 g, 5.0 mmol) in acetonitrile (6 ml). The resultant solution was heated to reflux for 16 hours. The reaction mixture was cooled then concentrated in vacuo. tert-Butyl-dimethyl ether (100 ml) and saturated sodium hydrogencarbonate (aqueous solution) (100 ml) were added and the layers were separated. The organic layer was washed with further saturated sodium hydrogencarbonate (aqueous solution) (50 ml) then water (20 ml). The organic layer was then dried over anhydrous MgSO₄ (s), filtered and evaporated in vacuo. Purification by column chromatography on silica gel eluting with heptane:toluene (9:1) to toluene (100%). Like fractions were evaporated in vacuo then azeotroped with ethyl acetate to afford the title compound as a colourless oil (475 mg, 31%).

¹HNMR (d₆-DMSO): 1.15 (d, 3H), 3.30 (s, 3H), 3.62-3.70 (m, 1H), 3.95 (d, 2H), 7.18-7.23 (m, 2H), 7.55 (dd, 1H).

Preparation 76

2-[5-Fluoro-2-(2-methoxypropoxy)-phenyl]-4,4,5,5-tetramethyl-[1,3,2]-dioxaborolane

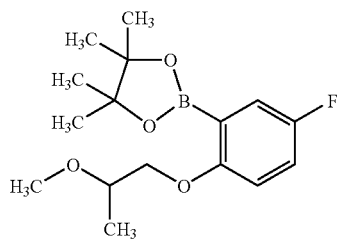

The mixture of 2-bromo-4-fluoro-1-(2-methoxypropoxy)-benzene (Preparation 75, 475 mg, 1.30 mmol), bis(pinacolato)diboron (420 mg, 1.66 mmol), potassium acetate (500 mg, 5.16 mmol) and 1,1'-[bis(diphenylphosphino)-ferrocene] dichloropalladium (II) (95 mg, 0.13 mmol) in N,N-dimethylformamide (4 ml) was degassed three times and heated at 100° C. for 8 hours. The reaction mixture was cooled then the solvent was removed in vacuo. The crude product was diluted with tert-butyl-dimethyl ether (60 ml) and saturated brine solution (30 ml) then filtered through Arbocel™. The organic layer washed with water (10 ml) then saturated brine solution (10 ml) before drying over anhydrous MgSO₄ (s). The solution was filtered then evaporated in vacuo to afford crude title compound as a dark brown oil (577 mg, >100%). Material was taken on with no further purification.

¹HNMR (d₆-DMSO): 1.20 (d, 3H), 1.30 (s, 12H), 3.30 (s, 3H), 3.58-3.63 (m, 1H), 3.80-3.85 (m, 2H), 6.90 (d, 1H), 7.15-7.22 (m, 1H).

Preparation 77

2-Bromo-1-(2-methoxypropoxy)-benzene

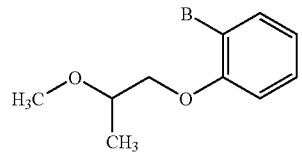

A solution of 2-bromophenol (790 mg, 4.14 mmol) in acetonitrile (6 ml) was treated as for preparation 75 to afford the title compound as a colourless oil (580 mg, 56%).

¹HNMR (d₆-DMSO): 1.20 (d, 3H), 3.35 (s, 3H), 3.62-3.70 (m, 1H), 4.00 (d, 2H), 6.90 (dt, 1H), 7.10 (dd, 1H), 7.30 (dt, 1H), 7.55 (dd, 1H).

Preparation 78

2-[2-(2-methoxypropoxy)-phenyl]-4,4,5,5-tetramethyl-[1,3,2]-dioxaborolane

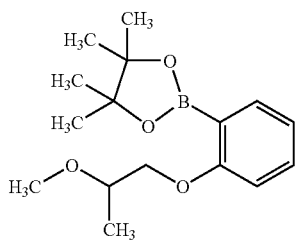

2-Bromo-1-(2-methoxypropoxy)-benzene (Preparation 77, 580 mg, 2.31 mmol) was treated as for preparation 76 to afford crude title compound as a dark brown oil (1.02 g, >100%). Material was taken on with no further purification.

¹HNMR (d₆-DMSO): 1.10 (d, 3H), 1.25 (s, 12H), 3.35 (s, 3H), 3.58-3.63 (m, 1H), 3.80-3.95 (m, 2H), 6.86-6.92 (m, 2H), 7.40 (t, 1H), 7.45 (d, 1H).

Preparation 79

2-Bromo-4-chloro-1-(2,2,2-trifluoroethoxy)-benzene

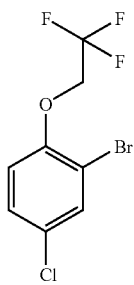

To a stirred solution of 2-bromo-4-chlorophenol (3.38 g, 16.3 mmol) in anhydrous 1-methyl-2-pyrrolidinone (25 ml) under an atmosphere of nitrogen, was added cesium carbonate (8.0 g, 24.4 mmol). The mixture was cooled to 0° C. before addition of 2,2,2-trifluoroethyl trifluoromethanesulfonate (3.78 g, 16.3 mmol) drop-wise over 2 minutes. The reaction was allowed to warm to room temperature and stirred for 14 hours. To encourage complete reaction the reaction mixture was warmed to 120° C. for 3 hours. The reaction mixture was cooled to room temperature then water (50 ml) was added. The layers were separated and the aqueous was extracted with heptane (3×50 ml). All organic extracts were combined then dried over anhydrous $Na_2SO_4$ (s), filtered and evaporated in vacuo to afford crude title compound as a yellow oil (4.20 g, 89%). Material was taken on without further purification.

$^1$HNMR ($CDCl_3$): 4.39 (q, 2H), 6.86 (dd, 1H), 7.25 (dd, 1H), 7.59 (s, 1H).

Preparation 80

2-[5-Chloro-2-(2,2,2-trifluoroethoxy)-phenyl]-4,4,5,5-tetramethyl-[1,3,2]-dioxaborolane

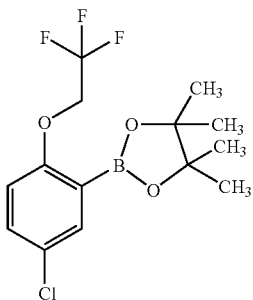

To a solution of the 2-bromo-4-chloro-1-(2,2,2-trifluoroethoxy)-benzene (Preparation 79, 0.110 g, 0.38 mmol), potassium acetate (0.336 g, 3.42 mmol) and Bis(pinacolato)diboron (0.290 g, 1.14 mmol) in degassed dimethoxyethane (4.5 ml) was added 1,1'-[bis(diphenylphosphino)-ferrocene]dichloropalladium (II) (0.009 g, 0.011 mmol). The reaction mixture was sealed into a 5 ml microwave vial before being irradiated in a microwave at 120° C. for 20 minutes with stirring. The tube was then allowed to cool to room temperature before the mixture was removed from the vessel and filtered through a pad of Arbocel™. This was then washed with dichloromethane (50 ml) before the collected solvent washings were concentrated in vacuo to afford crude title compound as a brown oil (128 mg, 100%). Material was taken on with no further purification.

Preparation 81

2-Bromo-4-fluoro-1-(2,2,2-trifluoroethoxy)-benzene

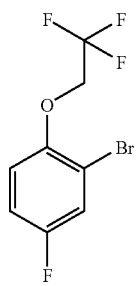

A solution of 2-bromo-4-fluorophenol (3.74 g, 19.6 mmol) in anhydrous 1-methyl-2-pyrrolidinone (25 ml) was treated as for preparation 79 to afford crude title compound as a yellow oil (4.60 g, 86%). Material was taken on without further purification.

$^1$HNMR ($CDCl_3$): 4.38 (q, 2H), 6.85-7.05 (m, 2H), 7.37 (d, 1H).

Preparation 82

2-[5-Fluoro-2-(2,2,2-trifluoroethoxy)-phenyl]-4,4,5,5-tetramethyl-[1,3,2]-dioxaborolane

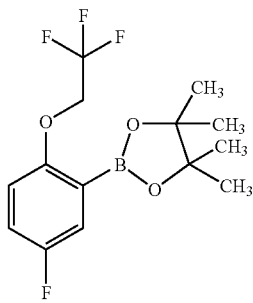

A solution of 2-bromo-4-fluoro-1-(2,2,2-trifluoroethoxy)-benzene (Preparation 81, 0.150 g, 0.52 mmol) was treated as for preparation 80 to afford crude title compound as a brown oil (145 mg, 100%). Material was taken on with no further purification.

Preparation 83

3-(2-Bromo-4-fluorophenoxy)-tetrahydrofuran

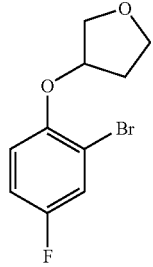

To a solution of 2-bromo-4-fluorophenol (500 mg, 2.62 mmol) in acetonitrile (5 ml) was added potassium carbonate (1090 mg, 7.85 mmol) followed by 3-bromotetrahydrofuran (1000 mg, 6.62 mmol) and the resulting solution was heated to 85° C. in a Reacti-vial™ for 72 hours. The reaction mixture was cooled then the solvents removed in vacuo. tert-Butyl-dimethyl ether (20 ml) and sodium hydroxide (10% aqueous solution) (10 ml) were added and the layers were separated. The organic layer was washed with further sodium hydroxide (10% aqueous solution) (10 ml) then saturated brine solution (10 ml). The organic layer was then dried over anhydrous $MgSO_4$ (s), filtered and evaporated in vacuo to afford crude title compound as a yellow oil (983 mg, >100%). Material was taken on without further purification.

$^1$HNMR ($d_6$-DMSO): 1.83-2.22 (m, 2H), 3.82-3.89 (m, 4H), 5.03-5.12 (m, 1H), 7.11-7.15 (m, 1H), 7.18-7.23 (m, 1H), 7.53-7.55 (dd, 1H).

Preparation 84

2-[5-Fluoro-2-(tetrahydrofuran-3-yloxy)-phenyl]-4,4,5,5-tetramethyl-[1,3,2]-dioxaborolane

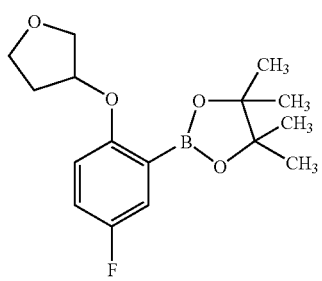

A solution of 3-(2-bromo-4-fluorophenoxy)-tetrahydrofuran (Preparation 83, 0.200 g, 0.77 mmol) was treated as for preparation 80 to afford crude title compound as a brown gum (191 mg, 81%). Material was taken on with no further purification.

$^1$HNMR ($d_6$-DMSO): 1.25 (s, 12H), 2.05-2.11 (m, 2H), 3.71-3.88 (m, 4H), 4.87-4.92 (m, 1H), 6.93-6.97 (m, 1H), 7.13-7.23 (m, 2H).

Preparation 85

2-Bromo-4-ethoxy-1-trifluoromethoxy-benzene

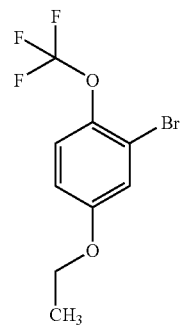

To a solution of the 3-bromo-4-trifluoromethoxyphenol (1.0 g, 2.48 mmol) in acetone (30 ml) was added ethyl iodide (0.795 ml, 9.94 mmol) followed by potassium carbonate (1.37 g, 9.94 mmol) and the reaction was heated to reflux for 12 hrs. The reaction mixture was cooled then filtered and concentrated in vacuo. Dichloromethane (20 ml) and water (20 ml) were added and the solution was filtered through a phase separation cartridge. The organic layer was collected, and evaporated in vacuo to afford crude title compound as a colourless oil (884 mg, 80%). Material was taken on without further purification.

LCMS (2 min) Rt=1.82 min, MS m/z 286 [MH]+

$^1$H-NMR ($d_6$-DMSO) 1H, 1.25 (t, 3H), 4.05 (q, 2H), 7.00 (dd, 1H), 7.35 (d, 1H), 7.40 (dd, 1H).

Preparation 86

[5-ethoxy-2-(trifluoromethoxy)phenyl]boronic acid

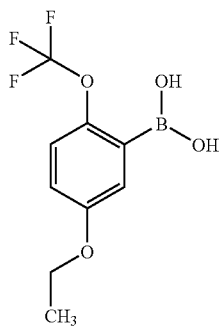

To a stirred solution of the 2-bromo-4-ethoxy-1-trifluoromethoxy-benzene (Preparation 85, 884 mg, 3.10 mmol) in anhydrous tetrahydrofuran (10 ml) was added n butyl lithium (2M solution in cyclohexanes, 2.33 ml, 4.65 mmol) while maintaining the temperature below −70° C. under an atmosphere of nitrogen. The solution was stirred at this temperature for 1 hour then tri-isopropylborate (875 mg, 4.65 mmol) was added, and the reaction maintained at −70° C. for a further 2 hours. The reaction mixture was then quenched by Preparation 87

2-Bromo-1-(2-chloroethoxy)-4-fluorobenzene

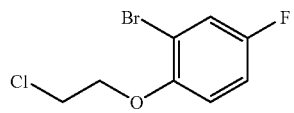

To a solution of toluene-4-sulfonic acid 2-chloroethyl ester (2.80 g, 11.93 mmol) in anhydrous N,N-dimethylformamide (10 ml) was added 2-bromo-4-fluorophenol (2.73 g, 14.30 mmol), and potassium carbonate (3.30 g, 23.90 mmol). The resulting solution was then heated at 50° C. with stirring for 6 hours. After cooling to room temperature, the reaction mixture was diluted with sodium hydroxide (1M aqueous solution, 30 ml) and tert-butyldimethyl ether (50 ml) was added. The layers were separated and the organic extract was washed with saturated brine solution (30 ml), prior to being dried over anhydrous MgSO$_4$ (s), filtered and evaporated in vacuo. Purification by column chromatography eluting with ethyl acetate:heptane 1:99 to 10:90 afforded the title compound as a colourless oil (1.50 g, 50%).

$^1$HNMR (CDCl$_3$): 3.82-3.85 (t, 2H), 4.23-4.26 (t, 2H), 6.87-6.92 (m, 1H), 6.69-7.02 (m, 1H), 7.31 (dd, 1H).

Preparation 88

2-Bromo-4-fluoro-1-vinyloxy-benzene

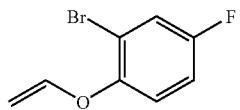

To an ice cooled solution of the 2-bromo-1-(2-chloroethoxy)-4-fluorobenzene (Preparation 87, 1.2 g, 4.73 mmol) in anhydrous tetrahydrofuran (15 ml) under nitrogen was added solid potassium tert-butoxide (1.06 g, 9.47 mmol) portionwise over 5 minutes. The resultant solution was allowed to attain room temperature then stirring was continued for 72 hours. The reaction mixture was evaporated in vacuo. tert-Butyldimethyl ether (25 ml) and water (25 ml) were added and the layers were separated. The organic extract was washed with saturated brine solution (20 ml) then dried over anhydrous MgSO$_4$ (s), filtered and evaporated in vacuo to afford the crude title compound as a yellow oil (745 mg, 73%). Material was taken on without further purification.

MS m/z 233 [M+NH$_4$]
$^1$HNMR (CDCl$_3$): 4.42 (d, 1H), 4.62 (d, 1H), 6.55 (dd, 1H), 6.69-7.02 (m, 2H), 7.30 (dd, 1H).

Preparation 89

2-Bromo-1-cyclopropoxy-4-fluoro-benzene

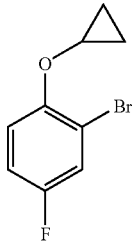

Diethyl zinc (1M in toluene, 23 ml, 23 mmol) was added under nitrogen with stirring to a solution of 2-bromo-4-fluoro-1-vinyloxy-benzene (Preparation 88, 1.0 g, 4.61 mmol) in dichloroethane (45 ml) at −10° C. (ice-salt-MeOH), taking care to maintain the temperature below 0° C. Diiodomethane (6.17 g, 23 mmol) in dichloroethane (10 ml) was then added via a syringe to the reaction mixture over 5 minutes ensuring that the reaction mixture remained at a temperature below +5° C. (internal temp). The reaction mixture was stirred at this temperature for twenty minutes and then allowed to attain room temperature and stirring was continued for 72 hours. The reaction was quenched with cold saturated ammonium chloride (aqueous solution) (5 ml) then the lower organic phase was removed, whilst the aqueous was extracted with a further dichloromethane (20 ml). The combined organic layers were dried over anhydrous Na$_2$SO$_4$ (s), filtered and evaporated in vacuo. Purification by column chromatography on silica gel eluting with tert-butyldimethyl ether:heptane 1:99 to 1:19 afforded almost pure title compound (93 mg, 9%).

$^1$HNMR (CDCl$_3$): 0.77-0.85 (m, 4H), 3.72-3.79 (m, 1H), 6.95-7.00 (m, 1H), 7.18 (dd, 2H), 7.25 (dd, 1H).

Preparation 90

2-(2-Cyclopropoxy-5-fluorophenyl)-4,4,5,5-tetramethyl-[1,3,2]-dioxaborolane

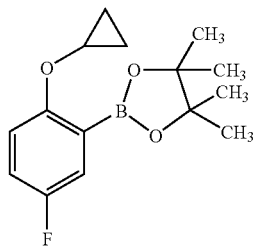

A solution of 2-bromo-1-cyclopropoxy-4-fluoro-benzene (Preparation 89, 0.100 g, 0.43 mmol) was treated as for preparation 80 to afford crude title compound as a brown oil (120 mg, 100%). Material was taken on with no further purification.

The ability of the pyridine derivatives of the formula (I) to inhibit the Na$_{V1.8}$ channel may be measured using the assay described below.

VIPR Assay for Nav1.8 Compounds

This screen is used to determine the effects of compounds on tetrodotoxin-resistant (TTX-R) sodium channels in Human Nav1.8 (HEK293) expressing cell line, utilising the technology of Aurora's fluorescent Voltage/Ion Probe Reader (VIPR). This experiment is based on FRET (Fluorescence Resonance Energy Transfer) and uses two fluorescent molecules. The first molecule, Oxonol (DiSBAC$_2$(3)), is a highly fluorescent, negatively charged, hydrophobic ion that "senses" the trans-membrane electrical potential. In response to changes in membrane potential, it can rapidly redistribute between two binding sites on opposite sides of the plasma membrane. The voltage dependent redistribution is transduced into a ratiometric fluorescent readout via a second fluorescent molecule (Coumarin (CC2-DMPE)) that binds specifically to one face of the plasma membrane and functions as a FRET partner to the mobile voltage-sensing ion. To enable the assay to work, the channels have to be pharmacologically held in the open state. This is achieved by treating the cells with either deltamethrin (for $Na_{V1.8}$) or veratridine (for the SHSY-5Y assay for TTX-S channels).

Cell Maintenance:

Human Nav1.8 cells are grown in T225 flasks, in a 5% CO2 humidified incubator to about 70% confluence. Media composition consists of DMEM/F-12, 10% FCS and 300 μg/ml Geneticine. They are split using cell dissociation fluid 1:5 to 1:20, depending on scheduling needs, and grown for 3-4 days before the next split.

Protocol:

Day One:

Plate-out HEK-Nav1.8 cells (100 μl per well) into poly-D-lysine coated plates prior to experimentation as follows:—24 hours @3.5×10$^4$ cells/well (3.5×10$^5$ cells/ml) or using the technology of Select.

Day Two: VIPR Assay:

1. Equilibrate buffers at room temperature for 2 hours or at 37° C. for 30 minutes prior to experimentation.
2. Prepare Coumarin dye (see below) and store in dark. Prime the plate washer with Na+ Free buffer and wash cells twice, Note: Plate washer deposits ~30 μl residual buffer per well. Add 100 μL Coumarin (CC2-DMPE) solution (see below) to cells and incubate for 45 minutes at room temperature avoiding bright light.
3. Prepare Oxonol (DiSBAC$_2$(3)) dye (see below):
4. Aspirate off Coumarin solution from the cells by washing in Na+ Free buffer.
5. Add 30 μl compound then add 30 μl Oxonol solution to the cells and incubate for 45 minutes at room temperature in the dark (total well volume ~90 μl).
6. Once the incubation is complete, the cells are ready to be assayed using the VIPR for sodium addback membrane potential.

The data was analyzed and reported as normalised ratios of intensities measured in the 460 nm and 580 nm channels. The process of calculating these ratios was performed as follows. An additional plate contained control solution with the same DisBAC2(3) concentrations as used in the cell plates, however no cells were included in the background plate. Intensity values at each wavelength were averaged for sample points 5-7 (initial) and 44-49 (final). These averages were subtracted from intensity values averaged over the same time periods in all assay wells. The initial ratio obtained from samples 3-8 (Ri) and the final ratio obtained from samples 45-50 (Rf) are defined as:

Ri=(Intensity 460 nm, samples 3-5–background 460 nm, samples 3-5)
(Intensity 580 nm, samples 3-5–background 580 nm, samples 3-5)
Rf=(Intensity 460 nm, samples 25-30–background 460 nm, samples 25-30)
(Intensity 580 nm, samples 25-30–background 580 nm, samples 25-30)

Final data are normalised to the starting ratio of each well and reported as Rf/Ri. This analysis is performed using a computerised specific programme designed for VIPR generated data.

Rf/Ri ratio values are plotted using Excel Labstats (curve fit) or analysed via ECADA to determine an IC50 value for each compound.

| Na+-Addback Buffer pH 7.4 (adjust with 5M NaOH) - 10X stock | | | | |
|---|---|---|---|---|
| Component: | Mwt/Conc$^n$: | weight/volume | 10X Conc. (mM) | 1X Conc: (mM): |
| NaCl | 58.44 | 93.5 g | 1600 | 160 |
| KCL | 74.55 | 3.35 g | 45.0 | 4.5 |
| CaCl$_2$ | 1M solution | 20 ml | 20.0 | 2 |
| MgCl$_2$ | 203.31 | 2.03 g | 10.0 | 1 |
| Hepes | 238.3 | 23.83 g | 100 | 10 |
| dH$_2$O | 1 L | | | |

| Na+-Free Buffer pH 7.4 (adjust with 5M KOH) - 10X stock | | | | |
|---|---|---|---|---|
| Component: | Mwt/Conc$^n$: | weight/volume | 10X Conc. (mM) | 1X Conc (mM): |
| Choline chloride | 139.6 | 223.36 g | 1600 | 160 |
| CaCl$_2$ | 1M solution | 1 ml | 1.0 | 0.1 |
| MgCl$_2$ | 203.31 | 2.03 g | 10.0 | 1.0 |
| Hepes | 238.3 | 23.83 g | 100 | 10 |
| dH$_2$O | 1 L | | | |

1×Na+ Free Buffer: –400 ml 10×+3600 ml dH2O
2×Na+ Free Buffer: –100 ml 10×+400 ml dH2O
1×Na+ Addback Buffer: –50 ml 10× Na+ Addback+450 ml dH2O

| Coumarin (CC2-DMPE): For 2 plates:- First mix 220 μl Coumarin (1 mM) + 22 μl Pluronic (20%) in a tube + 22 ml 1X Na+-Free Buffer, gently vortex. | | |
|---|---|---|
| | Solution Conc$^n$: | Final Assay Conc$^n$ |
| Coumarin (1 mM) | 10 μM | 10 μM |

| Oxonol (DiSBAC$_2$(3)): For 2 plates:- 48 μl Oxonol (5 mM) + 120ul Tartrazine (200 mM) Vortex 8.0 ml 2× Na+-Free Buffer Vortex 1.6 μl Deltamethrin (5 mM) Vortex | | |
|---|---|---|
| | Solution Conc$^n$: | Final Assay Conc$^n$ |
| Oxonol (5 mM) | 30 μM | 10 μM |
| Deltamethrin (5 mM) | 1 μM | 330 nM |
| Tartrazine (200 mM) | 3 mM | 1.0 mM |

TTX-S Assay

The TTX-S assay is performed in the SHSY-5Y cell line which constitutively express a number of tetrodotoxin-sensitive voltage-gated sodium channels including $Na_{V1.2}$, $Na_{V1.3}$ and $Na_{V1.7}$. The procedure detailed above for the $Na_{V1.8}$ assay was followed with the exception that veratridine was substituted for deltamethrin in the assay as an opener of the sodium channels, at a final assay concentration of 50 μM.

$Nav_{1.5}$ Assay

The $Nav_{1.5}$ assay is performed in HEK293 cells expressing Human $Nav_{1.5}$ in the same way as the $Nav_{1.8}$ assay.

| Example No. | $Na_{v1.8}$ IC50 (μM) | $Na_{v1.5}$ IC50 (μM) | TTX-S IC50 (μM) |
|---|---|---|---|
| 1 | 5.8 | 24 | >32 |
| 2 | 1.7 | >32 | 30 |
| 3 | 0.90 | 15 | 11 |
| 4 | 0.68 | — | — |
| 5 | 0.90 | >32 | >32 |
| 6 | 1.1 | 13 | 23 |
| 7 | 0.63 | 6.3 | 9.2 |
| 8 | 1.6 | 20 | 7.6 |
| 9 | 4.2 | 27 | >32 |
| 10 | 25 | >32 | >32 |
| 11 | 2.4 | 18 | 11 |
| 12 | 3.0 | >32 | >32 |
| 13 | 8.8 | >32 | >32 |
| 14 | 8.4 | >32 | >32 |
| 15 | 10 | 13 | 21 |
| 16 | 1.9 | 11 | 9.6 |
| 17 | 3.4 | 19 | 7.7 |
| 18 | 1.6 | 8.5 | 1.8 |
| 19 | 14 | >32 | 25 |
| 20 | 1.0 | 17 | 14 |
| 21 | 23 | | 27 |
| 22 | 1.0 | 4.6 | — |
| 23 | 1.6 | 17 | 9.4 |
| 24 | 0.44 | 8.5 | 11 |
| 25 | 1.6 | | 10 |
| 26 | 0.56 | 11 | 8.5 |
| 27 | 0.37 | 10 | 3.2 |
| 28 | 0.67 | 9.5 | — |
| 29 | 0.55 | 6.4 | 8.2 |
| 30 | 1.3 | 16 | 28 |
| 31 | 3.9 | 30 | 20 |
| 32 | 0.64 | 7.8 | 2.6 |
| 33 | 6.5 | >32 | 23 |
| 34 | 3.1 | 16 | 19 |
| 35 | 11 | >32 | >32 |
| 36 | 1.3 | 6.4 | 2.2 |
| 37 | 0.44 | 3.6 | 1.2 |
| 38 | 2.6 | 25 | 26 |
| 39 | 0.93 | 21 | 13 |
| 40 | 20 | 31 | 30 |
| 41 | 0.25 | 12 | 11 |
| 42 | 2.5 | >32 | 22 |
| 43 | 0.32 | 12 | 10 |
| 44 | 3.2 | — | 8.1 |
| 45 | 2.6 | — | 13 |
| 46 | 1.2 | — | 30 |
| 47 | 1.4 | 7.4 | 6.1 |
| 48 | 0.76 | 22 | 3.3 |
| 49 | 6.1 | — | 12 |
| 50 | 3.1 | 19 | 9.8 |
| 51 | 2.6 | — | 4.5 |
| 52 | 0.95 | 16 | 6.4 |
| 53 | 2.3 | 22 | 15 |
| 54 | 1.2 | 20 | 18 |
| 55 | 23 | >32 | >32 |
| 56 | 2.4 | 17 | 8.1 |
| 57 | 3.7 | >32 | 21 |
| 58 | 9.3 | 31 | 17 |
| 59 | 3.6 | 31 | 17 |
| 60 | 4.3 | 20 | >32 |
| 61 | 1.3 | 9.7 | 9.7 |
| 62 | 5.1 | 17 | 11 |
| 63 | 4.3 | 16 | 4.4 |
| 64 | 5.0 | 14 | 3.7 |
| 65 | 5.3 | 12 | 3.2 |
| 66 | 2.4 | — | 11 |
| 67 | 5.0 | 31 | 22 |
| 68 | 3.9 | 17 | 5.0 |
| 69 | 16 | 16 | 3.6 |
| 70 | 11 | 28 | 14 |
| 71 | >32 | >32 | >32 |
| 72 | 8.6 | — | 15 |
| 73 | 4.7 | >32 | 18 |
| 74 | 4.2 | — | 30 |
| 75 | 1.4 | — | 24 |
| 76 | 0.86 | — | 6.5 |
| 77 | 5.0 | — | >32 |
| 78 | 1.4 | 14 | 8.3 |
| 79 | 5.8 | — | 22 |
| 80 | 3.4 | 15 | 15 |
| 81 | 1.1 | 2.9 | 7.5 |
| 82 | 9.3 | >32 | >32 |
| 83 | 3.3 | 4.1 | 12 |
| 84 | 2.4 | 5.3 | 6.5 |
| 85 | 7.0 | 31 | 28 |
| 86 | 5.3 | 7.5 | 19 |
| 87 | 6.1 | 9.9 | 15 |
| 88 | 1.5 | 9.8 | 7.3 |
| 89 | 4.4 | >32 | >32 |
| 90 | 0.55 | >32 | >32 |
| 91 | 2.6 | >32 | >32 |
| 92 | 0.57 | 19 | 17 |
| 93 | 1.5 | >32 | 7.1 |
| 94 | >32 | 31 | 19 |
| 95 | >32 | >32 | 29 |
| 96 | 5.9 | 7.1 | 12 |
| 97 | 1.9 | — | 5.4 |
| 98 | 2.0 | — | 10 |
| 99 | 3.2 | 15 | 6.6 |
| 100 | 6.3 | — | 4.4 |
| 101 | 3.7 | — | 6.2 |
| 102 | 2.3 | — | 5.4 |
| 103 | 4.1 | — | 8.4 |
| 104 | 3.3 | — | 8.0 |
| 105 | 3.5 | — | 7.7 |
| 106 | 5.3 | 16 | 8.1 |
| 107 | 2.5 | 2.5 | 3.1 |
| 108 | 26 | >32 | 27 |
| 109 | 5.7 | 27 | — |
| 110 | 1.5 | 2.3 | — |
| 111 | 0.51 | 16 | 6.1 |
| 112 | 0.94 | 7.7 | 4.5 |
| 113 | 3.8 | 14 | 8.7 |
| 114 | 0.31 | 4.1 | 4.0 |
| 115 | 0.28 | 7.9 | 5.3 |
| 116 | 2.3 | 28 | 26 |
| 117 | 2.3 | 21 | 12 |
| 118 | 13 | 16 | 13 |
| 119 | 2.0 | 31 | 26 |
| 120 | 12 | 10 | 5.2 |
| 121 | 10 | 8.6 | 3.2 |
| 122 | 19 | 14 | 12 |
| 123 | 2.4 | >32 | — |
| 124 | 11 | 12 | 8.6 |
| 125 | 25 | >32 | — |
| 126 | 5.9 | >32 | — |
| 127 | >32 | 10 | >32 |
| 128 | 15 | >32 | >32 |
| 129 | 3.5 | 20 | — |
| 130 | 2.3 | 22 | — |
| 131 | 0.64 | 18 | — |
| 132 | 1.5 | >32 | — |
| 133 | 2.9 | >32 | — |
| 134 | 0.41 | 18 | — |
| 135 | 0.28 | 26 | — |
| 136 | 0.60 | 27 | — |
| 137 | 1.2 | 18 | — |

-continued

| Example No. | Na$_{v1.8}$ IC50 (μM) | Na$_{v1.5}$ IC50 (μM) | TTX-S IC50 (μM) |
|---|---|---|---|
| 138 | 1.0 | 23 | — |
| 139 | 2.1 | 7.5 | — |
| 140 | 0.43 | 18 | — |
| 141 | 5.4 | >32 | — |
| 142 | 0.96 | 17 | — |
| 143 | 0.97 | 24 | — |
| 144 | 0.53 | 23 | — |
| 145 | 1.5 | 28 | — |
| 146 | — | 13 | — |
| 147 | 12 | >32 | — |
| 148 | 0.56 | 10 | — |
| 149 | 4.0 | >32 | — |
| 150 | 2.5 | 19 | — |
| 151 | 5.1 | >32 | — |
| 152 | 1.9 | 31 | — |
| 153 | 8.8 | >32 | — |
| 154 | 0.47 | 10 | — |
| 155 | 18 | >32 | — |
| 156 | 3.1 | 31 | — |
| 157 | 9.5 | >32 | — |
| 158 | 15 | >32 | — |
| 159 | 4.7 | >32 | — |
| 160 | 13 | >32 | — |
| 161 | 6.7 | >32 | — |
| 162 | 0.09 | 7.7 | — |
| 163 | 0.48 | 9.9 | — |
| 164 | — | — | — |
| 165 | — | — | — |
| 166 | — | — | — |
| 167 | 11 | >32 | — |
| 168 | — | — | — |
| 169 | 4.9 | >32 | — |
| 170 | 0.90 | 21 | — |
| 171 | — | — | — |
| 172 | — | — | — |
| 173 | — | — | — |
| 174 | — | — | — |
| 175 | 23 | >32 | 20 |
| 176 | 1.4 | 10 | — |
| 177 | 1.3 | 12 | — |
| 178 | — | — | — |
| 179 | — | — | — |

Where replicate experiments were conducted resulting in multiple sets of data for a test compound, the data presented represent the average value from all replicate experiments.

The invention claimed is:

1. A compound of the formula (I):

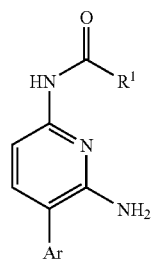

(I)

or a pharmaceutically acceptable salt thereof, wherein:
R$^1$ is selected from the group consisting of:
(i) phenyl, optionally substituted by one or more substituents each independently selected from the group consisting of halo, cyano, (C$_1$-C$_4$)alkyl, (C$_1$-C$_4$)alkoxy, halo(C$_1$-C$_4$)alkyl, halo(C$_1$-C$_4$)alkoxy, (C$_1$-C$_4$)alkoxy (C$_1$-C$_4$)alkyl, (C$_1$-C$_4$)alkylamino and di-((C$_1$-C$_4$)alkyl) amino; and (ii) a 5-membered heteroaryl group comprising either (a) from 1 to 4 nitrogen atoms or (b) one oxygen or one sulphur atom and 1 or 2 nitrogen atoms, and wherein the heteroaryl group is optionally substituted by one substituent selected from the group consisting of (C$_1$-C$_4$) alkyl, (C$_1$-C$_4$)alkoxy, halo(C$_1$-C$_4$)alkyl, halo(C$_1$-C$_4$) alkoxy, (C$_1$-C$_4$)alkoxy(C$_1$-C$_4$)alkyl, (C$_1$-C$_4$)alkylamino and di-((C$_1$-C$_4$)alkyl)amino; with the proviso that R$^1$ is not imidazolyl, oxazolyl or 1,2,4-triazolyl;

Ar is

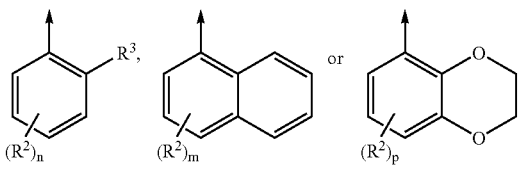

wherein → indicates the point of attachment to the pyridine ring;
each R$^2$ is independently selected from the group consisting of (C$_1$-C$_4$)alkyl, OR$^4$, (C$_1$-C$_4$)alkoxy(C$_1$-C$_4$)alkyl, halo(C$_1$-C$_4$)alkyl, cyano and halo;
n is 0 to 4;
m is 0 to 7;
p is 0 to 3;
R$^3$ is selected from the group consisting of hydrogen, (C$_1$-C$_4$)alkyl, OR$^4$, (C$_1$-C$_4$)alkoxy(C$_1$-C$_4$)alkyl, halo(C$_1$-C$_4$)alkyl, cyano and halo;
R$^4$ is selected from the group consisting of hydrogen, (C$_1$-C$_4$)alkyl, halo(C$_1$-C$_4$)alkyl, (C$_1$-C$_4$)alkoxy(C$_1$-C$_4$) alkyl, (C$_3$-C$_6$)cycloalkyl, (C$_3$-C$_6$)cycloalkyl(C$_1$-C$_4$) alkyl, Het$^1$-, and Het$^1$(C$_1$-C$_4$)alkyl-; and
Het$^1$ is a saturated 5- or 6-membered heterocyclic ring comprising one oxygen atom.

2. A compound according to claim 1, or a pharmaceutically acceptable salt thereof, wherein R$^1$ is selected from the group consisting of:
(i) phenyl, optionally substituted by one or more substituents each independently selected from the group consisting of halo, cyano, (C$_1$-C$_4$)alkyl, (C$_1$-C$_4$)alkoxy, halo(C$_1$-C$_4$)alkyl, and (C$_1$-C$_4$)alkoxy(C$_1$-C$_4$)alkyl; and
(ii) a 5-membered heteroaryl group selected from the group consisting of pyrazolyl, isoxazolyl, oxadiazolyl, and 1,2,3-triazolyl, each being optionally substituted with (C$_1$-C$_4$)alkyl, halo(C$_1$-C$_4$)alkyl, and (C$_1$-C$_4$) alkoxy(C$_1$-C$_4$)alkyl.

3. A compound according to claim 1, or a pharmaceutically acceptable salt thereof, wherein R$^1$ is a 5-membered heteroaryl group selected from the group consisting of:

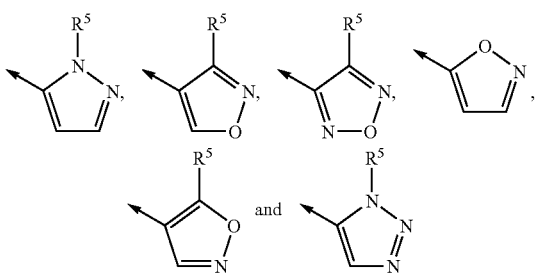

wherein → indicates the point of attachment to the carbonyl moiety and wherein R⁵ is selected from the group consisting of (C₁-C₄)alkyl, halo(C₁-C₄)alkyl, and (C₁-C₄)alkoxy(C₁-C₄)alkyl.

4. A compound according to claim 3, or a pharmaceutically acceptable salt thereof, wherein R⁵ is selected from the group consisting of methyl, ethyl, isopropyl, methoxymethyl, and trifluoromethyl.

5. A compound according to claim 1, or a pharmaceutically acceptable salt thereof, wherein Ar is

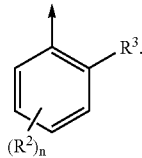

6. A compound according to claim 1, or a pharmaceutically acceptable salt thereof, wherein each R² is independently selected from the group consisting of (C₁-C₄)alkyl, OR⁴, (C₁-C₄)alkoxy(C₁-C₄)alkyl, halo(C₁-C₄)alkyl, and halo; and wherein R⁴ is selected from the group consisting of hydrogen, (C₁-C₄)alkyl, halo(C₁-C₄)alkyl, (C₁-C₄)alkoxy(C₁-C₄)alkyl, (C₃-C₆)cycloalkyl, and (C₃-C₆)cycloalkyl(C₁-C₄)alkyl.

7. A compound according to claim 1, or a pharmaceutically acceptable salt thereof, wherein each R² is independently selected from the group consisting of methyl, ethyl, propyl, hydroxy, methoxy, ethoxy, propoxy, butoxy, cyclopropyloxy, methoxymethyl, methoxyethoxy, methoxypropoxy, cyclopropylmethoxy, difluoromethyl, trifluoromethyl, 2,2,2-trifluoroethyl, difluoromethoxy, trifluoromethoxy, 2,2,2-trifluoroethoxy, chloro and fluoro.

8. A compound according to claim 1, or a pharmaceutically acceptable salt thereof, wherein R³ is selected from the group consisting of (C₁-C₄)alkyl, OR⁴, (C₁-C₄)alkoxy(C₁-C₄)alkyl, halo(C₁-C₄)alkyl, cyano and halo.

9. A compound according to claim 1, or a pharmaceutically acceptable salt thereof, wherein R³ is selected from the group consisting of methyl, ethyl, propyl, hydroxy, methoxy, ethoxy, propoxy, butoxy, cyclopropyloxy, methoxymethyl, methoxyethoxy, methoxypropoxy, cyclopropylmethoxy, difluoromethyl, trifluoromethyl, 2,2,2-trifluoroethyl, difluoromethoxy, trifluoromethoxy, 2,2,2-trifluoroethoxy, chloro and fluoro.

10. A compound according to claim 1 which is selected from the group consisting of:
N-[6-amino-5-(2-chloro-5-methoxyphenyl)pyridin-2-yl]-1-methyl-1H-pyrazole-5-carboxamide;
N-[6-amino-5-(2-chloro-5-methoxyphenyl)pyridin-2-yl]-3-methylisoxazole-4-carboxamide;
N-[6-amino-5-(7-chloro-2,3-dihydro-1,4-benzodioxin-5-yl)pyridin-2-yl]-3-methylisoxazole-4-carboxamide;
N-{6-amino-5-[5-chloro-2-(trifluoromethoxy)phenyl]pyridin-2-yl}-3-methylisoxazole-4-carboxamide;
N-{6-amino-5-[2-chloro-5-(trifluoromethoxy)phenyl]pyridin-2-yl}-3-methylisoxazole-4-carboxamide;
N-{6-amino-5[2-(trifluoromethoxy)phenyl]pyridin-2-yl}-3-methylisoxazole-4-carboxamide;
N-[6-amino-5-(2-chloro-5-methoxyphenyl)pyridin-2-yl]-1-ethyl-1H-pyrazole-5-carboxamide;
N-{6-amino-5-[5-fluoro-2-(trifluoromethoxy)phenyl]pyridin-2-yl}-3-methylisoxazole-4 -carboxamide;
N-[6-amino-5-(2-chloro-5-methoxyphenyl)pyridin-2-yl]-1-isopropyl-1H-pyrazole-5 -carboxamide;
N-[6-amino-5-(5-fluoro-2-propoxyphenyl)pyridin-2-yl]-3-methylisoxazole-4-carboxamide;
N-{6-amino-5-[5-chloro-2-(2,2,2-trifluoroethoxy)phenyl]pyridin-2-yl}-3-methylisoxazole -4-carboxamide;
N-{6-amino-5-[2-(cyclopropyloxy)-5-fluorophenyl]pyridin-2-yl}-1-methyl-1H-pyrazole-5-carboxamide;)
N-{6-amino-5-[2-(cyclopropyloxy)-5-fluorophenyl]pyridin-2-yl}-3-methylisoxazole-4 -carboxamide;
N-[6-amino-5-(2-chlorophenyl)pyridin-2-yl]-1-methyl-1H-pyrazole-5-carboxamide;
N-{6-amino-5-[2-(trifluoromethyl)phenyl]pyridin-2-yl}-3-methylisoxazole-4-carboxamide;
N-[6-amino-5-(2,5-dichlorophenyl)pyridin-2-yl]-1-methyl-1H-pyrazole-5-carboxamide;
N-[6-amino-5-(2,3,5-trichlorophenyl)pyridin-2-yl]-1-methyl-1H-pyrazole-5-carboxamide;
N-[6-amino-5-(2-chloro-5-fluorophenyl)pyridin-2-yl]-1-methyl-1H-pyrazole-5-carboxamide;
N-[6-amino-5-(2,3-dichloro-5-methoxyphenyl)pyridin-2-yl]-1-methyl-1H-pyrazole-5-carboxamide;
N-[6-amino-5-(2,5-dichloro-3-methoxyphenyl)pyridin-2-yl]-1-methyl-1H-pyrazole-5-carboxamide;
N-{6-amino-5-[2-(trifluoromethoxy)phenyl]pyridin-2-yl}-1-methyl-1H-pyrazole-5-carboxamide;
N-{6-amino-5-[5-fluoro-2-(trifluoromethyl)phenyl]pyridin-2-yl}-1-methyl-1H-pyrazole-5-carboxamide;)
N[6-amino-5-(2,4-dichlorophenyl)pyridin-2-yl]-1-methyl-1H-pyrazole-5-carboxamide;
N-{6-amino-5-[5-chloro-2-(trifluoromethoxy)phenyl]pyridin-2-yl}-1-methyl-1H-pyrazole-5-carboxamide;
N-[6-amino-5-(2-chlorophenyl)pyridin-2-yl]-5-methylisoxazole-4-carboxamide;
N-{6-amino-5[2-(trifluoromethoxy)phenyl]pyridin-2-yl}-5-methylisoxazole-4-carboxamide;
N-[6-amino-5-(2-chlorophenyl)pyridin-2-yl]-3-methylisoxazole-4-carboxamide;
N-[6-amino-5-(2,5-dichloro-3-methoxyphenyl)pyridin-2-yl]-3-methylisoxazole-4-carboxamide;
N-[6-amino-5-(2,3,5-trichlorophenyl)pyridin-2-yl]-3-methylisoxazole-4-carboxamide;
N-{6-amino-5-[2-(difluoromethoxy)phenyl]pyridin-2-yl}-3-methylisoxazole-4-carboxamide;
N-{6-amino-5-[5-fluoro-2-(trifluoromethyl)phenyl]pyridin-2-yl}-3-methylisoxazole-4-carboxamide;
N-[6-amino-5-(2-chloro-5-fluorophenyl)pyridin-2-yl]-3-methylisoxazole-4-carboxamide;
N-{6-amino-5-[2-(difluoromethyl)phenyl]pyridin-2-yl}-3-methylisoxazole-4-carboxamide;
N-[6-amino-5-(2-chloro-5-methoxyphenyl)pyridin-2-yl]-4-methyl-1,2,5-oxadiazole-3 -carboxamide;
N-{6-amino-5-[2-(trifluoromethoxy)phenyl]pyridin-2-yl}-4-methyl-1,2,5-oxadiazole-3 -carboxamide;
N-[6-amino-5-(2,5-dichloro-3-methoxyphenyl)pyridin-2-yl]-4-methyl-1,2,5-oxadiazole-3 -carboxamide;
N-[6-amino-5-(2-chlorophenyl)pyridin-2-yl]-1-ethyl-1H-pyrazole-5-carboxamide;
N-[6-amino-5-(2-chloro-5-fluorophenyl)pyridin-2-yl]-1-ethyl-1H-pyrazole-5-carboxamide;
N-{6-amino-5-[2-(trifluoromethoxy)phenyl]pyridin-2-yl}-1-ethyl-1H-pyrazole-5 -carboxamide;
N-{6-amino-5-[5-chloro-2-(trifluoromethoxy)phenyl]pyridin-2-yl}-1-ethyl-1H-pyrazole-5 -carboxamide;
N-[6-amino-5-(2-chlorophenyl)pyridin-2-yl]-1-isopropyl-1H-pyrazole-5-carboxamide;
N-[6-amino-5-(2-chloro-5-fluorophenyl)pyridin-2-yl]-1-isopropyl-1H-pyrazole-5 -carboxamide;

N-{6-amino-5-[2-(trifluoromethoxy)phenyl]pyridin-2-yl}-1-isopropyl-1H-pyrazole-5-carboxamide;
N-[6-amino-5-(2-chlorophenyl)pyridin-2-yl]-3-(methoxymethyl)isoxazole-4-carboxamide;
N-[6-amino-5-(2-chloro-5-fluorophenyl)pyridin-2-yl]-3-(methoxymethyl)isoxazole-4-carboxamide;
N-[6-amino-5-(2-chlorophenyl)pyridin-2-yl]-5-(methoxymethyl)isoxazole-4-carboxamide;
N-[6-amino-5-(2-chloro-5-fluorophenyl)pyridin-2-yl]-5-(methoxymethyl)isoxazole-4-carboxamide;
N-[6-amino-5-(2-chlorophenyl)pyridin-2-yl]-3-(trifluoromethyl)isoxazole-4-carboxamide;
N-{6-amino-5[2-(trifluoromethoxy)phenyl]pyridin-2-yl}-3-(trifluoromethyl)isoxazole-4-carboxamide;
N-[6-amino-5-(2-chloro-5-methoxyphenyl)pyridin-2-yl]-3-(trifluoromethyl)isoxazole-4-carboxamide;
N-{6-amino-5-[5-fluoro-2-(trifluoromethoxy)phenyl]pyridin-2-yl}-1-methyl-1H-pyrazole-5-carboxamide;
N-{6-amino-5-[2-(2,2,2-trifluoroethoxy)phenyl]pyridin-2-yl}-1-methyl-1H-pyrazole-5-carboxamide;
N-{6-amino-5-[2-(2,2,2-trifluoroethoxy)phenyl]pyridin-2-yl}-3-methylisoxazole-4-carboxamide;
N-[6-amino-5-(2-ethoxy-5-fluorophenyl)pyridin-2-yl]-3-methylisoxazole-4-carboxamide;
N-{6-amino-5-[5-methoxy-2-(trifluoromethoxy)phenyl]pyridin-2-yl}-1-methyl-1H-pyrazole-5-carboxamide;
N-{6-amino-5-[2-(2,2,2-trifluoroethyl)phenyl]pyridin-2-yl}-3-methylisoxazole-4-carboxamide;
N-[6-amino-5-(2-chloro-5-ethoxyphenyl)pyridin-2-yl]-3-methylisoxazole-4-carboxamide;
N-{6-amino-5-[5-chloro-2-(2,2,2-trifluoroethoxy)phenyl]pyridin-2-yl}-1-methyl-1H-pyrazole-5-carboxamide;
N-{6-amino-5-[5-fluoro-2-(2,2,2-trifluoroethoxy)phenyl]pyridin-2-yl}-1-methyl-1H-pyrazole-5-carboxamide;
N-{6-amino-5-[5-fluoro-2-(2,2,2-trifluoroethoxy)phenyl]pyridin-2-yl}-3-methylisoxazole-4-carboxamide;
or a pharmaceutically acceptable salt thereof.

11. A pharmaceutical composition comprising a compound of the formula (I), as defined in claim 1, or a pharmaceutically acceptable salt thereof, together with one or more pharmaceutically acceptable excipients.

12. The pharmaceutical composition of claim 11 wherein the compound of the formula (I) is selected from the group consisting of:
N-[6-amino-5-(2-chloro-5-methoxyphenyl)pyridin-2-yl]-1-methyl-1H-pyrazole-5-carboxamide;
N-[6-amino-5-(2-chloro-5-methoxyphenyl)pyridin-2-yl]-3-methylisoxazole-4-carboxamide;
N-[6-amino-5-(7-chloro-2,3-dihydro-1,4-benzodioxin-5-yl)pyridin-2-yl]-3-methylisoxazole-4-carboxamide;
N-{6-amino-5-[5-chloro-2-(trifluoromethoxy)phenyl]pyridin-2-yl}-3-methylisoxazole-4-carboxamide;
N-{6-amino-5-[2-chloro-5-(trifluoromethoxy)phenyl]pyridin-2-yl}-3-methylisoxazole-4-carboxamide;
N-{6-amino-5[2-(trifluoromethoxy)phenyl]pyridin-2-yl}-3-methylisoxazole-4-carboxamide;
N-[6-amino-5-(2-chloro-5-methoxyphenyl)pyridin-2-yl]-1-ethyl-1H-pyrazole-5-carboxamide;
N-{6-amino-5-[5-fluoro-2-(trifluoromethoxy)phenyl]pyridin-2-yl}-3-methylisoxazole-4-carboxamide;
N-[6-amino-5-(2-chloro-5-methoxyphenyl)pyridin-2-yl]-1-isopropyl-1H-pyrazole-5-carboxamide;
N-[6-amino-5-(5-fluoro-2-propoxyphenyl)pyridin-2-yl]-3-methylisoxazole-4-carboxamide;
N-{6-amino-5-[5-chloro-2-(2,2,2-trifluoroethoxy)phenyl]pyridin-2-yl}-3-methylisoxazole-4-carboxamide;
N-{6-amino-5-[2-(cyclopropyloxy)-5-fluorophenyl]pyridin-2-yl}-1-methyl-1H-pyrazole-5-carboxamide;)
N-{6-amino-5-[2-(cyclopropyloxy)-5-fluorophenyl]pyridin-2-yl}-3-methylisoxazole-4-carboxamide;
N-[6-amino-5-(2-chlorophenyl)pyridin-2-yl]-1-methyl-1H-pyrazole-5-carboxamide;
N-{6-amino-5-[2-(trifluoromethyl)phenyl]pyridin-2-yl}-3-methylisoxazole-4-carboxamide;
N-[6-amino-5-(2,5-dichlorophenyl)pyridin-2-yl]-1-methyl-1H-pyrazole-5-carboxamide;
N-[6-amino-5-(2,3,5-trichlorophenyl)pyridin-2-yl]-1-methyl-1H-pyrazole-5-carboxamide;
N-[6-amino-5-(2-chloro-5-fluorophenyl)pyridin-2-yl]-1-methyl-1H-pyrazole-5-carboxamide;
N-[6-amino-5-(2,3-dichloro-5-methoxyphenyl)pyridin-2-yl]-1-methyl-1H-pyrazole-5-carboxamide;
N-[6-amino-5-(2,5-dichloro-3-methoxyphenyl)pyridin-2-yl]-1-methyl-1H-pyrazole-5-carboxamide;
N-{6-amino-5-[2-(trifluoromethoxy)phenyl]pyridin-2-yl}-1-methyl-1H-pyrazole-5-carboxamide;
N-{6-amino-5-[5-fluoro-2-(trifluoromethyl)phenyl]pyridin-2-yl}-1-methyl-1H-pyrazole-5-carboxamide;)
N-[6-amino-5-(2,4-dichlorophenyl)pyridin-2-yl]-1-methyl-1H-pyrazole-5-carboxamide;
N-{6-amino-5-[5-chloro-2-(trifluoromethoxy)phenyl]pyridin-2-yl}-1-methyl-1H-pyrazole-5-carboxamide;
N-[6-amino-5-(2-chlorophenyl)pyridin-2-yl]-5-methylisoxazole-4-carboxamide;
N-{6-amino-5[2-(trifluoromethoxy)phenyl]pyridin-2-yl}-5-methylisoxazole-4-carboxamide;
N-[6-amino-5-(2-chlorophenyl)pyridin-2-yl]-3-methylisoxazole-4-carboxamide;
N-[6-amino-5-(2,5-dichloro-3-methoxyphenyl)pyridin-2-yl]-3-methylisoxazole-4-carboxamide;
N-[6-amino-5-(2,3,5-trichlorophenyl)pyridin-2-yl]-3-methylisoxazole-4-carboxamide;
N-{6-amino-5-[2-(difluoromethoxy)phenyl]pyridin-2-yl}-3-methylisoxazole-4-carboxamide;
N-{6-amino-5-[5-fluoro-2-(trifluoromethyl)phenyl]pyridin-2-yl}-3-methylisoxazole-4-carboxamide;
N-[6-amino-5-(2-chloro-5-fluorophenyl)pyridin-2-yl]-3-methylisoxazole-4-carboxamide;
N-{6-amino-5-[2-(difluoromethyl)phenyl]pyridin-2-yl}-3-methylisoxazole-4-carboxamide;
N-[6-amino-5-(2-chloro-5-methoxyphenyl)pyridin-2-yl]-4-methyl-1,2,5-oxadiazole-3-carboxamide;
N-{6-amino-5-[2-(trifluoromethoxy)phenyl]pyridin-2-yl}-4-methyl-1,2,5-oxadiazole-3-carboxamide;
N-[6-amino-5-(2,5-dichloro-3-methoxyphenyl)pyridin-2-yl]-4-methyl-1,2,5-oxadiazole-3-carboxamide;
N-[6-amino-5-(2-chlorophenyl)pyridin-2-yl]-1-ethyl-1H-pyrazole-5-carboxamide;
N-[6-amino-5-(2-chloro-5-fluorophenyl)pyridin-2-yl]-1-ethyl-1H-pyrazole-5-carboxamide;
N-{6-amino-5-[2-(trifluoromethoxy)phenyl]pyridin-2-yl}-1-ethyl-1H-pyrazole-5-carboxamide;
N-{6-amino-5-[5-chloro-2-(trifluoromethoxy)phenyl]pyridin-2-yl}-1-ethyl-1H-pyrazole-5-carboxamide;
N-[6-amino-5-(2-chlorophenyl)pyridin-2-yl]-1-isopropyl-1H-pyrazole-5-carboxamide;
N-[6-amino-5-(2-chloro-5-fluorophenyl)pyridin-2-yl]-1-isopropyl-1H-pyrazole-5-carboxamide;
N-{6-amino-5-[2-(trifluoromethoxy)phenyl]pyridin-2-yl}-1-isopropyl-1H-pyrazole-5-carboxamide;
N-[6-amino-5-(2-chlorophenyl)pyridin-2-yl]-3-(methoxymethyl)isoxazole-4-carboxamide;

N-[6-amino-5-(2-chloro-5-fluorophenyl)pyridin-2-yl]-3-(methoxymethyl)isoxazole-4-carboxamide;
N-[6-amino-5-(2-chlorophenyl)pyridin-2-yl]-5-(methoxymethypisoxazole-4-carboxamide;
N-[6-amino-5-(2-chloro-5-fluorophenyl)pyridin-2-yl]-5-(methoxymethypisoxazole-4 -carboxamide;
N-[6-amino-5-(2-chlorophenyl)pyridin-2-yl]-3-(trifluoromethypisoxazole-4-carboxamide;
N-{6-amino-5[2-(trifluoromethoxy)phenyl]pyridin-2-yl}-3-(trifluoromethypisoxazole-4 -carboxamide;
N-[6-amino-5-(2-chloro-5-methoxyphenyl)pyridin-2-yl]-3-(trifluoromethypisoxazole-4 -carboxamide;
N-{6-amino-5-[5-fluoro-2-(trifluoromethoxy)phenyl]pyridin-2-yl}-1-methyl-1H-pyrazole-5 -carboxamide;
N-{6-amino-5-[2-(2,2,2-trifluoroethoxy)phenyl]pyridin-2-yl}-1-methyl-1H-pyrazole-5 -carboxamide;
N-{6-amino-5-[2-(2,2,2-trifluoroethoxy)phenyl]pyridin-2-yl}-3-methylisoxazole-4 -carboxamide;
N-[6-amino-5-(2-ethoxy-5-fluorophenyl)pyridin-2-yl]-3-methylisoxazole-4-carboxamide;
N-{6-amino-5-[5-methoxy-2-(trifluoromethoxy)phenyl]pyridin-2-yl}-1-methyl-1H -pyrazole-5-carboxamide;
N-{6-amino-5-[2-(2,2,2-trifluoroethyl)phenyl]pyridin-2-yl}-3-methylisoxazole-4 -carboxamide;
N-[6-amino-5-(2-chloro-5-ethoxyphenyl)pyridin-2-yl]-3-methylisoxazole-4-carboxamide;
N-{6-amino-5-[5-chloro-2-(2,2,2-trifluoroethoxy)phenyl]pyridin-2-yl}-1-methyl-1H -pyrazole-5-carboxamide;
N-{6-amino-5-[5-fluoro-2-(2,2,2-trifluoroethoxy)phenyl]pyridin-2-yl}-1-methyl-1H -pyrazole-5-carboxamide;
N-{6-amino-5-[5-fluoro-2-(2,2,2-trifluoroethoxy)phenyl]pyridin-2-yl}-3-methylisoxazole-4 -carboxamide;
or a pharmaceutically acceptable salt thereof.

13. A method of treating pain in a mammal comprising administering to the mammal requiring such treatment an effective amount of a compound of the formula(I) as defined in claim 1, or a pharmaceutically acceptable salt thereof.

14. The method of claim 13 wherein the mammal is a human.

15. The method of claim 13 wherein the type of pain is selected from the group consisting of chronic, inflammatory, neuropathic, nociceptive and visceral pain.

16. The method of claim 13 wherein the compound of the formula 9l) is selected from the group consisting of: N-[6-amino-5-(2-chloro-5 -methoxyphenyl)pyridin-2-yl]-1-methyl-1H-pyrazole-5-carboxamide;
N-[6-amino-5-(2-chloro-5-methoxyphenyl)pyridin-2-yl]-3-methylisoxazole-4 -carboxamide;
N-[6-amino-5-(7-chloro-2,3-dihydro-1,4-benzodioxin-5-yl)pyridin-2-yl]-3 -methylisoxazole-4-carboxamide;
N-{6-amino-5-[5-chloro-2-(trifluoromethoxy)phenyl]pyridin-2-yl}-3-methylisoxazole-4 -carboxamide;
N-{6-amino-5-[2-chloro-5-(trifluoromethoxy)phenyl]pyridin-2-yl}-3-methylisoxazole-4 -carboxamide;
N-{6-amino-5[2-(trifluoromethoxy)phenyl]pyridin-2-yl}-3-methylisoxazole-4 -carboxamide;
N-[6-amino-5-(2-chloro-5-methoxyphenyl)pyridin-2-yl]-1-ethyl-1H-pyrazole-5 -carboxamide;
N-{6-amino-5-[5-fluoro-2-(trifluoromethoxy)phenyl]pyridin-2-yl}-3-methylisoxazole-4 -carboxamide;
N-[6-amino-5-(2-chloro-5-methoxyphenyl)pyridin-2-yl]-1-isopropyl-1H-pyrazole-5 -carboxamide;
N-[6-amino-5-(5-fluoro-2-propoxyphenyl)pyridin-2-yl]-3-methylisoxazole-4-carboxamide;
N-{6-amino-5-[5-chloro-2-(2,2,2-trifluoroethoxy)phenyl]pyridin-2-yl}-3-methylisoxazole-4 -carboxamide;
N-{6-amino-5-[2-(cyclopropyloxy)-5-fluorophenyl]pyridin-2-yl}-1-methyl-1H-pyrazole-5 -carboxamide;)
N-{6-amino-5-[2-(cyclopropyloxy)-5-fluorophenyl]pyridin-2-yl}-3-methylisoxazole-4 -carboxamide;
N-[6-amino-5-(2-chlorophenyl)pyridin-2-yl]-1-methyl-1H-pyrazole-5-carboxamide;
N-{6-amino-5-[2-(trifluoromethyl)phenyl]pyridin-2-yl}-3-methylisoxazole-4-carboxamide;
N-[6-amino-5-(2,5-dichlorophenyl)pyridin-2-yl]-1-methyl-1H-pyrazole-5-carboxamide;
N-[6-amino-5-(2,3,5-trichlorophenyl)pyridin-2-yl]-1-methyl-1H-pyrazole-5-carboxamide;
N-[6-amino-5-(2-chloro-5-fluorophenyl)pyridin-2-yl]-1-methyl-1H-pyrazole-5 -carboxamide;
N-[6-amino-5-(2,3-dichloro-5-methoxyphenyl)pyridin-2-yl]-1-methyl-1H-pyrazole-5 -carboxamide;
N-[6-amino-5-(2,5-dichloro-3-methoxyphenyl)pyridin-2-yl]-1-methyl-1H-pyrazole-5 -carboxamide;
N-{6-amino-5-[2-(trifluoromethoxy)phenyl]pyridin-2-yl}-1-methyl-1H-pyrazole-5 -carboxamide;
N-{6-amino-5-[5-fluoro-2-(trifluoromethyl)phenyl]pyridin-2-yl}-1-methyl-1H-pyrazole-5 -carboxamide;
N-[6-amino-5-(2,4-dichlorophenyl)pyridin-2-yl]-1-methyl-1H-pyrazole-5-carboxamide;
N-{6-amino-5-[5-chloro-2-(trifluoromethoxy)phenyl]pyridin-2-yl}-1-methyl-1H-pyrazole-5 -carboxamide;
N-[6-amino-5-(2-chlorophenyl)pyridin-2-yl]-5-methyl-isoxazole-4-carboxamide;
N-{6-amino-5[2-(trifluoromethoxy)phenyl]pyridin-2-yl}-5-methylisoxazole-4 -carboxamide;
N-[6-amino-5-(2-chlorophenyl)pyridin-2-yl]-3-methyl-isoxazole-4-carboxamide;
N-[6-amino-5-(2,5-dichloro-3-methoxyphenyl)pyridin-2-yl]-3-methylisoxazole-4 -carboxamide;
N-[6-amino-5-(2,3,5-trichlorophenyl)pyridin-2-yl]-3-methylisoxazole-4-carboxamide;
N-{6-amino-5-[2-(difluoromethoxy)phenyl]pyridin-2-yl}-3-methylisoxazole-4 -carboxamide;
N-{6-amino-5-[5-fluoro-2-(trifluoromethyl)phenyl]pyridin-2-yl}-3-methylisoxazole-4 -carboxamide;
N-[6-amino-5-(2-chloro-5-fluorophenyl)pyridin-2-yl]-3-methylisoxazole-4-carboxamide;
N-{6-amino-5-[2-(difluoromethyl)phenyl]pyridin-2-yl}-3-methylisoxazole-4-carboxamide;
N-[6-amino-5-(2-chloro-5-methoxyphenyl)pyridin-2-yl]-4-methyl-1,2,5-oxadiazole-3 -carboxamide;
N-{6-amino-5-[2-(trifluoromethoxy)phenyl]pyridin-2-yl}-4-methyl-1,2,5-oxadiazole-3 -carboxamide;
N-[6-amino-5-(2,5-dichloro-3-methoxyphenyl)pyridin-2-yl]-4-methyl-1,2,5-oxadiazole-3 -carboxamide;
N-[6-amino-5-(2-chlorophenyl)pyridin-2-yl]-1-ethyl-1H-pyrazole-5-carboxamide;
N-[6-amino-5-(2-chloro-5-fluorophenyl)pyridin-2-yl]-1-ethyl-1H-pyrazole-5-carboxamide;
N-{6-amino-5-[2-(trifluoromethoxy)phenyl]pyridin-2-yl}-1-ethyl-1H-pyrazole-5 -carboxamide;
N-{6-amino-5-[5-chloro-2-(trifluoromethoxy)phenyl]pyridin-2-yl}-1-ethyl-1H-pyrazole-5 -carboxamide;
N-[6-amino-5-(2-chlorophenyl)pyridin-2-yl]-1-isopropyl-1H-pyrazole-5-carboxamide;
N-[6-amino-5-(2-chloro-5-fluorophenyl)pyridin-2-yl]-1-isopropyl-1H-pyrazole-5 -carboxamide;
N-{6-amino-5-[2-(trifluoromethoxy)phenyl]pyridin-2-yl}-1-isopropyl-1H-pyrazole-5 -carboxamide;
N-[6-amino-5-(2-chlorophenyl)pyridin-2-yl]-3-(methoxymethyl)isoxazole-4-carboxamide;

N-[6-amino-5-(2-chloro-5-fluorophenyl)pyridin-2-yl]-3-(methoxymethyl)isoxazole-4-carboxamide;

N-[6-amino-5-(2-chlorophenyl)pyridin-2-yl]-5-(methoxymethyl)isoxazole-4-carboxamide;

N-[6-amino-5-(2-chloro-5-fluorophenyl)pyridin-2-yl]-5-(methoxymethyl)isoxazole-4-carboxamide;

N-[6-amino-5-(2-chlorophenyl)pyridin-2-yl]-3-(trifluoromethyl)isoxazole-4-carboxamide;

N-{6-amino-5[2-(trifluoromethoxy)phenyl]pyridin-2-yl}-3-(trifluoromethyl)isoxazole-4-carboxamide;

N-[6-amino-5-(2-chloro-5-methoxyphenyl)pyridin-2-yl]-3-(trifluoromethyl)isoxazole-4-carboxamide;

N-{6-amino-5-[5-fluoro-2-(trifluoromethoxy)phenyl]pyridin-2-yl}-1-methyl-1H-pyrazole-5-carboxamide;

N-{6-amino-5-[2-(2,2,2-trifluoroethoxy)phenyl]pyridin-2-yl}-1-methyl-1H-pyrazole-5-carboxamide;

N-{6-amino-5-[2-(2,2,2-trifluoroethoxy)phenyl]pyridin-2-yl}-3-methylisoxazole-4-carboxamide;

N-[6-amino-5-(2-ethoxy-5-fluorophenyl)pyridin-2-yl]-3-methylisoxazole-4-carboxamide;

N-{6-amino-5-[5-methoxy-2-(trifluoromethoxy)phenyl]pyridin-2-yl}-1-methyl-1H-pyrazole-5-carboxamide;

N-{6-amino-5-[2-(2,2,2-trifluoroethyl)phenyl]pyridin-2-yl}-3-methylisoxazole-4-carboxamide;

N-[6-amino-5-(2-chloro-5-ethoxyphenyl)pyridin-2-yl]-3-methylisoxazole-4-carboxamide;

N-{6-amino-5-[5-chloro-2-(2,2,2-trifluoroethoxy)phenyl]pyridin-2-yl}-1-methyl-1H-pyrazole-5-carboxamide;

N-{6-amino-5-[5-fluoro-2-(2,2,2-trifluoroethoxy)phenyl]pyridin-2-yl}-1-methyl-1H-pyrazole-5-carboxamide;

N-{6-amino-5-[5-fluoro-2-(2,2,2-trifluoroethoxy)phenyl]pyridin-2-yl}-3-methylisoxazole-4-carboxamide;

or a pharmaceutically acceptable salt thereof.

17. The method of claim 16 wherein the mammal is a human.

18. The method of claim 16 wherein the type of pain is selected from the group consisting of chronic, inflammatory, neuropathic, nociceptive and visceral pain.

19. A combination of a compound of the formula (I), or a pharmaceutically acceptable salt thereof, as defined in claim 1, and another pharmacologically active agent.

20. N-[6-amino-5-(2-chloro-5-methoxyphenyl)pyridin-2-yl]-1-methyl-1H-pyrazole-5-carboxamide, or a pharmaceutically acceptable salt thereof.

21. The pharmaceutical composition according to claim 11 in which said compound is N-[6-amino-5-(2-chloro-5-methoxyphenyl)pyridin-2-yl]-1-methyl-1H-pyrazole-5-carboxamide, or a pharmaceutically acceptable salt thereof.

22. The method according to claim 13 in which said compound is N-[6-amino-5-(2-chloro-5-methoxyphenyl)pyridin-2-yl]-1-methyl-1H-pyrazole-5-carboxamide, or a pharmaceutically acceptable salt thereof.

23. The method according to claim 15 in which said compound is N-[6-amino-5-(2-chloro-5-methoxyphenyl)pyridin-2-yl]-1-methyl-1H-pyrazole-5-carboxamide, or a pharmaceutically acceptable salt thereof.

* * * * *